(12) United States Patent
Dahmann et al.

(10) Patent No.: US 8,420,630 B2
(45) Date of Patent: Apr. 16, 2013

(54) PYRIMIDINE DERIVATIVES

(75) Inventors: Georg Dahmann, Attenweiler (DE); Frank Himmelsbach, Mittelbiberach (DE); Bernd Krist, Altenmuenster (DE); Martin Lenter, Ulm (DE); Alexander Pautsch, Ulm (DE); Gisela Schnapp, Biberach-Rindenmoos (DE); Martin Steegmaier, Reutlingen (DE); Helmut Wittneben, Schriesheim (DE); Anthony S. Prokopowicz, Stormville, NY (US); Walter Spevak, Oberrohrbach (AT); Andreas Schoop, Neuried (DE); Steffen Steurer, Vienna (AT)

(73) Assignees: Boehringer Ingelheim Pharma GmbH & Co. KG, Ingelheim am Rhein (DE); Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 12/711,364

(22) Filed: Feb. 24, 2010

(65) Prior Publication Data

US 2010/0152167 A1    Jun. 17, 2010

Related U.S. Application Data

(62) Division of application No. 11/313,380, filed on Dec. 21, 2005, now Pat. No. 7,709,480, which is a division of application No. 10/271,763, filed on Oct. 16, 2002, now Pat. No. 7,173, 028.

(60) Provisional application No. 60/330,145, filed on Oct. 17, 2001.

(51) Int. Cl.
*C07D 239/48* (2006.01)
*C07D 403/12* (2006.01)
*C07D 401/12* (2006.01)
*A61K 31/506* (2006.01)

(52) U.S. Cl.
USPC .......... 514/212.08; 514/218; 514/235.8; 514/252.02; 514/252.14; 514/252.18; 514/266.22; 514/275; 540/575; 540/601; 544/122; 544/238; 544/284; 544/295; 544/323; 544/324

(58) Field of Classification Search .......... 544/323, 544/122, 238, 284, 295, 324; 514/275, 212.08, 514/218, 235.8, 252.02, 252.14, 252.18, 514/266.22; 540/575, 601
See application file for complete search history.

(56) References Cited

U.S. PATENT DOCUMENTS

| | | | |
|---|---|---|---|
| 2,723,975 A | 11/1955 | Goldberg | |
| 4,189,581 A | 2/1980 | Scharwaechter et al. | |
| 4,215,216 A | 7/1980 | Scotese et al. | |
| 4,236,004 A | 11/1980 | Scotese et al. | |
| 4,245,094 A | 1/1981 | Scotese et al. | |
| 4,255,568 A | 3/1981 | Scotese et al. | |
| 4,279,899 A | 7/1981 | Gutsche et al. | |
| 4,301,281 A | 11/1981 | Scotese et al. | |
| 4,415,574 A | 11/1983 | Laruelle et al. | |
| 5,147,876 A | 9/1992 | Mizuchi et al. | |
| 5,491,234 A | 2/1996 | Coe et al. | |
| 5,620,981 A | 4/1997 | Blankley et al. | |
| 5,733,914 A | 3/1998 | Blankley et al. | |
| 6,096,747 A | 8/2000 | Beeley et al. | |
| 6,197,779 B1 | 3/2001 | Andries et al. | |
| 6,200,977 B1 | 3/2001 | Cushing et al. | |
| 6,235,746 B1 | 5/2001 | Davis et al. | |
| 6,498,163 B1 | 12/2002 | Boschelli et al. | |
| 6,908,920 B2 | 6/2005 | Thomas et al. | |
| 7,034,019 B2 | 4/2006 | Kukla et al. | |
| 7,105,530 B2 | 9/2006 | Boloor et al. | |
| 7,166,599 B2 * | 1/2007 | Bornemann et al. ....... 514/235.8 |
| 7,173,028 B2 | 2/2007 | Dahmann et al. | |
| 7,220,736 B2 | 5/2007 | Yamada et al. | |
| 7,273,868 B2 | 9/2007 | Yamada et al. | |

(Continued)

FOREIGN PATENT DOCUMENTS

DE    4029650 A1    3/1992
EP    0379806 A2    8/1990

(Continued)

OTHER PUBLICATIONS

Blain et al., Differential Interaction of the Cyclin-dependent Kinase (Cdk) Inhibitor p27Kip1 with Cyclin A-Cdk2 nad Cyclin D2-Cdk4, The Journal of Biological Chemistry, vol. 272, No. 41, pp. 25863-25872, 1997.*

(Continued)

*Primary Examiner* — Deepak Rao

(74) *Attorney, Agent, or Firm* — Michael P. Morris; Philip I. Datlow

(57) ABSTRACT

The present invention relates to trisubstituted pyrimidines of formula (I)

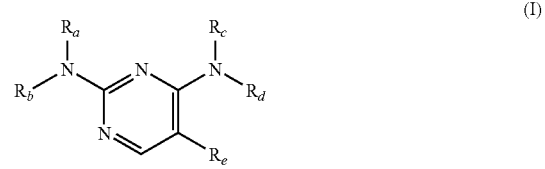

wherein $OR_a$ to $R_e$ are defined as in claim 1, which are suitable for the treatment of illnesses characterized by excessive or abnormal cell proliferation, the use thereof for preparing a pharmaceutical composition with the abovementioned properties, and processes for the preparation thereof.

12 Claims, No Drawings

U.S. PATENT DOCUMENTS

| | | | |
|---|---|---|---|
| 7,291,624 | B2 | 11/2007 | Brumby et al. |
| 7,557,210 | B2 | 7/2009 | Singh et al. |
| 7,598,260 | B2 | 10/2009 | Brumby et al. |
| 2002/0183335 | A1 | 12/2002 | Hewawasam et al. |
| 2003/0032647 | A1 | 2/2003 | Yamada et al. |
| 2003/0130286 | A1 | 7/2003 | Denny et al. |
| 2003/0171359 | A1 | 9/2003 | Dahmann et al. |
| 2003/0186990 | A1 | 10/2003 | Kukla et al. |
| 2003/0216406 | A1 | 11/2003 | Thomas et al. |
| 2003/0229089 | A1 | 12/2003 | Yamada et al. |
| 2004/0029902 | A1 | 2/2004 | Singh et al. |
| 2004/0102630 | A1 | 5/2004 | Brumby et al. |
| 2004/0142930 | A1 | 7/2004 | Yamada et al. |
| 2004/0224966 | A1 | 11/2004 | Brumby et al. |
| 2004/0242578 | A1 | 12/2004 | Boloor et al. |
| 2004/0242613 | A1 | 12/2004 | Cardozo et al. |
| 2006/0009474 | A1 | 1/2006 | Kukla et al. |
| 2006/0100227 | A1 | 5/2006 | Baenteli et al. |
| 2008/0027037 | A1 | 1/2008 | Yamada et al. |
| 2008/0039447 | A1 | 2/2008 | Brumby et al. |

FOREIGN PATENT DOCUMENTS

| | | | |
|---|---|---|---|
| EP | 0945443 | A1 | 9/1999 |
| EP | 1223170 | A1 | 7/2002 |
| FR | 2358148 | A1 | 2/1978 |
| GB | 910125 | A | 11/1962 |
| JP | 3127790 | A | 5/1991 |
| JP | 3918048 | | 5/2007 |
| WO | 9118887 | A1 | 12/1991 |
| WO | 9719065 | A1 | 5/1997 |
| WO | 9919305 | A2 | 4/1999 |
| WO | 9941253 | A1 | 8/1999 |
| WO | 9950250 | A1 | 10/1999 |
| WO | 0012485 | A1 | 3/2000 |
| WO | 0012486 | A1 | 3/2000 |
| WO | 0027825 | A1 | 5/2000 |
| WO | 0027826 | A1 | 5/2000 |
| WO | 0039101 | A1 | 7/2000 |
| WO | 0053595 | A1 | 9/2000 |
| WO | 0119825 | A1 | 3/2001 |
| WO | 0122938 | A1 | 4/2001 |
| WO | 0133989 | A1 | 5/2001 |
| WO | 0155148 | A1 | 8/2001 |
| WO | 0164653 | A1 | 9/2001 |
| WO | 0164654 | A1 | 9/2001 |
| WO | 0164655 | A1 | 9/2001 |
| WO | 0164656 | A1 | 9/2001 |
| WO | 0172717 | A1 | 10/2001 |
| WO | WO 02/04429 | * | 1/2002 |
| WO | 02066036 | A1 | 8/2002 |
| WO | 02096888 | A1 | 12/2002 |
| WO | WO 03/040141 | * | 5/2003 |
| WO | 03082855 | A1 | 10/2003 |

OTHER PUBLICATIONS

Traxler, Protein Tyrosine Kinase Inhibition in cancer treatment, Exp. Opin. Ther. Patents, 7(6), pp. 571-588, 1997.*

Douglas, Jr., Introduction to Viral Diseases, Cecil Textbook of Medicine, 20th Edition, vol. 2, pp. 1739-1744, 1996.*

LuValle et al., Cell Cycle Control in Growth Plate, Frontiers in Biosciences, 5, d493-503, May 2000.*

Simone, Oncology: Introduction, Cecil Textbook of Medicine, 20th Edition, vol. 1, pp. 1004-1010, 1996.*

Dahmann, G. et al; Chemical Abstracts, vol. 138:321292, 2003: Corresponds to US 2003/0171359.

Jill Murrell, et al. "A Mutation in the Amyloid Precursor Protein Associated with Hereditary Alzheimer's Disease" Science, vol. 25, pp. 97-99, 1991.

Barbara Cordell "B-Amyloid Formation as a Potential Therapeutic Target for Alzheimer's Disease" Annual Review Pharmacology and Toxicology, 1994, 34:69-89.

Marie-Christine Chartier-Harlin, et al. "Early-onset Alzheimer's Disease caused by Mutations at Codon 717 of the B-amyloid Precursor Protein Gene" Nature, vol. 353, pp. 844-846, 1991.

Martin Citron, et al. "Mutation of the B-amyloid Precursor Protein in Familial Alzheimer's Disease Increases B-protein Production" Nature, vol. 360, pp. 672-674, 1992.

George G. Glenner, et al. "Alzheimer's Disease: Initial Report of the Purification and Characterization of a Novel Cerebrovascular Amyloid Protein" Biochem. Biophys. Res. Comm., vol. 120, No. 3, pp. 885-890, 1984.

K. Johnson-Wood, et al. "Amyloid precursor protein processing and AB42 deposition in a transgenic mouse model of Alzheimer disease" Proc.Natl.Acad.Sci.USA, vol. 94, pp. 1550-1555, 1997.

Dennis J. Selkoe "Amyloid Protein and Alzheimer's Disease" Scientific American, Nov. 1991, pp. 68-78.

Hewawasam, P. et al; "2,4-Disubstituted Pyrimidine-5-Carboxamide Derivatives As KCNQ Potassium Channel Modulators"; US 2002/0183335 A1; Dec. 5, 2002.

Denny et al., Chemical Abstracts, vol. 134:237498, 2001: Corresponds to US 2003/0130286.

EP Patent Abstracts of Japan; Publication No. 01327790; Patent No. JP 3-127790 , (1991).

Boschelli, et al; "Synthesis and Tyrosine Kinase Inhibitory Activity of a Series of 2-Amino-8H-pyrido[2,3-d] pyrimidines: Identification of Potent, Selective Platelet-Derived Growth Factor Receptor Tyrosine Kinase Inhibitors"; J Med Chem 1998, 41, pp. 4365-4377.

Chemical Abstract: CA 117:48596 for German Patent DE 4029650 A1, (1992).

Yamada, K. et al; "Aromatic Nitrogen-Containing 6-Membered Cyclic Compounds"; US 2003/0032647 A1; Feb. 13, 2003.

Bornemann, K. et al; "Trisubstituted Pyrimidines"; U.S. Appl. No. 10/272,160; Filed Oct. 16, 2002.

Barbosa, Jr. et al, Pyrimidine Derivatives Useful as Inhibitors of αPKC-Theta; U.S. Appl. No. 11/175,476 filed Jul. 6, 2005 (Now U.S. 7,166,599).

Peters et al.; The Synthesis of Some 2,4,5-Trisubstituted Pyrimidines; Journal of Organic Chemistry; Dec. 1960; pp. 2137-2142.

Ghosh et al.; 2,4-Bis(arylamino)-5-methylpyrimidines as Antimicrobial Agents; Journal of Medicinal Chemistry; 1967; vol. 10; pp. 974-975.

O'Brien et al.; Pyrimidines. XVI. 2,4,5-Triaminopyrimidines and Related Compounds; Journal of Medicinal Chemistry; Jan. 1966; vol. 9; pp. 121-126.

Roy et al.; Synthesis of Some Arylamino- and Arylguanidinopyrimidines; Journal Organic Chemistry; Nov. 1960; vol. 25; pp. 1909-1912.

Schmidt et al.; A Convenient Synthesis of 2-Substituted 4-Amino-5-pyrimidinecarbonitriles; Journal of Heterocyclic Chemistry; Sep.-Oct. 1987; vol. 24; pp. 1305-1307.

Okumura et al.; Synthesis of Isokinetin, 2-N-furfurylaminopurine and its Leaf-growth Activity (Studies of Isokinetin and its Analogs. Part I); Bulletin Chemical Society Japan; Oct. 1960; vol. 33; No. 10; pp. 1471-1472.

Taylor et al.; Pyrimido[4,5-d]pyrimidines. Part I; Journal American Chemical Society; Nov. 5, 1960; vol. 82; pp. 5711-5718.

Dille et al.; *Purines v. the Preparation of Certain 2,9-Substituted Purines and Azapurines*; Journal of Organic Chemistry; Feb. 1955; vol. 20; pp. 171-177.

* cited by examiner

PYRIMIDINE DERIVATIVES

RELATED APPLICATIONS

This application is a Division of U.S. application Ser. No. 11/313,380, filed on Dec. 21, 2005, which is a division of U.S. application Ser. No. 10/271,763, filed on Oct. 16, 2002, now U.S. Pat. No. 7,173,028, which issued on Feb. 6, 2007, which claims the benefit of U.S. Provisional Application Ser. No. 60/330,145, filed on Oct. 17, 2001.

FIELD OF THE INVENTION

The invention relates to 2,4,5-trisubstituted pyrimidines of formula (I)

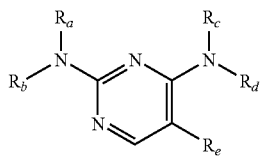

wherein the groups $R_a$ to $R_e$ have the meanings given in the claims and in the specification, processes for preparing them and the use thereof as pharmaceutical compositions, particularly as pharmaceutical compositions for the treatment of illnesses characterised by excessive or abnormal cell proliferation.

BACKGROUND OF THE INVENTION

International Patent Application WO 00/53595 describes the use of 2,4,5-substituted pyrimidines, with a heterocyclic group in the 4 position and an anilino group in the 2 position, which in turn carries a side chain with the length of at least one n-propyl group, as an active component with an anticancer activity.

Moreover, International Patent Application WO 00/39101 proposes the use of 2,4,5-substituted pyrimidines as compounds with an anticancer activity, which are linked in the 2 and 4 positions to an aromatic or heteroaromatic ring, at least one of which has a side chain with the length of at least one n-propyl group.

Antiviral 2,4,5-substituted pyrimidines, wherein the groups $R_c$ and $R_d$ at the nitrogen of the 4 position form a heteroaromatic five-membered ring, are known from International Patent Application WO 99/41253.

International Patent Application WO 97/19065 also proposes the use of 2,4,5-substituted pyrimidines, with a 3,4-dialkoxy-anilino group in the 2 position, as kinase inhibitors.

For 2,4,5-substituted pyrimidines which carry (hetero)aryls in the 2 and 4 positions (WO00/27825), as well as for 2,4,5-substituted pyrimidines which carry a (hetero)aryl group functionalised with a nitrile group in position 2 or 4 (EPO 945 443), an antiviral activity has been described.

The aim of the present invention is to find new active substances which can be used for the prevention and/or treatment of diseases characterised by excessive or abnormal cell proliferation.

DETAILED DESCRIPTION OF THE INVENTION

Surprisingly, it has now been found that the compounds of general formula (I)

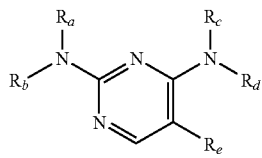

have valuable pharmacological properties, particularly an inhibiting activity on protein kinases such as SRC kinases, PLK kinase and particularly cyclin-dependent kinases (CDKs, such as e.g. CDK1, CDK2, CDK3, CDK4, CDK5, CDK6, CDK7, CDK8 and CDK9 with their specific cyclins A, B1, B2, C, D1 D2, D3, E, F, G1, G2, H, I, K and viral cyclin) as well as on the kinase activity of Aurora B. The compounds exhibit valuable pharmacological properties, such as neuroprotection and an inhibiting activity on the proliferation of cultivated human tumour cells.

In view of their biological properties the new compounds of general formula I, their isomers and their physiologically acceptable salts are suitable for treating diseases characterised by excessive or abnormal cell proliferation.

Such diseases include (with no claim to completeness): viral infections (e.g. HIV and Kaposi's sarcoma); infections caused by adeno, influenza or cytomegaly viruses); bacterial, fungal and/or parasitic infections; skin diseases (e.g. psoriasis, eczema, keratoses); bone diseases; cardiovascular diseases (e.g. restenosis and hypertrophism). They may also be useful in protecting proliferating cells (e.g. hair, intestinal, blood and progenitor cells) against DNA damage caused by radiation, UV treatment and/or cytostatic treatment (Davis et al., 2001, Science, 291, 134-137).

In addition, the compounds are useful for immunosuppression (e.g. in organ transplantation) and for the prevention or treatment of inflammation and autoimmune diseases (e.g. colitis, arthritis, Alzheimer's disease, glomerulonephritis and wound healing).

In particular, these compounds are useful as cytotoxic or cytostatic active substances for the treatment or prevention of diseases based on the proliferation of tumour cells.

The term "cytotoxic compound" denotes a chemical which has a toxic effect on living cells, particularly an active substance which destroys cancer cells. The term "cytostatic compound" denotes a compound which suppresses cell growth and division and thus also suppresses cell proliferation.

Accordingly, in another aspect, the invention relates to the use of a compound of the invention for preparing a pharmaceutical composition for the treatment of cancer. The invention further relates to a method for treating cancer by administering an effective amount of a pharmaceutical composition according to the invention to the patient. The indications include the treatment of cancer, in particular:

1) The treatment of malignant neoplasias and carcinomas including breast cancer, neoplasias of the digestive tract (colorectal carcinoma, anal carcinoma, pancreatic carcinoma, gastric carcinoma, oesophageal carcinoma, hepatocellular carcinoma, gall bladder carcinoma), lung cancer, tumours of the head and neck, ovarian tumours, tumours of the adnexa, endometrial carcinoma, prostate carcinoma, testicular tumours, urothelial carcinoma, kidney cell carcinoma, skin tumours, thyroid carcinoma and endocrinically active tumours.

2) Sarcomas of the bones and soft tissues: osteosarcoma, soft tissue sarcoma, Ewing's sarcoma, chondrosarcoma, fibrosarcoma, malignant fibrous histiocytoma (NFH), leiomyosarcomas and other soft tissue sarcomas;

3) Malignant tumours of haemopoiesis: Hodgkin's and non-Hodgkin's lymphomas; leukaemias, multiple myeloma, myeloproliferative and myelodysplastic syndromes;
4) Neuroectodermal tumours: peripheral nerve sheath tumours, medulloblastomas; neuroblastomas, retinoblastomas, astrocytomas and other brain tumours;
5) Melanomas;
6) Mesotheliomas.

The new compounds of formula I may also be used for the short-term or long-term treatment of the abovementioned diseases, optionally in combination with other "state-of-the-art" compounds such as other cytostatics, antibodies, targeted therapies such as inhibitors of the EGF, Her2 or VEGF signal transduction pathway or angiogenesis inhibitors. The CDK1 inhibitor olomoucine was found to have a synergistic effect with cytotoxic substances in cell culture (Ongkeko et al., 1995, J. Cell Sci., 108, 2897). The compounds mentioned may be administered before or after the administration of known antitumour drugs or cytotoxic substances. It is known that the cytotoxic activity of the CDK inhibitor flavopiridol in conjunction with cancer drugs is influenced by the sequence in which they are administered. (Cancer Research, 1997, 57, 3375).

Examples of cytostatics which are suitable for use in conjunction with the compounds of formula I are anthracycline such as doxorubicin, analogues of methotrexate such as methotrexate, pritrexime, trimetrexate or DDMP, melphalan, analogues of cisplatin such as cisplatin, J216, JM335, bis(platinum), oxaliplatin or carboplatin, analogues of purines and pyrimidines such as cytarabine, gemcitabine, azacitidine, 6-thioguanine, fludarabine or 2-deoxycoformycin and analogues of other chemotherapeutic agents such as 9-aminocamptothecin, D,L-aminoglutethimide, trimethoprim, pyrimethamine, mitomycin C, mitoxantrone, cyclophosphamide, 5-fluorouracil, capecitabine, estramustine, podophyllotoxin, bleomycin, epothilone A, B, C or D and derivatives of epothilone as described for example in U.S. Pat. No. 6,204,388, as well as taxane.

The present invention thus relates to the new 2,4,5-trisubstituted pyrimidines of formula (I)

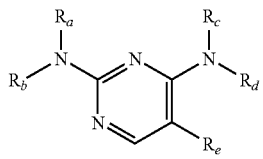
(I)

wherein
$R_a$ denotes a hydrogen atom or an alkyl group,
$R_b$ denotes an aralkyl group optionally substituted in the alkylene moiety by one or two alkyl groups, which may be substituted in the aryl moiety by a carboxy, alkoxycarbonyl, aminocarbonyl, alkylaminocarbonyl, dialkylaminocarbonyl, amino, alkylamino, dialkylamino, cyano, trifluoromethyl or nitro group or one or two fluorine, chlorine, bromine or iodine atoms or one or two hydroxy, alkyl or alkoxy groups, while the substituents may be identical or different, or by a 5- to 7-membered alkyleneimino group, while in each case one or two methylene groups adjacent to the nitrogen atom may be replaced in each case by a carbonyl group or in the abovementioned 6- to 7-membered alkyleneimino groups a methylene group in the 4-position may be replaced by an oxygen atom, by an imino, N-aryl-imino or N-alkyl-imino group, or
denotes a phenyl group optionally substituted by the groups $R_1$ to $R_3$, while
$R_1$ and $R_2$ in each case independently of one another denote a fluorine, chlorine, bromine or iodine atom, or
a $C_{1-2}$-alkyl or hydroxy group,
a $C_{3-7}$-cycloalkyl or $C_{4-7}$-cycloalkoxy group which may be substituted in each case by one or two alkyl groups or by an aryl group,
a $C_{2-5}$-alkenyl group optionally substituted by an aryl group,
a $C_{2-5}$-alkynyl group optionally substituted by an aryl group
an aryl, aryloxy, aralkyl, aralkoxy, alkylsulphenyl, alkylsulphinyl, alkylsulphonyl, alkylsulphonyloxy, trifluoromethylsulphenyl, trifluoromethylsulphinyl, trifluoromethylsulphonyl, arylsulphenyl, arylsulphinyl, arylsulphonyl, aralkylsulphenyl, aralkylsulphinyl or aralkylsulphonyl group,
a methyl or methoxy group substituted by 1 to 3 fluorine atoms,
a $C_{2-4}$-alkyl or $C_{2-4}$-alkoxy group substituted by 1 to 5 fluorine atoms,
a nitro, amino, alkylamino, dialkylamino, $C_{3-7}$-cycloalkylamino, N-alkyl-$C_{3-7}$-cycloalkylamino, arylamino, N-alkyl-arylamino, aralkylamino or N-alkyl-aralkylamino group,
a 4- to 7-membered alkyleneimino group optionally substituted by 1 to 4 alkyl groups, while in the abovementioned 5- to 7-membered alkyleneimino groups in each case one or two methylene groups adjacent to the nitrogen atom may be replaced in each case by a carbonyl group or in the abovementioned 6- to 7-membered alkyleneimino groups a methylene group in the 4-position may be replaced by an oxygen or sulphur atom, by a sulphinyl, sulphonyl, imino, N-alkyl-imino, N-alkylcarbonyl-imino, N-alkylsulphonyl-imino, N-arylcarbonyl-imino, N-arylsulphonyl-imino, N-aryl-imino or N-aralkyl-imino group,
an (alkyleneimino)carbonyl or (alkyleneimino)sulphonyl group with in each case 4 to 7 cyclic atoms in the alkyleneimino moiety, optionally substituted by 1 to 4 alkyl groups, while in the abovementioned 6- to 7-membered alkyleneimino moieties in each case a methylene group in the 4-position may be replaced by an oxygen or sulphur atom, by a sulphinyl, sulphonyl, imino, N-alkyl-imino, N-alkylcarbonyl-imino, N-alkylsulphonyl-imino, N-arylcarbonyl-imino, N-arylsulphonyl-imino, N-aryl-imino or N-aralkyl-imino group,
an alkylcarbonylamino, N-alkyl-alkylcarbonylamino, alkyl-sulphonylamino, N-alkyl-alkylsulphonylamino, arylcarbonylamino, N-alkyl-arylcarbonylamino, arylsulphonylamino, N-alkyl-arylsulphonylamino, aralkylcarbonylamino, N-alkyl-aralkylcarbonylamino, aralkylsulphonylamino, N-alkyl-aralkylsulphonylamino, perfluoroalkylsulphonylamino, N-alkyl-perfluoralkylsulphonylamino, alkylcarbonyl, arylcarbonyl, aralkylcarbonyl, arylhydroxymethyl, aralkyl-hydroxymethyl, carboxy, alkoxycarbonyl, aralkoxycarbonyl, aminocarbonyl, alkylaminocarbonyl, dialkylaminocarbonyl, arylaminocarbonyl, N-alkyl-arylaminocarbonyl, aralkylaminocarbonyl, N-alkyl-aralkylaminocarbonyl, N-hydroxy-aminocarbonyl, N-hydroxy-alkylaminocarbonyl, N-alkoxy-aminocarbonyl, N-alkoxy-alkylaminocarbonyl, cyano, azido, N-cyano-amino or N-cyano-alkylamino group,
a sulpho, alkoxysulphonyl, aminosulphonyl, alkylaminosulphonyl, dialkylaminosulphonyl, arylaminosulphonyl, pyridylaminosulphonyl, pyrimidinylaminosulphonyl, N-alkyl-arylaminosulphonyl, aralkylaminosulphonyl or N-alkyl-aralkylaminosulphonyl group,
a phosphono, O-alkyl-phosphono, O,O'-dialkyl-phosphono, O-aralkyl-phosphono or O,O'-diaralkyl-phosphono group,
a $C_{1-2}$ alkyl group substituted by $R_4$, wherein
$R_4$ denotes a hydroxy, alkoxy, aryloxy, aralkoxy, amino, alkylamino, haloalkylamino, dialkylamino, alkylsulphenyl, alkylsulphinyl, alkylsulphonyl, arylsulphenyl, arylsulphinyl, arylsulphonyl, aralkylsulphenyl, aralkylsulphinyl, aralkylsulphonyl, carboxy, alkoxycarbonyl, aminocarbonyl, alkylaminocarbonyl, dialkylaminocarbonyl or cyano group, a 4- to 7-membered alkyleneimino group optionally substituted by 1 to 4 alkyl groups, while in the abovementioned 5- to 7-membered alkyleneimino groups one or two methylene groups adjacent to the nitrogen atom may be replaced in each case by a carbonyl group or in the abovementioned 6- to 7-membered alkyleneimino groups a methylene group in the 4-position may be replaced by an oxygen or sulphur atom, by a sulphinyl, sulphonyl, imino, N-alkyl-imino, N-alkylcarbonyl-imino, N-alkylsulphonyl-imino, N-arylcarbonyl-imino, N-arylsulphonyl-imino, N-aryl-imino or N-aralkyl-imino group, or
a 4- to 7-membered alkyleneimino group optionally substituted by 1 to 4 alkyl groups, while in the abovementioned 5- to 7-membered alkyleneimino groups in each case one or two methylene groups adjacent to the nitrogen atom may be substituted by a carbonyl group or in the abovementioned 6- to 7-membered alkyleneimino groups may be substituted by one or two hydroxy, alkoxy, aminocarbonyl, alkylaminocarbonyl, dialkylaminocarbonyl, amino, alkylamino and dialkylamino group,
an (alkyleneimino)carbonyl group optionally substituted by 1 to 4 alkyl groups with 4 to 7 cyclic atoms in the alkyleneimino moiety in each case, while in the abovementioned 6- to 7-membered alkyleneimino moieties in each case a methylene group may be replaced in the 4-position by an oxygen or sulphur atom, by a sulphinyl, sulphonyl, imino, N-alkyl-imino, N-alkylcarbonyl-imino, N-alkylsulphonyl-imino, N-arylcarbonyl-imino, N-arylsulphonyl-imino, N-aryl-imino or N-aralkyl-imino group, or
a group of formula

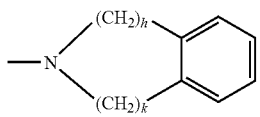

wherein
h and k, which may be identical or different, represent the numbers 1 to 3 or h denotes the number 0 and k denotes the number 2, 3 or 4, while additionally the above benzo moiety may be mono- or disubstituted by fluorine, chlorine, bromine or iodine atoms, by alkyl, trifluoromethyl, hydroxy, alkoxy, carboxy or cyano groups, while the substituents in each case may be identical or different, and the above saturated cyclic alkyleneimino moiety may be substituted by 1 or 2 alkyl groups,
$R_3$ denotes a fluorine, chlorine or bromine atom, a $C_{1-2}$ alkyl, $C_{1-2}$ alkoxy or trifluoromethyl group, or
a 5 or 6-membered heterocyclic, aromatic ring with at least one nitrogen atom and optionally a sulphur or oxygen atom which may be substituted by one or two alkyl, aryl or aralkyl groups, or
a sulpho, alkoxysulphonyl, aminosulphonyl, alkylaminosulphonyl, dialkylaminosulphonyl, arylaminosulphonyl, pyridylaminosulphonyl, pyrimidinylaminosulphonyl, N-alkyl-arylaminosulphonyl, aralkylaminosulphonyl or N-alkyl-aralkylaminosulphonyl group,
$R_2$ together with $R_3$, if they are bound to adjacent carbon atoms, denote
a methylenedioxy group optionally substituted by one or two alkyl groups, or
an n-$C_{3-6}$-alkylene group optionally substituted by one or two alkyl groups, wherein a methylene group may be replaced by an oxygen or sulphur atom, by a sulphinyl, sulphonyl, N-alkylcarbonyl-imino, N-alkylsulphonyl-imino, N-arylcarbonyl-imino or N-arylsulphonyl-imino group, or
a 1,3-butadien-1,4-diylene group optionally substituted by one or two fluorine, chlorine, bromine or iodine atoms, by one or two hydroxy, alkyl, alkoxy, trifluoromethyl, carboxy, alkoxycarbonyl, aminocarbonyl, alkylaminocarbonyl, dialkylaminocarbonyl or cyano groups, while the substituents may be identical or different, or
a group of formula

wherein
the methylene groups of the cyclic alkyleneimino moieties thus formed may additionally be substituted by 1 or 2 alkyl groups,
$R_5$ denotes a hydrogen atom or an alkyl, haloalkyl, aryl or aralkyl group, and m and n, which may be identical or different, represent the numbers 1, 2 or 3, while in the alkyleneimino moieties thus formed one or two methylene groups adjacent to the nitrogen atom may be replaced in each case by a carbonyl group, or
m denotes the number 0 and n denotes the number 2, 3 or 4, while in the alkyleneimino moieties thus formed in each case the methylene group adjacent to the nitrogen atom may be replaced by a carbonyl group, or
$R_2$ together with $R_3$ denotes a group of formula —NH—C(=O)—(CH$_2$)—, —NH—C(=O)—(CH$_2$)$_2$, —NH—N=N, —NH—N=CH, —NH—CH=N—, —O—CH=N, —S—CH=N or —NH—CH=CH— and the tautomers of the ring systems defined by —NH—N=N, —NH—N=CH, —NH—CH=N—, while each hydrogen atom may be substituted by an alkyl, aryl or aralkyl group, or
$R_a$ together with $R_1$, if $R_1$ is in the o-position to the nitrogen atom substituted by $R_a$, also denote an n-$C_{2-4}$-alkylene group optionally substituted by one or two alkyl groups, and $R_cNR_d$ denotes a 4- to 8-membered alkyleneimino group optionally substituted by 1 to 4 alkyl groups or 1 to 2 aryl groups, which is additionally substituted by the group $R_6$, while $R_6$ denotes a carboxy, alkoxycarbonyl, aminocarbonyl, alkylaminocarbonyl, dialkylaminocarbonyl, cyano, hydroxy, alkoxy, aryloxy, aralkoxy, alkylcarbonyloxy, arylcarbonyloxy, amino, alkylamino, hydroxy-$C_{2-4}$-alkylamino, dialkylamino, cyanamino, formylamino, N-(alkyl)-N-(hydroxy-$C_{2-4}$-alkyl)amino, bis-(hydroxy-$C_{2-4}$-alkyl)-amino group, alkylsulphenyl, alkylsulphinyl, alkylsulphonyl, arylsulphenyl, arylsulphinyl, arylsulphonyl, aralkylsulphenyl, aralkylsulphinyl, aralkylsulphonyl, an alkylcarbonylamino, N-alkyl-alkylcarbonylamino, alkylsulphonylamino, N-alkyl-alkylsulphonylamino, arylcarbonylamino, N-alkyl-arylcarbonylamino, arylsulphonylamino, N-alkyl-arylsulphonylamino, aralkylcarbonylamino, N-alkyl-aralkylcarbonylamino, aralkylsulphonylamino, N-alkyl-aralkylsulphonylamino, alkoxycarbonylamino, N-alkyl-alkoxycarbonylamino, alkoxycarbonylalkylamino, N-(alkyl)-N-(alkoxycarbonylalkyl)-amino, aralkoxycarbonylamino or N-alkyl-aralkoxycarbonylamino group, an $(NR_8R_9)CONR_7$ or $(NR_8R_9)SO2NR_7$-group, wherein
$R_7$, $R_8$ and $R_9$, which may be identical or different, in each case denote a hydrogen atom or an alkyl, aryl or pyridyl group, or
$R_7$ and $R_8$ together denote an n-$C_{2-4}$-alkylene group and $R_9$ denotes a hydrogen atom or an alkyl, aryl or pyridyl group, an (alkyleneimino)carbonyl group optionally substituted by 1 to 4 alkyl groups with in each case 4 to 7 cyclic atoms in the alkyleneimino moiety, while in the abovementioned 6- to 7-membered alkyleneimino moieties in each case a methylene group in the 4-position may be replaced by an oxygen or sulphur atom, by a sulphinyl, sulphonyl, imino, N-alkyl-imino, N-alkylcarbonyl-imino, N-alkylsulphonyl-imino, N-aryl-imino or N-aralkyl-imino group, a 4- to 7-membered alkyleneimino group optionally substituted by 1 to 4 alkyl groups or a hydroxyalkyl group, while in the abovementioned 5- to 7-membered alkyleneimino groups in each case one or two methylene groups adjacent to the nitrogen atom may be replaced by a carbonyl group, a 6 or 7-membered alkyleneimino group optionally substituted by 1 to 4 alkyl groups or a hydroxyalkyl group, while in each case a methylene group in the 4-position of the alkyleneimino moiety is replaced by an oxygen or sulphur atom, by a carbonyl, sulphinyl, sulphonyl, imino, N-alkylimino, N-alkylcarbonyl-imino, N-alkylsulphonyl-imino, N-arylimino or N-aralkyl-imino group and additionally in the alkyleneimino moiety of the abovementioned groups in each case one or two of the methylene groups adjacent to the nitrogen atoms may be replaced by a carbonyl group, a 4- to 7-membered alkyleneimino group substituted by a hydroxy, alkoxy, amino, alkylamino, dialkylamino, alkylcarbonylamino, N-alkyl-alkylcarbonylamino, alkylsulphonylamino, N-alkyl-alkylsulphonylamino, carboxy, alkoxycarbonyl, aminocarbonyl, alkylaminocarbonyl or dialkylaminocarbonyl group, an alkyl group substituted by a carboxy, alkoxycarbonyl, aminocarbonyl, alkylaminocarbonyl or dialkylaminocarbonyl, cyano, hydroxy, alkoxy, aryloxy, amino, alkylamino, dialkylamino, alkylcarbonylamino, N-alkyl-alkylcarbonylamino, alkoxycarbonylamino, N-alkyl-alkoxycarbonylamino, alkylsulphonylamino, N-alkyl-alkylsulphonylamino, arylcarbonylamino, N-alkyl-arylcarbonylamino, arylsulphonylamino, N-alkyl-arylsulphonylamino, aminocarbonylalkylamino, N-(alkyl)-N-(aminocarbonylalkyl)-amino, alkylaminocarbonylalkylamino, N-(alkyl)-N-(alkylaminocarbonylalkyl)-amino, dialkylaminocarbonylalkylamino, N-(alkyl)-N-(dialkylaminocarbonylalkyl)-amino, dialkylaminoalkoxy, alkylsulphenyl, alkylsulphinyl, alkylsulphonyl, arylsulphenyl, arylsulphinyl or arylsulphonyl group, an (alkyleneimino)alkyl group optionally substituted by 1 to 4 alkyl groups with in each case 4 to 7 cyclic atoms in the alkyleneimino moiety, while in the abovementioned 6- to 7-membered alkyleneimino moieties a methylene group in the 4-position may be replaced in each case by an oxygen or sulphur atom, by a sulphinyl, sulphonyl, imino, N-alkyl-imino or N-alkylcarbonyl-imino group, an (alkyleneimino)carbonylalkyl group optionally substituted by 1 to 4 alkyl groups with in each case 4 to 7 cyclic atoms in the alkyleneimino moiety, while in the abovementioned 6- to 7-membered alkyleneimino moieties a methylene group in the 4-position may be replaced in each case by an oxygen or sulphur atom, by a sulphinyl, sulphonyl, imino or N-alkyl-imino group, a (carboxyalkyl)oxy, (alkoxycarbonylalkyl)oxy, (aminocarbonylalkyl)oxy, (alkylaminocarbonylalkyl)oxy or (dialkylaminocarbonylalkyl)oxy group, an [(alkyleneimino)carbonylalkyl]oxy-group optionally substituted by 1 to 4 alkyl groups with in each case 4 to 7 cyclic atoms in the alkyleneimino moiety, while in the abovementioned 6- to 7-membered alkyleneimino moieties a methylene group in the 4-position may be replaced in each case by an oxygen or sulphur atom, by a sulphinyl, sulphonyl, imino or N-alkyl-imino group, a $C_{5-7}$-cycloalkyl group wherein a methylene group is replaced by an oxygen or sulphur atom, by a sulphinyl, sulphonyl, imino or N-alkyl-imino, alkylcarbonylimino or alkylsulphonylimino group, a 3,4-dihydro-1H-quinazolin-2-on-3-yl or 1H-benzimidazol-2-on-1-yl-group optionally substituted in the aryl moiety by one or two fluorine, chlorine, bromine or iodine atoms or one or two nitro, alkyl, alkoxy or cyano groups in each case, while the substituents may be identical or different, or $R_cNR_d$ denotes a 6- to 8-membered alkyleneimino group optionally substituted by 1 to 4 alkyl groups or by an aryl group, which may additionally be substituted by the group $R_6$, while in the abovementioned alkyleneimino groups a methylene group in the 4-position is replaced by an oxygen or sulphur atom, by a carbonyl, sulphinyl, sulphonyl, N-oxido-N-alkylimino or $R_{10}$N-group in each case, while $R_{10}$ denotes a hydrogen atom, an alkyl, hydroxy-$C_{2-4}$-alkyl, alkoxy-$C_{2-4}$-alkyl, amino-$C_{2-4}$-alkyl, alkylamino-$C_{2-4}$-alkyl, dialkylamino-$C_{2-4}$-alkyl, (hydroxy-$C_{2-4}$-alkoxy)-$C_{2-4}$-alkyl, aminocarbonylalkyl, alkylaminocarbonylalkyl, dialkylaminocarbonylalkyl, aryl, formyl, alkylcarbonyl, alkylsulphonyl, arylcarbonyl, aryl-sulphonyl, aralkylcarbonyl, aralkylsulphonyl, alkoxycarbonyl, aralkoxycarbonyl, cyano, aminocarbonyl, alkylaminocarbonyl or dialkylaminocarbonyl group, an amino-alkylcarbonyl, alkylamino-alkylcarbonyl, dialkylamino-alkylcarbonyl group, an alkyl group substituted by one, two or three aryl groups, an 8-alkyl-8-aza-bicyclo[3.2.1]oct-3-yl group, an aryl or a 2-, 3- or 4-pyridyl group or 2-, 4- or 5-pyrimidinyl group an (alkyleneimino)carbonyl or (alkyleneimino)carbonylalkyl group with 4 to 7 cyclic atoms in the alkyleneimino moiety in each case, while in the abovementioned 6- to 7-membered alkyleneimino moieties a methylene group in the 4-position may be replaced in each case by an oxygen or sulphur atom, by a sulphinyl, sulphonyl, imino, N-alkyl-imino, N-alkylcarbonyl-imino or N-aralkyl-imino group, or $R_c NR_d$ denotes a 3-thiazolidinyl-group substituted in the 4-position by a carboxy, alkoxycarbonyl, aminocarbonyl, alkylaminocarbonyl, dialkylaminocarbonyl group, or $R_c NR_d$ denotes a 1-pyrrolidinyl group optionally substituted by 1 to 4 alkyl groups, wherein two hydrogen atoms on the carbon skeleton are replaced by a straight-chain alkylene bridge, this bridge containing 2 to 6 carbon atoms if the two hydrogen atoms are located on the same carbon atom, or 1 to 5 carbon atoms if the two hydrogen atoms are located on adjacent carbon atoms, or 2 to 4 carbon atoms if the two hydrogen atoms are located on carbon atoms separated by one atom, while the abovementioned 1-pyrrolidinyl groups are additionally substituted by the group $R_6$, which is as hereinbefore defined, a 1-piperidinyl or 1-azacyclohept-1-yl group optionally substituted by 1 to 4 alkyl groups, wherein two hydrogen atoms on the carbon skeleton are replaced by a straight-chain alkylene bridge, this bridge containing 2 to 6 carbon atoms if the two hydrogen atoms are located on the same carbon atom, or 1 to 5 carbon atoms if the two hydrogen atoms are located on adjacent carbon atoms, or 1 to 4 carbon atoms if the two hydrogen atoms are located on carbon atoms separated by an atom, or 1 to 3 carbon atoms if the two hydrogen atoms are located on carbon atoms separated by two atoms, while the abovementioned 1-piperidinyl- and 1-azacyclohept-1-yl groups are additionally substituted by the group $R_6$, which is as hereinbefore defined, a 1-pyrrolidinyl group optionally substituted by 1 to 4 alkyl groups, wherein two hydrogen atoms in the 3 position are substituted by a —O—CH$_2$CH$_2$—O or —O—CH$_2$CH$_2$CH$_2$—O-group, a 1-piperidinyl or 1-azacyclohept-1-yl group optionally substituted by 1 to 4 alkyl groups, wherein in the 3 position or in the 4 position two hydrogen atoms are substituted by a —O—CH$_2$CH$_2$—O or —O—CH$_2$CH$_2$CH$_2$—O-group in each case, a 1-azetidinyl group optionally substituted by an alkyl group, wherein the two hydrogen atoms of a methylene group are replaced by a straight-chain $C_{4-6}$-alkylene bridge, while in each case a methylene group in the $C_{4-6}$-alkylene bridge is replaced by a $R_{10}$N-group, where $R_{10}$ is as hereinbefore defined, while the bicyclic ring thus formed may additionally be substituted by a hydroxy, alkoxy, amino, alkylamino, dialkylamino, cyano, alkylcarbonylamino, alkylsulphonylamino, alkoxycarbonylamino, arylcarbonyl, carboxy, alkoxycarbonyl, aminocarbonyl, alkylaminocarbonyl or dialkylaminocarbonyl group, a 1-pyrrolidinyl, 1-piperidinyl or 1-azacyclohept-1-yl group optionally substituted by 1 to 2 alkyl groups, wherein the two hydrogen atoms of a methylene group are replaced by a straight-chain $C_{3-6}$-alkylene bridge, while in each case a methylene group in the $C_{3-6}$-alkylene bridge is replaced by a $R_{10}$N-group, while $R_{10}$ is as hereinbefore defined, while the bicyclic ring thus formed may additionally be substituted by a hydroxy, alkoxy, amino, alkylamino, dialkylamino, cyano, alkylcarbonylamino, alkylsulphonylamino, alkoxycarbonylamino, arylcarbonyl, carboxy, alkoxycarbonyl, aminocarbonyl, alkylaminocarbonyl or dialkylaminocarbonyl group, a group of the structure

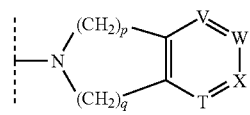

optionally substituted in the alkylene moieties by 1 or 2 alkyl groups, wherein p and q, which may be identical or different, represent the number 1 or 2, and the unit —V=W—X=Y— denotes one of the groups (a), (b), (c), (d) or (e):

 (a),

 (b),

 (c),

 (d),

 (e), or —V=W— taken together represent an oxygen or sulphur atom and —X=Y— represents one of the groups —N=C, —C=N or —C=C—, or —V=W— taken together represent an imino, N-alkyl-imino, N-aralkyl-imino or N-aryl-imino group and —X=Y— represents one of the groups —N=N, —N=C, —C=N or —C=C—, or, if p and q are not the same, —X=Y— taken together represent an oxygen or sulphur atom and —V=W— represents one of the groups —N=C, —C=N or —C=C—, or —X=Y— taken together represent an imino, N-alkyl-imino, N-aralkyl-imino or N-aryl-imino-group and —V=W— represents one of the groups —N=N, —N=C, —C=N or —C=C—, while one or two of the available carbon atoms of the unit —V=W—X=Y— may be substituted in each case by a hydroxy, alkoxy, amino, alkylamino, dialkylamino, carboxy, alkoxycarbonyl, aminocarbonyl, alkylaminocarbonyl, dialkylaminocarbonyl or hydrazinocarbonyl group, while the substituents may be identical or different, and the remaining available carbon atoms of the unit —V=W—X=Y— are substituted by a hydrogen atom, an alkyl, aralkyl or aryl group, or $R_c$ denotes a hydrogen atom or a $C_{1-8}$-alkyl group, a $C_{3-7}$-cycloalkyl, $C_{3-7}$-cycloalkyl-alkyl or aralkyl group which may be substituted in each case by one or two alkyl groups or by an aryl group, an alkyl group which is substituted by a hydroxy, alkoxy, aryloxy, aralkoxy, alkylsulphenyl, alkylsulphinyl, alkylsulphonyl, arylsulphenyl, arylsulphinyl, arylsulphonyl, amino, alkylamino, dialkylamino, alkylcarbonylamino, N-alkyl-alkylcarbonylamino, alkylsulphonylamino, N-alkyl-alkylsulphonylamino, trifluoromethylsulphonylamino, N-alkyl-trifluoromethylsulphonylamino, carboxy, alkoxycarbonyl, aralkoxycarbonyl, aminocarbonyl, alkylaminocarbonyl, dialkylaminocarbonyl, cyano group,
by a 2-, 3- or 4-pyridyl group,
by an alkyleneimino or (alkyleneimino)carbonyl group with in each case 4 to 7 cyclic atoms in the alkyleneimino moiety, optionally substituted by 1 to 4 alkyl groups, while in the abovementioned 6- to 7-membered alkyleneimino groups a methylene group may be replaced in the 4-position by an oxygen or sulphur atom, by an imino, N-alkyl-imino, N-aryl-imino, N-aralkyl-imino, N-arylcarbonyl-imino or N-alkylcarbonyl-imino group,
a $C_{3-5}$-alkenyl group optionally substituted by an aryl group, while the vinyl moiety may not be attached to the nitrogen atom of the $R_cNR_d$ group,
a $C_{3-5}$-alkynyl group optionally substituted by an aryl group, while the ethynyl moiety may not be attached to the nitrogen atom of the $R_cNR_d$ group, and $R_d$ denotes a $C_{1-16}$-alkyl group which is substituted by a group selected from the groups (a) to (n):
(a) a carboxy, alkoxycarbonyl, aminocarbonyl, alkylaminocarbonyl, dialkylaminocarbonyl, hydroxy-$C_{2-4}$-alkylaminocarbonyl, cyano, hydroxy, alkoxy, aryloxy, aralkoxy, $C_{2-4}$-alkylenedioxy, alkylcarbonyloxy, arylcarbonyloxy, formylamino, alkylcarbonylamino, arylcarbonylamino, amino, alkylamino, dialkylamino, naphthylamino, aralkylamino, diaralkylamino or N-alkyl-aralkylamino group,
(b) a phenylamino, N-alkyl-N-phenylamino, pyridylamino or N-alkyl-N-pyridylamino group optionally substituted in the aryl moiety by one or two fluorine, chlorine, bromine or iodine atoms or one or two nitro, trifluoromethyl, alkyl, hydroxy, alkoxy, amino, alkylamino, dialkylamino, carboxy, alkoxycarbonyl, aminocarbonyl, alkylaminocarbonyl, dialkylaminocarbonyl or cyano groups, while the substituents may be identical or different,
(c) an alkoxy group substituted by one, two or three aryl groups,
(d) a hydroxy-C2-4-alkylaminocarbonyl, alkoxy-C2-4-alkylaminocarbonyl, amino-C2-4-alkylaminocarbonyl, alkylamino-C2-4-alkylaminocarbonyl, dialkylamino-C2-4-alkylaminocarbonyl, carboxyalkylaminocarbonyl, alkoxycarbonylalkylaminocarbonyl, aminocarbonylalkylaminocarbonyl, alkylaminocarbonylalkylaminocarbonyl, dialkylaminocarbonylalkylaminocarbonyl, arylaminocarbonyl, N-alkyl-arylaminocarbonyl, aralkylaminocarbonyl, N-alkyl-aralkylaminocarbonyl,
(e) a group of formula —C(=NH)NH₂ or —NH—C(=NH) NH₂, which is optionally substituted by a cyano or alkoxycarbonyl group,
(f) an (alkyleneimino)carbonyl group optionally substituted by 1 to 4 alkyl groups with in each case 4 to 7 cyclic atoms in the alkyleneimino moiety, while in a 6 or 7-membered alkyleneimino moiety a methylene group in the 4-position may be replaced in each case by an oxygen or sulphur atom, by a sulphinyl, sulphonyl, imino, N-alkyl-imino, N-alkylcarbonyl-imino, N-alkylsulphonyl-imino, N-aryl-imino or N-aralkyl-imino group,
(g) a 4- to 7-membered alkyleneimino group optionally substituted by 1 to 4 alkyl groups, while in the abovementioned 6 or 7-membered alkyleneimino groups a methylene group in the 4-position may be replaced in each case by an oxygen or sulphur atom, by a sulphinyl, sulphonyl or $R_{10}N$ group, where $R_{10}$ is as hereinbefore defined, and additionally in the abovementioned 5- to 7-membered alkyleneimino groups in each case one or two methylene groups adjacent to the nitrogen atoms may be replaced by a carbonyl group,
(h) a 5- to 7-membered alkyleneimino group optionally substituted by 1 to 2 alkyl groups which is substituted by a hydroxyalkyl, aminoalkyl, alkylaminoalkyl or dialkylaminoalkyl group,
(i) an alkylsulphonylamino, N-alkyl-alkylsulphonylamino, arylcarbonylamino, N-alkyl-arylcarbonylamino, alkylcarbonylamino, N-alkyl-alkylcarbonylamino, arylsulphonylamino, N-alkyl-arylsulphonylamino, aralkylcarbonylamino, N-alkyl-aralkylcarbonylamino, alkoxyalkylcarbonylamino, alkoxyalkyl-N-alkyl-carbonylamino, dialkylamino-alkylcarbonylamino, alkylamino-alkylcarbonylamino, amino-alkylcarbonylamino, aralkylsulphonylamino, N-alkyl-aralkylsulphonylamino, alkoxycarbonylamino, N-alkyl-alkoxycarbonylamino, aralkoxycarbonylamino or N-alkyl-aralkoxycarbonylamino group,
(j) a $(R_9NR_8)$—CO—$NR_7$ or $(R_9NR_8)$—SO2-$NR_7$ group, where $R_7$, $R_8$ and $R_9$ are as hereinbefore defined,
(k) an alkylsulphenyl, alkylsulphinyl, alkylsulphonyl, arylsulphenyl, arylsulphinyl, arylsulphonyl, aralkylsulphenyl, aralkylsulphinyl or aralkylsulphonyl group,
(l) a $C_{4-7}$-cycloalkyl group substituted by $R_6$ and optionally additionally by 1 to 4 alkyl groups, where $R_6$ is as hereinbefore defined,
(m) an $C_{5-7}$-cycloalkyl group optionally substituted by 1 to 4 alkyl groups wherein a methylene group is replaced by an oxygen or sulphur atom, by a sulphinyl, sulphonyl or $NR_{10}$ group, where $R_{10}$ is as hereinbefore defined,
(n) a 4-piperidinyl-alkyl group optionally substituted by 1 to 4 alkyl groups, which is substituted in the 1 position by $R_{10}$ and additionally in the 4-position by a hydroxy group, where $R_{10}$ is as hereinbefore defined, and wherein additionally hydrogen atoms in positions 2 and 6 of the piperidinyl structure are together replaced by a $C_{2-3}$-alkylene bridge,
a methyl group substituted by a 3-hydroxy-1,3-dihydro-indol-2-on-3-yl or 2-aminocarbonyl-1,3-dihydro-isoindol-5-yl-group,
a group of the structure

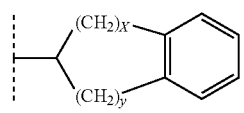

substituted in the aryl moiety by a carboxy, alkoxycarbonyl, aminocarbonyl, alkylaminocarbonyl, dialkylaminocarbonyl, carboxyalkyl, alkoxycarbonylalkyl, aminocarbonylalkyl, alkylaminocarbonylalkyl or dialkylaminocarbonylalkyl group and optionally additionally substituted in the alkylene moiety by 1 or 2 alkyl groups
wherein x and y, which may be identical or different, independently of one another represent the number 0, 1 or 2, but x and y together must yield at least the number 2,
a $C_{3-8}$-alkyl group substituted by a hydroxy group and additionally by an amino, alkylamino, dialkylamino, hydroxy, alkoxy, 1-pyrrolidinyl, 1-piperidinyl or morpholino group,
a $C_{2-8}$-alkyl group substituted by a carboxy group and additionally by an amino, hydroxy, aminocarbonyl or benzyloxycarbonylamino group,
a $C_{2-4}$-alkyl group which is substituted by a $C_{2-4}$-alkylsulphenyl or $C_{2-4}$-alkoxy group, which is substituted in the ω-position by an amino, hydroxy or alkoxy group, a $C_{2-4}$-alkyl group which is substituted by a $C_{2-4}$-alkoxy-$C_{2-4}$-alkoxy group, which is substituted in the ω-position by an amino or hydroxy group, a cyclopropyl group which is substituted by a carboxy, alkoxycarbonyl, aminocarbonyl, alkylaminocarbonyl or dialkylaminocarbonyl group or by an (alkyleneimino)carbonyl group optionally substituted by 1 to 4 alkyl groups with 4 to 7 cyclic atoms in the alkyleneimino moiety in each case, while in the abovementioned 6 or 7-membered alkyleneimino moieties a methylene group in the 4-position may be replaced in each case by an oxygen or sulphur atom, by a sulphinyl, sulphonyl, imino, N-alkyl-imino, N-alkylcarbonyl-imino, N-alkylsulphonyl-imino, N-arylimino or N-aralkyl-imino group, a $C_{4-7}$-cycloalkyl group optionally substituted by 1 to 4 alkyl groups, which is additionally substituted by $R_6$, which is as hereinbefore defined, a $C_{5-7}$-cycloalkyl group optionally substituted by 1 to 2 alkyl groups which is additionally substituted by a N,N-dialkyl-N-oxido-amino group, a $C_{4-7}$-cycloalkyl group optionally substituted by 1 to 4 alkyl groups which may additionally be substituted by $R_6$, while in the cycloalkyl moiety a methylene group is replaced by an oxygen or sulphur atom, by a sulphinyl, sulphonyl, N-alkyl-N-oxido-imino or $R_{10}$N group, where $R_6$ and $R_{10}$ are as hereinbefore defined, a $C_5$-$C_7$-cycloalkyl or $C_5$-$C_7$-cycloalkylalkyl group optionally substituted by 1 to 4 alkyl groups, wherein in each case a methylene group in the cycloalkyl moiety is replaced by a carbonyl group, a cyclopentyl or cyclopentylalkyl group optionally substituted by 1 to 4 alkyl groups, wherein in each case two hydrogen atoms in the cyclopentyl moiety are replaced by a straight-chain alkylene bridge, this bridge containing 2 to 6 carbon atoms, if the two hydrogen atoms are located on the same carbon atom, or 1 to 5 carbon atoms, if the two hydrogen atoms are located on adjacent carbon atoms, or 2 to 4 carbon atoms if the two hydrogen atoms are located on carbon atoms separated by a carbon atom, while the abovementioned rings are additionally substituted by the group R6, which is as hereinbefore defined, a cyclohexyl, cyclohexylalkyl, cycloheptyl or cycloheptylalkyl group optionally substituted by 1 to 4 alkyl groups, wherein two hydrogen atoms in the cycloalkyl moiety are replaced by a straight-chain alkylene bridge in each case, this bridge containing 2 to 6 carbon atoms if the two hydrogen atoms are located on the same carbon atom, or 1 to 5 carbon atoms if the two hydrogen atoms are located on adjacent carbon atoms, or 1 to 4 carbon atoms if the two hydrogen atoms are located on carbon atoms separated by a carbon atom, or 1 to 3 carbon atoms if the two hydrogen atoms are located on carbon atoms separated by two carbon atoms, while the abovementioned rings are additionally substituted by the group $R_6$, which is as hereinbefore defined, an alkyl group substituted by a 3-hydroxy-1,3-dihydro-indol-2-on-3-yl or 2-aminocarbonyl-1,3-dihydro-isoindol-5-yl group, a $C_{1-10}$-alkyl group substituted by an aryl group, while the abovementioned aryl moiety is substituted by an alkoxycarbonyl, carboxy, carboxyalkyl, aminosulphonyl, trifluoromethoxy, cyano, aminoalkyl, amino, alkylamino, dialkylamino, nitro, 2H-pyridazin-3-on-6-yl, hydroxyphenyl, hydroxyalkyl, hydroxy or alkoxy group, an aralkyl group which is substituted in the aryl moiety by a hydroxy or alkoxy group and additionally by a carboxy, alkoxycarbonyl, hydroxy or alkoxy group, a $C_{1-10}$-alkyl group substituted by a pyrrolyl, imidazolyl, pyrazolyl, pyridyl, pyrimidinyl, pyrazinyl, indolyl or benzimidazolyl group, while the abovementioned heteroaryl moieties on the available carbon atoms may additionally be substituted in each case by one or two groups selected from fluorine, chlorine, bromine or iodine atoms, alkyl, alkoxycarbonyl, carboxy, trifluoromethyl, trifluoromethoxy, cyano, amino, alkylamino, dialkylamino, nitro, hydroxy or alkoxy groups, while the substituents may be identical or different, a $C_{1-10}$-alkyl group substituted by a carboxy, alkoxycarbonyl, aminocarbonyl, alkylaminocarbonyl, dialkylaminocarbonyl, aralkylaminocarbonyl, cyano, hydroxy, alkoxy, aryloxy, amino, alkylamino, dialkylamino, alkylcarbonylamino or alkoxycarbonylamino group, which is additionally substituted by one or two aryl groups or a pyrrolyl, imidazolyl, pyrazolyl, pyridyl, pyrimidinyl, pyrazinyl, indolyl or benzimidazolyl group, while the abovementioned aryl or heteroaryl moieties at the available carbon atoms may additionally be substituted in each case by one or two groups selected from fluorine, chlorine, bromine or iodine atoms, alkyl, alkoxycarbonyl, carboxy, trifluoromethyl, trifluoromethoxy, cyano, amino, alkylamino, dialkylamino, nitro, hydroxy or alkoxy groups, while the substituents may be identical or different, a $C_{1-6}$-alkyl group substituted by an aryl group which is substituted in the aryl moiety by a hydroxy or amino group and additionally by two fluorine, chlorine, bromine or iodine atoms, while the substituents may be identical or different, a $C_{2-6}$-alkyl group substituted by a carboxy or alkoxycarbonyl group, which is additionally substituted by an amino, alkylamino, dialkylamino, alkylcarbonylamino, N-alkyl-alkylcarbonylamino, alkylsulphonylamino, N-alkyl-alkylsulphonylamino, arylcarbonylamino, N-alkyl-arylcarbonylamino, arylsulphonylamino, N-alkyl-arylsulphonylamino, aralkylcarbonylamino, N-alkyl-aralkylcarbonylamino, aralkylsulphonylamino, N-alkyl-aralkylsulphonylamino, alkoxycarbonylamino, N-alkyl-alkoxycarbonylamino, aralkoxycarbonylamino or N-alkyl-aralkoxycarbonylamino group, a 3-quinuclidinyl, 4-quinuclidinyl, 2-quinuclidinyl-alkyl, 3-quinuclidinyl-alkyl or 4-quinuclidinyl-alkyl group, or $R_c$ denotes a hydrogen atom or an alkyl group and $R_d$ denotes a hydroxy or alkoxy group, and $R_e$ denotes a fluorine, chlorine, bromine or iodine atom, a cyano, nitro, alkyl, alkoxy, dialkylamino, alkylamino, alkylcarbonyl, alkylsulphenyl, alkylsulphinyl, alkylsulphonyl, alkoxyalkyl-alkylcarbonyl-N-alkyl-aminoalkyl, alkylcarbonyl-aminoalkyl, alkylsulphonyl-aminoalkyl, aminocarbonyl, alkylaminocarbonyl, dialkylaminocarbonyl, aminoalkyl, alkylaminoalkyl or dialkylaminoalkyl group, a methyl, methylsulphenyl or methoxy group substituted by 1 to 3 fluorine atoms, a $C_{2-4}$-alkyl, $C_{2-4}$-alkylsulphenyl or $C_{2-4}$-alkoxy group substituted by 1 to 5 fluorine atoms, an $C_{3-6}$-cycloalkyl-$C_{1-3}$-alkyl group optionally substituted by 1-6 fluorine atoms, a $C_{2-5}$-alkenyl or $C_{3-5}$-alkenyloxy group, while the vinyl moiety may not be attached to the oxygen atom, a $C_{2-6}$-alkynyl or $C_{3-6}$-alkynyloxy group, while the ethynyl moiety may not be attached to the oxygen atom, an alkyleneimino or alkyleneimino-alkyl group with in each case 4 to 7 cyclic atoms in the alkyleneimino moiety optionally substituted by 1 to 4 alkyl groups, while in a 6- or 7-membered alkyleneimino moiety a methylene group in the 4-position may be replaced in each case by an oxygen or sulphur atom, by a sulphinyl, sulphonyl, imino, N-alkyl-imino, N-alkylcarbonyl-imino, N-alkylsulphonyl-imino, N-aryl-imino or N-aralkyl-imino group, optionally in the form of the tautomers, racemates, enantiomers, diastereomers and mixtures thereof, and optionally also the pharmacologically acceptable acid addition salts thereof, while, unless otherwise stated, by the aryl moieties mentioned in the definition of the abovementioned groups is meant a phenyl group, wherein one or two carbon atoms may be replaced by a nitrogen atom in each case, while the abovementioned aryl moieties in each case may be monosubstituted by $R_{11}$, mono-, di- or trisubstituted by $R_{12}$ or monosubstituted by $R_{11}$ and additionally mono- or disubstituted by $R_{12}$, while the substituents may be identical or different, and $R_{11}$ denotes a cyano, carboxy, aminocarbonyl, alkylaminocarbonyl, dialkylaminocarbonyl, alkoxycarbonyl, alkylcarbonyl, alkylsulphenyl, alkylsulphinyl, alkylsulphonyl, alkylsulphonyloxy, perfluoroalkyl, perfluoroalkoxy, nitro, amino, alkylcarbonylamino, N-alkyl-alkylcarbonylamino, alkylamino, dialkylamino, hydroxy-$C_{2-4}$-alkylamino, N-alkyl-(hydroxy-$C_{2-4}$-alkyl)amino, bis-(hydroxy-$C_{2-4}$-alkyl)amino, phenylalkylcarbonylamino, phenylcarbonylamino, alkylsulphonylamino, phenylalkylsulphonylamino, phenylsulphonylamino, N-alkyl-phenylalkylcarbonylamino, N-alkyl-phenylcarbonylamino, N-alkyl-alkylsulphonylamino, N-alkyl-phenylalkylsulphonylamino, N-alkyl-phenylsulphonylamino, aminosulphonyl, alkylaminosulphonyl, dialkylaminosulphonyl, $(R_9NR_8)$—CO—$NR_7$ or $(R_9NR_8)$—SO2-$NR_7$ group, where $R_7$, $R_8$ and $R_9$ are as hereinbefore defined, a 5- to 7-membered alkyleneimino group optionally substituted by 1 to 4 alkyl groups or a hydroxyalkyl group, while in the abovementioned 6- to 7-membered alkyleneimino groups a methylene group in the 4-position may be replaced in each case by an oxygen atom or an $R_{10}N$ group, where $R_{10}$ is as hereinbefore defined, a 5- to 7-membered alkyleneimino group optionally substituted by 1 to 4 alkyl groups or a hydroxyalkyl group, while in each case one or two methylene groups adjacent to the nitrogen atom is replaced by a carbonyl group in each case, and $R_{12}$ denotes an alkyl, hydroxy or alkoxy group, a fluorine, chlorine, bromine or iodine atom, while two groups $R_{12}$, if they are bound to adjacent carbon atoms, may also denote an alkylene group with 3 to 6 carbon atoms, a 1,3-butadien-1,4-diylene group or a methylenedioxy group, and, unless stated to the contrary, the abovementioned alkyl, alkylene and alkoxy moieties each contain 1 to 4 carbon atoms, while, unless otherwise stated, each carbon atom in the abovementioned alkyl, alkylene or cycloalkylene moieties, which is bound to a nitrogen, oxygen or sulphur atom, cannot be bound to any other halogen, nitrogen, oxygen or sulphur atom.

Preferred compounds of formula I are those wherein $R_a$ denotes a hydrogen atom or an alkyl group, $R_b$ denotes an aralkyl group which may be substituted in the aryl moiety by a carboxy, alkoxycarbonyl, aminocarbonyl, alkylaminocarbonyl, dialkylaminocarbonyl, amino, alkylamino, dialkylamino, cyano, trifluoromethyl or nitro group or one or two fluorine, chlorine, bromine or iodine atoms or one or two hydroxy, alkyl or alkoxy groups, while the substituents may be identical or different, or by a 5- to 7-membered alkyleneimino group, while in each case one or two methylene groups adjacent to the nitrogen atom may be replaced in each case by a carbonyl group or in the abovementioned 6- to 7-membered alkyleneimino groups a methylene group in the 4-position may be replaced by an oxygen atom, by an imino, N-aryl-imino or N-alkyl-imino group, and wherein the alkylene moiety of the abovementioned aralkyl groups may be substituted by one or two alkyl groups, or a phenyl group optionally substituted by the groups $R_1$ to $R_3$, while $R_1$ denotes a fluorine, chlorine, bromine or iodine atom, a $C_{1-2}$-alkyl or hydroxy group, a $C_{3-6}$-cycloalkyl or $C_{5-6}$-cycloalkoxy group, a $C_{2-5}$-alkenyl group, a $C_{2-5}$-alkynyl group, an aryl, aryloxy, aralkyl, aralkoxy, alkylsulphenyl, alkylsulphinyl, alkylsulphonyl, alkylsulphonyloxy, trifluoromethylsulphenyl, trifluoromethylsulphonyl, arylsulphenyl, arylsulphinyl, arylsulphonyl, aralkylsulphenyl, aralkylsulphinyl or aralkylsulphonyl group, a methyl or methoxy group substituted by 1 to 3 fluorine atoms, a $C_{2-4}$-alkyl or $C_{2-4}$-alkoxy group substituted by 1 to 5 fluorine atoms, a nitro, amino, alkylamino, dialkylamino, $C_{3-6}$-cycloalkylamino, N-alkyl-$C_{3-6}$-cycloalkylamino, arylamino, N-alkyl-arylamino, aralkylamino or N-alkyl-aralkylamino group, a 5- to 7-membered alkyleneimino group, while in each case one or two methylene groups adjacent to the nitrogen atom may be replaced in each case by a carbonyl group or in the abovementioned 6- to 7-membered alkyleneimino groups a methylene group in the 4-position may be replaced by an oxygen atom, by an imino, N-aryl-imino or N-alkyl-imino group and the alkyleneimino groups may additionally be substituted by 1-2 methyl groups, an (alkyleneimino)carbonyl or (alkyleneimino)sulphonyl group with in each case 5 to 7 cyclic atoms in the alkyleneimino moiety, while in the abovementioned 6- to 7-membered alkyleneimino moieties a methylene group in the 4-position may be replaced in each case by an oxygen atom, by an imino, N-aryl-imino or N-alkyl-imino group, an alkylcarbonylamino, N-alkyl-alkylcarbonylamino, alkyl-sulphonylamino, N-alkyl-alkylsulphonylamino, arylcarbonylamino, N-alkyl-arylcarbonylamino, arylsulphonylamino, N-alkyl-arylsulphonylamino, aralkylcarbonylamino, N-alkyl-aralkylcarbonylamino, aralkylsulphonylamino, N-alkyl-aralkylsulphonylamino, trifluoromethylsulphonylamino, N-alkyl-trifluoromethylsulphonylamino, alkylcarbonyl, arylcarbonyl, aralkylcarbonyl, carboxy, alkoxycarbonyl, aminocarbonyl, alkylaminocarbonyl, dialkylaminocarbonyl, arylaminocarbonyl, N-alkyl-arylaminocarbonyl, aralkylaminocarbonyl, N-alkyl-aralkylaminocarbonyl, N-hydroxy-aminocarbonyl, N-hydroxy-alkylaminocarbonyl, N-alkoxy-aminocarbonyl, N-alkoxy-alkylaminocarbonyl, cyano, azido, N-cyano-amino or N-cyano-alkylamino group, a sulpho, aminosulphonyl, alkylaminosulphonyl, dialkylaminosulphonyl, arylaminosulphonyl, pyridylaminosulphonyl, N-alkyl-arylaminosulphonyl, aralkylaminosulphonyl or N-alkyl-aralkylaminosulphonyl group, or a $C_{1-2}$ alkyl group substituted by $R_4$, wherein R$_4$ denotes a hydroxy, alkoxy, aryloxy, amino, alkylamino, fluoroalkylamino, dialkylamino, alkylsulphenyl, alkylsulphinyl, alkylsulphonyl, arylsulphenyl, arylsulphinyl, arylsulphonyl, carboxy, alkoxycarbonyl, aminocarbonyl, alkylaminocarbonyl, dialkylaminocarbonyl or cyano group, a 5- to 7-membered alkyleneimino group optionally substituted by one or two alkyl groups, while in the abovementioned 6- to 7-membered alkyleneimino groups a methylene group in the 4-position may be replaced by an oxygen or sulphur atom, by an imino, N-alkyl-imino, N-alkylcarbonyl-imino, N-alkylsulphonyl-imino, N-arylcarbonyl-imino, N-arylsulphonyl-imino, N-aryl-imino or N-aralkyl-imino group, or may be substituted by a hydroxy, alkoxy, aminocarbonyl, alkylaminocarbonyl, dialkylaminocarbonyl, amino, alkylamino- and dialkylamino group, or an (alkyleneimino)carbonyl group with in each case 5 to 7 cyclic atoms in the alkyleneimino moiety optionally substituted by one or two alkyl groups, while in the abovementioned 6- to 7-membered alkyleneimino moieties a methylene group in the 4-position may be replaced in each case by an oxygen or sulphur atom, by an imino, N-alkyl-imino or N-alkylcarbonyl-imino group, or a group of formula wherein

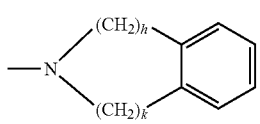

h and k, which may be identical or different, represent the numbers 1 to 2 or h denotes the number 0 and k denotes the number 2 or 3, while additionally the above benzo portion may be substituted by a fluorine, chlorine, bromine or iodine atom or by an alkyl, trifluoromethyl, hydroxy, alkoxy, carboxy or cyano group and the above saturated cyclic imino moiety may be substituted by 1 or 2 alkyl groups, R$_2$ denotes a fluorine, chlorine or bromine atom, a C$_{1-2}$ alkyl, trifluoromethyl, hydroxy, amino, alkylamino, dialkylamino, alkylcarbonylamino, N-alkyl-alkylcarbonylamino, alkylsulphonylamino, N-alkyl-alkylsulphonylamino, trifluoromethylsulphonylamino, N-alkyl-trifluoromethylsulphonylamino or cyano group, and R$_3$ denotes a fluorine, chlorine or bromine atom, a C$_{1-2}$ alkyl, trifluoromethyl or alkoxy group, a group of the structure

wherein the point of attachment may be a carbon or a nitrogen atom and up to three carbon atoms may be replaced by a nitrogen atom and the ring may be substituted, via each of the atoms, by one or two alkyl, aryl or aralkyl groups, or a sulpho, aminosulphonyl, alkylaminosulphonyl, dialkylaminosulphonyl, arylaminosulphonyl, pyridylaminosulphonyl, N-alkyl-arylaminosulphonyl, aralkylaminosulphonyl or N-alkyl-aralkylaminosulphonyl group R$_2$ together with R$_3$, if they are bound to adjacent carbon atoms, denote a methylenedioxy group optionally substituted by one or two alkyl groups, or an n-C$_{3-5}$-alkylene group optionally substituted by one or two alkyl groups wherein a methylene group may be replaced by an oxygen atom, by an imino, N-alkyl-imino or N-aralkyl-imino group, or a 1,3-butadiene-1,4-diylene group optionally substituted by a fluorine, chlorine or bromine atom, by a hydroxy, alkyl, alkoxy, trifluoromethyl, carboxy or cyano group or a group of formula —NH—C(=O)—(CH$_2$) or —NH—C(=O)—(CH$_2$)$_2$, which may additionally be substituted in the alkylene moiety by 1 or 2 alkyl groups, or a group of formula —NH—N=N, —NH—N=CH, —NH—CH=N—, —O—CH=N, —S—CH=N, —NH—CH=CH— and the tautomers thereof, while each hydrogen atom may be substituted by an alkyl, aryl or aralkyl group, or a group of formula —(CH$_2$)$_m$—NR$_5$—(CH$_2$)$_n$—, wherein m and n which may be identical or different in each case represent 1 or 2, and R$_5$ denotes hydrogen, C$_{1-6}$ alkyl or C$_{1-6}$ fluoroalkyl, or R$_a$ together with R$_1$, if R$_1$ is in the o-position to the nitrogen atom substituted by R$_a$, also denote an n-C$_{2-3}$-alkylene group optionally substituted by one or two alkyl groups, and R$_c$NR$_d$ represents a 4- to 7-membered alkyleneimino group optionally substituted by 1 to 2 alkyl or aryl groups which is additionally substituted by the group R$_6$, where R$_6$ denotes a carboxy, alkoxycarbonyl, aminoalkyl, aminocarbonyl, alkylaminocarbonyl, dialkylaminocarbonyl, cyano, hydroxy, alkoxy, aryloxy, aralkoxy, alkylcarbonyloxy, arylcarbonyloxy, amino, alkylamino, hydroxy-C$_{2-4}$-alkylamino, dialkylamino, cyanamino, formylamino, alkylsulphenyl, alkylsulphinyl, alkylsulphonyl, arylsulphenyl, arylsulphinyl, arylsulphonyl, aralkylsulphenyl, aralkylsulphinyl or aralkylsulphonyl group, an alkylcarbonylamino, N-alkyl-alkylcarbonylamino, alkylsulphonylamino, N-alkyl-alkylsulphonylamino, arylcarbonylamino, N-alkyl-arylcarbonylamino, arylsulphonylamino, N-alkyl-arylsulphonylamino, aralkylcarbonylamino, N-alkyl-aralkylcarbonylamino, aralkylsulphonylamino, N-alkyl-aralkylsulphonylamino, alkoxycarbonylamino, N-alkyl-alkoxycarbonylamino, alkoxycarbonylalkylamino, N-(alkyl)-N-(alkoxycarbonylalkyl)-amino, aralkoxycarbonylamino or N-alkyl-aralkoxycarbonylamino group, a (NR$_8$R$_9$)CONR$_7$ group wherein R$_7$ and R$_8$ in each case denote a hydrogen atom or an alkyl group and R$_9$ denotes a hydrogen atom or an alkyl, aryl or pyridyl group, while the groups R$_7$, R$_8$ and R$_9$ may be identical or different, or R$_7$ and R$_8$ together denote a n-C$_{2-4}$-alkylene group and R$_9$ is a hydrogen atom or an alkyl, aryl or pyridyl group, an alkyleneimino group with 5 to 7 cyclic atoms in the alkyleneimino moiety optionally substituted by 1 to 2 alkyl groups, while in the abovementioned 6- to 7-membered alkyleneimino moieties a methylene group in the 4-position of the alkyleneimino moiety may be replaced in each case by an oxygen or sulphur atom, by a carbonyl, sulphinyl, sulphonyl, imino, N-alkylimino, N-alkylcarbonyl-imino, N-alkylsulphonyl-imino, N-arylimino or N-aralkyl-imino group, an (alkyleneimino)carbonyl group with in each case 4 to 7 cyclic atoms in the alkyleneimino moiety optionally substituted by 1 to 2 alkyl groups, while in the abovementioned 6- to 7-membered alkyleneimino moieties a methylene group in the 4-position may be replaced in each case by an oxygen or sulphur atom, by a sulphinyl, sulphonyl, imino, N-alkyl-imino, N-alkylcarbonyl-imino, N-alkylsulphonyl-imino, N-aryl-imino or N-aralkyl-imino group, a 4- to 7-membered alkyleneimino group substituted by a hydroxy, alkoxy, amino, alkylamino, dialkylamino, alkylcarbonylamino, N-alkyl-alkylcarbonylamino, alkylsulphonylamino, N-alkyl-alkylsulphonylamino, hydroxyalkyl, carboxy, alkoxycarbonyl, aminocarbonyl, alkylaminocarbonyl or dialkylaminocarbonyl group, an alkyl group substituted by a carboxy, alkoxycarbonyl, aminocarbonyl, alkylaminocarbonyl, dialkylaminocarbonyl, cyano, hydroxy, alkoxy, aryloxy, amino, alkylamino, dialkylamino, alkylcarbonylamino, N-alkyl-alkylcarbonylamino, alkoxycarbonylamino, N-alkyl-alkoxycarbonylamino, alkylsulphonylamino, N-alkyl-alkylsulphonylamino, arylcarbonylamino, N-alkyl-arylcarbonylamino, arylsulphonylamino, N-alkyl-arylsulphonylamino, dialkylaminocarbonylalkylamino, N-(alkyl)-N-(dialkylaminocarbonylalkyl)-amino, dialkylaminoalkoxy, alkylsulphenyl, alkylsulphinyl, alkylsulphonyl, arylsulphenyl, arylsulphinyl or arylsulphonyl group, an (alkyleneimino)alkyl group with in each case 4 to 7 cyclic atoms in the alkyleneimino moiety optionally substituted by 1 to 2 alkyl groups, while in the abovementioned 6- to 7-membered alkyleneimino moieties a methylene group in the 4-position may be replaced in each case by an oxygen or sulphur atom, by a sulphinyl, sulphonyl, imino, N-alkyl-imino or N-alkylcarbonyl-imino group, an (alkyleneimino)carbonylalkyl group with in each case 4 to 7 cyclic atoms in the alkyleneimino moiety optionally substituted by 1 to 2 alkyl groups, while in the abovementioned 6- to 7-membered alkyleneimino moieties a methylene group in the 4-position may be replaced in each case by an oxygen or sulphur atom, by a sulphinyl, sulphonyl, imino or N-alkyl-imino group, a (carboxyalkyl)oxy, (alkoxycarbonylalkyl)oxy, (aminocarbonylalkyl)oxy, (alkylaminocarbonylalkyl)oxy or (dialkylaminocarbonylalkyl)oxy group, a 3,4-dihydro-1H-quinazolin-2-on-3-yl or 1H-benzimidazol-2-on-1-yl group optionally substituted in the aryl moiety by one or two fluorine, chlorine, bromine or iodine atoms or one or two nitro, alkyl, alkoxy or cyano groups in each case, while the substituents may be identical or different, or $R_cNR_d$ denotes a 6- to 7-membered alkyleneimino group optionally substituted by 1 to 2 alkyl groups or by an aryl group, which may additionally be substituted by the group $R_6$, while in the abovementioned alkyleneimino groups a methylene group in the 4-position is replaced in each case by an oxygen or sulphur atom, by a carbonyl, sulphinyl, sulphonyl or $R_{10}N$ group, where $R_{10}$ denotes a hydrogen atom, an alkyl, hydroxy-$C_{2-4}$-alkyl, amino-$C_{2-4}$-alkyl, alkylamino-$C_{2-4}$-alkyl, dialkylamino-$C_{2-4}$-alkyl, (hydroxy-$C_{2-4}$-alkoxy)-$C_{2-4}$-alkyl, aminocarbonylalkyl, alkylaminocarbonylalkyl, dialkylaminocarbonylalkyl, aryl, formyl, alkylcarbonyl, alkyl-sulphonyl, arylcarbonyl, arylsulphonyl, aralkylcarbonyl, aralkylsulphonyl, alkoxycarbonyl, aralkoxycarbonyl, cyano, aminocarbonyl, alkylaminocarbonyl or dialkylaminocarbonyl group, an amino-alkylcarbonyl, alkylamino-alkylcarbonyl, dialkylamino-alkylcarbonyl-group, a methyl group substituted by one or two aryl groups, while the aryl moieties may be substituted independently of one another by one or two fluorine, chlorine, bromine or iodine atoms or one or two nitro, alkyl, hydroxy or alkoxy groups in each case, while the substituents may be identical or different, a 2-, 3- or 4-pyridyl group, a 2-, 4- or 5-pyrimidyl group, a phenyl group optionally substituted by one or two fluorine, chlorine, bromine or iodine atoms or one or two nitro, trifluoromethyl, alkyl, hydroxy, alkoxy, amino, alkylamino, dialkylamino, carboxy, alkoxycarbonyl, aminocarbonyl, alkylaminocarbonyl, dialkylaminocarbonyl or cyano groups, while the substituents may be identical or different, a 8-methyl-8-aza-bicyclo[3.2.1]oct-3-yl group, or an (alkyleneimino)carbonyl or (alkyleneimino)carbonylalkyl group with in each case 5 to 7 cyclic atoms in the alkyleneimino moiety, while in the abovementioned 6- to 7-membered alkyleneimino moieties a methylene group in the 4-position may be replaced in each case by an oxygen or sulphur atom, by a sulphinyl, sulphonyl, imino, N-alkyl-imino, N-alkylcarbonyl-imino or N-aralkyl-imino group, or $R_cNR_d$ denotes a 3-thiazolidinyl group substituted in the 4-position by a carboxy, alkoxycarbonyl, aminocarbonyl, alkylaminocarbonyl or dialkylaminocarbonyl group, or $R_cNR_d$ denotes a 1-piperidinyl group optionally substituted by 1 to 2 alkyl groups, wherein two hydrogen atoms on the carbon skeleton are replaced by a straight-chain alkylene bridge, this bridge containing 2 to 6 carbon atoms, if the two hydrogen atoms are located on the same carbon atom, or 1 to 5 carbon atoms if the two hydrogen atoms are located on adjacent carbon atoms, or 1 to 4 carbon atoms if the two hydrogen atoms are located on carbon atoms which are separated by one atom, or 1 to 3 carbon atoms if the two hydrogen atoms are located on carbon atoms which are separated by two atoms, while the abovementioned 1-piperidinyl groups are additionally substituted by the group $R_6$, which is as hereinbefore defined, a 1-pyrrolidinyl or 1-piperidinyl group optionally substituted by 1 to 2 alkyl groups, wherein the two hydrogen atoms of a methylene group are replaced by a straight-chain $C_{3-6}$-alkylene bridge, while in each case a methylene group in the $C_{3-6}$-alkylene bridge is replaced by a $R_{10}N$ group, where $R_{10}$ is as hereinbefore defined, while the bicyclic ring thus formed is optionally additionally substituted by a hydroxy, alkoxy, amino, alkylamino, dialkylamino, cyano, alkylcarbonylamino, alkylsulphonylamino, alkoxycarbonylamino, arylcarbonyl, carboxy, alkoxycarbonyl, aminocarbonyl, alkylaminocarbonyl or dialkylaminocarbonyl group, a group of the structure

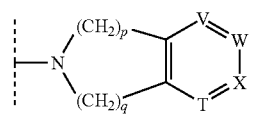

optionally substituted by 1 or 2 alkyl groups in the alkylene moieties wherein
p and q, which may be identical or different, independently of one another denote the number 1 or 2, and
the unit —V=W—X=Y— denotes one of the groups (a) or (b):

 (a),

 (b), while one of the available carbon atoms of the groups (a) or (b) may be substituted by a hydroxy, alkoxy, amino, alkylamino or dialkylamino group and the remaining available carbon atoms of the groups (a) or (b) are substituted by a hydrogen atom, an alkyl or aryl group, or —V=W— taken together represent an oxygen or sulphur atom or an imino, N-alkyl-imino or N-aryl-imino group and —X=Y— represents one of the groups —N=C or —C=N—, or, if n and m are not the same, —X=Y— taken together represent an oxygen or sulphur atom or an imino, N-alkyl-imino or N-aryl-imino group and —V=W— represents one of the groups —N=C or —C=N—, or $R_c$ represents a hydrogen atom, an aralkyl or a $C_{1-6}$-alkyl group, an alkyl group which is substituted
  by a hydroxy, alkoxy, aryloxy, aralkoxy, amino, alkylamino, dialkylamino, alkylcarbonylamino, N-alkyl-alkylcarbonylamino, alkylsulphonylamino, N-alkyl-alkylsulphonylamino, trifluoromethylsulphonylamino, N-alkyl-trifluoromethylsulphonylamino, carboxy, alkoxycarbonyl, aminocarbonyl, alkylaminocarbonyl, dialkylaminocarbonyl, cyano or by a 2-, 3- or 4-pyridyl group with the proviso that the hetero atoms are separated from the nitrogen atom of the $R_cNR_d$ group by two or more carbon atoms,
a $C_{3-5}$-alkenyl group, while the vinyl moiety may not be attached to the nitrogen atom of the $R_cNR_d$ group,
a $C_{3-5}$-alkynyl group, while the ethynyl moiety may not be attached to the nitrogen atom of the $R_cNR_d$ group, and
$R_d$ denotes a $C_{1-10}$-alkyl group which is substituted by a group selected from the groups (a) to (n):
  (a) a carboxy, alkoxycarbonyl, aminocarbonyl, alkylaminocarbonyl, dialkylaminocarbonyl, cyano, hydroxy, alkoxy, aryloxy, aralkoxy, alkylcarbonylamino, amino, alkylamino, dialkylamino, naphthylamino, aralkylamino, diaralkylamino or N-alkyl-aralkylamino group,
  (b) a phenylamino or pyridylamino group optionally substituted in the aryl moiety by a fluorine, chlorine, bromine or iodine atom or a nitro, trifluoromethyl, alkyl, hydroxy, alkoxy, amino, alkylamino, dialkylamino, carboxy, alkoxycarbonyl, aminocarbonyl, alkylaminocarbonyl, dialkylaminocarbonyl or cyano group,
  (c) a methoxy group substituted by one, two or three aryl groups,
  (d) a carboxyalkylaminocarbonyl, alkoxycarbonylalkylaminocarbonyl, amino-carbonylalkylaminocarbonyl, alkylaminocarbonylalkylaminocarbonyl, dialkylaminocarbonylalkylaminocarbonyl, arylaminocarbonyl, N-alkyl-arylaminocarbonyl, aralkylaminocarbonyl, N-alkyl-aralkylaminocarbonyl,
  (e) a group of formula —C(=NH)NH$_2$,
  (f) an (alkyleneimino)carbonyl group with in each case 5 to 7 cyclic atoms in the alkyleneimino moiety optionally substituted by 1 to 2 alkyl groups, while in the abovementioned 6- to 7-membered alkyleneimino groups a methylene group in the 4-position may be replaced in each case by an oxygen or sulphur atom, by a sulphinyl, sulphonyl, imino, N-alkyl-imino, N-alkylcarbonyl-imino, N-alkylsulphonyl-imino, N-aryl-imino or N-aralkyl-imino group,
  (g) a 4- to 7-membered alkyleneimino group optionally substituted by 1 to 2 alkyl groups, while in the abovementioned 6- to 7-membered alkyleneimino groups a methylene group in the 4-position may be replaced in each case by an oxygen or sulphur atom, by a sulphinyl, sulphonyl or $R_{10}N$ group, where $R_{10}$ is as hereinbefore defined, and additionally in the abovementioned 5- to 7-membered alkyleneimino groups a methylene group adjacent to the nitrogen atoms may be replaced by a carbonyl group in each case,
  (h) a 5- to 7-membered alkyleneimino group optionally substituted by 1 to 2 alkyl groups which is substituted by a hydroxyalkyl, aminoalkyl, alkylaminoalkyl or dialkylaminoalkyl group,
  (i) an alkylsulphonylamino, N-alkyl-alkylsulphonylamino, arylcarbonylamino, N-alkyl-arylcarbonylamino, alkylcarbonylamino, N-alkyl-alkylcarbonylamino, alkoxy-alkylcarbonylamino, dialkylamino-alkylcarbonylamino, arylsulphonylamino, N-alkyl-arylsulphonylamino, aralkylcarbonylamino, N-alkylaralkylcarbonylamino, aralkylsulphonylamino, N-alkyl-aralkylsulphonylamino, alkoxycarbonylamino, N-alkyl-alkoxycarbonylamino, aralkoxycarbonylamino or N-alkyl-aralkoxycarbonylamino group,
  (j) a $(R_9NR_8)$—CO—$NR_7$ group, where $R_7$, $R_8$ and $R_9$ are as hereinbefore defined,
  (k) a 2-aza-bicyclo[2.2.1]hept-5-en-2-yl group,
  (l) an alkylsulphenyl, alkylsulphinyl, alkylsulphonyl, arylsulphenyl, arylsulphinyl or arylsulphonyl group,
  (m) a $C_{4-7}$-cycloalkyl group substituted by $R_6$ and optionally additionally substituted by 1 to 2 alkyl groups, while $R_6$ is as hereinbefore defined,
  (n) a $C_{5-7}$-cycloalkyl group optionally substituted by 1 to 4 alkyl groups wherein a methylene group is replaced by an oxygen atom or a $NR_{10}$ group, while $R_{10}$ is as hereinbefore defined,
a 4-piperidinyl-methyl group which is substituted in the 1-position by $R_{10}$ and additionally in the 4-position by a hydroxy group, where $R_{10}$ is as hereinbefore defined, and wherein additionally a hydrogen atom in each of positions 2 and 6 of the piperidinyl structure are together replaced by a $C_{2-3}$-alkylene bridge,
a methyl group substituted by a 3-hydroxy-1,3-dihydro-indol-2-on-3-yl or 2-aminocarbonyl-1,3-dihydro-isoindol-5-yl group,
a group of the structure

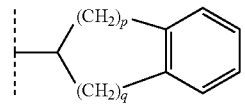

substituted in the aryl moiety by a carboxy or carboxyalkyl group and optionally additionally substituted in the alkylene moiety by 1 or 2 alkyl groups
  while p and q, which may be identical or different, denote the number 0, 1 or 2, but p and q together must at least yield the number 2,
a $C_{3-6}$-alkyl group substituted by a hydroxy group and additionally substituted by an amino, alkylamino, dialkylamino, hydroxy, alkoxy, 1-pyrrolidinyl, 1-piperidinyl or morpholino group, a C$_{2-6}$-alkyl group substituted by a carboxy group and additionally substituted by an amino, hydroxy, aminocarbonyl or benzyloxycarbonylamino group, a C$_{2-4}$-alkyl group which is substituted by a C$_{2-4}$-alkylsulphenyl group, which is substituted in the ω-position by a ω-amino group, a C$_{2-4}$-alkyl group which is substituted by a C$_{2-4}$-alkoxy group, which is substituted in the ω-position by an amino, hydroxy or alkoxy group, a C$_{2-4}$-alkyl group which is substituted by a C$_{2-4}$-alkoxy-C$_{2-4}$-alkoxy group, which is substituted in the ω-position by an amino or hydroxy group, a C$_{4-7}$-cycloalkyl group optionally substituted by 1 to 2 alkyl groups, which is additionally substituted by R$_6$, which is as hereinbefore defined, a C$_{4-7}$-cycloalkyl group optionally substituted by 1 to 2 alkyl groups, which may additionally be substituted by R$_6$, while in the cycloalkyl moiety a methylene group is replaced by an oxygen or sulphur atom, by a sulphinyl, sulphonyl or R$_{10}$N group, while R$_6$ and R$_{10}$ are as hereinbefore defined, a methyl group substituted by a 3-hydroxy-1,3-dihydro-indol-2-on-3-yl or 2-aminocarbonyl-1,3-dihydro-isoindol-5-yl group, a C$_{1-6}$-alkyl group substituted by an aryl group, while the abovementioned aryl moiety is substituted by an alkoxycarbonyl, carboxy, carboxyalkyl, aminosulphonyl, trifluoromethoxy, cyano, aminoalkyl, amino, alkylamino, dialkylamino, nitro, 2H-pyridazin-3-on-6-yl, hydroxyphenyl, hydroxyalkyl, hydroxy or alkoxy group, an aralkyl group which is substituted in the aryl moiety by an alkoxy or hydroxy group and additionally by an alkoxycarbonyl, carboxy, alkoxy or hydroxy group, a C$_{1-6}$-alkyl group substituted by a 2-pyridyl, 3-pyridyl, 4-pyridyl, 2-pyrazinyl-, 1H-pyrrol-2-yl, 1H-pyrazol-4-yl-, 1H-pyrazol-5-yl, 1H-imidazol-1-yl, 1H-imidazol-4-yl, 1H-indol-3-yl or 1H-benzimidazol-2-yl group, while the abovementioned heteroaryl moieties at the available carbon atoms may additionally be substituted in each case by one or two groups selected from fluorine, chlorine, bromine or iodine atoms, alkyl, alkoxycarbonyl, carboxy, trifluoromethyl, trifluoromethoxy, cyano, amino, alkylamino, dialkylamino, nitro, hydroxy or alkoxy groups, while the substituents may be identical or different, a C$_{1-6}$-alkyl group substituted by a carboxy, alkoxycarbonyl, aminocarbonyl, alkylaminocarbonyl, dialkylaminocarbonyl, aralkylaminocarbonyl, cyano, hydroxy, alkoxy, aryloxy, amino, alkylamino, dialkylamino, alkylcarbonylamino or alkoxycarbonylamino group, which is additionally substituted by one or two aryl groups or a heteroaryl group, while the heteroaryl group denotes a 2-pyridyl, 3-pyridyl, 4-pyridyl, 2-pyrazinyl-, 1H-pyrrol-2-yl, 1H-pyrazol-4-yl-, 1H-pyrazol-5-yl, 1H-imidazol-1-yl, 1H-imidazol-4-yl, 1H-indol-3-yl or 1H-benzimidazol-2-yl group, while the abovementioned aryl or heteroaryl moieties at the available carbon atoms may additionally be substituted in each case by one or two groups selected from fluorine, chlorine, bromine or iodine atoms, alkyl, alkoxycarbonyl, carboxy, trifluoromethyl, trifluoromethoxy, cyano, amino, alkylamino, dialkylamino, nitro, hydroxy or alkoxy groups, while the substituents may be identical or different, a C$_{1-6}$-alkyl group substituted by an aryl group which is substituted in the aryl moiety by a hydroxy or amino group and is additionally substituted by two fluorine, chlorine, bromine or iodine atoms, while the substituents may be identical or different, a C$_{2-6}$-alkyl group substituted by a carboxy or alkoxycarbonyl group which is additionally substituted by an amino, alkylamino, dialkylamino, alkylcarbonylamino, arylcarbonylamino, arylsulphonylamino, alkoxycarbonylamino or aralkoxycarbonylamino group, a 3-quinuclidinyl or 4-quinuclidinyl group, and R$_e$ denotes a fluorine, chlorine, bromine or iodine atom, an alkyl, alkoxy, dialkylamino, allyl, ethynyl, methylsulphenyl, methylsulphonyl, alkoxymethyl, nitro, cyano or dialkylaminomethyl group, a methyl, ethyl, methylsulphenyl or methoxy group substituted by 1 to 3 fluorine atoms, an alkyleneimino or alkyleneimino-methyl group with 4 to 7 cyclic atoms in the alkyleneimino moiety in each case, while in a 6 or 7-membered alkyleneimino moiety a methylene group in the 4-position may be replaced in each case by an oxygen or sulphur atom, by an N-alkyl-imino, N-alkylcarbonyl-imino, N-alkylsulphonyl-imino, N-arylimino or N-aralkyl-imino group, while, unless otherwise specified, the abovementioned alkyl, alkylene and alkoxy moieties in each case contain 1 to 4 carbon atoms, optionally in the form of the tautomers, racemates, enantiomers, diastereomers and mixtures thereof, and optionally also the pharmacologically acceptable acid addition salts thereof, while, unless otherwise stated, each carbon atom in the abovementioned alkyl, alkylene or cycloalkylene moieties which is bound to a nitrogen, oxygen or sulphur atom, cannot be bound to any other halogen, nitrogen, oxygen or sulphur atom.

Particularly preferred compounds of formula I are those wherein

R$_a$ denotes a hydrogen atom or a methyl group,

R$_b$ denotes a naphthyl group optionally substituted by a fluorine, chlorine or bromine atom or by a carboxy, C$_{1-2}$ alkyl, C$_{1-2}$ alkoxy, cyano or trifluoromethyl group, a benzyl or 2-phenethyl group optionally substituted in the aryl moiety by a hydroxy, cyano, trifluoromethyl, nitro, carboxy, alkoxycarbonyl, aminocarbonyl, alkylaminocarbonyl, dialkylaminocarbonyl, amino, alkylamino or dialkylamino group or one or two fluorine, chlorine or bromine atoms or one or two alkyl or alkoxy groups, while the substituents may be identical or different, and while the alkylene moiety of the abovementioned aralkyl groups may be substituted by one or two methyl groups, or a 5- or 6-indazolyl or 1,3-dihydro-2-oxo-indol-6-yl group or a phenyl group optionally substituted by the groups R$_1$ to R$_3$, where R$_1$ denotes a fluorine, chlorine, bromine or iodine atom, a C$_{1-2}$ alkyl, trifluoromethyl, aminocarbonyl, carboxy, alkoxycarbonyl, cyano, phenylaminocarbonyl, benzylaminocarbonyl, aminosulphonyl, methylaminosulphonyl, dimethylaminosulphonyl, morpholinosulphonyl, N-methylpiperazinosulphonyl, homopiperazinosulphonyl, 2,6-dimethylpiperazin-4-yl, 2-aminopyridyl-N-sulphonyl, morpholino, 4-methyl-1-piperazinyl, (N-methyl-N-methylsulphonyl)amino, 2-carboxy-1-ethyl, dimethylamino-1-ethyl or nitro group, a methyl group which is substituted by a 1,2,4,5-tetrahydro-benzo[d]azepin-3-yl, a dialkylamino or a pyrrolidino, piperidino, 2,6-dimethyl-piperidino-1-yl, 4-methoxy-piperidino-1-yl, morpholino, S-dioxo-thiomorpholino, piperazino or 4-methyl-1-piperazinyl group, a fluoroalkylamino group of formula —(CH$_2$)$_r$—(CF$_2$)$_s$-Q, wherein
r denotes 0 or an integer from 1 to 3,
s denotes an integer from 1 to 3, and
Q denotes hydrogen, fluorine or chlorine,
$R_2$ denotes a fluorine or chlorine atom, a hydroxy, amino or methyl group and
$R_3$ denotes a chlorine atom, or
a tetrazolyl, triazolyl, imidazolyl or pyrazolyl group,
wherein the point of attachment is a carbon atom or a nitrogen atom and on the ring a hydrogen atom may be replaced by an alkyl group, or
an aminosulphonyl, methylaminosulphonyl, dimethylaminosulphonyl, morpholinosulphonyl, N-methylpiperazinosulphonyl, homopiperazinosulphonyl or 2-aminopyridyl-N-sulphonyl group,
$R_2$ and $R_3$ taken together represent a group of the formula —(CH$_2$)$_m$—NR$_5$—(CH$_2$)$_n$ wherein n and m independently of each other denote 1 or 2, and
$R_5$ denotes a fluoroalkyl group of formula —(CH$_2$)$_{r'}$—(CF$_2$)$_{s'}$-Q', wherein
r' denotes 0 or an integer from 1 to 3,
s' denotes an integer from 1 to 3, and
Q' denotes hydrogen, fluorine or chlorine,
the group $R_c NR_d$
denotes a 5- to 7-membered alkyleneimino group substituted by the group $R_6$,
while $R_6$ denotes a hydroxy, alkoxy, aryloxy, amino, alkylamino, dialkylamino, alkylcarbonylamino, N-alkyl-alkylcarbonylamino, alkoxycarbonylalkylamino, N-(alkyl)-N-(alkoxycarbonylalkyl)-amino, alkylsulphenyl, alkylsulphinyl, alkylsulphonyl, arylsulphenyl, arylsulphinyl, arylsulphonyl, carboxy, alkoxycarbonyl, aminocarbonyl, alkylaminocarbonyl, dialkylaminocarbonyl or cyano group,
an alkyl group which is substituted by a hydroxy, amino, alkylamino, dialkylamino, alkylcarbonylamino, N-alkyl-alkylcarbonylamino, dialkylaminocarbonylalkylamino, N-(alkyl)-N-(dialkylaminocarbonylalkyl)-amino, alkoxycarbonyl, carboxy or dialkylaminoalkoxy group or by a 5- to 7-membered alkyleneimino group, while in the abovementioned 6- to 7-membered alkyleneimino groups a methylene group in the 4-position may be replaced by an oxygen or sulphur atom or by an imino, N-alkyl-imino or N-alkylcarbonyl-imino group,
an alkyleneimino group with 5 to 7 cyclic atoms in the alkyleneimino moiety, while in the abovementioned 6- to 7-membered alkyleneimino moieties a methylene group in the 4-position may be replaced in each case by an oxygen or sulphur atom, by an N-alkyl-imino, N-alkylcarbonyl-imino or N-aralkyl-imino group,
an alkyleneimino group with 5 to 7 cyclic atoms in the alkyleneimino moiety substituted by a hydroxy, amino, alkylamino, dialkylamino, carboxy, alkoxycarbonyl, aminocarbonyl, alkylaminocarbonyl or dialkylaminocarbonyl group,
a 3,4-dihydro-1H-quinazolin-2-on-3-yl or a 1H-benzimidazol-2-on-1-yl group optionally substituted in the aryl moiety by a fluorine, chlorine or bromine atom or a nitro, alkyl, alkoxy or cyano group in each case,
a 6- to 7-membered alkyleneimino group optionally substituted by 1 or 2 alkyl groups, while a methylene group in the 4-position is replaced by an oxygen or sulphur atom, by a sulphinyl, sulphonyl or an NR$_{10}$ group, where $R_{10}$ denotes a hydrogen atom or an alkyl, aralkyl, amino-C$_{2-4}$-alkyl, hydroxy-C$_{2-4}$-alkyl, alkylcarbonyl, aralkoxycarbonyl, alkylsulphonyl, arylcarbonyl, arylsulphonyl,
an (alkyleneimino)carbonylalkyl group with 5 to 7 cyclic atoms in the alkyleneimino moiety, while in the abovementioned 6- to 7-membered alkyleneimino moieties a methylene group in the 4-position may be replaced in each case by an oxygen or sulphur atom, by an N-alkyl-imino, N-alkylcarbonyl-imino or N-aralkyl-imino group,
a 2-, 3- or 4-pyridyl group,
a 2-, 3- or 4-pyrimidyl group,
a phenyl group optionally substituted by one or two fluorine, chlorine, bromine or iodine atoms or one or two nitro, alkyl, hydroxy, alkoxy, amino, alkylamino, dialkylamino, carboxy, alkoxycarbonyl, aminocarbonyl, alkylaminocarbonyl, dialkylaminocarbonyl or cyano groups, while the substituents may be identical or different,
an 8-methyl-8-aza-bicyclo[3.2.1]oct-3-yl group,
a benzhydryl group, wherein independently of one another each phenyl moiety may be substituted by a fluorine, chlorine, bromine or iodine atom or a nitro, alkyl, hydroxy, alkoxy group, while the substituents may be identical or different,
a 6- or 7-membered alkyleneimino group substituted by a phenyl group, which is additionally substituted by a hydroxy, carboxy, alkoxycarbonyl or cyano group or wherein a methylene group in the 4-position is replaced by a carbonyl group,
a 3-thiazolidinyl group substituted in the 4-position by a carboxy, alkoxycarbonyl, aminocarbonyl, alkylaminocarbonyl or dialkylaminocarbonyl group,
a group of the structure

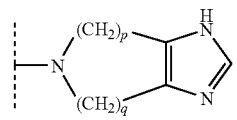

wherein p and q, which may be identical or different, independently of one another represent the number 1 or 2, while the imidazo ring may be substituted by one or two alkyl or aryl groups, while the substituents may be identical or different,
a 1-pyrrolidinyl or 1-piperidinyl group, wherein the two hydrogen atoms of a methylene group are replaced by a straight-chain C$_{3-5}$-alkylene bridge, while in each case a methylene group in the C$_{3-5}$-alkylene bridge is replaced by an imino, N-alkyl-imino or N-(aralkyl)imino group, while the bicyclic ring thus formed is optionally additionally substituted by a hydroxy group,
a 1-piperidinyl group which is substituted in the 4-position by a hydroxy, alkoxy or aralkoxy group and wherein additionally one of the hydrogen atoms in each of positions 2 and 6 of the piperidinyl structure are together replaced by an ethylene bridge, or
$R_c$ denotes a hydrogen atom or a C$_{1-6}$-alkyl group,
an alkyl group substituted by a phenyl or a 2-, 3- or 4-pyridyl group,
a C$_{2-4}$-alkyl group substituted by a hydroxy or alkoxy group, and
$R_d$ represents a C$_{1-6}$-alkyl group which is substituted by a group selected from the groups (a) to (j):

(a) a group of formula —C(=NH)NH$_2$,
(b) a carboxy, alkoxycarbonyl, carboxymethylaminocarbonyl, aminocarbonyl, alkylaminocarbonyl, alkylcarbonylamino, dialkylaminocarbonyl, arylaminocarbonyl, N-alkyl-arylaminocarbonyl, aralkylaminocarbonyl, N-alkyl-aralkylaminocarbonyl or cyano group,
(c) a hydroxy, amino, alkoxy, alkylamino, dialkylamino, alkylcarbonylamino, N-alkyl-alkylcarbonylamino, alkoxycarbonylamino, alkoxyacetylamino, dialkylaminoacetylamino, N-alkyl-alkoxycarbonylamino, alkylsulphonylamino, N-alkyl-alkylsulphonylamino, arylamino, naphthylamino, aralkylamino, diaralkylamino, N-alkyl-aralkylamino or alkylsulphenyl group,
(d) a nitro-2-pyridyl-amino group,
(e) a methoxy group substituted by one, two or three aryl groups,
(f) a 4- to 7-membered alkyleneimino group, while in the abovementioned 6- to 7-membered alkyleneimino groups a methylene group in the 4-position may be replaced in each case by an oxygen or sulphur atom, by an imino, N-alkyl-imino, N-(hydroxy-C$_{2-4}$-alkyl)-imino or N-(amino-C$_{2-4}$-alkyl)-imino group, and additionally in the abovementioned 5- to 7-membered alkyleneimino groups a methylene group adjacent to the nitrogen atoms may be replaced in each case by a carbonyl group,
(g) a 1-piperidinyl group substituted by a dialkylaminoalkyl group,
(h) a 2-aza-bicyclo[2.2.1]hept-5-en-2-yl group,
(i) a 5- to 7-membered (alkyleneimino)carbonyl group, while in the abovementioned 6- to 7-membered alkyleneimino groups a methylene group in the 4-position may be replaced by an oxygen or sulphur atom or by an imino or N-alkyl-imino group, and
(j) a (R$_8$R$_9$)CONR$_7$ group wherein
   R$_7$, R$_8$ and R$_9$, which may be identical or different, in each case denote a hydrogen atom or a methyl group or
   R$_7$ and R$_8$ together denote a n-C$_{2-3}$-alkylene group and R$_9$ denotes a hydrogen atom or a methyl or 4-pyridyl group or
   R$_7$ and R$_8$ denote a hydrogen atom and R$_9$ denotes a phenyl group,
a cyclohexyl group substituted in the 2-, 3- or 4-position by a hydroxy, amino, alkylamino, dialkylamino, aminomethyl, hydroxymethyl, alkoxycarbonyl, aminocarbonyl, alkylaminocarbonyl, dialkylaminocarbonyl or carboxy group,
a cyclohexyl group substituted in the 4-position by a carboxyalkyl group,
an ethyl group substituted in the 2-position by a 2-amino-1-ethylthio, 2-hydroxy-1-ethoxy, 2-(2-amino-1-ethoxy)-1-ethoxy or 2-(2-hydroxy-1-ethoxy)-1-ethoxy group,
a propyl group substituted in the 3-position by a 3-amino-1-propoxy or 2-(3-amino-1-propoxy)-1-ethoxy group,
a C$_{1-2}$-alkyl group substituted by a C$_{5-6}$-cycloalkyl group, while the cycloalkyl moiety is substituted by a hydroxy, aminomethyl, dimethylaminomethyl, 2-carboxyethyl or tert.-butyloxycarbonylaminomethyl group or wherein in the cycloalkyl moiety a methylene group is replaced by an oxygen atom, an N-alkyl-imino or N-(2-dialkylaminoacetyl)imino group,
a 4-piperidinyl-methyl group which is substituted in the 1-position by an alkyl or aralkyl group and additionally in the 4-position by a hydroxy group and wherein additionally in each case a hydrogen atom in each of positions 2 and 6 of the piperidinyl structure are together replaced by an ethylene bridge,
a 3-pyrrolidinyl or a 3- or 4-piperidinyl group which is substituted in each case in the 1-position by an alkyl, aralkyl or arylsulphonyl group,
a 4-piperidinyl group which is substituted in the 1-position by an alkyl, aralkyl or aryl group and is additionally substituted in the 4-position by a carboxy group,
an aralkyl group which is substituted in the aryl moiety by a hydroxy, aminosulphonyl, carboxy, nitro, amino, aminomethyl, 2-amino-1-ethyl, alkoxycarbonyl, 4-hydroxyphenyl or 2H-pyridazin-3-on-6-yl group,
a methyl group substituted by a 3-hydroxy-1,3-dihydro-indol-2-on-3-yl or 2-aminocarbonyl-1,3-dihydro-isoindol-5-yl group,
a 2-indanyl group substituted in the aryl moiety by a 3-carboxy-1-propyl group,
an alkyl group substituted by a 1H-2-benzimidazolyl or 4-amino-3,5-dichlorophenyl group,
an aralkyl group which is substituted in the alkyl moiety by a hydroxy, amino, alkylamino, dialkylamino, aminocarbonyl, alkylaminocarbonyl, dialkylaminocarbonyl, aralkylaminocarbonyl, carboxy or cyano group and is optionally additionally substituted in the aryl moiety by one or two fluorine, chlorine or bromine atoms or one or two hydroxy or alkoxy groups, while the substituents may be identical or different,
an alkyl group substituted by a carboxy group and additionally by two phenyl groups,
a C$_{2-6}$-alkyl group substituted by a carboxy group and additionally substituted by a hydroxy, aminocarbonyl, 1H-imidazol-4-yl or benzyloxycarbonylamino group,
an alkyl group substituted by an alkoxycarbonyl group and additionally by a pyridyl group,
a C$_{3-6}$-alkyl group substituted by a hydroxy group and additionally by an amino, alkylamino, dialkylamino, hydroxy, alkoxy, 1-pyrrolidinyl, 1-piperidinyl or morpholino group,
an aralkyl group which is substituted in the aryl moiety by an alkoxy and additionally by a carboxy or hydroxy group,
an alkyl group substituted by a 2-pyridyl, 3-pyridyl, 4-pyridyl, 2-pyrazinyl, 3-chloro-5-trifluoromethyl-2-pyridyl, 1-methyl-1H-pyrrol-2-yl, 1H-pyrazol-4-yl, 4-ethoxycarbonyl-1H-pyrazol-5-yl, 1H-imidazol-1-yl, 1H-imidazol-4-yl, 1H-indol-3-yl or 6-methoxy-1H-benzimidazol-2-yl group,
a 1-pentyl group substituted in the 5-position by an alkoxycarbonyl group, which is additionally substituted in the 5 position by an amino, alkylcarbonylamino, arylcarbonylamino, arylsulphonylamino, alkoxycarbonylamino or aralkoxycarbonylamino group,
R$_e$ denotes a fluorine, chlorine bromine or iodine atom,
an alkyl, alkoxy, dimethylamino, allyl, ethynyl, trifluoromethyl, methyldifluoromethylene, methylsulphenyl, trifluoromethylsulphenyl, methylsulphonyl, methoxymethyl, nitro, cyano or dimethylaminomethyl group,
while, unless otherwise specified, the abovementioned alkyl, alkylene and alkoxy moieties each contain 1 to 4 carbon atoms,
optionally in the form of the tautomers, racemates, enantiomers, diastereomers and mixtures thereof, and optionally also the pharmacologically acceptable acid addition salts thereof,
while, unless otherwise stated, each carbon atom in the abovementioned alkyl, alkylene or cycloalkylene moieties which is bound to a nitrogen, oxygen or sulphur atom cannot be bound to any other halogen, nitrogen, oxygen or sulphur atom.
Most particularly preferred compounds of formula I are those wherein $R_a$ denotes a hydrogen atom, $R_b$ denotes a 1-naphthyl group or a 2-naphthyl group optionally substituted in the 5 position by a carboxy group, a benzyl group optionally substituted in the 2 position of the phenyl moiety by a chlorine or bromine atom, a 1,3-dihydro-2-oxo-indol-6-yl, benzotriazol-5-yl, benzimidazol-5-yl, indazol-5-yl or indazol-6-yl group, a phenyl group optionally substituted in the 4 position of the phenyl moiety by a fluorine, chlorine or bromine atom, by a cyano, aminosulphonyl, methylaminosulphonyl, dimethylaminosulphonyl, morpholinosulphonyl, N-methylpiperazinosulphonyl, homopiperazinosulphonyl, 2,6-dimethylpiperazin-4-yl, 2-aminopyridyl-N-sulphonyl, carboxy, piperidinomethyl, 1,2,4,5-tetrahydro-benzo[d] azepin-3-yl-methyl, 2-carboxy-1-ethyl, phenylaminocarbonyl, benzylaminocarbonyl, aminocarbonyl, methoxycarbonyl, (N-methyl-N-methylsulphonyl)amino, diethylaminomethyl, 3-diethylamino-1-propyloxy, morpholino, 4-methyl-1-piperazinyl, 2-H-tetrazol-5-yl, 1-H-imidazol-4-yl or nitro group, a phenyl group substituted in the 3 position of the phenyl moiety by a chlorine or bromine atom, by a cyano, aminocarbonyl, carboxy, ethoxycarbonyl or nitro group or by a group of formula

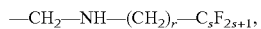

—CH$_2$—NH—(CH$_2$)$_r$—C$_s$F$_{2s+1}$, wherein r denotes 1 or 2 and s denotes 1, 2 or 3, a 3,4-dichlorophenyl, 3,5-dichlorophenyl, 4-amino-3,5-dichlorophenyl, 3-chloro-4-fluorophenyl, 4-chloro-3-methylphenyl, 4-chloro-3-trifluoromethylphenyl, 4-bromo-3-chlorophenyl or 3-hydroxy-4-methylphenyl group, or a group of formula

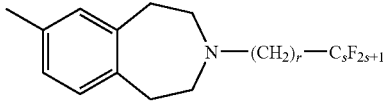

wherein r denotes 1 or 2 and s denotes 1, 2 or 3, the group $R_cNR_d$ denotes a 1-pyrrolidinyl group substituted in the 2 position by a hydroxymethyl, 1-pyrrolidinylmethyl or 2-ethoxycarbonyl-1-ethyl group, a 1-pyrrolidinyl group substituted in the 3 position by an amino, acetylamino, N-methyl-acetylamino or tert.butyloxycarbonylamino, a 4-carboxy-3-thiazolidinyl, a 7-methyl-2,7-diaza-spiro[4.4] non-2-yl or a 5-hydroxy-2-methyl-2,8-diaza-spiro[5.5]undec-8-yl group, a morpholino or S-oxido-thiomorpholino group a 1-piperidinyl group substituted in the 2 position by a ethoxycarbonyl, hydroxymethyl, 3-hydroxypropyl, 3-diethylamino-1-propyl or 2-(2-diethylaminoethoxy)-1-ethyl group, a 1-piperidinyl group substituted in the 3 position by a hydroxy, hydroxymethyl, 3-diethylamino-1-propyl, aminocarbonyl, dimethylaminocarbonyl, carboxy, 1-pyrrolidinylmethyl, 4-(1-pyrrolidinyl)-1-butyl, methoxycarbonylmethyl or acetylaminomethyl group, a 1-piperidinyl group substituted in the 4-position by an ethoxycarbonyl, 3-hydroxypropyl, hydroxy, aminomethyl, 2-(2-diethylamino)-1-ethyl, 2-carboxy-1-ethyl, N-(2-methoxycarbonyl-1-ethyl)-N-methyl-amino, 2-(N-(dimethylaminocarbonylmethyl)-N-methyl-amino)-1-ethyl, N-acetyl-N-methyl-aminomethyl, 8-methoxy-3,4-dihydro-1H-quinazolin-2-on-3-yl, 1-piperidinyl, 3-hydroxy-1-piperidinyl or 4-ethoxycarbonyl-1-piperidinyl group, a 3,5-dimethyl-1-piperazinyl, 1,4,6,7-tetrahydro-imidazo[4,5-c]pyridin-5-yl, 2-methyl-1,4,6,7-tetrahydro-imidazo[4,5-c]pyridin-5-yl, 1,4,5,6,7,8-hexahydro-imidazo[4,5-d]azepin-6-yl, 2-methyl-1,4,5,6,7,8-hexahydro-imidazo[4,5-d]azepin-6-yl, 3-phenyl-azepan-4-on-1-yl or 4-carboxy-4-phenyl-1-piperidinyl group, a 1-piperazinyl group which is optionally substituted in the 4-position by a methyl, acetyl, benzyloxycarbonyl, 2-pyridyl, 2-pyrimidinyl, 2-nitrophenyl, 3-methoxyphenyl, 4-cyanophenyl, 3,4-dimethoxyphenyl, 4-[bis-(4-methoxyphenyl)]-methyl, 8-methyl-8-aza-bicyclo[3.2.1]oct-3-yl, morpholinocarbonylmethyl, 2-amino-1-ethyl or 3-hydroxy-1-propyl group, a 1-homopiperazinyl group which is optionally substituted in the 4-position by a methyl group, a 3-hydroxy-8-aza-bicyclo[3.2.1]oct-8-yl group, or $R_c$ denotes a hydrogen atom or a methyl, ethyl, 2-methoxyethyl, 2-hydroxyethyl, i-propyl, n-propyl, n-butyl, benzyl or 3-pyridylmethyl group, and $R_d$ denotes a methyl group substituted by a group of formula —C(=NH)NH$_2$ or a cyano, carboxyl, ethoxycarbonyl, aminocarbonyl, carboxymethylaminocarbonyl, 1-hydroxy-1-cyclohexyl, aminomethylcyclohexyl, 3-hydroxy-8-methyl-8-aza-bicyclo[3.2.1]oct-3-yl, 3-hydroxy-1,3-dihydro-indol-2-on-3-yl, 2-aminocarbonyl-1,3-dihydro-isoindol-5-yl, 2-tetrahydrofuryl, 1-ethyl-2-pyrrolidinyl, 1H-imidazol-4-yl, 1-methyl-4-piperidinyl, 1-(2-dimethylaminoacetyl)-4-piperidinyl, 2-pyridyl, 3-pyridyl, 4-pyridyl, 2-pyrazinyl, 3-chloro-5-trifluoromethyl-2-pyridyl, 4-ethoxycarbonyl-1H-pyrazol-5-yl, 2-carboxyphenyl, 3-carboxyphenyl, 2-hydroxyphenyl, 4-hydroxyphenyl, 2-nitrophenyl, 3-nitrophenyl, 4-nitrophenyl, 3-aminophenyl, 4-aminophenyl, 4-(aminosulphonyl)phenyl, 4'-hydroxybiphenyl, 4-(aminomethyl)phenyl or 4-hydroxy-3-methoxyphenyl group, a $C_{2-5}$-alkyl group substituted by a carboxy group, a $C_{2-5}$-alkyl group substituted by a hydroxy, acetylamino, amino or dimethylamino group, with the proviso that the hetero atoms of the abovementioned substituents are separated from the nitrogen atom of the $R_cNR_d$ group by at least two carbon atoms, a benzyl group substituted in the methylene moiety by a carboxy or cyano group, a methyl group substituted by a carboxy group and a 4-hydroxyphenyl group, an ethyl group substituted in the 1-position by a methoxycarbonyl or a 1H-benzimidazol-2-yl group, an ethyl group substituted in the 2 position by a methoxy, diphenylmethoxy, methylthio, methylamino, diethylamino, diisopropylamino, acetylamino, N-methylacetylamino, 2-methoxyacetylamino, 2-dimethylaminoacetylamino, isopropylcarbonylamino, tert.-butyloxycarbonylamino, methylsulphonylamino, benzoylamino, phenylamino, 1-naphthylamino, 4-nitro-2-pyridyl-amino, cyano, ethoxycarbonyl, aminocarbonyl, methylaminocarbonyl, dimethylaminocarbonyl, 2-hydroxy-1-ethoxy, 2-(2-amino-1-ethoxy)-1-ethoxy, 2-(2-hydroxy-1-ethoxy)-1-ethoxy, 2-amino-1-ethylthio, 1-methyl-2-pyrrolidinyl, 1-pyrrolidinyl, 2-oxo-pyrrolidin-1-yl, 1-piperidinyl, 2-oxo-piperidin-1-yl, morpholino, 4-(2-hydroxyethyl)-1-piperazinyl, 2-(2-dimethylaminoethyl)-1-piperidinyl, 4-methyl-1-piperazinocarbonyl, 3-carboxy-2-methoxy-phenyl, 2-hydroxyphenyl, 3-hydroxyphenyl, 4-hydroxyphenyl, 4-(aminosulphonyl)phenyl, 4-nitrophenyl-1,3-methoxycarbonylphenyl, 2-(2-amino-1-ethyl) phenyl, 4-pyridyl, 1H-imidazol-1-yl-, 1H-imidazol-4-yl, 1H-pyrazol-4-yl, 1-methyl-1H-pyrrol-2-yl, 1H-indol-3-yl, 6-methoxy-1H-benzimidazol-2-yl, 4-(2H-pyridazin-3-on-6-yl)-phenyl or imidazolidin-2-on-1-yl group, an ethyl group substituted in the 1-position by a carboxy group and additionally substituted in the 2 position by a hydroxy, aminocarbonyl, 2-chlorophenyl, 4-chlorophenyl, 1H-imidazol-4-yl or 4-hydroxyphenyl group, an ethyl group substituted in the 1-position by an aminocarbonyl group and additionally substituted in the 2 position by a 4-methoxyphenyl group, an ethyl group substituted in the 1-position by a 4-phenyl-1-butylaminocarbonyl group and additionally substituted in the 2 position by a phenyl group, an ethyl group substituted in the 2 position by a hydroxy group and additionally substituted in the 2 position by a phenyl, 3-hydroxyphenyl, 4-hydroxyphenyl or 4-hydroxy-3-methoxyphenyl group, an ethyl group substituted in the 1-position by a phenyl group and additionally substituted in the 2 position by a hydroxy or carboxy group, an ethyl group substituted in the 1-position by a 3-pyridyl group and additionally substituted in the 2 position by an ethoxycarbonyl group, an ethyl group substituted in the 1-position by a carboxy group and additionally substituted in the 2 position by two phenyl groups, an n-propyl group substituted in the 2 position by a hydroxy group and additionally substituted in the 3 position by an amino, hydroxy or morpholino group, an n-propyl group substituted in the 3 position by a methoxy, isopropylamino, methylamino, diethylamino, dibenzylamino, 1-pyrrolidinyl, 1-piperidinyl, morpholino, 4-methyl-1-piperazinyl, -tert.-butyloxycarbonylamino, 2-oxo-1-pyrrolidinyl, 2-oxo-piperidin-1-yl, ethoxycarbonyl, 4-pyridyl, 4-amino-3,5-dichlorophenyl, 3-amino-1-propoxy, 2-(3-amino-1-propoxy)-1-ethoxy, 1H-imidazol-1-yl, 2-aza-bicyclo[2.2.1]hept-5-en-2-yl, 4-(3-amino-1-propyl)-1-piperazinyl or 2-diethylaminomethyl-1-piperidinyl group, an n-butyl group substituted in the 4-position by a 4-hydroxyphenyl group, an n-butyl group substituted in the 4-position by a dimethylamino group and additionally substituted in the 2 position by a phenyl group, a 2-methyl-2-butyl group substituted in the 3 position by a phenylaminocarbonylamino or a 1-(4-pyridyl)-3-imidazolin-2-on-3-yl, an n-pentyl group substituted in the 1-position by a carboxy group and additionally substituted in the 5 position by a benzyloxycarbonylamino group, a 1-pentyl group substituted in the 5 position by a methoxycarbonyl group and additionally substituted in the 5 position by an acetylamino group, an n-hexyl group substituted in the 6 position by a hydroxy, amino, tert.-butyloxycarbonylamino or N-methyl-N-phenethylamino group, a cyclohexyl group substituted in the 2 position by a hydroxy, amino, dimethylamino or hydroxymethyl group, a cyclohexyl group substituted in the 3 position by an amino or carboxy group, a cyclohexyl group substituted in the 4 position by a hydroxy, amino, carboxy, 2-carboxyethyl, 3-carboxypropyl, methoxycarbonyl or dimethylamino group, a cyclohexylmethyl group substituted in the 3 position of the cyclohexyl moiety by an aminomethyl or a tert.-butyloxycarbonylaminomethyl group, a cyclohexylmethyl group substituted in the 4-position of the cyclohexyl moiety by an aminomethyl, dimethylaminomethyl or 2-carboxyethyl group, a 4-piperidinyl group substituted in the 1-position by a methyl, benzyl or phenylsulphonyl group, a 1-methyl-4-carboxy-4-piperidinyl group, a 1-ethyl-3-piperidinyl, 1-benzyl-3-pyrrolidinyl or 5-(3-carboxy-1-propyl)-indan-2-yl) group, and $R_e$ denotes a bromine atom or a methyl, ethyl, ethynyl, trifluoromethyl, methylsulphenyl, trifluoromethylsulphenyl, cyano or nitro group, optionally in the form of the tautomers, racemates, enantiomers, diastereomers and mixtures thereof, and optionally also the pharmacologically acceptable acid addition salts thereof.

Most preferred are the compounds of formula I wherein $R_a$ denotes hydrogen.

Particularly preferred are those compounds of formulae I to 5, wherein:

$R_b$ denotes a phenyl group optionally substituted in the 4 position of the phenyl moiety by a fluorine, chlorine or bromine atom, by a cyano, aminosulphonyl, dimethylaminosulphonyl, carboxy, piperidinomethyl, 1,2,4,5-tetrahydro-benzo[d]azepin-3-yl-methyl, 2-carboxy-1-ethyl, phenylaminocarbonyl, benzylaminocarbonyl, aminocarbonyl, methoxycarbonyl, (N-methyl-N-methylsulphonyl)amino, diethylaminomethyl, 3-diethylamino-1-propyloxy, morpholino, 4-methyl-1-piperazinyl, 2-H-tetrazol-5-yl, 1-H-imidazol-4-yl, or nitro group, or a phenyl group substituted in the 3 position of the phenyl moiety by a chlorine or bromine atom, a cyano, aminocarbonyl, carboxy, ethoxycarbonyl or nitro group or a group of the formula

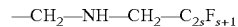
$$-CH_2-NH-CH_2-C_{2s}F_{s+1}$$

wherein s denotes 1 or 2, or a 3,4-dichlorophenyl, 3,5-dichlorophenyl, 4-amino-3,5-dichlorophenyl, 3-chloro-4-fluorophenyl, 4-chloro-3-methylphenyl, 4-chloro-3-trifluoromethylphenyl, 4-bromo-3-chlorophenyl, 3-hydroxy-4-methylphenyl group, benzotriazol-5-yl, benzimidazol-5-yl, indazol-5-yl or indazol-6-yl or a group of the formula

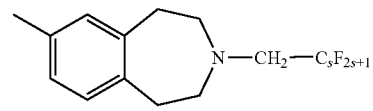

wherein s denotes 1 or 2.

Most preferred of all are compounds of formula I wherein $R_e$ denotes a trifluoromethyl, ethyl, ethynyl or nitro group, particularly a trifluoromethyl or nitro group.

The best results are achieved with compounds of formula I wherein:

the group $R_cNR_d$ is selected from the following groups:

2-amino-1-ethylamino, 2-acetylamino-ethylamino, 2-aminocarbonyl-1-ethylamino, 2-methoxy-1-ethylamino, 2-morpholino-1-ethylamino, 3-aminopropyl-amino, 1-carboxy-2-propylamino, 4-aminobutylamino, 5-hydroxy-1-pentylamino, 3-(3-aminopropoxy-1-propylamino, 2-(3-hydroxyphenyl)-1-ethyl-amino, 2-(4-hydroxy-3-methoxy-phenyl)-2-hydroxy-1-ethylamino, 2-(2-(2-amino-1-ethyl)-phenyl)-1-ethyl-amino, 4-hydroxycyclohexylamino, 3-amino-cyclohexylamino, 4-aminomethyl-cyclohexylmethylamino, 4-dimethylamino-cyclohexylamino, 1-methyl-piperidin-4-yl-methylamino, N-(4-methyl-piperidin-4-yl)-N-methyl-amino, 3-(2-oxo-pyrrolidin-1-yl)-propyl-1-amino, 1,4,6,7-tetrahydro-imidazo[4,5-c]pyridin-5-yl, 2-hydroxymethyl-pyrrolidin-1-yl, 4-aminomethyl-piperidin-1-yl, 3-hydroxymethyl-piperidin-1-yl, 3-acetylaminomethyl-piperidin-1-yl, 4-(N-acetyl-N-methyl-aminomethyl)-piperidin-1-yl, 3-(4-(pyrrolidin-1-yl)butyl)-piperidin-1-yl, 3-(2-aza-bicyclo[2.2.1]hept-5-en-2-yl)-propylamino and 7-methyl-2,7-diaza-spiro[4.4]non-2-yl.

The invention further relates to the physiologically acceptable salts of the compounds of the formula.

The invention also relates to the compounds of formula I for use as pharmaceutical compositions.

In another aspect the invention relates to a process for preparing the compounds of formula I, wherein
a. a compound of general formula

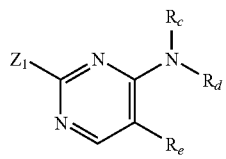 (II)

wherein
$R_c$ to $R_e$ are as hereinbefore defined and
$Z_1$ denotes a leaving group,
is reacted with an amine of general formula

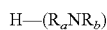 (III)

wherein
$R_a$ and $R_b$ are as hereinbefore defined; or
b. a compound of general formula IV

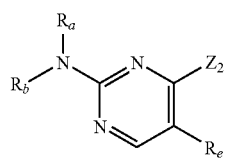 (IV)

wherein
$R_a$, $R_b$ and $R_e$ are as hereinbefore defined, and
$Z_2$ denotes a leaving group, is reacted with an amine of general formula

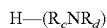 (V)

wherein
$R_c$ and $R_d$ are as hereinbefore defined.

The reaction is expediently carried out in a solvent such as ethanol, isopropanol, butanol, tetrahydrofuran, dioxan, toluene, chlorobenzene, dimethylformamide, dimethylsulphoxide, ethylenglycolmonomethylether, ethylenglycoldiethylether or sulpholane optionally in the presence of an inorganic base, e.g. sodium carbonate or potassium hydroxide, or a tertiary organic base, e.g. triethylamine, N-ethyl-diisopropylamine or pyridine, while the latter may simultaneously also act as solvent, and optionally in the presence of a reaction accelerator such as a copper salt, a corresponding amine-hydrohalide or alkali metal halide at temperatures between 0 and 250° C., preferably however at temperatures between 20 and 200° C. The reaction may however also be carried out without a solvent or in an excess of the compound of formula III or V used.

Moreover the compounds of general formula I obtained as mentioned hereinbefore may be resolved into their enantiomers and/or diastereomers. Thus, for example, cis-/trans mixtures may be resolved into their cis- and trans-isomers, and compounds with at least one optically active carbon atom are resolved into their enantiomers.

Thus, for example, the cis/trans mixtures obtained may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, N-acetylglutamic acid, aspartic acid, N-acetylaspartic acid or quinic acid. An optically active alcohol may be for example (+)- or (-)-menthol and an optically active acyl group in amides, for example, may be a (+)- or (-)-menthyloxycarbonyl group.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid or maleic acid.

Moreover, if the new compounds of formula I thus obtained contain an acid group such as a carboxy group, they may subsequently, if desired, be converted into the salts thereof, with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formulae II to V used as starting materials are known from the literature in some cases or may be obtained by methods known from the literature.

As already mentioned, the compounds of formula I according to the invention and the physiologically acceptable salts thereof have valuable pharmacological properties, particularly an inhibitory effect on the proliferation of cells, particularly endothelial cells. This effect of the new compounds was tested by the following standard procedure, as follows:

The invention also relates to the use of compounds of formula (I) for preparing a medicament for the treatment and prevention of diseases characterised by excessive or anomalous cell proliferation, as well as pharmaceutical compositions which are characterised by a content of one or more compounds of formula I.

Some procedures for preparing the compounds according to the invention will be described in detail hereinafter by way of example. The following Examples of synthesis are intended solely as a detailed illustration without restricting the object of the invention thereto.

Preparation of the Starting Compounds:

The following starting compounds may be prepared according to the reference cited in each case:

Synthesis of 2-chloro-4-thiocyanato-5-nitro-pyrimidine: Takahashi et al., Chem. Pharm. Bull. (1958) 334

Synthesis of 2,4-dichloro-5-trifluoromethylsulphanyl-pyrimidine: Haas, A.; Lieb, M.; J. Heterocycl. Chem. (1986) 1079-1084;

2,4-dichloro-5-methylsulphanyl-pyrimidine:
a) Ishikawa, Katsutoshi et al.; Preparation and fungicidal activity of halothiocyanopyrimidines. JP 62 053973
b) Maggiali, C. et al., Farmaco, Ed. Sci. (1988), 43(3), 277-91.

Synthesis of 2,4-dichloro-5-trifluoromethyl-pyrimidine: Shen; Lewis; Ruyle; J. org. Chem. 30 (1965) 835

Synthesis of 2,4-dichloro-5-nitro-pyrimidine: Albert et al.; J. Chem. Soc. (1951) 474

Synthesis of 4,5,6,7-tetrahydro-1(3)H-imidazo[4,5-c]pyridine: Dale; Dudley; J. Pharmacol. exper. Therap.; 18; 106; Chem. Zentralbl.; GE; 93; I; 1922; 770. Lit 2: Fraenkel; Zeimer; Biochem. Z.; 110; 1920; 238.

Synthesis of (N-(trans-4-hydroxy-cyclohexyl)-N-methylamine: U.S. Pat. No. 2,152,960.

HPLC Methods

Method A: The HPLC/MS data were obtained using an HP-1100-MSD apparatus.

The following was used as the mobile phase:
A: water with 0.1% formic acid
B: acetonitrile with 0.1% formic acid

| time in min | % A | % B | flow rate in ml/min |
|---|---|---|---|
| 0.0 | 95 | 5 | 0.400 |
| 0.5 | 95 | 5 | 0.400 |
| 5.5 | 5 | 95 | 0.400 |
| 8.5 | 5 | 95 | 0.400 |
| 9.5 | 95 | 5 | 0.400 |

The stationary phase used was a Waters X-Terra™ MS $C_{18}$ column, 2.5 μm, 2.1 mm×50 mm (column temperature: constant at 30° C. (±0.5° C.))

The UV detection was carried out at two wavelengths: signal A at 230 nm (±2 nm), signal B at 254 nm (±2 nm).

Range of mass-spectrometric detection: m/z 100 to m/z 1000

Method B:

ThermoFinnigan LCQ Deca, Surveyor-HPLC
The following was used as the mobile phase:
A: water with 0.1% trifluoroacetic acid
B: acetonitrile with 0.1% trifluoroacetic acid

| time in min | % A | % B | flow rate in ml/min |
|---|---|---|---|
| 0.0 | 95 | 5 | 0.500 |
| 4.5 | 2 | 98 | 0.500 |
| 5.5 | 2 | 98 | 0.500 |
| 5.6 | 95 | 5 | 0.500 |
| 7.0 | 95 | 5 | 0.500 |

The stationary phase used was a Waters X-Terra™ MS $C_{18}$ column, 2.5 μm, 2.1 mm×50 mm (column temperature: constant at 40° C.)

The diode array detection was carried out in a wavelength range from 210-500 nm Range of mass-spectrometric detection: m/z 150 to m/z 1500

Method C:

Analogous to method B with the gradient:

| time in min | % A | % B | flow rate in ml/min |
|---|---|---|---|
| 0.0 | 95 | 5 | 0.6 |
| 4.0 | 5 | 95 | 0.6 |
| 6.0 | 5 | 95 | 0.6 |
| 8.0 | 95 | 5 | 0.6 |
| 1 min post run | 95 | 5 | 0.6 |

Method D:

Analogous to Method B with the gradient:

| time in min | % A | % B | flow rate in ml/min |
|---|---|---|---|
| 0.0 | 95 | 5 | 0.4 |
| 5.5 | 5 | 95 | 0.4 |
| 9.5 | 5 | 95 | 0.4 |
| 3 min post run | 95 | 5 | 0.4 |

Method E:

Analogous to Method B with the gradient:

| time in min | % A | % B | flow rate in ml/min |
|---|---|---|---|
| 0.0 | 90 | 10 | 0.7 |
| 4.0 | 5 | 95 | 0.7 |
| 4.5 | 5 | 95 | 0.7 |
| 6.0 | 90 | 10 | 0.7 |

Method F:

The mobile phase used was:
A: water containing 0.1% formic acid
B: Acetonitrile containing 0.1% formic acid

| time in min | % A | % B | flow rate in ml/min |
|---|---|---|---|
| 0.5 | 95 | 5 | 1.5 |
| 5.0 | 0 | 100 | 1.5 |

The stationary phase used was a Develosil RPAqueous 4.6×50 mm column. UV detection was carried out at 254 nm Method G:
Analogous to Method F with the gradient:

| time in min | % A | % B | flow rate in ml/min |
|---|---|---|---|
| 0.5 | 90 | 10 | 1.5 |
| 5.0 | 0 | 100 | 1.5 |

Method H:
Analogous to Method F with the gradient:

| time in min | % A | % B | flow rate in ml/min |
|---|---|---|---|
| 0.5 | 80 | 20 | 1.5 |
| 5.0 | 0 | 100 | 1.5 |

Method I:
Analogous to Method F with the gradient:

| time in min | % A | % B | flow rate in ml/min |
|---|---|---|---|
| 0.5 | 70 | 30 | 1.5 |
| 5.0 | 0 | 100 | 1.5 |

Method J:
Analogous to Method F with the gradient:

| time in min | % A | % B | flow rate in ml/min |
|---|---|---|---|
| 0.5 | 95 | 5 | 1.5 |
| 4.5 | 70 | 30 | 1.5 |
| 5.0 | 0 | 100 | 1.5 |

Method K:
Analogous to Method F with the gradient:

| time in min | % A | % B | flow rate in ml/min |
|---|---|---|---|
| 0.5 | 60 | 40 | 1.5 |
| 5.0 | 0 | 100 | 1.5 |

Method L:
Analogous to Method F with the gradient:

| time in min | % A | % B | flow rate in ml/min |
|---|---|---|---|
| 0.5 | 40 | 60 | 1.5 |
| 5.0 | 0 | 100 | 1.5 |

Method M:
Analogous to Method F with the gradient:

| time in min | % A | % B | flow rate in ml/min |
|---|---|---|---|
| 0.5 | 30 | 70 | 1.5 |
| 5.0 | 0 | 100 | 1.5 |

Example I 2-(3,4-dichlorophenylamino)-4-thiocyanato-5-nitro-pyrimidine 2.47 g of 3,4-dichloroaniline in 12 ml ethanol are added to 3.00 g of 2-chloro-4-thiocyanato-5-nitro-pyrimidine in 40 ml toluene at ambient temperature. The mixture is stirred for another 16 hours, the solid is suction filtered, washed twice with 30 ml toluene and then once with 30 ml of ethanol and dried.

Yield: 2.86 g (60% of theory), Melting point: 240-242° C.

The following compounds are obtained analogously to Example I:

(1) 2-(4-amino-3,5-dichlorophenylamino)-4-thiocyanato-5-nitro-pyrimidine
(2) 2-(4-aminosulphonyl-phenylamino)-4-thiocyanato-5-nitro-pyrimidine
(3) 2-(4-chlorophenylamino)-4-thiocyanato-5-nitro-pyrimidine
Melting point: 2-(4-226° C.
(4) 2-(4-carboxyphenylamino)-4-thiocyanato-5-nitro-pyrimidine
(5) 2-(3-chloro-4-fluoro-phenylamino)-4-thiocyanato-5-nitro-pyrimidine
(6) 2-(3-aminocarbonyl-phenylamino)-4-thiocyanato-5-nitro-pyrimidine
(7) 2-(4-phenylaminocarbonyl-phenylamino)-4-thiocyanato-5-nitro-pyrimidine
(8) 2-(4-nitro-phenylamino)-4-thiocyanato-5-nitro-pyrimidine
(9) 2-(4-cyano-phenylamino)-4-thiocyanato-5-nitro-pyrimidine
(10) 2-(3-bromo-phenylamino)-4-thiocyanato-5-nitro-pyrimidine
(11) 2-(4-bromo-phenylamino)-4-thiocyanato-5-nitro-pyrimidine
(12) 2-(3-nitro-phenylamino)-4-thiocyanato-5-nitro-pyrimidine
(13) 2-(4-(2-carboxy-1-ethyl)phenylamino)-4-thiocyanato-5-nitro-pyrimidine
(14) 2-(4-aminocarbonyl-phenylamino)-4-thiocyanato-5-nitro-pyrimidine
(15) 2-(4-chloro-3-methyl-phenylamino)-4-thiocyanato-5-nitro-pyrimidine
(16) 2-(4-methoxycarbonyl-phenylamino)-4-thiocyanato-5-nitro-pyrimidine
(17) 2-(3-cyano-phenylamino)-4-thiocyanato-5-nitro-pyrimidine
(18) 2-(4-benzylaminocarbonyl-phenylamino)-4-thiocyanato-5-nitro-pyrimidine
(19) 2-(4-fluoro-phenylamino)-4-thiocyanato-5-nitro-pyrimidine
(20) 2-(benzylamino)-4-thiocyanato-5-nitro-pyrimidine
(21) 2-(2-chlorobenzylamino)-4-thiocyanato-5-nitro-pyrimidine
(22) 2-(3-carboxyphenylamino)-4-thiocyanato-5-nitro-pyrimidine
(23) 2-(3-ethoxycarbonyl-phenylamino)-4-thiocyanato-5-nitro-pyrimidine Example II 2-chloro-4-(2-acetylamino-ethylamino)-5-trifluoromethyl-pyrimidine 1.84 g of 2-acetylamino-ethylamine dissolved in 10 ml of dioxane are added to 3.91 g of 2,4-dichloro-5-trifluoromethyl-pyrimidine in 20 ml dioxane at ambient temperature. Then 3.7 ml of 5 M potassium carbonate solution are added and the mixture is stirred for three days at ambient temperature. It is then filtered through Alox B and washed with dioxane. The filtrate is concentrated by evaporation and the residue separated by chromatography through a silica gel column with cyclohexane:ethyl acetate:methanol (5:4:1).

Yield: 2.30 g (45% of theory); Melting point: 185° C.

The following compounds are obtained analogously to Example II:

(1) 2-chloro-4-(2-acetylamino-ethylamino)-5-nitro-pyrimidine

Prepared from 2,4-dichloro-5-nitro-pyrimidine in the presence of 2N sodium hydroxide solution.

(2) 2-chloro-4-(2-acetylamino-ethylamino)-5-methylsulphanyl-pyrimidine

Prepared from 2,4-dichloro-5-methylsulphanyl-pyrimidine.

(3) 2-chloro-4-(2-acetylamino-ethylamino)-5-trifluoromethylsulphanyl-pyrimidine $R_f$=0.15 (silica gel; methylene chloride:methanol=20:1)

Prepared from 2,4-dichloro-5-trifluoromethylsulphanyl-pyrimidine.

(4) 2-chloro-4-(2-acetylamino-ethylamino)-5-bromo-pyrimidine

Prepared from 2,4-dichloro-5-bromo-pyrimidine.

$R_f$=0.16 (silica gel; ethyl acetate:cyclohexane=1:1)

(5) 2-chloro-4-(N-(trans-4-hydroxy-cyclohexyl)-N-methyl-amino)-5-nitro-pyrimidine (6) 2-chloro-4-(trans-4-hydroxy-cyclohexylamino)-5-nitro-pyrimidine (7) 2-chloro-4-(2-pyridyl-methylamino)-5-nitro-pyrimidine (8) 2-chloro-4-(ethoxycarbonyl-methylamino)-5-nitro-pyrimidine (9) 2-chloro-4-[N-(2-hydroxyethyl)-N-methyl-amino]-5-nitro-pyrimidine

(10) N-[2-(2-Chloro-5-trimethylsilanylethynyl-pyrimidin-4-ylamino)-ethyl]acetamide UVmax (ethanol)=215, 265, 314 nm 1H-NMR ($D_6$-DMSO, 400 MHz) δ: 0.27 (s, 9H), 1.82 (s, 3H), 3.26 (m, 2H), 3.43 (m, 2H), 7.50 (t, 1H), 8.08 (t, 1H), 8.14 (s, 1H).

(11) 2-chloro-4-[3-(2-oxo-pyrrolidin-1-yl)-propylamino]-5-bromo-pyrimidine 5.0 g 5-bromo-2,4-dichloro-pyrimidine are placed in 50 ml of 1,4-dioxane together with 3.1 g of 1-(3-aminopropyl)-pyrrolidin-2-one. At ambient temperature 4.39 ml of 5 M potassium carbonate solution are added and the mixture is stirred for 1 hour. Then the reaction mixture is evaporated down completely, taken up in methanol, filtered through aluminium oxide and evaporated down again. The crystalline residue is taken up in 170 ml ethyl acetate, filtered, concentrated by evaporation and recrystallised from ethyl acetate. 5.45 g (75%) of the desired product are obtained.

Rf (methylene chloride/methanol=9:1; SiO2)=0.51; (M+H)+=333/335/337 (Cl, Br);

1H-NMR (D6-DMSO, 400 MHz) δ: 1.72 (quint, 2H), 1.95 (quint, 2H), 2.22 (t, 2H), 3.20 (t, 2H), 3.28-3.40 (m, 4H), 7.71 (t, 1H), 8.22 (s, 1H).

(12) 2-chloro-4-(2-acetylamino-ethylamino)-5-methyl-pyrimidine 1.0 g of 2,4-dichloro-5-methyl-pyrimidine is placed in DMA (0.1 M) and combined at 0° C. with a solution of 0.69 g (1.2 eq.) of N-acetylethylenediamine and 2.0 ml (2 eq.) of ethyldiisopropylamine in DMA. The reaction mixture is stirred for 1-2 hours at ambient temperature and then evaporated to dryness. After the addition of saturated sodium hydrogen carbonat solution the mixture is extracted with ethyl acetate and the organic phase is then dried over sodium sulphate and evaporated down. To purify it further the crude product is chromatographed on silica gel. 78% of the desired product are obtained.

1H-NMR (D6-DMSO, 300 MHz) δ: 1.80 (s, 3H), 1.94 (s, 3H), 3.23 (m, 2H), 3.36 (m, 2H), 7.31 (s, 1H), 7.77 (s, 1H), 7.97 (s, 1H).

(13) 2-chloro-4-(2-acetylamino-ethylamino)-5-chloro-pyrimidine-2-chloro-4-(2-acetylamino-ethylamino)-5-chloro-pyrimidine is obtained analogously to II (12) from 2,4,5-trichloro-pyrimidine in a yield of 58%.

HPLC/MS (method F): RT=3.40 min.; [M+H]+=249/251; Abs. λ max=247.5 nm

1H-NMR (D6-DMSO, 300 MHz) δ: 8.15 (s, 1H); 8.00-7.92 (m, 2H, N—H); 3.40 (q, J=5.8 Hz, 2H); 3.24 (q, J=5.8 Hz, 2H); 1.79 (s, 3H).

(14) 2-chloro-4-(2-acetylamino-ethylamino)-5-methoxy-pyrimidine 1.0 g of 2,4-dichloro-5-methoxy-pyrimidine is quickly added to a solution of 0.69 g (1.2 eq.) of N-acetylethylenediamine and 1.2 ml (1.25 eq.) of ethyldiisopropylamine in 20 ml of ethanol. The reaction mixture is stirred for 2-15 hours at ambient temperature and then evaporated to dryness. After the addition of ethyl acetate the mixture is extracted with saturated sodium hydrogen carbonate solution and saturated sodium chloride solution and the organic phase is then dried over sodium sulphate. For further purification the crude product is chromatographed on silica gel. 793 mg (58%) of the desired product are obtained.

1H-NMR (D6-DMSO, 300 MHz) δ: 1.79 (s, 3H), 3.21 (q, 2H), 3.34 (q, 2H), 3.83 (s, 3H), 7.53 (t, 1H), 7.67 (s, 1H), 7.96 (t, 1H).

(15) 2-chloro-4-(1,4,6,7-tetrahydro-imidazo[4,5-c]pyridin-5-yl)-5-chloro-pyrimidine 2-chloro-4-(1,4,6,7-tetrahydro-imidazo[4,5-c]pyridin-5-yl)-5-chloro-pyrimidine is obtained analogously to II (12) from 2,4,5-trichloro-pyrimidine in a yield of 20%.

HPLC/MS (Method F): RT=3.35 min.; [M+H]+=270/272; Abs. λ max=211.4 nm

1H-NMR (D6-DMSO, 300 MHz) δ: 12.0 (bs, 1H); 8.30 (s, 1H); 7.49 (s, 1H); 4.59 (m, 2H); 3.94 (m, 2H); 2.79 (m, 2H).

(16) 2-chloro-4-(2-acetylamino-ethylamino)-5-methylsulphonyl-pyrimidine 2-chloro-4-(2-acetylamino-ethylamino)-5-methylsulphonyl-pyrimidine is obtained analogously to II (14) from 2,4-dichloro-5-methylsulphonyl-pyrimidine in a yield of 50%.

1H-NMR (D6-DMSO, 300 MHz) δ: 1.79 (s, 3H), 3.16-3.29 (m, 5H), 3.53 (q, 2H), 7.84 (t, 1H), 7.99 (t, 1H), 8.41 (s, 1H).

(17) 2-chloro-4-(2-acetylamino-ethylamino)-5-dimethylamino-pyrimidine 2-chloro-4-(2-acetylamino-ethylamino)-5-dimethylamino-pyrimidine is obtained analogously to II (14) from 2,4-dichloro-5-dimethylamino-pyrimidine in a yield of 49%.

1H-NMR (D6-DMSO, 300 MHz) δ: 1.80 (s, 3H), 2.57 (s, 6H), 3.24 (q, 2H), 3.38 (q, 2H), 7.30 (t, 1H), 7.71 (s, 1H), 7.97 (t, 1H).

(18) 2-chloro-4-(2-acetylamino-ethylamino)-5-isopropoxy-pyrimidine 2-chloro-4-(2-acetylamino-ethylamino)-5-isopropoxy-pyrimidine is obtained analogously to II (14) from 2,4-dichloro-5-isopropoxy-pyrimidine in a yield of 66%.

1H-NMR (D6-DMSO, 300 MHz) δ: 1.28 (d, 6H), 1.80 (s, 3H), 3.22 (q, 2H), 3.35 (q, 2H), 4.58 (sept, 1H), 7.35 (t, 1H), 7.69 (s, 1H), 7.98 (t, 1H).

(19) 2-chloro-4-(2-acetylamino-ethylamino)-5-isopropyl-pyrimidine 2-chloro-4-(2-acetylamino-ethylamino)-5-isopropyl-pyrimidine is obtained analogously to II (14) from 2,4-dichloro-5-isopropyl-pyrimidine in a yield of 70%.

1H-NMR (D6-DMSO, 300 MHz) δ: 1.15 (d, 6H), 1.81 (s, 3H), 2.82 (sept, 1H), 3.23 (q, 2H), 3.39 (q, 3H), 7.41 (t, 1H), 7.84 (s, 1H), 7.99 (t, 1H).

(20) 2-chloro-4-[3-(2-oxo-pyrrolidin-1-yl)-propylamino]-5-chloro-pyrimidine 2-chloro-4-[3-(2-oxo-pyrrolidin-1-yl)-propylamino]-5-chloro-pyrimidine is obtained analogously to II (12) from 2,4,5-trichloro-pyrimidine in a yield of 68%.

HPLC/MS (Method F): RT=3.96 min.; [M+H]+=289/291; Abs. λ max=249.4 nm

1H-NMR (D6-DMSO, 300 MHz) δ: 8.13 (s, 1H); 7.88 (bs, 1H, N—H), 3.31 (m, 4H); 3.16 (m, 2H); 2.22 (t, J=7.9 Hz, 2H); 1.93 (m, 2H); 1.72 (m, 2H).

(21) 2-chloro-4-[3-(2-oxo-pyrrolidin-1-yl)-propylamino]-5-methoxy-pyrimidine 1.0 g of 2,4-dichloro-5-methoxy-pyrimidine is added quickly to a solution of 0.95 g (1.2 eq.) of 1-(3-aminopropyl)-pyrrolidin-2-one and 1.2 ml (1.25 eq.) of ethyldiisopropylamine in 20 ml of ethanol. The reaction mixture is stirred for 15 hours at ambient temperature and then evaporated to dryness. After the addition of ethyl acetate it is extracted with saturated sodium hydrogen carbonate solution and saturated sodium chloride solution and the organic phase is then dried over sodium sulphate. For further purification the crude product is chromatographed on silica gel. 1.15 g (72%) of the desired product is obtained.

1H-NMR (D6-DMSO, 300 MHz) δ: 1.70 (m, 2H), 1.93 (m, 2H), 2.22 (t, 2H), 3.38-3.17 (m, 6H), 3.84 (s, 3H), 7.50 (m, 1H), 7.65 (s, 1H).

(22) 2-chloro-4-[3-(2-oxo-pyrrolidin-1-yl)-propylamino]-5-methyl-pyrimidine 2-chloro-4-[3-(2-oxo-pyrrolidin-1-yl)-propylamino]-5-methyl-pyrimidine is obtained analogously to II (12) from 2,4-dichloro-5-methyl-pyrimidine in a yield of 46%.

HPLC/MS (Method F): RT=3.15 min.; [M+H]+=269/271

1H-NMR (D6-DMSO, 300 MHz) δ: 1.72 (m, 2H), 1.93 (m, 2H), 1.96 (s, 3H), 2.22 (t, 2H), 3.22 (t, 2H), 3.26-3.38 (m, 4H), 7.23 (s, 1H), 7.77 (s, 1H).

(23) 2-chloro-4-[3-(2-oxo-pyrrolidin-1-yl)-propylamino]-5-methylsulphonyl-pyrimidine 2-chloro-4-[3-(2-oxo-pyrrolidin-1-yl)-propylamino]-5-methylsulphonyl-pyrimidine is obtained analogously to II (21) from 2,4-dichloro-5-methylsulphonyl-pyrimidine in a yield of 34%.

1H-NMR (D6-DMSO, 300 MHz) δ: 1.76 (quint, 2H), 1.94 (quint, 2H), 2.32 (t, 2H), 3.23 (t, 2H), 3.26-3.49 (m, 7H), 7.84 (t, 1H), 8.39 (s, 1H).

(24) 2-chloro-4-[3-(2-oxo-pyrrolidin-1-yl)-propylamino]-5-dimethylamino-pyrimidine 2-chloro-4-[3-(2-oxo-pyrrolidin-1-yl)-propylamino]-5-dimethylamino-pyrimidine is obtained analogously to II (21) from 2,4-dichloro-5-dimethylamino-pyrimidine in a yield of 59%.

1H-NMR (D6-DMSO, 300 MHz) δ: 1.71 (quint, 2H), 1.93 (quint, 2H), 2.22 (t, 2H), 2.58 (s, 6H), 3.19-3.38 (m, 6H), 7.30 (t, 1H), 7.70 (s, 1H).

(25) 2-chloro-4-[3-(2-oxo-pyrrolidin-1-yl)-propylamino]-5-isopropoxy-pyrimidine 2-chloro-4-[3-(2-oxo-pyrrolidin-1-yl)-propylamino]-5-isopropoxy-pyrimidine is obtained analogously to II (21) from 2,4-dichloro-5-isopropoxy-pyrimidine in a yield of 83%.

1H-NMR (D6-DMSO, 300 MHz) δ: 1.28 (d, 6H), 1.69 (quint, 2H), 1.93 (quint, 2H), 2.23 (t, 2H), 3.18-3.38 (m, 6H), 4.86 (sept, 1H), 7.29 (t, 1H), 7.68 (s, 1H).

(26) 2-chloro-4-[3-(2-oxo-pyrrolidin-1-yl)-propylamino]-5-isopropyl-pyrimidine 2-chloro-4-[3-(2-oxo-pyrrolidin-1-yl)-propylamino]-5-isopropyl-pyrimidine is obtained analogously to II (21) from 2,4-dichloro-5-isopropyl-pyrimidine in a yield of 54%.

1H-NMR (D6-DMSO, 300 MHz) δ: 1.16 (d, 6H), 1.71 (quint, 2H), 1.94 (quint, 2H), 2.24 (t, 2H), 2.84 (sept, 1H), 3.22 (t, 2H), 3.26-3.34 (m, 4H), 7.34 (t, 1H), 7.83 (s, 1 H).

(27) 2-chloro-4-(4,5,7,8-tetrahydro-1H-imidazo[4,5-d]azepin-6-yl)-5-chloro-pyrimidine 1.0 g of 2,4,5-trichloro-pyrimidine in isopropanol (0.1 M) is combined at 0° C. with a solution of 0.69 g (1.2 eq.) of 4,5,7,8-tetrahydro-1H-imidazo[4,5-d]azepine and 2 ml (2 eq.) of ethyldiisopropylamine in isopropanol. The reaction mixture is stirred for 1-2 hours at ambient temperature and then evaporated to dryness. After the addition of saturated sodium hydrogen carbonate solution the mixture is extracted with dichloromethane and ethyl acetate and the organic phase is then dried over sodium sulphate and evaporated down. For further purification the crude product is chromatographed on silica gel. 95% of the desired product is obtained.

HPLC/MS (Method F): RT=3.32 min.; [M+H]+=284/286; Abs. λ max=260.8 nm

1H-NMR (D6-DMSO, 300 MHz) δ: 8.18 (s, 1H); 7.37 (s, 1H); 4.11-4.08 (m, 4H); 2.89-2.86 (m, 4H).

(28) 2-chloro-4-(4,5,7,8-tetrahydro-1H-imidazo[4,5-d]azepin-6-yl)-5-methyl-pyrimidine 2-chloro-4-(4,5,7,8-tetrahydro-1H-imidazo[4,5-d]azepin-6-yl)-5-methyl-pyrimidine is obtained analogously to II (27) from 2,4-dichloro-5-methyl-pyrimidine in a yield of 36%.

HPLC/MS (Method F): RT=3.22 min.; [M+H]+=264/266

1H-NMR (D6-DMSO, 300 MHz) δ: 2.30 (s, 3H), 2.83 (m, 4H), 3.93 (m, 4H), 7.39 (s, 1H), 7.87 (s, 1H).

(29) 2-chloro-4-(1,4,6,7-tetrahydro-imidazo[4,5-c]pyridin-5-yl)-5-methyl-pyrimidine 2-chloro-4-(1,4,6,7-tetrahydro-imidazo[4,5-c]pyridin-5-yl)-5-methyl-pyrimidine is obtained analogously to II (12) from 2,4-dichloro-5-methyl-pyrimidine in a yield of 26%.

HPLC/MS (Method F): RT=3.19 min.; [M+H]+=250/252

1H-NMR (D6-DMSO, 300 MHz) δ: 2.24 (s, 3H), 2.74 (m, 2H), 3.74 (m, 2H), 4.46 (m, 2H), 7.48 (s, 1H), 8.01 (s, 1H), 11.82 (s, 1H).

(30) 2-chloro-4-(1,4,6,7-tetrahydro-imidazo[4,5-c]pyridin-5-yl)-5-methoxy-pyrimidine 2-chloro-4-(1,4,6,7-tetrahydro-imidazo[4,5-c]pyridin-5-yl)-5-methoxy-pyrimidine is obtained analogously to II (21) from 2,4-dichloro-5-methoxy-pyrimidine in a yield of 88%.

1H-NMR (D6-DMSO, 300 MHz) δ: 2.71 (m, 2H), 3.87 (s, 3H), 3.97 (m, 2H), 4.67 (m, 2H), 7.49 (s, 1H), 7.91 (s, 1H), 11.86 (s, 1H).

(31) 2-chloro-4-(4,5,7,8-tetrahydro-1H-imidazo[4,5-d]azepin-6-yl)-5-bromo-pyrimidine 2-chloro-4-(4,5,7,8-tetrahydro-1H-imidazo[4,5-d]azepin-6-yl)-5-bromo-pyrimidine is obtained analogously to II (27) from 2,4-dichloro-5-bromo-pyrimidine in a yield of 98%.

HPLC/MS (Method F): RT=3.66 min.; [M+H]+=328/330/332

1H-NMR (D6-DMSO, 300 MHz) δ: 2.89 (m, 4H), 4.12 (m, 4H), 7.36 (d, 1H), 8.30 (s, 1H), 11.61 (s, 1H).

(32) 2-chloro-4-(1,4,6,7-tetrahydro-imidazo[4,5-c]pyridin-5-yl)-5-bromo-pyrimidine 2-chloro-4-(1,4,6,7-tetrahydro-imidazo[4,5-c]pyridin-5-yl)-5-bromo-pyrimidine is obtained analogously to II (12) from 2,4-dichloro-5-bromo-pyrimidine in a yield of 32%.

HPLC/MS (Method F): RT=3.47 min

1H-NMR (D6-DMSO, 300 MHz) δ: 2.80 (m, 2H), 3.94 (m, 2H), 4.58 (m, 2H), 7.51 (s, 1H), 8.42 (s, 1H), 11.89 (s, 1H).

(33) 2-chloro-4-(1,4,6,7-tetrahydro-imidazo[4,5-c]pyridin-5-yl)-5-dimethylamino-pyrimidine 2-chloro-4-(1,4,6,7-tetrahydro-imidazo[4,5-c]pyridin-5-yl)-5-dimethylamino-pyrimidine is obtained from 2,4-dichloro-5-dimethylamino-pyrimidine analogously to II (21) in a yield of 43%.

1H-NMR (D6-DMSO, 300 MHz) δ: 2.64 (s, 6H), 2.76 (m, 2H), 3.97 (t, 2H), 4.69 (s, 2H), 7.48 (s, 1H), 7.86 (s, 1H), 11.85 (s, 1H).

(34) 2-chloro-4-(1,4,6,7-tetrahydro-imidazo[4,5-c]pyridin-5-yl)-5-isopropyl-pyrimidine 2-chloro-4-(1,4,6,7-tetrahydro-imidazo[4,5-c]pyridin-5-yl)-5-isopropyl-pyrimidine is obtained analogously to II (21) from 2,4-dichloro-5-isopropyl-pyrimidine in a yield of 50%.

1H-NMR (D6-DMSO, 300 MHz) δ: 1.26 (d, 6H), 2.79 (m, 2H), 3.00 (sept., 1H), 3.66 (m, 2H), 4.35 (m, 2H), 7.50 (s, 1H), 8.30 (s, 1H), 11.88 (s, 1H).

Example III 2-(3,4-dichlorophenylamino)-4-chloro-5-trifluoromethyl-pyrimidine 4.86 g of 3,4-dichloroaniline dissolved in 10 ml of dioxane are added to 6.51 g of 2,4-dichloro-5-trifluoromethyl-pyrimidine in 40 ml of dioxane at ambient temperature. Then 6 ml of 5 M potassium carbonate solution are added and the mixture is stirred for three days at ambient temperature. It is then filtered through Alox B (20 ml) and washed with dioxane. The filtrate is concentrated by evaporation, the residue dissolved in 50 ml methylene chloride and this solution is cooled in a bath of dry ice and acetone. The precipitate is suction filtered and the filtrate is cooled again. After suction filtering again the precipitates are combined and the filtrate is concentrated by evaporation. The residue is separated by chromatography through an RP18 column (gradient: acetonitrile: H2O=20:80 to 80:20).

The precipitates and the product obtained by chromatography of the filtrate are combined.

Yield: 3.90 g (38% of theory)

The following compounds are obtained analogously to Example III:
(1) 2-(3-chlorophenylamino)-4-chloro-5-trifluoromethyl-pyrimidine
(2) 2-(phenylamino)-4-chloro-5-trifluoromethyl-pyrimidine
(3) 2-(4-chlorophenylamino)-4-chloro-5-trifluoromethyl-pyrimidine
$R_f$=0.88 (silica gel; methylene chloride)
(4) 2-(4-bromophenylamino)-4-chloro-5-trifluoromethyl-pyrimidine
(5) 2-(3-bromophenylamino)-4-chloro-5-trifluoromethyl-pyrimidine
(6) 2-(4-carboxyphenylamino)-4-chloro-5-trifluoromethyl-pyrimidine
(7) 2-(4-(2-carboxy-1-ethyl-)phenylamino)-4-chloro-5-trifluoromethyl-pyrimidine
(8) 2-(2-naphthylamino)-4-chloro-5-trifluoromethyl-pyrimidine
(9) 2-(3,5-dichlorophenylamino)-4-chloro-5-trifluoromethyl-pyrimidine
(10) 2-(4-(1-piperidinyl-methyl-)phenylamino)-4-chloro-5-trifluoromethyl-pyrimidine
Prepared using 4-(piperidin-1-yl)-methyl-aniline. The chromatography was carried out using silica gel.
(11) 2-(3,4-dichlorophenylamino)-4-chloro-5-cyano-pyrimidine
Prepared using of 2,4-dichloro-5-cyano-pyrimidine.
(12) 2-[4-(1,2,4,5-tetrahydro-benzo[d]azepin-3-yl-methyl)-phenylamino]-4-chloro-5-trifluoromethyl-pyrimidine
(13) (6) 2-(4-aminocarbonylphenylamino)-4-chloro-5-trifluoromethyl-pyrimidine Example IV 4-(3,5-dimethyl-piperazin-1-sulphonyl)-phenylamine 3 g of 4-nitrobenzenesulphonylchloride are dissolved in 100 ml of dioxane, and 1.56 g of 2,6-dimethylpiperazine and 2.8 ml of a 5 M aqueous potassium carbonate solution are pipetted in. The mixture is stirred at ambient temperature for 3 hours. The precipitate formed is filtered off, rinsed with fresh dioxane and the combined organic solution is evaporated down.

Yield 3.3 g

Rf value 0.26 (silica gel, dichloromethane:methanol=95:5)

The intermediate product 4-(3,5-dimethyl-piperazin-1-sulphonyl)-nitrobenzene is taken up in 25 ml of ethanol and combined with 0.3 g of palladium on charcoal (10%). At ambient temperature and under 5 bars of hydrogen the mixture is hydrogenated until total conversion is achieved. After the catalyst has been filtered off and the solvent eliminated, the product is obtained as a yellowish solid.

Yield: 3.0 g

Rf value 0.19 (silica gel, dichloromethane:methanol=95:5)

Example V 4-(4-tert-butyl-oxycarbonyl-homo-piperazin-1-sulphonyl)-phenylamine 2.8 g of 4-nitrobenzenesulphonylchloride are placed in 90 ml dichloromethane and to this are added dropwise 5 g of N-(tert.-butyl-oxycarbonyl)-homopiperazine and 5.1 ml of triethylamine. The mixture is stirred at ambient temperature for 1.5 hours. The organic solution is washed with 1 M aqueous sodium acetate and water and then concentrated by evaporation.

Yield 4.8 g

Rf value 0.61 (silica gel, dichloromethane:methanol=95:5)

The intermediate product is taken up in 25 ml of methanol and 10 ml of ethanol and combined with 0.5 g of palladium on charcoal (10%). At ambient temperature and under 5 bars of hydrogen the mixture is hydrogenated until fully converted. After the catalyst has been filtered off and the solvent eliminated, the product is obtained as a yellowish solid.

Yield: 3.9 g

Rf value 0.41 (silica gel, dichloromethane: methanol=95:5)

Example VI

1-[2-(methylamino)-ethyl]-pyrrolidin-2-one 48 ml of N-methyl-ethylenediamine and 42 ml of butyrolactone are heated together to 250° C. for 7 hours in an autoclave. The product distils out of the resulting brown oil at 150-155° C. and at 0.01 Torr. Yield 8.8 g Rf value 0.29 (silica gel, ethyl acetate:methanol=1:1)

Example VII

4-(N-methyl-N-methylsulphonyl-amino)-phenylamine 4.3 g of 4-(N-methylsulphonylamino)-nitrobenzene are dissolved in 40 ml of DMSO and stirred with 2.5 g of potassium-tert-butoxide for 1 hour at RT. 4.2 g of methyl iodide in 10 ml of DMSO are added dropwise to the solution and stirred overnight at ambient temperature. The mixture is then poured onto about 120 ml of ice water and extracted with ethyl acetate. The organic phase is washed with water three times, then dried over sodium sulphate and concentrated by evaporation. The residue is triturated with diethylether, suction filtered and dried. Yield: 4.6 g Melting point 105-106° C.

Rf value 0.52 (silica gel, toluene:ethyl acetate=7:3)

4.1 g of 4-(N-methyl-N-methylsulphonyl-amino)-nitrobenzene are taken up in 80 ml of methanol, combined with 1 g of palladium charcoal and hydrogenated at ambient temperature under 5 bar. After 30 minutes the catalyst is filtered off, the mixture is evaporated down and the remaining product is triturated with diethylether. Yield: 3.6 g Melting point 116° C.

Rf value 0.14 (silica gel, toluene:ethyl acetate=7:3)

Example VIII

2-methyl-4,5,7,8-tetrahydro-1H-imidazo[4,5-d]azepine 3 equivalents (4.463 g) of sodium methoxide are placed in MeOH at ambient temperature, 7.8 g of acetamidine-hydrochloride are added and the mixture is stirred for 30 min. Then 10 g of N-benzyl-5-bromohexahydro-4-azepinone are added. After another 30 minutes an additional 2 eq. (2.976 g) of sodium methoxide are added to the mixture which is refluxed for 11 hours. After cooling to ambient temperature the mixture is fully concentrated by evaporation in vacuo, the material remaining is triturated with about 140 ml of isopropanol, filtered and the filtrate is evaporated down again. The crude product is taken up in 50 ml of 1N $K_2CO_3$ solution and extracted 3× with 40 ml of $CH_2Cl_2$. The organic phases are dried with $MgSO_4$, filtered off and evaporated to dryness. The residue is chromatographed over silica gel ($CH_2Cl_2$/MeOH=87:13 to 70:30). Yield: 1.7 g

MS (M+H)+=242

1H-NMR (D6-DMSO; 400 MHz) δ: 2.13 (s, 3H), 2.58 (t, 4H), 2.79 (t, 4H), 3.72 (s, 2H), 7.20-7.40 (m, 5H), 11.11 (br s, 1H).

The N-benzylated 2-methyl-4,5,7,8-tetrahydro-1H-imidazo[4,5-d]azepine is dissolved in 55 ml ethanol and combined with 500 mg of palladium on charcoal (5%). The mixture is hydrogenated in a shaking autoclave at ambient temperature under 50 psi of pressure for 48 hours. The catalyst is then filtered off and the mixture is evaporated down in vacuo.

Yield: 900 mg
MS (M+H)+=152

Example IX

3-pyrrolidin-1-ylmethyl-piperidine

The educt 3-(1-pyrrolidinylmethyl)-pyridine (24.6 g) is taken up in 250 ml glacial acetic acid and hydrogenated with 2 g of $PtO_2$ under 3 bar $H_2$ at ambient temperature. The solution filtered off is evaporated down, combined with ice and made alkaline with solid KOH while cooling. After extracting three times with 250 ml of diethylether the crude product is dried with $MgSO_4$. After the $MgSO_4$ has been filtered off the solvent is eliminated and the amine is distilled in a water jet vacuum at a boiling point of 123° C.

Yield: 17.9 g
Melting point: 47° C.
CHN analysis
calculated: 71.37%/11.98%/16.65%
found: 71.00%/12.04%/16.01%

Example X

N,N-dimethyl-2-[methyl-(2-piperidin-4-yl-ethyl)-amino]-acetamide

4-[2-(methylamino)ethyl]pyridine (34.4 g) and 29.18 g of chloroacetic acid-dimethylamide are dissolved in 200 ml of methanol. After the addition of 20 g of sodium bicarbonate the mixture is refluxed for 5 hours with stirring. For working up the mixture is combined with 1000 ml of tetrahydrofuran, decanted off from the precipitated salts and the solution is filtered through active charcoal. After the limination of the solvent, N,N-dimethyl-2-[methyl-(2-pyridine-4-yl-ethyl)-amino]-acetamide is obtained as a crude product.

Of the crude N,N-dimethyl-2-[methyl-(2-pyridine-4-yl-ethyl)-amino]-acetamide, 44 g are dissolved in 500 ml of glacial acetic acid and hydrogenated with 4 g of PtO2 at ambient temperature under 3 bar H2. After the catalyst has been removed by suction filtering the filtrate is evaporated down. The residue is made alkaline with 50% potassium hydroxide solution while cooling with ice and the product obtained is taken up in ether. The ether solution is dried over sodium sulphate, filtered and the solution is evaporated down. The product is left as a yellow oil. Yield: 42 g

Example XI

2-methyl-2,8-diaza-spiro[5.5]undecan-5-ol 87 g of acrylonitrile are added dropwise at ambient temperature, with stirring, to 75 ml of Triton B and 277 g of ethyl 1-methyl-4-oxo-piperidin-3-carboxylate in 1500 ml of dioxane, while the temperature of the mixture rises to 48° C. The solution is stirred for a further 4 hours at ambient temperature before the solvent is distilled off in vacuo. The residue is combined with diethylether and extracted twice with saturated saline solution.

After the organic phase has been dried the solvent is distilled off. The product is distilled under a high vacuum.

Yield: 220.5 g.

In the autoclave 90 g of ethyl 3-(2-cyano-ethyl)-1-methyl-4-oxo-piperidin-3-carboxylate are hydrogenated in 1800 ml of methanolic ammonia and 15 g of Raney nickel (3 bar). When the mixture is no longer absorbing any hydrogen the catalyst is removed by suction filtering and the filtrate in vacuo. The product is obtained after chromatography on silica gel.

Yield: 42.6 g

Of the 11-hydroxy-8-methyl-2,8-diaza-spiro[5.5]undecan-1-one obtained, 2 g are taken up in 20 ml of absolute tetrahydrofuran; this solution is added dropwise, with stirring, to 1 g of LiAlH4 in 50 ml of absolute tetrahydrofuran. The temperature rises to 36° C., while hydrogen is given off in copious amounts. After another 3 hours at ambient temperature the mixture is refluxed for 10 hours. The reaction is stopped by the addition of 2 ml of water and 2 ml 1N aqueous sodium hydroxide solution while cooling with ice. The product is extracted with ethyl acetate and the solvent is eliminated in vacuo. Then the amine is precipitated from absolute ethanol with HCl gas, in the form of the hydrochloride. Yield 1.44 g.

Analysis: Melting point 293-295° C. decomposition

Example XII

2,4-dichloro-5-trimethylsilanylethynyl-pyrimidine 66.55 g of 2,4-dichloro-5-iodo-pyrimidine is stirred for three hours in 1.2 litres of absolute THF with 70 ml of triethylamine, 4.9 g of palladium chloride, 13.3 g of triphenylphosphine, 4 g of copper iodide and 39.3 ml of trimethylsilylacetylene at 40° C. After the reaction has ended the solvent is eliminated in vacuo and the dark red oil remaining is subjected to fractional distillation. The product is distilled over at 0.01 Torr and 100° C.

1H-NMR (D6-DMSO, 400 MHz) δ: 0.20 (s, 9H), 8.90 (s, 1H)

Example XIII

2,4-dichloro-5-methylsulphonyl-pyrimidine

The compound is prepared from 5-bromouracil by a 3-step synthesis.

5-thiomethyl-uracil 126 g of 5-bromouracil are refluxed in 1.0 litres of a 21% aqueous sodium thiomethoxide solution for 5 hours. After the reaction has ended the mixture is cooled to 10° C. and slowly adjusted to pH 7 with 330 ml of conc. hydrochloric acid (temperature should not exceed 30° C.). The reaction mixture is left to stand overnight at ambient temperature, the precipitate is filtered off, washed with 300 ml of cold water and the solid is dried (100 g; 96%) in the drying cupboard at 80° C.

Rf=0.29 (silica gel; n-butanol)

2,4-dichloro-5-thiomethyl-pyrimidine 100 g of 5-thiomethyluracil are added to 580 ml of phosphorus oxychloride. 80 ml of dimethylaniline are added at ambient temperature and the reaction mixture is refluxed for 3 hours. Then the excess phosphorus oxychloride is evaporated off, the residue is poured onto 500 ml of ice water and the aqueous phase is extracted three times with 400 ml of diethylether. The ether extracts are washed four times with 75 ml of water, dried over sodium sulphate and evaporated down. A solid is left, which is recrystallised twice from cyclohexane (20.0 g; 16%).

2,4-dichloro-5-methylsulphonyl-pyrimidine

A solution of 51.2 g of 3-chloroperbenzoic acid (98%) in 450 ml of methylene chloride is added dropwise to 20.0 g of 2,4-dichloro-5-thiomethyl-pyrimidine in 250 ml methylene chloride at −5° C. within 1 hour. The reaction mixture is left to thaw at ambient temperature and stirred for 24 hours. Then the precipitate is filtered off, the filtrate is washed successively with 50 ml of saturated sodium sulphite solution, 50 ml of saturated sodium hydrogen carbonate solution and 50 ml of water. The organic phase is dried over sodium sulphate and evaporated down, whereupon the product is obtained as a crystalline precipitate antfällt (18.5 g; 80%). No further purification is required.

Rf=0.49 (silica gel; cyclohexane/ethyl acetate=1:1)
GC/MS: (M+H)⁺=226/228 (2Cl);
1H-NMR (D6-DMSO, 400 MHz) δ: 3.42 (s, 3H), 9.18 (s, 1H).

Example XIV

2,4-dichloro-5-isopropoxy-pyrimidine

The compound is prepared from chloracetic acid and thiourea.

Methyl Isopropoxyacetate 116.5 g of the sodium salt of chloracetic acid are slowly added at 80° C. to a sodium isopropoxide solution (freshly prepared from 23 g of sodium and 250 ml of isopropylalcohol). The reaction mixture is refluxed for 2 hours and then combined with 500 ml of water. The mixture is evaporated down to a total volume of 200 ml and adjusted to pH1 with conc. sulphuric acid. The precipitate formed is filtered off, the two phases of the filtrate are and the organic phase is fractionally distilled in vacuo (101-103° C./10 Torr; 83 g; 70%). The 2-isopropoxy-acetic acid thus obtained is heated together with 0.2 ml of conc. sulphuric acid in 57 ml of methanol and 200 ml benzene for 7 hours using a water separator. After the excess methanol has been distilled off the residue is fractionally distilled in vacuo (50-55° C./10 Torr; 81.6 g; 88%).

4-hydroxy-5-isopropoxy-2-mercapto-pyrimidine 81.6 g of methyl isopropoxyacetate are added together with 50.3 ml of ethylformate to a previously prepared suspension of 14.2 g of sodium in 200 ml of toluene. The reaction mixture is left to stand overnight, the toluene is decanted off and the unpurified residue of the 2-isopropoxy-2-methoxycarbonyl-sodium ethoxide is used without any further purification for the next step.

The complete residue is dissolved in 150 ml of ethanol with heating. Then 47.0 g of thiourea are added thereto and the reaction mixture is refluxed for 5 hours. After the solvent has been eliminated using the rotary evaporator the residue is taken up in 300 ml of water and adjusted to pH 2, whereupon the desired product is obtained as a precipitate, filtered off and dried overnight (60.8 g; 53%).

5-Isopropoxyuracil 60.8 g of 4-hydroxy-5-isopropoxy-2-mercapto-pyrimidine are refluxed together with 60 g of chloroacetic acid in 1.2 litres of water for 2.5 hours, during which time the precipitate dissolves completely. 200 ml of conc. hydrochloric acid are added and the mixture is refluxed for a further 7 hours. Then the reaction mixture is evaporated down to 500 ml, whereupon the desired product is obtained as a precipitate, filtered off and dried overnight at 70° C. (28.6 g; 52%).

2,4-dichloro-5-isopropoxy-pyrimidine 28.6 g of 5-isopropoxyuracil are refluxed for 2 hours together with 140 ml of phosphorus oxychloride and 44 ml of dimethylaniline. Then the excess phosphorus oxychloride is distilled off in vacuo. The residue is poured onto 300 ml of ice water, extracted twice with 250 ml of diethylether, washed four times with 50 ml of water and the ether extracts are dried over sodium sulphate. The solvent is eliminated using the rotary evaporator and the residue is fractionally distilled under a high vacuum (82-85° C./10$^{-2}$ Torr; 19.0 g; 55%).

Rf=0.62 (cyclohexane/ethyl acetate=1:1);
GC-MS (M+H)$^+$=206/208 (2Cl);
1H-NMR (D6-DMSO; 400 MHz) δ: 1.38 (s, 6H), 4.89 (m, 1H), 8.65 (s, 1H).

Example XV 2,4-dichloro-5-isopropyl-pyrimidine 23.0 g of 5-isopropyluracil are refluxed for 4 hours together with 139 ml of phosphorus oxychloride and 38.8 ml of dimethylaniline. Then the excess phosphorus oxychloride is distilled off in vacuo. The residue is poured onto 400 ml of ice water and extracted twice je 250 ml of diethylether, washed three times with 50 ml of water and the ether extracts are dried over sodium sulphate. The solvent is eliminated using the rotary evaporator and the residue is fractionally distilled under a high vacuum (70-78° C./10$^{-2}$ Torr; 25.6 g; 90%).

Rf=0.69 (ethyl acetate);
GC-MS (M+H)$^+$=190/192 (2Cl);
1H-NMR (D6-DMSO; 400 MHz) δ: 1.33 (s, 6H), 3.22 (m, 1H), 8.80 (s, 1H).

Example XVI 3-phenyl-perhydro-azepin-4-one 281 g of ethyl 4-bromobutyrate, 305 g of potassium carbonate and 5.5 g of potassium iodide are added to 313 g of ethyl 3-benzylamino-2-phenyl-propionate in 800 ml of methylethylketone and the mixture is refluxed for 24 hours. For working up the precipitate is filtered off, washed with acetone and the combined organic solutions are evaporated down. The residue is taken up in 1000 ml of diethylether, combined with 500 ml of 3N hydrochloric acid and the aqueous phase and the hydrochloride extracted with oil are isolated. The ethereal phase is extracted twice with 3 N hydrochloric acid, the combined aqueous phases are made alkaline again with concentrated aqueous ammonia and extracted twice with ether. After the organic phase has been dried over magnesium sulphate and evaporated in vacuo the product is obtained as a clear oil.

Yield: 314 g 87.3 g of NaH is suspended in 1300 ml of toluene, 7.7 ml of ethanol are quickly added dropwise thereto. Within 10 minutes 199 g of ethyl 4-[benzyl-(2-ethoxycarbonyl-2-phenylethyl)-amino]-butyrate in 230 ml of toluene are added dropwise thereto and the mixture is refluxed for three hours with stirring. After cooling to 40° C., 160 ml of ethanol is added dropwise and then the mixture is poured onto 700 ml of ice-cooled 6N HCl. The aqueous phase and the oily hydrochloride are separated off and the toluene phase is extracted three times with 300 ml of water. The combined acid phases, as well as the isolated oil, are heated to 140° C. for 90 minutes and then stirred overnight at ambient temperature. The mixture is then made alkaline with conc. aqueous ammonia, while cooling with ice, extracted twice with diethyl ether, the organic phase is dried over magnesium sulphate and evaporated down. The product can be recrystallised from petroleum ether. Yield: 85.8 g.

22.1 g of 1-benzyl-3-phenyl-perhydro-azepin-4-one hydrochloride are dissolved in 250 ml of methanol and 10 ml of water and hydrogenated with 2.5 g of Pd/C (10%) for 3 hours under 5 bar of H$_2$. Then another 2.5 g of catalyst are added and the hydrogenation step is repeated. The catalyst is filtered off and the mixture is evaporated down. The residue is recrystallised from ethanol. Yield: 8.2 g MS: [M]+=189
CHNCl analysis
calculated 63.85%/7.14%/6.21%/15.71%
found 61.90%/7.13%/5.94%/16.79%
Melting point: 187° C. decomposition Example XVII 3-(4-aminomethyl-cyclohexyl)-propionic acid 11.2 g of methyl 3-[4-(acetylamino-methyl)-phenyl]-propionate are dissolved in 130 ml of methanol and 24 ml of 8 N aqueous sodium hydroxide solution are added with stirring. After 2 hours at ambient temperature the mixture is neutralised with glacial acetic acid and concentrated by evaporation. The residue is taken up in water and adjusted with 2 N aqueous hydrochloric acid to a pH value of 1-2. The white precipitate formed is suction filtered and washed with water.

Yield 12.6 g
Melting point 144-147° C.

The intermediate product 3-[4-(acetylamino-methyl)-phenyl]-propionic acid (12.6 g) is dissolved in 200 ml of methanol and hydrogenated with 1.2 g of Rh/Pt catalyst under 3 bar H$_2$ atmosphere. After 90 minutes at ambient temperature the catalyst is filtered off and the solution is evaporated to dryness. Yield 13 g Melting point 91-94° C.

13 g of 3-[4-(acetylamino-methyl)-cyclohexyl]-propionic acid are added to 200 ml of semi-concentrated aqueous hydrochloric acid and the resulting solution is refluxed overnight. The mixture is combined with acetone, recrystallised and the precipitate is separated off. When the mother liquor is concentrated step by step further fractions of the crystallin product are isolated. The fractions are combined, recrystallised with isopropanol and then dried.

Yield: 10.9 g.

Example XVIII

Methyl 4-[(pyridine-3-ylmethyl)-amino]-cyclohexane-carboxylate 6.13 g of pyridine-3-aldehyde, 5.77 g of triethylamine and 9 g of methyl 4-amino-cyclohexanecarboxylate are mixed into 250 ml of methanol. 3 g of Raney nickel are added thereto in order to hydrogenate the mixture, with stirring, for about 6.5 hours at 50° C. and 3 bar. After the catalyst has been eliminated by suction filtering the filtrate is evaporated down. The crude product is purified through silica gel with methylene chloride/methanol.

Yield 4.1 g.
Melting point 47° C.

Example 1

2-(3,4-dichlorophenylamino)-4-(2-acetylamino-ethylamino)-5-nitro-pyrimidine 716 mg of 2-acetylamino-ethylamine in 8 ml of DMF are added to 800 mg of 2-(3,4-dichlorophenylamino)-4-thiocyanato-5-nitro-pyrimidine (compound of Example I) in 5 ml dimethylformamide (DMF) at ambient temperature. The mixture goes into solution with a slightly exothermic reaction, and after 1.5 hours a yellowish precipitate is formed. After 3.5 h 30 ml of water are added. The precipitate is suction filtered and dried. The residue is stirred with 30 ml of methylene chloride, suction filtered and dried.

Yield: 795 mg (88% of theory)
Melting point: 232° C.
R$_f$=0.6 (silica gel; methylene chloride:methanol=9:1)

The following compounds are obtained analogously to Example 1:

(1) 2-(3,4-dichlorophenylamino)-4-(4-aminomethyl-cyclohexylmethylamino)-5-nitro-pyrimidine
Melting point: 210° C. (decomposition)
R$_f$=0.3 (silica gel; methylene chloride:methanol:conc.ammonia=9:1:0.1)
Prepared from the compound of Example I.

(2) 2-(3,4-dichlorophenylamino)-4-(2-acetylamino-ethylamino)-5-cyano-pyrimidine
Melting point: 281° C.
R$_f$=0.6 (silica gel; cyclohexane:ethyl acetate:methanol=5:4:2)
Prepared from the compound (11) of Example III, carried out in DMSO under microwave irradiation (900 Watt).

(3) 2-(2-naphthylamino)-4-(3-(2-oxo-pyrrolidin-1-yl)-propyl-1-amino)-5-trifluoromethyl-pyrimidine
Melting point: 142° C.
HPLC/MS (Method A): RT=6.13 min.; [M+H]+=430.2
R$_f$=0.5 (silica gel; cyclohexane:ethyl acetate:methanol=5:4:1)
Prepared from compound (8) of Example III, carried out in DMSO.

(4) 2-(4-chlorophenylamino)-4-(1,4,6,7-tetrahydro-imidazo[4,5-c]pyridin-5-yl)-5-trifluoromethyl-pyrimidine
Melting point: 230° C.
HPLC/MS (Method A): RT=5.54 min.; [M+H]+=395.1
Prepared from compound (3) of Example III using DMF, dioxane and Hünig base.

(5) 2-(3-chlorophenylamino)-4-(1,4,6,7-tetrahydro-imidazo[4,5-c]pyridin-5-yl)-5-trifluoromethyl-pyrimidine
Melting point: 210° C.
HPLC/MS (Method A): RT=5.61 min.; [M+H]+=395.1
R$_f$=0.26 (silica gel; cyclohexane:ethyl acetate:methanol=5:4:1)
Prepared from compound (1) of Example III using DMSO and 2N NaOH.

(6) 2-(4-(1-piperidinyl-methyl-)phenylamino)-4-(1,4,6,7-tetrahydro-imidazo[4,5-c]pyridin-5-yl)-5-trifluoromethyl-pyrimidine
Melting point: 105° C.
HPLC/MS (Method A): RT=4.75 min.; [M+H]+=458.3
R$_f$=0.21 (silica gel; methylene chloride:methanol:conc.ammonia=9:1:0.1)
Prepared from compound (10) of Example III using DMSO and 2N NaOH.

(7) 2-(4-amino-3,5-dichlorophenylamino)-4-(bis-(2-hydroxy-ethyl)-amino)-5-nitro-pyrimidine
HPLC/MS (Method A): RT=5.67 min.; [M+H]+=403.1

(8) 2-(4-aminosulphonyl-phenylamino)-4-(3-(2-oxo-pyrrolidin-1-yl)-propyl-1-amino)-5-nitro-pyrimidine
HPLC/MS (Method A): RT=5.4 min.; [M+H]+=436.1

(9) 2-(3,4-dichlorophenylamino)-4-(3-(2-aza-bicyclo[2.2.1]hept-5-en-2-yl)-propylamino)-5-trifluoro-methyl-pyrimidine

(10) 2-(4-chlorophenylamino)-4-(1,4,6,7-tetrahydro-imidazo[4,5-c]pyridin-5-yl)-5-nitro-pyrimidine
HPLC/MS (Method A): RT=5.38 min.; [M+H]+=372.1

(11) 2-(4-chlorophenylamino)-4-(3-(2-oxo-pyrrolidin-1-yl)-propyl-1-amino)-5-trifluoromethyl-pyrimidine
HPLC/MS (Method A): RT=6.12 min.; [M+H]+=414.1
Melting point: 260-262° C.

R$_f$ value: 0.82 (silica gel; cyclohexane/EE/MeOH=5:4:1)
HPLC/MS (Method D): RT=5.837 min.; [M+H]+=414; Abs./max 250 nm

(12) 2-(3-chlorophenylamino)-4-(3-aminopropyl-amino)-5-trifluoromethyl-pyrimidine
HPLC/MS (Method A): RT=5.13 min.; [M+H]+=346.1

(13) 2-(4-carboxyphenylamino)-4-[N-(3-dimethylaminopropyl-)N-methyl]-amino-5-nitro-pyrimidine
HPLC/MS (Method A): RT=4.83 min.; [M+H]+=375.2

(14) 2-(3,5-dichlorophenylamino)-4-(1,4,6,7-tetrahydro-imidazo[4,5-c]pyridin-5-yl)-5-trifluoromethyl-pyrimidine
HPLC/MS (Method A): RT=5.85 min.; [M+H]+=429.1

(15) 2-(3-chloro-4-fluoro-phenylamino)-4-(1,4,6,7-tetrahydro-imidazo[4,5-c]pyridin-5-yl)-5-nitro-pyrimidine
HPLC/MS (Method A): RT=5.39 min.; [M+H]+=390.1

(16) 2-(3,4-dichloro-phenylamino)-4-(2-nitrobenzylamino)-5-trifluoromethyl-pyrimidine
HPLC/MS (Method A): RT=7.77 min.; [M+H]+=458.1

(17) 2-(4-carboxy-phenylamino)-4-(1,4,6,7-tetrahydro-imidazo[4,5-c]pyridin-5-yl)-5-trifluoromethyl-pyrimidine
HPLC/MS (Method A): RT=5.12 min.; [M+H]+=405.1

(18) 2-(4-carboxy-phenylamino)-4-(trans-4-dimethylamino-cyclohexylamino)-5-nitro-pyrimidine
HPLC/MS (Method A): RT=4.97 min.; [M+H]+=401.2

(19) 2-(4-bromo-phenylamino)-4-(1,4,6,7-tetrahydro-imidazo[4,5-c]pyridin-5-yl)-5-trifluoromethyl-pyrimidine
HPLC/MS (Method A): RT=5.61 min.; [M+H]+=439.1

(20) 2-(3,5-dichloro-phenylamino)-4-(3-amino-cyclohexylamino)-5-trifluoromethyl-pyrimidine
HPLC/MS (Method A): RT=5.71 min.; [M+H]+=420.1

(21) 2-(4-carboxy-phenylamino)-4-(3-(2-oxo-pyrrolidin-1-yl)-propyl-1-amino)-5-trifluoromethyl-pyrimidine
HPLC/MS (Method A): RT=5.44 min.; [M+H]+=424.2

(22) 2-(3-aminocarbonyl-phenylamino)-4-(1,4,6,7-tetrahydro-imidazo[4,5-c]pyridin-5-yl)-5-nitro-pyrimidine
HPLC/MS (Method A): RT=4.71 min.; [M+H]+=381.2

(23) 2-(4-(2-carboxy-1-ethyl-)phenylamino)-4-(1,4,6,7-tetrahydro-imidazo[4,5-c]pyridin-5-yl)-5-trifluoromethyl-pyrimidine
HPLC/MS (Method A): RT=5.13 min.; [M+H]+=433.2

(24) 2-(3-bromo-phenylamino)-4-(3-amino-propylamino)-5-trifluoromethyl-pyrimidine
HPLC/MS (Method A): RT=5.16 min.; [M+H]+=390.1

(25) 2-(3,4-dichloro-phenylamino)-4-(2-aminocarbonyl-1-ethylamino)-5-trifluoromethyl-pyrimidine
HPLC/MS (Method A): RT=6.36 min.; [M+H]+=394.1

(26) 2-(4-phenylaminocarbonyl-phenylamino)-4-(1,4,6,7-tetrahydro-imidazo[4,5-c]pyridin-5-yl)-5-nitro-pyrimidine
HPLC/MS (Method A): RT=5.3 min.; [M+H]+=457.2

(27) 2-(4-nitro-phenylamino)-4-(1,4,6,7-tetrahydro-imidazo[4,5-c]pyridin-5-yl)-5-nitro-pyrimidine
HPLC/MS (Method A): RT=5.21 min.; [M+H]+=383.2

(28) 2-(4-chloro-phenylamino)-4-(3-(4-(pyrrolidin-1-yl)butyl)-piperidin-1-yl)-5-nitro-pyrimidine
HPLC/MS (Method A): RT=5.89 min.; [M+H]+=459.2

(29) 2-(4-carboxy-phenylamino)-4-(1,4,6,7-tetrahydro-imidazo[4,5-c]pyridin-5-yl)-5-nitro-pyrimidine
HPLC/MS (Method A): RT=4.85 min.; [M+H]+=382.1

(30) 2-(3,4-dichloro-phenylamino)-4-(1-methyl-piperidin-4-yl-methylamino)-5-trifluoromethyl-pyrimidine
HPLC/MS (Method A): RT=5.58 min.; [M+H]+=434.1

(31) 2-phenylamino-4-(3-(2-oxo-pyrrolidin-1-yl)-propyl-1-amino)-5-trifluoromethyl-pyrimidine
HPLC/MS (Method A): RT=5.36 min.; [M+H]+=380.2

(32) 2-(4-cyano-phenylamino)-4-(1,4,6,7-tetrahydro-imidazo[4,5-c]pyridin-5-yl)-5-nitro-pyrimidine HPLC/MS (Method A): RT=5.11 min.; [M+H]+=363.1
(33) 2-phenylamino-4-(4-aminomethyl-cyclohexylmethylamino)-5-trifluoromethyl-pyrimidine
HPLC/MS (Method A): RT=4.93 min.; [M+H]+=380.2
(34) 2-(4-chloro-phenylamino)-4-(3-amino-cyclohexylamino)-5-nitro-pyrimidine
HPLC/MS (Method A): RT=5.41 min.; [M+H]+=363.1
(35) 2-(3,4-dichloro-phenylamino)-4-(3-amino-propylamino)-5-trifluoromethyl-pyrimidine
HPLC/MS (Method A): RT=5.45 min.; [M+H]+=380.1
(36) 2-(4-chloro-phenylamino)-4-(3-amino-propylamino)-5-trifluoromethyl-pyrimidine
HPLC/MS (Method A): RT=5.02 min.; [M+H]+=346.1
(37) 2-(3,4-dichloro-phenylamino)-4-(cis-4-hydroxy-cyclohexylamino)-5-trifluoromethyl-pyrimidine
HPLC/MS (Method A): RT=6.84 min.; [M+H]+=421.1
(38) 2-(3-bromo-phenylamino)-4-(1,4,6,7-tetrahydro-imidazo[4,5-c]pyridin-5-yl)-5-trifluoromethyl-pyrimidine
HPLC/MS (Method A): RT=5.6 min.; [M+H]+=439.1
(39) 2-(2-naphthylamino)-4-(3-amino-cyclohexylamino)-5-trifluoromethyl-pyrimidine
HPLC/MS (Method A): RT=5.34 min.; [M+H]+=402.2
(40) 2-(3,4-dichloro-phenylamino)-4-(3-acetylaminomethyl-piperidin-1-yl)-5-trifluoromethyl-pyrimidine
HPLC/MS (Method A): RT=7.12 min.; [M+H]+=462.1
(41) 2-(3,4-dichloro-phenylamino)-4-(3-(2-oxo-pyrrolidin-1-yl)-propyl-1-amino)-5-trifluoromethyl-pyrimidine
HPLC/MS (Method A): RT=6.85 min.; [M+H]+=448.1D
(42) 2-(3-bromo-phenylamino)-4-(4-aminomethyl-piperidin-1-yl)-5-nitro-pyrimidine
HPLC/MS (Method A): RT=5.36 min.; [M+H]+=407.1
(43) 2-(4-bromo-phenylamino)-4-(4-aminomethyl-piperidin-1-yl)-5-nitro-pyrimidine
HPLC/MS (Method A): RT=5.53 min.; [M+H]+=430.1
(44) 2-(4-chloro-phenylamino)-4-(N-(1-methyl-piperidin-4-yl)-N-methyl-amino)-5-nitro-pyrimidine
HPLC/MS (Method A): RT=5.32 min.; [M+H]+=377.2
(45) 2-(3,4-dichloro-phenylamino)-4-(5-hydroxy-1-pentylamino)-5-trifluoromethyl-pyrimidine
HPLC/MS (Method A): RT=6.79 min.; [M+H]+=409.1
(46) 2-(4-(2-carboxy-1-ethyl)-phenylamino)-4-(2-(3-hydroxyphenyl)-1-ethyl-amino)-5-trifluoromethyl-pyrimidine
HPLC/MS (Method A): RT=5.64 min.; [M+H]+=447.1
(47) 2-(3-bromo-phenylamino)-4-(3-(2-oxo-pyrrolidin-1-yl)-propyl-1-amino)-5-trifluoromethyl-pyrimidine
HPLC/MS (Method A): RT=6.37 min.; [M+H]+=458.1D
(48) 2-(4-chloro-phenylamino)-4-((1S)-1-carboxy-1-ethylamino)-5-nitro-pyrimidine
HPLC/MS (Method B): RT=2.5 min.; [M+H]+=338
(49) 2-(3,5-dichloro-phenylamino)-4-(3-(2-oxo-pyrrolidin-1-yl)-propyl-1-amino)-5-trifluoromethyl-pyrimidine
HPLC/MS (Method A): RT=7.15 min.; [M+H]+=448.1
(50) 2-(3-nitro-phenylamino)-4-(3-hydroxymethyl-piperidin-1-yl)-5-nitro-pyrimidine
HPLC/MS (Method A): RT=6.39 min.; [M+H]+=375.2
(51) 2-(4-bromo-phenylamino)-4-(3-amino-propylamino)-5-trifluoromethyl-pyrimidine
HPLC/MS (Method A): RT=5.12 min.; [M+H]+=390.1
(52) 2-(4-chloro-phenylamino)-4-(4-(N-acetyl-N-methyl-aminomethyl)-piperidin-1-yl)-5-nitro-pyrimidine
HPLC/MS (Method A): RT=6.61 min.; [M+H]+=419.2
(53) 2-(3,4-dichloro-phenylamino)-4-(2-(4-hydroxy-3-methoxy-phenyl)-2-hydroxy-1-ethylamino)-5-trifluoromethyl-pyrimidine
HPLC/MS (Method A): RT=6.79 min.; [M+H]+=489.1
(54) 2-(4-carboxy-phenylamino)-4-(trans-4-dimethylamino-cyclohexylamino)-5-trifluoromethyl-pyrimidine
HPLC/MS (Method A): RT=4.93 min.; [M+H]+=424.2
(55) 2-(4-chloro-phenylamino)-4-((2S)-2-hydroxymethyl-pyrrolidin-1-yl)-5-nitro-pyrimidine
HPLC/MS (Method A): RT=6.59 min.; [M+H]+=350.1
Prepared using L-prolinol.
(56) 2-(4-bromo-phenylamino)-4-(3-(2-oxo-pyrrolidin-1-yl)-propyl-1-amino)-5-trifluoromethyl-pyrimidine
HPLC/MS (Method A): RT=6.19 min.; [M+H]+=458.1
(57) 2-(3,4-dichloro-phenylamino)-4-(3-amino-cyclohexylamino)-5-trifluoromethyl-pyrimidine
HPLC/MS (Method A): RT=5.66 min.; [M+H]+=420.1
(58) 2-(3,4-dichloro-phenylamino)-4-(3-(isopropylamino)-1-propylamino)-5-trifluoromethyl-pyrimidine
HPLC/MS (Method A): RT=5.66 min.; [M+H]+=422.1
(59) 2-(4-chloro-phenylamino)-4-(2-(3-hydroxy-phenyl)-2-hydroxy-1-ethylamino)-5-nitro-pyrimidine
HPLC/MS (Method A): RT=6.49 min.; [M+H]+=402.1
(60) 2-(3,4-dichloro-phenylamino)-4-(1,4,6,7-tetrahydro-imidazo[4,5-c]pyridin-5-yl)-5-trifluoromethyl-pyrimidine
HPLC/MS (Method A): RT=5.78 min.; [M+H]+=429.1
(61) 2-(3,4-dichloro-phenylamino)-4-(trans-4-carboxy-cyclohexylamino)-5-trifluoromethyl-pyrimidine
HPLC/MS (Method A): RT=6.99 min.; [M+H]+=449.1
(62) 2-(3,4-dichloro-phenylamino)-4-(1,1-dimethyl-2-hydroxy-1-ethylamino)-5-trifluoromethyl-pyrimidine
HPLC/MS (Method A): RT=7.34 min.; [M+H]+=395.1
(63) 2-(3,4-dichloro-phenylamino)-4-(5-amino-pentylamino)-5-trifluoromethyl-pyrimidine
HPLC/MS (Method A): RT=5.57 min.; [M+H]+=408.1
(64) 2-(4-amino-3,5-dichlorophenylamino)-4-(3-hydroxymethyl-piperidin-1-yl)-5-nitro-pyrimidine
HPLC/MS (Method A): RT=6.43 min.; [M+H]+=413.1
(65) 2-(3,4-dichloro-phenylamino)-4-(6-hydroxy-1-hexylamino)-5-trifluoromethyl-pyrimidine
HPLC/MS (Method A): RT=7.06 min.; [M+H]+=423.1
(66) 2-(3,4-dichloro-phenylamino)-4-((1S)-1-carboxy-2-(1H-imidazol-4-yl)-ethylamino)-5-trifluoromethyl-pyrimidine
HPLC/MS (Method A): RT=5.51 min.; [M+H]+=461.1
Prepared using L-histidine.
(67) 2-(3-chloro-phenylamino)-4-(3-(2-oxo-pyrrolidin-1-yl)-propyl-1-amino)-5-trifluoromethyl-pyrimidine
HPLC/MS (Method A): RT=6.24 min.; [M+H]+=414.2
(68) 2-(3,4-dichlorophenylamino)-4-(2-(1H-imidazol-4-yl)-ethylamino)-5-trifluoromethyl-pyrimidine
HPLC/MS (Method A): RT=5.55 min.; [M+H]+=417.1
(69) 2-(3,4-dichloro-phenylamino)-4-(4-hydroxy-but-1-ylamino)-5-trifluoromethyl-pyrimidine
HPLC/MS (Method A): RT=6.66 min.; [M+H]+=395.1
(70) 2-(4-aminosulphonyl-phenylamino)-4-(4-aminomethyl-piperidin-1-yl)-5-nitro-pyrimidine
HPLC/MS (Method A): RT=4.66 min.; [M+H]+=408.2
(71) 2-(3,4-dichloro-phenylamino)-4-(4-carboxy-1-butylamino)-5-trifluoromethyl-pyrimidine
HPLC/MS (Method A): RT=6.78 min.; [M+H]+=423.1
(72) 2-(3,4-dichloro-phenylamino)-4-(1-methyl-4-piperidinyl-amino)-5-trifluoromethyl-pyrimidine
HPLC/MS (Method A): RT=5.58 min.; [M+H]+=420.1
(73) 2-(3,4-dichloro-phenylamino)-4-(3-(3-aminopropoxy)-1-propylamino)-5-trifluoromethyl-pyrimidine
HPLC/MS (Method A): RT=5.65 min.; [M+H]+=438.1
(74) 2-(4-carboxy-phenylamino)-4-(1-hydroxy-2-propylamino)-5-nitro-pyrimidine
HPLC/MS (Method A): RT=5.55 min.; [M+H]+=334.1

(75) 2-(4-aminosulphonyl-phenylamino)-4-(4-aminomethyl-cyclohexylmethylamino)-5-nitro-pyrimidine
HPLC/MS (Method A): RT=4.93 min.; [M+H]+=436.2

(76) 2-(3,4-dichloro-phenylamino)-4-(2-(3-hydroxy-phenyl)-2-hydroxy-1-ethylamino)-5-trifluoromethyl-pyrimidine
HPLC/MS (Method A): RT=6.85 min.; [M+H]+=459.1

(77) 2-(3-chloro-phenylamino)-4-(5-amino-1-pentylamino)-5-trifluoromethyl-pyrimidine
HPLC/MS (Method A): RT=5.19 min.; [M+H]+=374.1

(78) 2-(3,4-dichlorophenylamino)-4-(4-nitrobenzylamino)-5-trifluoromethyl-pyrimidine
HPLC/MS (Method A): RT=7.72 min.; [M+H]+=458.1

(79) 2-(4-chloro-phenylamino)-4-(5-amino-pentyl-1-amino)-5-trifluoromethyl-pyrimidine
HPLC/MS (Method A): RT=5.12 min.; [M+H]+=374.1

(80) 2-(3,4-dichloro-phenylamino)-4-(2-amino-1-ethylamino)-5-trifluoromethyl-pyrimidine
100 mg of (4-chloro-5-trifluoromethyl-pyrimidin-2-yl)-(3,4-dichloro-phenyl)-amine, tert-butyl (2-amino-ethyl)-carbaminate (1 eq.) and diisopropylethylamine (2 eq.) were stirred in 2 ml of isopropanol for several hours at ambient temperature. The reaction mixture was mixed with 2 ml of saturated NaHCO3 solution and extracted with ethyl acetate. The organic phase was dried over MgSO4 and evaporated down. The crude product was washed with diethyl ether and dichloromethane and purified by chromatography (CH$_2$Cl$_2$/MeOH gradient, silica gel). The product was then treated with TFA/CH2Cl2 (1:1), mixed with NaHCO3, extracted with ethyl acetate, dried over MgSO4 and evaporated down.
HPLC/MS (Method A): RT=5.54 min.; [M+H]+=366.1
Melting point: 115-117° C.
R$_f$=0.13 (silica gel; methylene chloride:methanol=4:1)
HPLC/MS (Method F): RT=3.84 min.; [M+H]+=367; Abs. λ max=258.9 nm

(81) 2-(3,4-dichloro-phenylamino)-4-(4-dimethylaminomethyl-cyclohexylmethylamino)-5-trifluoromethyl-pyrimidine
HPLC/MS (Method A): RT=5.78 min.; [M+H]+=476.2

(82) 2-(4-chloro-phenylamino)-4-(N-methyl-N-(2-cyano-1-ethyl)-amino)-5-nitro-pyrimidine
HPLC/MS (Method A): RT=6.74 min.; [M+H]+=333.1

(83) 2-(4-chloro-phenylamino)-4-(3-acetylaminomethyl-piperidin-1-yl)-5-nitro-pyrimidine
HPLC/MS (Method A): RT=6.46 min.; [M+H]+=405.2

(84) 2-(4-carboxy-phenylamino)-4-(4-(2-pyridyl)-piperazin-1-yl)-5-nitro-pyrimidine
HPLC/MS (Method A): RT=5.04 min.; [M+H]+=422.2

(85) 2-(3,4-dichloro-phenylamino)-4-(2-(1-methyl-2-pyrrolidinyl)-1-ethylamino)-5-trifluoromethyl-pyrimidine
R$_f$=0.16 (silica gel; methylene chloride:methanol=9:1)
HPLC/MS (Method G): RT=3.66 min.; [M+H]+=435; Abs./max 266.5 nm

(86) 2-(4-chloro-phenylamino)-4-(4-carboxy-1-butylamino)-5-nitro-pyrimidine
HPLC/MS (Method A): RT=6.55 min.; [M+H]+=366.1

(87) 2-(3,4-dichloro-phenylamino)-4-(bis-(2-hydroxyethyl)-amino)-5-trifluoromethyl-pyrimidine
HPLC/MS (Method A): RT=6.4 min.; [M+H]+=411.1

(88) 2-(3-bromo-phenylamino)-4-(4-aminomethyl-cyclohexylmethylamino)-5-trifluoromethyl-pyrimidine
HPLC/MS (Method A): RT=5.46 min.; [M+H]+=458.1

(89) 2-(3,4-dichloro-phenylamino)-4-(2-(4-hydroxy-phenyl)-2-hydroxy-1-ethylamino)-5-trifluoromethyl-pyrimidine
HPLC/MS (Method A): RT=6.73 min.; [M+H]+=459.1

(90) 2-(3,4-dichloro-phenylamino)-4-(4-aminomethyl-piperidin-1-yl)-5-trifluoromethyl-pyrimidine
HPLC/MS (Method A): RT=5.78 min.; [M+H]+=420.1

(91) 2-(4-aminocarbonyl-phenylamino)-4-(2-(3-hydroxypropyl)-piperidin-1-yl)-5-nitro-pyrimidine
HPLC/MS (Method A): RT=5.65 min.; [M+H]+=401.2

(92) 2-(3-nitro-phenylamino)-4-(4-aminomethyl-cyclohexylmethylamino)-5-nitro-pyrimidine
HPLC/MS (Method A): RT=5.41 min.; [M+H]+=402.2

(93) 2-(3,4-dichloro-phenylamino)-4-(2-methoxy-1-ethylamino)-5-trifluoromethyl-pyrimidine
HPLC/MS (Method A): RT=7.37 min.; [M+H]+=381.1

(94) 2-(4-methoxycarbonyl-phenylamino)-4-(4-aminomethyl-cyclohexylmethylamino)-5-nitro-pyrimidine
HPLC/MS (Method A): RT=5.37 min.; [M+H]+=415.2

(95) 2-(4-chloro-phenylamino)-4-(3-(2-oxo-pyrrolidin-1-yl)-propyl-1-amino)-5-nitro-pyrimidine
HPLC/MS (Method A): RT=6.43 min.; [M+H]+=391.2

(96) 2-(3,4-dichloro-phenylamino)-4-(3-hydroxymethyl-piperidin-1-yl)-5-trifluoromethyl-pyrimidine
HPLC/MS (Method A): RT=7.42 min.; [M+H]+=421.1

(97) 2-(3-cyano-phenylamino)-4-(1,4,6,7-tetrahydro-imidazo[4,5-c]pyridin-5-yl)-5-nitro-pyrimidine
HPLC/MS (Method A): RT=5.12 min.; [M+H]+=363.2

(98) 2-(4-benzylaminocarbonyl-phenylamino)-4-(4-aminomethyl-cyclohexylmethylamino)-5-nitro-pyrimidine
HPLC/MS (Method A): RT=5.45 min.; [M+H]+=490.3

(99) 2-(3,4-dichloro-phenylamino)-4-(2-(4-(2-hydroxyethyl)-piperazin-1-yl)-1-ethylamino))-5-trifluoromethyl-pyrimidine
HPLC/MS (Method A): RT=5.42 min.; [M+H]+=479.2

(100) 2-(4-amino-3,5-dichlorophenylamino)-4-(4-aminomethyl-cyclohexylmethylamino)-5-nitro-pyrimidine
HPLC/MS (Method A): RT=5.44 min.; [M+H]+=440.2

(101) 2-(4-aminocarbonyl-phenylamino)-4-(3-hydroxymethyl-piperidin-1-yl)-5-nitro-pyrimidine
HPLC/MS (Method A): RT=5.44 min.; [M+H]+=373.2

(102) 2-(3,4-dichloro-phenylamino)-4-(2-(3-hydroxyphenyl)-1-ethylamino)-5-trifluoromethyl-pyrimidine
HPLC/MS (Method A): RT=7.32 min.; [M+H]+=443.1

(103) 2-(3,4-dichloro-phenylamino)-4-(3-hydroxy-piperidin-1-yl)-5-trifluoromethyl-pyrimidine
HPLC/MS (Method A): RT=7.31 min.; [M+H]+=407.1

(104) 2-(3,4-dichloro-phenylamino)-4-(2-morpholino-1-ethylamino)-5-trifluoromethyl-pyrimidine (105) 2-(4-bromo-phenylamino)-4-(4-aminomethyl-cyclohexylmethylamino)-5-trifluoromethyl-pyrimidine
HPLC/MS (Method A): RT=5.42 min.; [M+H]+=458.1

(106) 2-(4-chloro-phenylamino)-4-(5-aminopentylamino)-5-nitro-pyrimidine
HPLC/MS (Method A): RT=5.41 min.; [M+H]+=351.1

(107) 2-(4-chloro-phenylamino)-4-(4-aminomethyl-cyclohexylmethylamino)-5-nitro-pyrimidine
HPLC/MS (Method A): RT=5.33 min.; [M+H]+=414.2

(108) 2-(3-nitro-phenylamino)-4-(2-(3-hydroxypropyl)-piperidin-1-yl)-5-nitro-pyrimidine
HPLC/MS (Method A): RT=6.68 min.; [M+H]+=403.2

(109) 2-(3,4-dichlorophenylamino)-4-(4-amino-cyclohexylamino)-5-trifluoromethyl-pyrimidine
HPLC/MS (Method A): RT=5.55 min.; [M+H]+=420.1

(110) 2-(4-chloro-phenylamino)-4-(2-methoxy-1-ethylamino)-5-nitro-pyrimidine
Melting point: 153-155° C.

(111) 2-(4-carboxyphenylamino)-4-(4-amino-cyclohexylamino)-5-trifluoromethyl-pyrimidine
HPLC/MS (Method A): RT=4.93 min.; [M+H]+=396.2

(112) 2-(4-(2-carboxy-1-ethyl)-phenylamino)-4-(1,4,6,7-tetrahydro-imidazo[4,5-c]pyridin-5-yl)-5-nitro-pyrimidine
HPLC/MS (Method A): RT=4.98 min.; [M+H]+=410.2
(113) 2-(4-amino-3,5-dichlorophenylamino)-4-(1,4,6,7-tetrahydro-imidazo[4,5-c]pyridin-5-yl)-5-nitro-pyrimidine
HPLC/MS (Method A): RT=5.24 min.; [M+H]+=421.1
(114) 2-(4-aminocarbonyl-phenylamino)-4-(1,4,6,7-tetrahydro-imidazo[4,5-c]pyridin-5-yl)-5-nitro-pyrimidine
HPLC/MS (Method A): RT=4.67 min.; [M+H]+=381.2
(115) 2-(4-chloro-3-methyl-phenylamino)-4-(4-aminomethyl-cyclohexylmethylamino)-5-nitro-pyrimidine
HPLC/MS (Method A): RT=5.66 min.; [M+H]+=405.2
(116) 2-(4-bromophenylamino)-4-(1,4,6,7-tetrahydro-imidazo[4,5-c]pyridin-5-yl)-5-nitro-pyrimidine
HPLC/MS (Method A): RT=5.41 min.; [M+H]+=416.1
(117) 2-(3,4-dichlorophenylamino)-4-(7-methyl-2,7-diazaspiro[4.4]non-2-yl)-5-trifluoromethyl-pyrimidine
(118) 2-phenylamino-4-(1,4,6,7-tetrahydro-imidazo[4,5-c]pyridin-5-yl)-5-trifluoromethyl-pyrimidine
HPLC/MS (Method A): RT=5.23 min.; [M+H]+=361.2
(119) 2-(3-bromophenylamino)-4-(1,4,6,7-tetrahydro-imidazo[4,5-c]pyridin-5-yl)-5-nitro-pyrimidine
HPLC/MS (Method A): RT=5.4 min.; [M+H]+=416.1
(120) 2-(3,4-dichlorophenylamino)-4-(4-dimethylamino-cyclohexylamino)-5-trifluoromethyl-pyrimidine
HPLC/MS (Method A): RT=5.62 min.; [M+H]+=448.1
(121) 2-(3,4-dichlorophenylamino)-4-(2-(imidazol-1-yl)-1-ethylamino)-5-trifluoromethyl-pyrimidine
HPLC/MS (Method A): RT=5.63 min.; [M+H]+=417.1
(122) 2-(3-nitro-phenylamino)-4-(1,4,6,7-tetrahydro-imidazo[4,5-c]pyridin-5-yl)-5-nitro-pyrimidine
HPLC/MS (Method A): RT=5.2 min.; [M+H]+=383.1
(123) 2-(4-chloro-phenylamino)-4-(N-(2-hydroxybenzyl)-N-methyl-amino)-5-nitro-pyrimidine
HPLC/MS (Method A): RT=7.07 min.; [M+H]+=386.1
(124) 2-(4-phenylaminocarbonyl-phenylamino)-4-(4-aminomethyl-cyclohexylmethylamino)-5-nitro-pyrimidine
HPLC/MS (Method A): RT=5.5 min.; [M+H]+=476.3
(125) 2-(4-fluoro-phenylamino)-4-(1,4,6,7-tetrahydro-imidazo[4,5-c]pyridin-5-yl)-5-nitro-pyrimidine
HPLC/MS (Method A): RT=5.13 min.; [M+H]+=356.1
(126) 2-(3,4-dichlorophenylamino)-4-(3-(3-hydroxy-8-methyl-8-aza-bicyclo[3.2.1]octyl)-methylamino)-5-trifluoromethyl-pyrimidine
HPLC/MS (Method A): RT=5.61 min.; [M+H]+=476.1
(127) 2-(4-carboxy-phenylamino)-4-(4-ethoxycarbonyl-piperidin-1-yl)-5-nitro-pyrimidine
HPLC/MS (Method A): RT=6.37 min.; [M+H]+=416.2
(128) 2-(3,4-dichlorophenylamino)-4-(trans-4-hydroxy-cyclohexylamino)-5-trifluoromethyl-pyrimidine
HPLC/MS (Method A): RT=6.87 min.; [M+H]+=421.1
(129) 2-(3,4-dichlorophenylamino)-4-(2-(1H-pyrazol-4-yl)-1-ethylamino)-5-trifluoromethyl-pyrimidine
(130) 2-(phenylamino)-4-(1-methyl-piperidin-4-yl-methylamino)-5-trifluoromethyl-pyrimidine
HPLC/MS (Method A): RT=4.68 min.; [M+H]+=352.2
(131) 2-(4-chloro-phenylamino)-4-(1-methyl-piperidin-4-yl-methylamino)-5-trifluoromethyl-pyrimidine
HPLC/MS (Method A): RT=5.23 min.; [M+H]+=386.2
(132) 2-(4-bromo-phenylamino)-4-(1-methyl-piperidin-4-yl-methylamino)-5-trifluoromethyl-pyrimidine
HPLC/MS (Method A): RT=5.32 min.; [M+H]+=430.1D
(133) 2-(3-bromo-phenylamino)-4-(1-methyl-piperidin-4-yl-methylamino)-5-trifluoromethyl-pyrimidine
HPLC/MS (Method A): RT=5.39 min.; [M+H]+=430.1
(134) 2-(3-chloro-phenylamino)-4-(4-aminomethyl-piperidin-1-yl)-5-trifluoromethyl-pyrimidine
HPLC/MS (Method A): RT=5.50 min.; [M+H]+=386.2
(135) 2-(phenylamino)-4-(4-aminomethyl-piperidin-1-yl)-5-trifluoromethyl-pyrimidine
HPLC/MS (Method A): RT=5.05 min.; [M+H]+=352.2
(136) 2-(4-chloro-phenylamino)-4-(4-aminomethyl-piperidin-1-yl)-5-trifluoromethyl-pyrimidine
HPLC/MS (Method A): RT=5.45 min.; [M+H]+=386.1
(137) 2-(3-bromo-phenylamino)-4-(4-aminomethyl-piperidin-1-yl)-5-trifluoromethyl-pyrimidine
HPLC/MS (Method A): RT=5.54 min.; [M+H]+=430.1
(138) 2-(3-chloro-phenylamino)-4-(4-aminomethyl-cyclohexylmethylamino)-5-trifluoromethyl-pyrimidine
HPLC/MS (Method A): RT=5.40 min.; [M+H]+=414.2
(139) 2-(3-chloro-phenylamino)-4-(2-amino-cyclohexylamino)-5-trifluoromethyl-pyrimidine
HPLC/MS (Method A): RT=5.63 min.; [M+H]+=386.2
(140) 2-(4-chlorophenylamino)-4-(2-amino-1-ethylamino)-5-nitro-pyrimidine
Rf value: 0.30 (silica gel; methylene chloride/methanol/conc. aqueous ammonia=9:1:0.1)
(141) 2-(4-chlorophenylamino)-4-[2-(acetylamino)-1-ethylamino]-5-nitro-pyrimidine
Prepared from compound 140 of Example 1 by subsequent reaction with acetic anhydride/triethylamine
Melting point: 224-226° C.
(142) 2-(4-chlorophenylamino)-4-[4-(dimethylamino)butylamino]-5-nitro-pyrimidine
Melting point: 131-132° C.
(143) 2-(3,4-dichlorophenylamino)-4-(1-carboxy-1-ethylamino)-5-trifluoromethyl-pyrimidine
HPLC/MS (Method A): RT=7.04 min.; [M+H]+=395.0
(144) 2-(4-carboxy-phenylamino)-4-[N-(2-hydroxyethyl)-N-benzylamino]-5-nitro-pyrimidine
HPLC/MS (Method A): RT=6.05 min.; [M+H]+=410.2
(145) 2-(3,4-dichlorophenylamino)-4-((1R)-1-carboxy-2-(1H-imidazol-4-yl)-1-ethylamino)-5-trifluoromethyl-pyrimidine
HPLC/MS (Method A): RT=5.51 min.; [M+H]+=461.0
Prepared using D-histidine.
(146) 2-(3,4-dichlorophenylamino)-4-(3-hydroxy-1,3-dihydro-2-oxo-indol-3-yl-methylamino)-5-trifluoromethyl-pyrimidine
HPLC/MS (Method A): RT=6.83 min.; [M+H]+=484.1
(147) 2-(3,4-dichlorophenylamino)-4-(4-(2-carboxy-1-ethyl)-cyclohexylamino)-5-trifluoromethyl-pyrimidine
HPLC/MS (Method A): RT=7.42 min.; [M+H]+=477.1
(148) 2-(4-chlorophenylamino)-4-(trans-4-carboxy-cyclohexylamino)-5-nitro-pyrimidine
HPLC/MS (Method A): RT=6.86 min.; [M+H]+=392.1
(149) 2-(4-chloro-phenylamino)-4-((2R)-2-hydroxymethyl-pyrrolidin-1-yl)-5-nitro-pyrimidine
HPLC/MS (Method A): RT=6.59 min.; [M+H]+=350.1
Prepared using D-prolinol.
(150) 2-(4-carboxy-phenylamino)-4-(3-(2-oxo-pyrrolidin-1-yl)-propyl-1-amino)-5-nitro-pyrimidine
HPLC/MS (Method A): RT=5.57 min.; [M+H]+=401.1
(151) 2-(4-chloro-phenylamino)-4-(2-morpholino-1-ethylamino)-5-nitro-pyrimidine HPLC/MS (Method B): RT=2.16 min.; [M+H]+=379.1
(152) 2-(2-naphthylamino)-4-(1,4,6,7-tetrahydro-imidazo[4,5-c]pyridin-5-yl)-5-trifluoromethyl-pyrimidine
HPLC/MS (Method A): RT=5.66 min.; [M+H]+=411.2
(153) 2-(4-chloro-phenylamino)-4-(2-(1H-imidazol-4-yl)-ethylamino)-5-nitro-pyrimidine HPLC/MS (Method B): RT=2.21 min.; [M+H]+=360.1
(154) 2-(4-chloro-phenylamino)-4-(2-(4-hydroxy-phenyl)-2-hydroxy-1-ethylamino)-5-nitro-pyrimidine HPLC/MS (Method B): RT=2.81 min.; [M+H]+=402.1
(155) 2-(4-chloro-phenylamino)-4-(2-(4-hydroxy-3-methoxy-phenyl)-2-hydroxy-1-ethylamino)-5-nitro-pyrimidine
HPLC/MS (Method B): RT=2.68 min.; [M+H]+=432.2
(156) 2-(4-chloro-phenylamino)-4-(2-(1-methyl-2-pyrrolidinyl)-1-ethylamino)-5-nitro-pyrimidine
HPLC/MS (Method B): RT=2.29 min.; [M+H]+=377.2
(157) 2-(4-chloro-phenylamino)-4-(4-hydroxy-butylamino)-5-nitro-pyrimidine
Melting point: 178-182° C.
(158) 2-(4-chloro-phenylamino)-4-(6-hydroxy-1-hexylamino)-5-nitro-pyrimidine
HPLC/MS (Method B): RT=2.96 min.; [M+H]+=366.2
(159) 2-(4-chloro-phenylamino)-4-(5-hydroxy-1-pentylamino)-5-nitro-pyrimidine
HPLC/MS (Method B): RT=2.97 min.; [M+H]+=352.2
(160) 2-(4-chloro-phenylamino)-4-(1,1-dimethyl-2-hydroxy-1-ethylamino)-5-nitro-pyrimidine
HPLC/MS (Method B): RT=2.66 min.; [M+H]+=338.17
(161) 2-(4-carboxyphenylamino)-4-(2-(3-hydroxy-phenyl)-1-ethylamino)-5-nitro-pyrimidine
HPLC/MS (Method B): RT=2.4 min.; [M+H]+=396.3
(162) 2-(benzylamino)-4-(4-aminomethyl-cyclohexylmethylamino)-5-nitro-pyrimidine
Melting point: 169° C.
(163) 2-(benzylamino)-4-(4-aminomethyl-cyclohexylmethylamino)-5-trifluoromethyl-pyrimidine
Melting point: 119° C.
(164) 2-(4-carboxyphenylamino)-4-(2-(4-hydroxy-phenyl)-1-ethylamino)-5-nitro-pyrimidine
HPLC/MS (Method B): RT=2.36 min.; [M+H]+=396.2
(165) 2-(2-chlorobenzylamino)-4-(4-aminomethyl-cyclohexylmethylamino)-5-nitro-pyrimidine
Melting point: 189° C.
(166) 2-(3-carboxyphenylamino)-4-(2-(4-hydroxy-phenyl)-1-ethylamino)-5-nitro-pyrimidine
HPLC/MS (Method B): RT=2.34 min.; [M+H]+=396.2
(167) 2-(4-chloro-phenylamino)-4-(4-aminomethyl-cyclohexylmethylamino)-5-nitro-pyrimidine
(168) 2-(3-carboxyphenylamino)-4-(2-(3-hydroxy-phenyl)-1-ethylamino)-5-nitro-pyrimidine
HPLC/MS (Method B): RT=2.41 min.; [M+H]+=396.3
(169) 2-(4-chloro-phenylamino)-4-(2-(imidazolidin-2-on-1-yl)-1-ethylamino)-5-nitro-pyrimidine
HPLC/MS (Method B): RT=2.5 min.; [M+H]+=378.2
(170) 2-(4-bromo-phenylamino)-4-(2-(1H-imidazol-4-yl)-1-ethylamino)-5-trifluoromethyl-pyrimidine
HPLC/MS (Method B): RT=2 min.; [M+H]+=427.1
(171) 2-(3-bromo-phenylamino)-4-(4-aminomethyl-cyclohexylmethylamino)-5-nitro-pyrimidine
HPLC/MS (Method B): RT=2.56 min.; [M+H]+=435.2
(172) 2-(4-bromo-phenylamino)-4-(4-aminomethyl-cyclohexylmethylamino)-5-nitro-pyrimidine
HPLC/MS (Method B): RT=2.66 min.; [M+H]+=435.2
(173) 2-(4-chloro-phenylamino)-4-(1-methyl-4-piperidinylamino)-5-nitro-pyrimidine
HPLC/MS (Method B): RT=2.24 min.; [M+H]+=363.2
(174) 2-(4-chloro-phenylamino)-4-(6-amino-1-hexylamino)-5-nitro-pyrimidine
HPLC/MS (Method B): RT=2.46 min.; [M+H]+=365.2
(175) 2-(4-chloro-phenylamino)-4-(3-aminomethyl-cyclohexylmethylamino)-5-nitro-pyrimidine
HPLC/MS (Method B): RT=2.56 min.; [M+H]+=391.2
(176) 2-(4-benzylaminocarbonyl-phenylamino)-4-(4-acetyl-1-piperazinyl)-5-nitro-pyrimidine
HPLC/MS (Method B): RT=2.53 min.; [M+H]+=476.2
(177) 2-(3-carboxy-phenylamino)-4-(4-aminosulphonyl-benzylamino)-5-nitro-pyrimidine
HPLC/MS (Method B): RT=2.31 min.; [M+H]+=445.1
(178) 2-(4-chloro-phenylamino)-4-[N-(1-methyl-4-piperidinyl-methyl)-N-methyl-amino]-5-nitro-pyrimidine
HPLC/MS (Method B): RT=2.31 min.; [M+H]+=391.2
(179) 2-(3-carboxy-phenylamino)-4-(4-aminomethyl-cyclohexylmethylamino)-5-nitro-pyrimidine (mixture of isomers)
HPLC/MS (Method B): RT=1.97 min.; [M+H]+=401.2
(180) 2-(3-ethoxycarbonyl-phenylamino)-4-(4-aminomethyl-cyclohexylmethylamino)-5-nitro-pyrimidine (mixture of isomers)
HPLC/MS (Method B): RT=2.42 min.; [M+H]+=429.3
(181) 2-(4-benzylaminocarbonyl-phenylamino)-4-(4-carboxy-4-phenyl-1-piperidinyl)-5-nitro-pyrimidine
HPLC/MS (Method B): RT=3.11 min.; [M+H]+=553.3
(182) 2-(3,4-dichlorophenylamino)-4-(2-(3-carboxy-2-methoxy-phenyl)-1-ethylamino)-5-trifluoromethyl-pyrimidine
HPLC/MS (Method B): RT=2.96 min.; [M+H]+=501.2
(183) 2-(4-chlorophenylamino)-4-(7-methyl-2,7-diaza-spiro[4.4]non-2-yl)-5-nitro-pyrimidine
HPLC/MS (Method B): RT=2.34 min.; [M+H]+=389.2
(184) 2-(4-carboxy-phenylamino)-4-(4-hydroxy-benzylamino)-5-nitro-pyrimidine
HPLC/MS (Method B): RT=2.2 min.; [M+H]+=382.1
(185) 2-(3,4-dichlorophenylamino)-4-(3-carboxy-cyclohexylamino)-5-trifluoromethyl-pyrimidine HPLC/MS (Method B): RT=2.9 min.; [M+H]+=449.2
(186) 2-(3,4-dichlorophenylamino)-4-(4-aminomethyl-cyclohexylmethylamino)-5-trifluoromethyl-pyrimidine
HPLC/MS (Method B): RT=2.35 min.; [M+H]+=448.1
(187) 2-(3,4-dichlorophenylamino)-4-(1-carboxy-2,2-diphenyl-1-ethylamino)-5-trifluoromethyl-pyrimidine
HPLC/MS (Method B): RT=3.17 min.; [M+H]+=547.28
(188) 2-(3,4-dichlorophenylamino)-4-(3-aminomethyl-cyclohexylmethylamino)-5-trifluoromethyl-pyrimidine
HPLC/MS (Method B): RT=2.15 min.; [M+H]+=448.0
Melting point: 140-142° C.
$R_f$=0.08 (silica gel; methylene chloride:methanol=4:1)
HPLC/MS (Method G): RT=3.78 min.; [M+H]+=449; Abs. λ max=260.8 nm
(189) 2-(benzylamino)-4-(2-(3-hydroxyphenyl)-1-ethylamino)-5-trifluoromethyl-pyrimidine
(190) 2-(4-chloro-phenylamino)-4-(3-hydroxy-piperidin-1-yl)-5-nitro-pyrimidine
HPLC/MS (Method B): RT=2.9 min.; [M+H]+=350.2
(191) 2-(4-chloro-phenylamino)-4-(trans-4-hydroxy-cyclohexylamino)-5-nitro-pyrimidine
HPLC/MS (Method B): RT=2.92 min.; [M+H]+=364.2
(192) 2-(4-chloro-phenylamino)-4-(4-amino-cyclohexylamino)-5-nitro-pyrimidine
HPLC/MS (Method B): RT=2.4 min.; [M+H]+=393.2
(193) 2-(4-chloro-phenylamino)-4-(4-dimethylamino-cyclohexylamino)-5-nitro-pyrimidine
HPLC/MS (Method B): RT=2.36 min.; [M+H]+=391.2
(194) 2-(4-chloro-phenylamino)-4-((1R)-1-carboxy-1-ethylamino)-5-nitro-pyrimidine
HPLC/MS (Method B): RT=2.51 min.; [M+H]+=338.14
(195) 2-(4-chloro-phenylamino)-4-(3-amino-propylamino)-5-nitro-pyrimidine
HPLC/MS (Method B): RT=2.15 min.; [M+H]+=323.1
(196) 2-(4-chloro-phenylamino)-4-(3-(3-aminopropoxy-1-propylamino)-5-nitro-pyrimidine
(197) 2-(4-chlorine-phenylamino)-4-(4-aminomethyl-piperidin-1-yl)-5-nitro-pyrimidine (198) 2-(4-chloro-phenylamino)-4-(3-(isopropylamino)-1-propylamino)-5-nitro-pyrimidine
HPLC/MS (Method B): RT=2.32 min.; [M+H]+=365.1
(199) 2-(4-chloro-phenylamino)-4-(2-(4-(2-hydroxyethyl)-piperazin-1-yl)-1-ethylamino))-5-nitro-pyrimidine
(200) 2-(4-chloro-phenylamino)-4-(3-(3-hydroxy-8-methyl-8-aza-bicyclo[3.2.1]octyl)-methylamino)-5-nitro-pyrimidine
HPLC/MS (Method B): RT=2.17 min.; [M+H]+=419.2
(201) 2-(4-chloro-phenylamino)-4-(3-hydroxy-1,3-dihydro-2-oxo-indol-3-yl-methylamino)-5-nitro-pyrimidine
(202) 2-(4-chloro-phenylamino)-4-(2-(3-carboxy-2-methoxy-phenyl)-1-ethylamino)-5-nitro-pyrimidine
HPLC/MS (Method B): RT=3.2 min.; [M+H]+=444.1
(203) 2-(4-chloro-phenylamino)-4-(3-hydroxymethyl-piperidin-1-yl)-5-nitro-pyrimidine
HPLC/MS (Method B): RT=2.97 min.; [M+H]+=364.2
(204) 2-(4-chloro-phenylamino)-4-(bis-(2-hydroxy-ethyl)-amino)-5-nitro-pyrimidine
HPLC/MS (Method B): RT=2.41 min.; [M+H]+=354.1
(205) 2-(4-chloro-phenylamino)-4-(4-nitrobenzylamino)-5-nitro-pyrimidine
HPLC/MS (Method B): RT=3.49 min.; [M+H]+=401.2
(206) 2-(4-chloro-phenylamino)-4-(2-aminocarbonyl-1-ethylamino)-5-nitro-pyrimidine
(207) 2-(4-chloro-phenylamino)-4-(1-carboxy-2-(1H-imidazol-4-yl)-1-ethylamino)-5-nitro-pyrimidine
HPLC/MS (Method B): RT=1.67 min.; [M+H]+=404.15
(208) 2-(4-chloro-phenylamino)-4-(1-carboxy-2,2-diphenyl-1-ethylamino)-5-nitro-pyrimidine
HPLC/MS (Method B): RT=3.25 min.; [M+H]+=490.2
(209) 2-(4-chloro-phenylamino)-4-(3-carboxy-cyclohexylamino)-5-nitro-pyrimidine
HPLC/MS (Method B): RT=3.15 min.; [M+H]+=392.2
(210) 2-(4-chloro-phenylamino)-4-(4-(2-carboxy-1-ethyl)-cyclohexylamino)-5-nitro-pyrimidine
HPLC/MS (Method B): RT=3.41 min.; [M+H]+=420.3
(211) 2-(4-chloro-phenylamino)-4-(2-(3-hydroxyphenyl)-1-ethylamino)-5-nitro-pyrimidine
HPLC/MS (Method B): RT=3.29 min.; [M+H]+=386.2
(212) 2-(4-chloro-phenylamino)-4-(2-(1H-pyrazol-4-yl)-1-ethylamino)-5-nitro-pyrimidine
HPLC/MS (Method B): RT=2.38 min.; [M+H]+=360.1
(213) 2-(4-chloro-phenylamino)-4-(3-(2-aza-bicyclo[2.2.1]hept-5-en-2-yl)-propylamino)-5-nitro-pyrimidine
(214) 2-(4-chloro-phenylamino)-4-(1-methyl-piperidin-4-yl-methylamino)-5-nitro-pyrimidine
HPLC/MS (Method B): RT=2.28 min.; [M+H]+=377.2
(215) 2-(4-chloro-phenylamino)-4-(cis-4-hydroxy-cyclohexylamino)-5-nitro-pyrimidine
HPLC/MS (Method B): RT=2.92 min.; [M+H]+=364.2
(216) 2-(4-chloro-phenylamino)-4-(4-dimethylaminomethyl-cyclohexylmethylamino)-5-nitro-pyrimidine
HPLC/MS (Method B): RT=2.15 min.; [M+H]+=357.1
(217) 2-(4-chloro-phenylamino)-4-(2-(imidazol-1-yl)-1-ethylamino)-5-nitro-pyrimidine
HPLC/MS (Method B): RT=2.26 min.; [M+H]+=371.1
(218) 2-(3,4-dichloro-phenylamino)-4-(6-amino-1-hexylamino)-5-trifluoromethyl-pyrimidine
HPLC/MS (Method B): RT=2.31 min.; [M+H]+=422.1
(219) 2-(3,4-dichloro-phenylamino)-4-(N-(1-methyl-piperidin-4-yl)-N-methyl-amino)-5-trifluoromethyl-pyrimidine
HPLC/MS (Method B): RT=2.46 min.; [M+H]+=434.1
(220) 2-(3,4-dichloro-phenylamino)-4-(N-methyl-N-(2-hydroxybenzyl)-amino)-5-trifluoromethyl-pyrimidine
HPLC/MS (Method B): RT=3.3 min.; [M+H]+=443.1

(221) 2-(3,4-dichlorophenylamino)-4-(N-methyl-N-(2-cyano-1-ethyl)-amino)-5-trifluoromethyl-pyrimidine
HPLC/MS (Method B): RT=3.27 min.; [M+H]+=390.1
(222) 2-(3,4-dichlorophenylamino)-4-(3-(4-(1-pyrrolidinyl)-butyl)-piperidin-1-yl)-5-trifluoromethyl-pyrimidine
HPLC/MS (Method B): RT=2.87 min.; [M+H]+=516.1
(223) 2-(3,4-dichlorophenylamino)-4-((2S)-2-hydroxymethyl-pyrrolidin-1-yl)-5-trifluoromethyl-pyrimidine
HPLC/MS (Method B): RT=2.85 min.; [M+H]+=407.2
(224) 2-(3,4-dichlorophenylamino)-4-((2R)-2-hydroxymethyl-pyrrolidin-1-yl)-5-trifluoromethyl-pyrimidine
HPLC/MS (Method B): RT=2.62 min.; [M+H]+=407.2
(225) 2-(3,4-dichlorophenylamino)-4-(2-(imidazolidin-2-on-1-yl)-1-ethylamino)-5-trifluoromethyl-pyrimidine
HPLC/MS (Method B): RT=2.49 min.; [M+H]+=435.1
(226) 2-(3,4-dichlorophenylamino)-4-(4-(N-acetyl-N-methyl-aminomethyl)-piperidin-1-yl)-5-trifluoromethyl-pyrimidine
HPLC/MS (Method B): RT=2.59 min.; [M+H]+=476.3
(227) 2-(3,4-dichlorophenylamino)-4-[N-(1-methyl-4-piperidinyl-methyl)-N-methyl-amino]-5-trifluoromethyl-pyrimidine
HPLC/MS (Method B): RT=2.4 min.; [M+H]+=434.2
(228) 2-(3,4-dichlorophenylamino)-4-(4-methylpiperazino)-5-trifluoromethyl-pyrimidine
HPLC/MS (Method B): RT=2.41 min.; [M+H]+=406.2
(229) 2-(3,4-dichlorophenylamino)-4-(4-hydroxy-1-piperidinyl)-5-trifluoromethyl-pyrimidine
HPLC/MS (Method B): RT=2.63 min.; [M+H]+=407.2
(230) 2-(3,4-dichlorophenylamino)-4-(2-dimethylamino-1-ethylamino)-5-trifluoromethyl-pyrimidine
HPLC/MS (Method B): RT=2.24 min.; [M+H]+=394.1
(231) 2-(3,4-dichlorophenylamino)-4-(3-(4-morpholinyl)-1-propylamino)-5-trifluoromethyl-pyrimidine
HPLC/MS (Method B): RT=2.15 min.; [M+H]+=450.1
(232) 2-(3,4-dichlorophenylamino)-4-(2-carboxy-1-ethylamino)-5-trifluoromethyl-pyrimidine
HPLC/MS (Method B): RT=2.34 min.; [M+H]+=395.2
(233) 2-(3,4-dichlorophenylamino)-4-(3-(1H-1-imidazolyl)-1-propylamino)-5-trifluoromethyl-pyrimidine
HPLC/MS (Method B): RT=2.01 min.; [M+H]+=431.1
(234) 2-(3,4-dichlorophenylamino)-4-(3-dimethylamino-1-propylamino)-5-trifluoromethyl-pyrimidine
HPLC/MS (Method B): RT=1.87 min.; [M+H]+=408.1
(235) 2-(3,4-dichlorophenylamino)-4-(2-diisopropylamino-1-ethylamino)-5-trifluoromethyl-pyrimidine
HPLC/MS (Method B): RT=2.5 min.; [M+H]+=450.3
(236) 2-(3,4-dichlorophenylamino)-4-(bis-(2-methoxyethyl)amino)-5-trifluoromethyl-pyrimidine
HPLC/MS (Method B): RT=3.44 min.; [M+H]+=439.2
(237) 2-(3,4-dichlorophenylamino)-4-(N-methyl-N-(2-methylamino-1-ethyl)-amino)-5-trifluoromethyl-pyrimidine
HPLC/MS (Method B): RT=2.56 min.; [M+H]+=394.0
(238) 2-(3,4-dichlorophenylamino)-4-(2-(4-pyridyl)-1-ethylamino)-5-trifluoromethyl-pyrimidine
HPLC/MS (Method B): RT=2.17 min.; [M+H]+=428.1
(239) 2-(3,4-dichlorophenylamino)-4-(4-aminosulphonyl-benzylamino)-5-trifluoromethyl-pyrimidine
HPLC/MS (Method B): RT=2.72 min.; [M+H]+=492.2
(240) 2-(3,4-dichlorophenylamino)-4-(2-acetylamino-ethylamino)-5-chloro-pyrimidine
Prepared analogously to Example 1(80). Melting point: 147° C.
$R_f$=0.12 (silica gel; methylene chloride:methanol=4:1)
HPLC/MS (Method G): RT=3.76 min.; [M+H]+=381; Abs. λ max=270.3 nm (241) 2-(3,4-dichlorophenylamino)-4-(4-pyridyl-methylamino)-5-trifluoromethyl-pyrimidine
HPLC/MS (Method B): RT=2.31 min.; [M+H]+=414.2

(242) 2-(3,4-dichlorophenylamino)-4-((3-chloro-5-trifluoromethyl-2-pyridyl)-methylamino)-5-trifluoromethyl-pyrimidine (243) 2-(3,4-dichlorophenylamino)-4-((4-ethoxycarbonyl-1H-pyrazol-5-yl)-methylamino)-5-trifluoromethyl-pyrimidine (244) 2-(3,4-dichlorophenylamino)-4-(3-nitrobenzylamino)-5-trifluoromethyl-pyrimidine
HPLC/MS (Method B): RT=3.3 min.; [M+H]+=458.2

(245) 2-(3,4-dichlorophenylamino)-4-(4-(2-carboxy-1-ethyl)-1-piperidinyl)-5-trifluoromethyl-pyrimidine
HPLC/MS (Method B): RT=3.11 min.; [M+H]+=463.2

(246) 243.4-dichlorophenylamino)-4-(3-(1-pyrrolidinyl)-1-propylamino)-5-trifluoromethyl-pyrimidine
HPLC/MS (Method B): RT=2.26 min.; [M+H]+=434.1

(247) 2-(3,4-dichlorophenylamino)-4-(5-acetylamino-5-methoxycarbonyl-1-pentylamino)-5-trifluoromethyl-pyrimidine
HPLC/MS (Method B): RT=2.4 min.; [M+H]+=508.2

(248) 2-(3,4-dichlorophenylamino)-4-((1-hydroxy-1-cyclohexyl)-methylamino)-5-trifluoromethyl-pyrimidine
HPLC/MS (Method B): RT=3.16 min.; [M+H]+=435.1

(249) 2-(3,4-dichlorophenylamino)-4-(2-(1H-indol-3-yl)-1-ethylamino)-5-trifluoromethyl-pyrimidine
HPLC/MS (Method B): RT=3.26 min.; [M+H]+=466.2

(250) 2-(3,4-dichlorophenylamino)-4-(2-(4-nitro-2-pyridyl-amino)-1-ethylamino)-5-trifluoromethyl-pyrimidine
HPLC/MS (Method B): RT=2.99 min.; [M+H]+=488.1

(251) 2-(3,4-dichlorophenylamino)-4-(2-hydroxy-2-phenyl-1-ethylamino)-5-trifluoromethyl-pyrimidine
HPLC/MS (Method B): RT=3.02 min.; [M+H]+=443.1

(252) 2-(3,4-dichlorophenylamino)-4-(2-phenylamino-1-ethylamino)-5-trifluoromethyl-pyrimidine
HPLC/MS (Method B): RT=3.16 min.; [M+H]+=442.2

(253) 2-(3,4-dichlorophenylamino)-4-(2-(4-hydroxyphenyl)-1-ethylamino)-5-trifluoromethyl-pyrimidine
HPLC/MS (Method B): RT=2.91 min.; [M+H]+=443.2

(254) 2-(3,4-dichlorophenylamino)-4-(2-(4-aminosulphonylphenyl)-1-ethylamino)-5-trifluoromethyl-pyrimidine
HPLC/MS (Method B): RT=2.74 min.; [M+H]+=506.1

(255) 2-(3,4-dichlorophenylamino)-4-(2-(1-naphthylamino)-1-ethylamino)-5-trifluoromethyl-pyrimidine
HPLC/MS (Method B): RT=3.6 min.; [M+H]+=492.2

(256) 2-(3,4-dichlorophenylamino)-4-(2-(4-nitrophenyl)-1-ethylamino)-5-trifluoromethyl-pyrimidine
HPLC/MS (Method B): RT=3.33 min.; [M+H]+=472.2

(257) 2-(3,4-dichlorophenylamino)-4-(3-ethoxycarbonyl-1-propylamino)-5-trifluoromethyl-pyrimidine
HPLC/MS (Method B): RT=3.14 min.; [M+H]+=437.2

(258) 2-(3,4-dichlorophenylamino)-4-(aminocarbonylmethylamino)-5-trifluoromethyl-pyrimidine
HPLC/MS (Method B): RT=2.33 min.; [M+H]+=380.1

(259) 2-(3,4-dichlorophenylamino)-4-(2-acetylamino-ethylamino)-5-ethyl-pyrimidine
Melting point: 211-213° C.
$R_f$=0.04 (silica gel; methylene chloride:methanol=4:1)
HPLC/MS (Method F): RT=2.79 min.; [M+H]+=341; Abs. λ max=277.9 nm (260) 2-(3,4-dichlorophenylamino)-4-(2-tert.-butyloxycarbonylamino-1-ethylamino)-5-trifluoromethyl-pyrimidine
HPLC/MS (Method B): RT=2.96 min.; [M+H]+=466.1

(261) 2-(3,4-dichlorophenylamino)-4-(1-ethyl-2-pyrrolidinyl-methylamino)-5-trifluoromethyl-pyrimidine
HPLC/MS (Method B): RT=2.52 min.; [M+H]+=434.2

(262) 2-(3,4-dichlorophenylamino)-4-(2-(1-pyrrolidinyl)-1-ethylamino)-5-trifluoromethyl-pyrimidine
HPLC/MS (Method B): RT=2.33 min.; [M+H]+=420.2

(263) 2-(3,4-dichlorophenylamino)-4-(2-tetrahydrofuryl-methylamino)-5-trifluoromethyl-pyrimidine (264) 2-(3,4-dichlorophenylamino)-4-(2-(1-piperidinyl)-1-ethylamino)-5-trifluoromethyl-pyrimidine
HPLC/MS (Method B): RT=2.4 min.; [M+H]+=434.2

(265) 2-(3,4-dichlorophenylamino)-4-(2-hydroxy-1-propylamino)-5-trifluoromethyl-pyrimidine
HPLC/MS (Method B): RT=2.63 min.; [M+H]+=381.1

(266) 2-(3,4-dichlorophenylamino)-4-(2,3-dihydroxy-1-propylamino)-5-trifluoromethyl-pyrimidine
HPLC/MS (Method B): RT=2.31 min.; [M+H]+=397.2

(267) 2-(3,4-dichlorophenylamino)-4-(2-diethylamino-1-ethylamino)-5-trifluoromethyl-pyrimidine
HPLC/MS (Method B): RT=2.39 min.; [M+H]+=422.1

(268) 2-(3,4-dichlorophenylamino)-4-(2-(2-hydroxy-ethoxy)-1-ethylamino)-5-trifluoromethyl-pyrimidine
HPLC/MS (Method B): RT=2.5 min.; [M+H]+=411.2

(269) 2-(3,4-dichlorophenylamino)-4-(2-hydroxy-1-ethylamino)-5-trifluoromethyl-pyrimidine
HPLC/MS (Method B): RT=2.46 min.; [M+H]+=367.2

(270) 2-(3,4-dichlorophenylamino)-4-(3-diethylamino-1-propylamino)-5-trifluoromethyl-pyrimidine
HPLC/MS (Method B): RT=2.26 min.; [M+H]+=436.2

(271) 2-(3,4-dichlorophenylamino)-4-(3-hydroxy-1-propylamino)-5-trifluoromethyl-pyrimidine
HPLC/MS (Method B): RT=2.49 min.; [M+H]+=381.2

(272) 2-(3,4-dichlorophenylamino)-4-(2-(1-methyl-M-pyrrol-2-yl)-1-ethylamino)-5-trifluoromethyl-pyrimidine
HPLC/MS (Method B): RT=3.23 min.; [M+H]+=430.1

(273) 2-(3,4-dichlorophenylamino)-4-(4-hydroxy-3-methoxy-benzylamino)-5-trifluoromethyl-pyrimidine
HPLC/MS (Method B): RT=2.89 min.; [M+H]+=459.1

(274) 2-(3,4-dichlorophenylamino)-4-(2-methylsulphanyl-1-ethylamino)-5-trifluoromethyl-pyrimidine
HPLC/MS (Method B): RT=3.17 min.; [M+H]+=397.1

(275) 2-(3,4-dichlorophenylamino)-4-(3-methoxy-1-propylamino)-5-trifluoromethyl-pyrimidine
HPLC/MS (Method B): RT=3.06 min.; [M+H]+=395.2

(276) 2-(3,4-dichlorophenylamino)-4-(2,2-dimethyl-3-dimethylamino-1-propylamino)-5-trifluoromethyl-pyrimidine
HPLC/MS (Method B): RT=2.41 min.; [M+H]+=436.1

(277) 2-(3,4-dichlorophenylamino)-4-(2,2-dimethyl-3-hydroxy-1-propylamino)-5-trifluoromethyl-pyrimidine
HPLC/MS (Method B): RT=3.03 min.; [M+H]+=409.2

(278) 2-(3,4-dichlorophenylamino)-4-cyanomethylamino-5-trifluoromethyl-pyrimidine
HPLC/MS (Method B): RT=2.66 min.; [M+H]+=362.2

(279) 2-(3,4-dichlorophenylamino)-4-(3-aminocarbonyl-1-piperidinyl)-5-trifluoromethyl-pyrimidine
HPLC/MS (Method B): RT=2.6 min.; [M+H]+=434.2

(280) 2-(3,4-dichlorophenylamino)-4-(4-acetyl-1-piperazinyl)-5-trifluoromethyl-pyrimidine
HPLC/MS (Method B): RT=2.81 min.; [M+H]+=434.2

(281) 2-(3,4-dichlorophenylamino)-4-(4-(1-piperidinyl)-1-piperidinyl)-5-trifluoromethyl-pyrimidine
HPLC/MS (Method B): RT=2.45 min.; [M+H]+=474.2

(282) 2-(3,4-dichlorophenylamino)-4-(4-(morpholinocarbonylmethyl)-1-piperazinyl)-5-trifluoromethyl-pyrimidine
HPLC/MS (Method B): RT=2.41 min.; [M+H]+=519.2

(283) 2-(3,4-dichlorophenylamino)-4-piperazino-5-trifluoromethyl-pyrimidine
HPLC/MS (Method B): RT=2.31 min.; [M+H]+=392.2

(284) 2-(3,4-dichlorophenylamino)-4-(3-(4-(3-amino-1-propyl)-1-piperazinyl)-1-propylamino)-5-trifluoromethyl-pyrimidine
HPLC/MS (Method B): RT=1.7 min.; [M+H]+=506.2
(285) 2-(3,4-dichloro-phenylamino)-4-(cis-4-carboxy-cyclohexylamino)-5-trifluoromethyl-pyrimidine
(286) 2-(3,4-dichlorophenylamino)-4-(3-dibenzylamino-1-propylamino)-5-trifluoromethyl-pyrimidine
HPLC/MS (Method B): RT=2.65 min.; [M+H]+=560.1
(287) 2-(3,4-dichloro-phenylamino)-4-(N-[4-methoxycarbonyl-cyclohexyl]-N-[3-pyridylmethyl]amino)-5-trifluoromethyl-pyrimidine
HPLC/MS (Method B): RT=2.5 min.; [M+H]+=554.1
(288) 2-(3,4-dichlorophenylamino)-4-(2-acetylamino-ethylamino)-5-methoxymethyl-pyrimidine
(289) 2-(3,4-dichlorophenylamino)-4-(2-phenyl-1-(4-phenyl-1-butyl-aminocarbonyl)-1-ethylamino)-5-trifluoromethyl-pyrimidine
HPLC/MS (Method B): RT=3.73 min.; [M+H]+=602.28
(290) 2-(3,4-dichlorophenylamino)-4-(1-aminocarbonyl-2-(4-methoxyphenyl)-1-ethylamino)-5-trifluoromethyl-pyrimidine
HPLC/MS (Method B): RT=2.61 min.; [M+H]+=500.24
(291) 2-(3,4-dichlorophenylamino)-4-(1-dimethylaminomethylcarbonyl-4-piperidinyl-methylamino)-5-trifluoromethyl-pyrimidine
(292) 2-(3,4-dichloro-phenylamino)-4-(N-ethyl-N-(4-pyridylmethyl)-amino)-5-trifluoromethyl-pyrimidine
HPLC/MS (Method B): RT=2.66 min.; [M+H]+=435.2
(293) 2-(3,4-dichloro-phenylamino)-4-(3-phenyl-azepan-4-on-1-yl)-5-trifluoromethyl-pyrimidine
HPLC/MS (Method B): RT=2.49 min.; [M+H]+=381.2
(294) 2-(3,4-dichlorophenylamino)-4-(2-(3-hydroxy-1-propyl)-1-piperidinyl)-5-trifluoromethyl-pyrimidine
HPLC/MS (Method B): RT=3.2 min.; [M+H]+=449.0
(295) 2-(3,4-dichlorophenylamino)-4-(4-(8-methoxy-3,4-dihydro-1H-quinazolin-2-on-3-yl)-1-piperidinyl)-5-trifluoromethyl-pyrimidine
HPLC/MS (Method B): RT=3.1 min.; [M+H]+=567.08
(296) 2-(3,4-dichlorophenylamino)-4-(4-(2-nitrophenyl)-1-piperazinyl)-5-trifluoromethyl-pyrimidine
Melting point: 228-229° C.
Rf=0.07 (silica gel; methylene chloride:methanol=4:1)
HPLC/MS (Method G): RT=2.61 min.; [M+H]+=409; Abs. λ max=276 nm
(297) 2-(3,4-dichlorophenylamino)-4-(4-(3,4-dimethoxyphenyl)-1-piperazinyl)-5-trifluoromethyl-pyrimidine
HPLC/MS (Method B): RT=3.02 min.; [M+H]+=443.1
(298) 2-(3,4-dichlorophenylamino)-4-(4-(4-cyanophenyl)-1-piperazinyl)-5-trifluoromethyl-pyrimidine
HPLC/MS (Method B): RT=2.41 min.; [M+H]+=396.3
(299) 2-(3,4-dichlorophenylamino)-4-(1-benzyl-3-pyrrolidinyl-amino)-5-trifluoromethyl-pyrimidine
HPLC/MS (Method B): RT=2.54 min.; [M+H]+=482.2
(300) 2-(3,4-dichlorophenylamino)-4-(1-hydroxy-2-propylamino)-5-trifluoromethyl-pyrimidine
HPLC/MS (Method B): RT=2.48 min.; [M+H]+=381.2
(301) 2-(3,4-dichlorophenylamino)-4-(3-(1-piperidinyl)-1-propylamino)-5-trifluoromethyl-pyrimidine
HPLC/MS (Method B): RT=2.08 min.; [M+H]+=448.1
(302) 2-(3,4-dichlorophenylamino)-4-(1-benzyl-4-piperidinyl-amino)-5-trifluoromethyl-pyrimidine
HPLC/MS (Method B): RT=2.41 min.; [M+H]+=496.2
(303) 2-(3,4-dichlorophenylamino)-4-(4-aminomethyl-benzylamino)-5-trifluoromethyl-pyrimidine
HPLC/MS (Method B): RT=2.14 min.; [M+H]+=442.1
(304) 2-(3,4-dichlorophenylamino)-4-(4-aminobutylamino)-5-trifluoromethyl-pyrimidine
HPLC/MS (Method B): RT=2.11 min.; [M+H]+=394.1
(305) 2-(3,4-dichlorophenylamino)-4-(3-amino-2,2-dimethyl-1-propylamino)-5-trifluoromethyl-pyrimidine
HPLC/MS (Method B): RT=2.4 min.; [M+H]+=408.1
(306) 2-(3,4-dichlorophenylamino)-4-(trans-2-amino-cyclohexylamino)-5-trifluoromethyl-pyrimidine
HPLC/MS (Method B): RT=2.61 min.; [M+H]+=420.1
(307) 2-(3,4-dichlorophenylamino)-4-(2-(2-(2-amino-1-ethoxy)-1-ethoxy)-1-ethylamino)-5-trifluoromethyl-pyrimidine
HPLC/MS (Method B): RT=2.25 min.; [M+H]+=454.0
(308) 2-(3,4-dichlorophenylamino)-4-(3-amino-benzylamino)-5-trifluoromethyl-pyrimidine
HPLC/MS (Method B): RT=2.16 min.; [M+H]+=428.2
(309) 2-(3,4-dichlorophenylamino)-4-(3-amino-2-hydroxy-1-propylamino)-5-trifluoromethyl-pyrimidine
HPLC/MS (Method B): RT=2.11 min.; [M+H]+=396.1
(310) 2-(3,4-dichlorophenylamino)-4-(2-(2-amino-1-ethyl-sulphanyl)-1-ethylamino)-5-trifluoromethyl-pyrimidine
HPLC/MS (Method B): RT=2.28 min.; [M+H]+=426.0
(311) 2-(3,4-dichlorophenylamino)-4-(N-[2-dimethylamino-1-ethyl]-N-ethyl-amino)-5-trifluoromethyl-pyrimidine
HPLC/MS (Method B): RT=2.76 min.; [M+H]+=422.1
(312) 2-(3,4-dichlorophenylamino)-4-(N-[3-dimethylamino-1-propyl]-N-methyl-amino)-5-trifluoromethyl-pyrimidine
HPLC/MS (Method B): RT=2.39 min.; [M+H]+=422.0
(313) 2-(3,4-dichlorophenylamino)-4-(3-(4-methyl-1-piperazinyl)-1-propylamino)-5-trifluoromethyl-pyrimidine
HPLC/MS (Method B): RT=2.09 min.; [M+H]+=463.1
(314) 2-(3,4-dichloro-phenylamino)-4-(N-[2-cyano-1-ethyl]-N-[3-pyridylmethyl]-amino)-5-trifluoromethyl-pyrimidine
HPLC/MS (Method B): RT=2.4 min.; [M+H]+=467.0
(315) 2-(3,4-dichloro-phenylamino)-4-(4-(2-pyridyl)-1-piperazinyl)-5-trifluoromethyl-pyrimidine
HPLC/MS (Method B): RT=2.48 min.; [M+H]+=469.1
(316) 2-(3,4-dichloro-phenylamino)-4-(4-[bis-(4-methoxyphenyl)]-methyl-1-piperazinyl)-5-trifluoromethyl-pyrimidine
(317) 2-(3,4-dichloro-phenylamino)-4-(4-(3-methoxy-phenyl)-1-piperazinyl)-5-trifluoromethyl-pyrimidine
HPLC/MS (Method B): RT=2.4 min.; [M+H]+=396.3
(318) 2-(3,4-dichloro-phenylamino)-4-(N-benzyl-N-[2-cyano-1-ethyl]-amino)-5-trifluoromethyl-pyrimidine
HPLC/MS (Method B): RT=3.92 min.; [M+H]+=466.2
(319) 2-(3,4-dichloro-phenylamino)-4-(N-benzyl-N-[2-hydroxy-1-ethyl]-amino)-5-trifluoromethyl-pyrimidine
HPLC/MS (Method B): RT=3.4 min.; [M+H]+=457.1
(320) 2-(3,4-dichlorophenylamino)-4-(3-carboxy-1-propylamino)-5-trifluoromethyl-pyrimidine
(321) 2-(3,4-dichloro-phenylamino)-4-(N-benzyl-N-[ethoxycarbonylmethyl]-amino)-5-trifluoromethyl-pyrimidine
HPLC/MS (Method B): RT=4.11 min.; [M+H]+=499.2
(322) 2-(3,4-dichloro-phenylamino)-4-(N-[4-nitrobenzyl]-N-propyl-amino)-5-trifluoromethyl-pyrimidine
HPLC/MS (Method B): RT=4.03 min.; [M+H]+=500.2
(323) 2-(3,4-dichloro-phenylamino)-4-(cyano-phenyl-methylamino)-5-trifluoromethyl-pyrimidine
(324) 2-(3,4-dichloro-phenylamino)-4-(N-benzyl-N-[4-hydroxy-1-butyl]-amino)-5-trifluoromethyl-pyrimidine
HPLC/MS (Method B): RT=3.43 min.; [M+H]+=485.2

(325) 2-(3,4-dichloro-phenylamino)-4-(N-benzyl-N-[2-hydroxymethyl-1-cyclohexyl]-amino)-5-trifluoromethyl-pyrimidine
HPLC/MS (Method B): RT=2.8 min.; [M+H]+=525.26

(326) tert-butyl N-1-[2-(3,4-dichloro-phenylamino)-5-trifluoromethyl-pyrimidin-4-yl]-pyrrolidin-3-yl)-carbaminate
Prepared analogously to Example 1(80)
Melting point: 198-200° C.
Rf=0.44 (silica gel; methylene chloride:methanol=99:1)
HPLC/MS (Method K): RT=4.37 min.; [M+H]+=493; Abs. λ max=270.3 nm (327) 2-(3,4-dichloro-phenylamino)-4-((1S)-1-carboxy-2-hydroxy-1-ethyl-amino)-5-trifluoromethyl-pyrimidine
HPLC/MS (Method B): RT=2 min.; [M+H]+=411

(328) 2-(3,4-dichloro-phenylamino)-4-(5-carboxy-1-pentylamino)-5-trifluoromethyl-pyrimidine
HPLC/MS (Method B): RT=2.7 min.; [M+H]+=437.0

(329) 2-(3,4-dichloro-phenylamino)-4-(2-aminocarbonyl-1-carboxy-1-ethylamino)-5-trifluoromethyl-pyrimidine (330) 2-(3,4-dichloro-phenylamino)-4-(2-carboxy-2-propylamino)-5-trifluoromethyl-pyrimidine
HPLC/MS (Method B): RT=2.5 min.; [M+H]+=409

(331) 2-(3,4-dichloro-phenylamino)-4-(1-carboxy-3-methyl-1-propylamino)-5-trifluoromethyl-pyrimidine (332) 2-(3,4-dichloro-phenylamino)-4-((1R)-1-carboxy-2-hydroxy-1-ethylamino)-5-trifluoromethyl-pyrimidine (333) 2-(3,4-dichlorophenylamino)-4-(4-(2-amino-1-ethyl)-1-piperazinyl)-5-trifluoromethyl-pyrimidine
HPLC/MS (Method B): RT=2.36 min.; [M+H]+=435.2

(334) 2-(3,4-dichloro-phenylamino)-4-(3,5-dimethyl-1-piperazinyl)-5-trifluoromethyl-pyrimidine
HPLC/MS (Method B): RT=2.7 min.; [M+H]+=420.1

(335) 2-(3,4-dichlorophenylamino)-4-(cis-2-amino-cyclohexylamino)-5-trifluoromethyl-pyrimidine
HPLC/MS (Method B): RT=2.68 min.; [M+H]+=420.2

(336) 2-(3,4-dichloro-phenylamino)-4-(N-methyl-N-[3-methylamino-1-propyl]-amino)-5-trifluoromethyl-pyrimidine (337) 2-(3,4-dichloro-phenylamino)-4-(3-hydroxy-8-aza-bicyclo[3.2.1]oct-8-yl)-5-trifluoromethyl-pyrimidine
HPLC/MS (Method B): RT=2.75 min.; [M+H]+=433.2

(338) 2-(3,4-dichloro-phenylamino)-4-(3-amino-1-pyrrolidinyl)-5-trifluoromethyl-pyrimidine
HPLC/MS (method B): RT=2.24 min.; [M+H]+=392.2
melting point: 157-158° C.
R$_f$=0.03 (silica gel; methylene chloride:methanol=9:1)
HPLC/MS (method G): RT=3.63 min.; [M+H]+=393; Abs. λ max=272.2 nm (339) 2-(3,4-dichlorophenylamino)-4-(4-benzyloxycarbonyl-1-piperazinyl)-5-trifluoromethyl-pyrimidine
HPLC/MS (method B): RT=3.99 min.; [M+H]+=526.2

(340) 2-(3,4-dichlorophenylamino)-4-(3-(2-(3-amino-1-propoxy)-1-ethoxy)-1-propylamino)-5-trifluoromethyl-pyrimidine
HPLC/MS (method B): RT=2.35 min.; [M+H]+=482.1

(341) 2-(3,4-dichlorophenylamino)-4-(N-benzyl-N-[2-hydroxy-1-phenyl-1-ethyl]-amino)-5-trifluoromethyl-pyrimidine
HPLC/MS (Method B): RT=3.27 min.; [M+H]+=533.0

(342) 2-(3,4-dichlorophenylamino)-4-(1-homopiperazinyl)-5-trifluoromethyl-pyrimidine
HPLC/MS (Method B): RT=2.48 min.; [M+H]+=406.1

(343) 2-(3,4-dichlorophenylamino)-4-(2-(2-(2-hydroxy-1-ethoxy)-1-ethoxy)-1-ethylamino)-5-trifluoromethyl-pyrimidine
HPLC/MS (method B): RT=2.56 min.; [M+H]+=455.2

(344) 2-(3,4-dichlorophenylamino)-4-(2-(3-methoxycarbonylphenyl)-1-ethyl-amino)-5-trifluoromethyl-pyrimidine
HPLC/MS (method B): RT=3.37 min.; [M+H]+=485.2

(345) 2-(3,4-dichloro-phenylamino)-4-(2-hydroxy-3-(4-morpholinyl)-1-propyl-amino)-5-trifluoromethyl-pyrimidine
HPLC/MS (method B): RT=2.19 min.; [M+H]+=466.1

(346) 2-(3,4-dichlorophenylamino)-4-(N-methyl-N-[2-nitrobenzyl]-amino)-5-trifluoromethyl-pyrimidine
HPLC/MS (method B): RT=3.7 min.; [M+H]+=472.1

(347) 2-(3,4-dichlorophenylamino)-4-(2-carboxy-1-phenyl-1-ethyl-amino)-5-trifluoromethyl-pyrimidine
HPLC/MS (method B): RT=3.15 min.; [M+H]+=471.1

(348) 2-(3,4-dichlorophenylamino)-4-(N-methyl-N-[6-[N-methyl-N-(2-phenyl-1-ethyl)-amino]-1-hexyl]-amino)-5-trifluoromethyl-pyrimidine
HPLC/MS (method B): RT=2.92 min.; [M+H]+=554.1

(349) 2-(3,4-dichlorophenylamino)-4-(2-(2-(2-amino-1-ethyl)-phenyl)-1-ethyl-amino)-5-trifluoromethyl-pyrimidine
HPLC/MS (method B): RT=2.27 min.; [M+H]+=470.0

(350) 2-(3,4-dichlorophenylamino)-4-(N-[2-diethylamino-1-ethyl]-N-ethyl-amino)-5-trifluoromethyl-pyrimidine
HPLC/MS (method B): RT=2.86 min.; [M+H]+=450.1

(351) 2-(3,4-dichlorophenylamino)-4-(2-ethoxycarbonyl-1-piperidinyl)-5-trifluoromethyl-pyrimidine
HPLC/MS (method B): RT=4.01 min.; [M+H]+=463.2

(352) 2-(3,4-dichlorophenylamino)-4-(4-methyl-1-homopiperazinyl)-5-trifluoromethyl-pyrimidine
HPLC/MS (method B): RT=2.52 min.; [M+H]+=420.1

(353) 2-(3,4-dichlorophenylamino)-4-(N-cyanomethyl-N-butyl-amino)-5-trifluoromethyl-pyrimidine (354) 2-(3,4-dichlorophenylamino)-4-(N-[2-dimethylamino-1-ethyl]-N-methyl-amino)-5-trifluoromethyl-pyrimidine
HPLC/MS (method B): RT=2.58 min.; [M+H]+=408.1

(355) 2-(3,4-dichlorophenylamino)-4-(2-(1-pyrrolidinyl-methyl)-1-pyrrolidinyl)-5-trifluoromethyl-pyrimidine
HPLC/MS (method B): RT=2.67 min.; [M+H]+=460.1

(356) 2-(3,4-dichlorophenylamino)-4-(3-methoxycarbonyl-methyl-1-piperidinyl)-5-trifluoromethyl-pyrimidine
HPLC/MS (method B): RT=3.59 min.; [M+H]+=463.3

(357) 2-(3,4-dichlorophenylamino)-4-(3-(3-diethylamino-1-propyl)-1-piperidinyl)-5-trifluoromethyl-pyrimidine
HPLC/MS (method B): RT=2.94 min.; [M+H]+=504.1

(358) 2-(3,4-dichlorophenylamino)-4-(5-hydroxy-2-methyl-2,8-diaza-spiro[5.5]undec-8-yl)-5-trifluoromethyl-pyrimidine
HPLC/MS (method B): RT=2.6 min.; [M+H]+=490.2

(359) 2-(3,4-dichlorophenylamino)-4-(3-(1-pyrrolidinyl-methyl)-1-piperidinyl)-5-trifluoromethyl-pyrimidine
HPLC/MS (method B): RT=2.74 min.; [M+H]+=474.1

(360) 2-(3,4-dichlorophenylamino)-4-(3-carboxy-1-piperidinyl)-5-trifluoromethyl-pyrimidine
HPLC/MS (method B): RT=3.12 min.; [M+H]+=435.2

(361) 2-(3,4-dichlorophenylamino)-4-(2-(2-(2-dimethylamino-1-ethyl)-1-piperidinyl)-1-ethylamino)-5-trifluoromethyl-pyrimidine
HPLC/MS (method B): RT=2.2 min.; [M+H]+=505.2

(362) 2-(3,4-dichlorophenylamino)-4-(3-(2-diethylaminomethyl-1-piperidinyl)-1-propylamino)-5-trifluoromethyl-pyrimidine
HPLC/MS (method B): RT=2.21 min.; [M+H]+=533.2

(363) 2-(3,4-dichlorophenylamino)-4-(4-(8-methyl-8-aza-bicyclo[3.2.1]oct-3-yl)-1-piperazinyl)-5-trifluoromethyl-pyrimidine
HPLC/MS (method B): RT=2.16 min.; [M+H]+=515.2

(364) 2-(3,4-dichlorophenylamino)-4-(1-carboxy-2-(4-chlorophenyl)-1-ethyl-amino)-5-trifluoromethyl-pyrimidine
HPLC/MS (method B): RT=3.14 min.; [M+H]+=505.04
(365) 2-(3,4-dichlorophenylamino)-4-(carboxymethylaminocarbonylmethylamino)-5-trifluoromethyl-pyrimidine
HPLC/MS (method B): RT=1.8 min.; [M+H]+=438
(366) 2-(3,4-dichlorophenylamino)-4-(carboxy-phenyl-methylamino)-5-trifluoromethyl-pyrimidine
HPLC/MS (method B): RT=2.85 min.; [M+H]+=457.22
(367) 2-(3,4-dichlorophenylamino)-4-(4'-hydroxy-biphenyl-4-ylmethylamino)-5-trifluoromethyl-pyrimidine
HPLC/MS (method B): RT=3.28 min.; [M+H]+=505.1
(368) 2-(3,4-dichlorophenylamino)-4-(N-[4-amino-benzyl]-N-[2-methoxy-1-ethyl]-amino)-5-trifluoromethyl-pyrimidine
HPLC/MS (method B): RT=2.64 min.; [M+H]+=486.0
(369) 2-(3,4-dichlorophenylamino)-4-(4-hydroxy-benzylamino)-5-trifluoromethyl-pyrimidine
HPLC/MS (method B): RT=2.9 min.; [M+H]+=429.1
(370) 2-(3,4-dichlorophenylamino)-4-(2-diphenylmethoxy-1-ethylamino)-5-trifluoromethyl-pyrimidine
(371) 2-(3,4-dichlorophenylamino)-4-(N-aminocarbonylmethyl-N-methyl-amino)-5-trifluoromethyl-pyrimidine
HPLC/MS (method B): RT=2.55 min.; [M+H]+=394.1
(372) 2-(3,4-dichlorophenylamino)-4-(2-methylaminocarbonyl-1-ethylamino)-5-trifluoromethyl-pyrimidine
HPLC/MS (method B): RT=2.5 min.; [M+H]+=408.1
(373) 2-(3,4-dichlorophenylamino)-4-(2-dimethylaminocarbonyl-1-ethylamino)-5-trifluoromethyl-pyrimidine
HPLC/MS (method B): RT=2.69 min.; [M+H]+=422.1
(374) 2-(3,4-dichlorophenylamino)-4-(2-(4-methyl-1-piperazinyl)-carbonyl-1-ethylamino)-5-trifluoromethyl-pyrimidine
HPLC/MS (method B): RT=2.2 min.; [M+H]+=477.1
(375) 2-(3,4-dichlorophenylamino)-4-(4-carboxy-3-thiazolidinyl)-5-trifluoromethyl-pyrimidine
HPLC/MS (method B): RT=2.84 min.; [M+H]+=439.11
(376) 2-(3,4-dichlorophenylamino)-4-((R)carboxy-(4-hydroxyphenyl)-methylamino)-5-trifluoromethyl-pyrimidine
HPLC/MS (method B): RT=2.4 min.; [M+H]+=473.13
(377) 2-(3,4-dichlorophenylamino)-4-(1-carboxy-5-benzyloxycarbonylamino-1-pentylamino)-5-trifluoromethyl-pyrimidine
HPLC/MS (method B): RT=2.84 min.; [M+H]+=586.12
(378) 2-(3,4-dichlorophenylamino)-4-(1-(1H-benzimidazol-2-yl)-1-ethylamino)-5-trifluoromethyl-pyrimidine
HPLC/MS (method B): RT=2.65 min.; [M+H]+=467.1
(379) 2-(3,4-dichlorophenylamino)-4-(4-(4-ethoxycarbonyl-1-piperidinyl)-1-piperidinyl)-5-trifluoromethyl-pyrimidine
HPLC/MS (method B): RT=2.84 min.; [M+H]+=546.2
(380) 2-(3,4-dichlorophenylamino)-4-(4-(3-hydroxy-1-piperidinyl)-1-piperidinyl)-5-trifluoromethyl-pyrimidine
HPLC/MS (method B): RT=2.56 min.; [M+H]+=490.2
(381) 2-(3,4-dichlorophenylamino)-4-(N-methyl-N-[2-pyrazinyl-methyl]-amino)-5-trifluoromethyl-pyrimidine
HPLC/MS (method B): RT=3.06 min.; [M+H]+=429.2
(382) 2-(3,4-dichlorophenylamino)-4-((S)carboxy-(4-hydroxyphenyl)-methylamino)-5-trifluoromethyl-pyrimidine
HPLC/MS (method B): RT=2.39 min.; [M+H]+=473.33
(383) 2-(3,4-dichlorophenylamino)-4-(1-phenylsulphonyl-4-piperidinylamino)-5-trifluoromethyl-pyrimidine
(384) 2-(3,4-dichlorophenylamino)-4-(4-(4-hydroxyphenyl)-1-butylamino)-5-trifluoromethyl-pyrimidine
HPLC/MS (method B): RT=3.14 min.; [M+H]+=471.3
(385) tert-butyl (2-[2-(3,4-dichloro-phenylamino)-5-trifluoromethyl-pyrimidin-4-ylamino]-ethyl)-methyl-carbaminate
melting point: 140-141° C.
$R_f$=0.43 (silica gel; methylene chloride:methanol=9:1)
HPLC/MS (method K): RT=3.58 min.; [M+H]+=481; Abs. λ max=266.5 nm
(386) 2-(3,4-dichlorophenylamino)-4-(4-(3-carboxy-1-propyl)-cyclohexylamino)-5-trifluoromethyl-pyrimidine
HPLC/MS (method B): RT=2.36 min.; [M+H]+=396.2
(387) 2-(3,4-dichlorophenylamino)-4-(4-(2-carboxy-1-ethyl)-cyclohexylmethylamino)-5-trifluoromethyl-pyrimidine
HPLC/MS (method B): RT=3.05 min.; [M+H]+=491.3
(388) 2-(3,4-dichlorophenylamino)-4-(1-carboxy-2-propylamino)-5-trifluoromethyl-pyrimidine
HPLC/MS (method B): RT=2.76 min.; [M+H]+=409.2
(389) 2-(3,4-dichlorophenylamino)-4-(2-(2-hydroxyphenyl)-1-ethylamino)-5-trifluoromethyl-pyrimidine
HPLC/MS (method B): RT=3.16 min.; [M+H]+=443.2
(390) tert. butyl (1-[2-(4-carbamoyl-phenylamino)-5-trifluoromethyl-pyrimidin-4-yl]-pyrrolidin-3-yl)-carbaminate
melting point: 225-228° C.
$R_f$=0.20 (silica gel; methylene chloride:methanol=9:1)
HPLC/MS (method G): RT=3.70 min.; [M+H]+=467; Abs. λ max=283.6 nm
(391) 2-(3,4-dichlorophenylamino)-4-(3-carboxy-benzylamino)-5-trifluoromethyl-pyrimidine
HPLC/MS (method B): RT=2.91 min.; [M+H]+=457.2
(392) 2-(3,4-dichlorophenylamino)-4-(6-tert.-butyloxycarbonylamino-1-hexylamino)-5-trifluoromethyl-pyrimidine
HPLC/MS (method B): RT=3.47 min.; [M+H]+=522.0
(393) 2-(3,4-dichlorophenylamino)-4-(3-tert.-butyloxycarbonylamino-1-propylamino)-5-trifluoromethyl-pyrimidine
HPLC/MS (method B): RT=3.28 min.; [M+H]+=480.0
(394) 2-(3,4-dichlorophenylamino)-4-(4-carboxy-1-methyl-4-piperidinylamino)-5-trifluoromethyl-pyrimidine
HPLC/MS (method B): RT=2.09 min.; [M+H]+=464.1
(395) 2-(3,4-dichlorophenylamino)-4-(1-carboxy-2-(2-chlorophenyl)-1-ethylamino)-5-trifluoromethyl-pyrimidine
HPLC/MS (method B): RT=2.96 min.; [M+H]+=504.77
(396) 2-(3,4-dichlorophenylamino)-4-(N-benzyl-N-[1-methoxycarbonyl-1-ethyl]-amino)-5-trifluoromethyl-pyrimidine
(397) 2-(3,4-dichlorophenylamino)-4-(N-[ethoxycarbonylmethyl]-N-isopropyl-amino)-5-trifluoromethyl-pyrimidine
HPLC/MS (method B): RT=3.7 min.; [M+H]+=451
(398) 2-(3,4-dichlorophenylamino)-4-(2-(2-ethoxycarbonyl-1-ethyl)-1-pyrrolidinyl)-5-trifluoromethyl-pyrimidine
HPLC/MS (method B): RT=3.42 min.; [M+H]+=477.2
(399) 2-(3,4-dichlorophenylamino)-4-(carbamimidoyl-methylamino)-5-trifluoromethyl-pyrimidine
HPLC/MS (method B): RT=1.74 min.; [M+H]+=379.13
(400) 2-(3,4-dichlorophenylamino)-4-(N-[4-hydroxycyclohexyl]-N-methylamino)-5-trifluoromethyl-pyrimidine
HPLC/MS (method B): RT=2.86 min.; [M+H]+=435.2
(401) 2-(3,4-dichlorophenylamino)-4-(2-(6-methoxy-1H-benzimidazol-2-yl)-1-ethyl)-5-trifluoromethyl-pyrimidine
HPLC/MS (method B): RT=2.31 min.; [M+H]+=497.0
(402) 2-(3,4-dichlorophenylamino)-4-(2-carboxy-benzylamino)-5-trifluoromethyl-pyrimidine
HPLC/MS (method B): RT=2.59 min.; [M+H]+=457.26

(403) 2-(3,4-dichlorophenylamino)-4-(2-aminocarbonyl-1,3-dihydro-isoindol-5-yl-methylamino)-5-trifluoromethyl-pyrimidine
HPLC/MS (method B): RT=2.68 min.; [M+H]+=497.2
(404) 2-(3,4-dichlorophenylamino)-4-(3-(tert.-butyloxycarbonylaminomethyl)-cyclohexylmethylamino)-5-trifluoromethyl-pyrimidine
HPLC/MS (method B): RT=3.61 min.; [M+H]+=548.0
(405) 2-(3,4-dichlorophenylamino)-4-(2-methyl-4-phenylaminocarbonylamino-2-butylamino)-5-trifluoromethyl-pyrimidine
(406) 2-(3,4-dichlorophenylamino)-4-(3-dimethylaminocarbonyl-1-piperidinyl)-5-trifluoromethyl-pyrimidine
HPLC/MS (method B): RT=3.1 min.; [M+H]+=462.2
(407) 2-(3,4-dichlorophenylamino)-4-(2-hydroxy-cyclohexylamino)-5-trifluoromethyl-pyrimidine
HPLC/MS (method B): RT=2.96 min.; [M+H]+=421.2
(408) 2-(3,4-dichlorophenylamino)-4-(2-hydroxymethyl-1-piperidinyl)-5-trifluoromethyl-pyrimidine
HPLC/MS (method B): RT=2.62 min.; [M+H]+=421.1
(409) 2-(3,4-dichlorophenylamino)-4-(N-methyl-N-[2-pyridyl-methyl]-amino)-5-trifluoromethyl-pyrimidine
HPLC/MS (method B): RT=2.48 min.; [M+H]+=428.1
(410) 2-(3,4-dichlorophenylamino)-4-(N-methyl-N-[3-pyridyl-methyl]-amino)-5-trifluoromethyl-pyrimidine
HPLC/MS (method B): RT=2.91 min.; [M+H]+=443.2
(411) 2-(3,4-dichlorophenylamino)-4-(1-ethyl-3-piperidinylamino)-5-trifluoromethyl-pyrimidine
HPLC/MS (method B): RT=3.6 min.; [M+H]+=492.2
(412) 2-(3,4-dichlorophenylamino)-4-(2-dimethylamino-cyclohexylamino)-5-trifluoromethyl-pyrimidine
HPLC/MS (method B): RT=2.74 min.; [M+H]+=506.1
(413) 2-(3,4-dichlorophenylamino)-4-(4-(3-hydroxy-1-propyl)-1-piperidinyl)-5-trifluoromethyl-pyrimidine
HPLC/MS (method B): RT=2.46 min.; [M+H]+=367.2
(414) 2-(3,4-dichlorophenylamino)-4-(4-(3-hydroxy-1-propyl)-1-piperazinyl)-5-trifluoromethyl-pyrimidine
HPLC/MS (method B): RT=2.5 min.; [M+H]+=411.2
(415) 2-(3,4-dichlorophenylamino)-4-(N-methyl-N-[3-(4-pyridyl)-1-propyl]-amino)-5-trifluoromethyl-pyrimidine
HPLC/MS (method B): RT=2.5 min.; [M+H]+=456.1
(416) 2-(3,4-dichlorophenylamino)-4-(4-dimethylamino-2-phenyl-1-butylamino)-5-trifluoromethyl-pyrimidine
HPLC/MS (method B): RT=2.37 min.; [M+H]+=498.1
(417) 2-(3,4-dichlorophenylamino)-4-(2-(3-diethylamino-1-propyl)-1-piperidinyl)-5-trifluoromethyl-pyrimidine
HPLC/MS (method B): RT=2.92 min.; [M+H]+=504.1
(418) 2-(3,4-dichlorophenylamino)-4-(bis-[3-pyridylmethyl]-amino)-5-trifluoromethyl-pyrimidine
HPLC/MS (method B): RT=2.01 min.; [M+H]+=505.2
(419) 2-(3,4-dichlorophenylamino)-4-(4-(N-methyl-N-[2-methoxycarbonyl-1-ethyl]-amino)-1-piperidinyl)-5-trifluoromethyl-pyrimidine
HPLC/MS (method B): RT=2.23 min.; [M+H]+=506.12
(420) 2-(3,4-dichlorophenylamino)-4-(2-(4-(2H-pyridazin-3-on-6-yl)-phenyl)-1-ethylamino)-1-piperidinyl)-5-trifluoromethyl-pyrimidine
(421) 2-(3,4-dichlorophenylamino)-4-(3-(4-amino-3,5-dichlorophenyl)-1-propylamino)-5-trifluoromethyl-pyrimidine
HPLC/MS (method B): RT=3.6 min.; [M+H]+=524.0
(422) 2-(3,4-dichlorophenylamino)-4-(4-(2-(N-[dimethylaminocarbonylmethyl]-N-methyl-amino)-1-ethyl-amino)-1-piperidinyl)-5-trifluoromethyl-pyrimidine
HPLC/MS (method B): RT=2.13 min.; [M+H]+=533.03

(423) 2-(3,4-dichlorophenylamino)-4-(2-(2-(2-diethylamino-1-ethoxy)-1-ethyl)-1-piperidinyl)-5-trifluoromethyl-pyrimidine
HPLC/MS (method B): RT=3.02 min.; [M+H]+=534.2
(424) 2-(3,4-dichlorophenylamino)-4-(4-(2-(2-diethylamino-1-ethoxy)-1-ethyl)-1-piperidinyl)-5-trifluoromethyl-pyrimidine
HPLC/MS (method B): RT=2.67 min.; [M+H]+=534.2
(425) 2-(3,4-dichlorophenylamino)-4-(5-(3-carboxy-1-propyl)-indan-2-yl-amino)-5-trifluoromethyl-pyrimidine
HPLC/MS (method B): RT=3.16 min.; [M+H]+=525.2
(426) 2-(3,4-dichlorophenylamino)-4-(2-ethoxycarbonyl-1-(3-pyridyl)-1-ethyl-amino)-5-trifluoromethyl-pyrimidine
HPLC/MS (method B): RT=2.78 min.; [M+H]+=500.2
(427) 2-(3,4-dichlorophenylamino)-4-(1,1-dimethyl-3-(2-oxo-3-pyridin-4-yl-imidazolidin-1-yl)-propylamino)-5-trifluoromethyl-pyrimidine
HPLC/MS (method B): RT=2.05 min.; [M+H]+=554.3
(428) 2-(4-chlorophenylamino)-4-(4-methylpiperazino)-5-nitro-pyrimidine
melting point: 178-180° C.
(429) 2-(4-chlorophenylamino)-4-(4-hydroxy-1-piperidinyl)-5-nitro-pyrimidin
HPLC/MS (method B): RT=2.76 min.; [M+H]+=350.2
(430) 2-(4-chlorophenylamino)-4-[2-(dimethylamino)-1-ethylamino]-5-nitro-pyrimidine
melting point: 179-181° C.
(431) 2-(4-chlorophenylamino)-4-(3-(4-morpholinyl)-1-propylamino)-5-nitro-pyrimidine
HPLC/MS (method B): RT=2.23 min.; [M+H]+=393.2
(432) 2-(4-chlorophenylamino)-4-(2-carboxy-1-ethylamino)-5-nitro-pyrimidine
Prepared from compound 632 of Example 1 by subsequently reacting with 1N sodium hydroxide solution in tetrahydrofuran.
melting point: >300° C.
Rf value: 0.40 (silica gel; methylene chloride/methanol=9:1)
(433) 2-(4-chlorophenylamino)-4-(3-(1H-imidazolyl)-1-propylamino)-5-nitro-pyrimidine
HPLC/MS (method B): RT=2.28 min.; [M+H]+=374.2
(434) 2-(4-chlorophenylamino)-4-(3-dimethylamino-1-propylamino)-5-nitro-pyrimidine
melting point: 148-150° C.
(435) 2-(4-chlorophenylamino)-4-(2-diisopropylamino-1-ethylamino)-5-nitro-pyrimidine
HPLC/MS (method B): RT=2.4 min.; [M+H]+=393.2
(436) 2-(4-chlorophenylamino)-4-(bis-(2-methoxyethyl)amino)-5-nitro-pyrimidine
HPLC/MS (method B): RT=3.31 min.; [M+H]+=382.1
(437) 2-(4-chlorophenylamino)-4-(N-methyl-N-(2-methylamino-1-ethyl)-amino)-5-nitro-pyrimidine
HPLC/MS (method B): RT=2.4 min.; [M+H]+=337.0
(438) 2-(4-chlorophenylamino)-4-(2-(4-pyridyl)-1-ethylamino)-5-nitro-pyrimidine
HPLC/MS (method B): RT=2.26 min.; [M+H]+=371.1
(439) 2-(4-chlorophenylamino)-4-(4-aminosulphonyl-benzylamino)-5-nitro-pyrimidine
HPLC/MS (method B): RT=2.89 min.; [M+H]+=435.2
(440) 2-(3,4-dichlorophenylamino)-4-(2-acetylamino-ethylamino)-5-fluor-pyrimidin
(441) 2-(4-chlorophenylamino)-4-(4-pyridyl-methylamino)-5-nitro-pyrimidine
HPLC/MS (method B): RT=2.15 min.; [M+H]+=357.1
(442) 2-(4-chlorophenylamino)-4-((3-chlor-5-trifluoromethyl-2-pyridyl)-methylamino)-5-nitro-pyrimidine
HPLC/MS (method B): RT=3.91 min.; [M+H]+=459.1

(443) 2-(4-chlorophenylamino)-4-((4-ethoxycarbonyl-1H-pyrazol-5-yl)-methylamino)-5-nitro-pyrimidine
(444) 2-(4-chlorophenylamino)-4-(3-nitrobenzylamino)-5-nitro-pyrimidine
HPLC/MS (method B): RT=3.31 min.; [M+H]+=401.2
(445) 2-(4-chlorophenylamino)-4-(4-(2-carboxy-1-ethyl)-1-piperidinyl)-5-nitro-pyrimidine
HPLC/MS (method B): RT=3.08 min.; [M+H]+=406.2
(446) 2-(4-chlorophenylamino)-4-(3-(1-pyrrolidinyl)-1-propylamino)-5-nitro-pyrimidine
HPLC/MS (method B): RT=2.31 min.; [M+H]+=377.2
(447) 2-(4-chlorophenylamino)-4-(5-acetylamino-5-methoxycarbonyl-1-pentylamino)-5-nitro-pyrimidine
HPLC/MS (method B): RT=2.66 min.; [M+H]+=451.2
(448) 2-(4-chlorophenylamino)-4-((1-hydroxy-1-cyclohexyl)-methylamino)-5-nitro-pyrimidine
HPLC/MS (method B): RT=3.45 min.; [M+H]+=378.2
(449) 2-(4-chlorophenylamino)-4-(2-(1H-indol-3-yl)-1-ethylamino)-5-nitro-pyrimidine
HPLC/MS (method B): RT=3.64 min.; [M+H]+=409.2
(450) 2-(4-chlorophenylamino)-4-(2-(4-nitro-2-pyridyl-amino)-1-ethylamino)-5-nitro-pyrimidine
HPLC/MS (method B): RT=3.05 min.; [M+H]+=431.1
(451) 2-(4-chlorophenylamino)-4-(2-hydroxy-2-phenyl-1-ethylamino)-5-nitro-pyrimidine
HPLC/MS (method B): RT=3.3 min.; [M+H]+=386.3
(452) 2-(4-chlorophenylamino)-4-(2-phenylamino-1-ethylamino)-5-nitro-pyrimidine
HPLC/MS (method B): RT=3.08 min.; [M+H]+=385.1
(453) 2-(4-chlorophenylamino)-4-(2-(4-hydroxyphenyl)-1-ethylamino)-5-nitro-pyrimidine
HPLC/MS (method B): RT=3.24 min.; [M+H]+=386.2
(454) 2-(4-chlorophenylamino)-4-(2-(4-aminosulphonylphenyl)-1-ethylamino)-5-nitro-pyrimidine
HPLC/MS (method B): RT=2.85 min.; [M+H]+=449.1
(455) 2-(4-chlorophenylamino)-4-(2-(1-naphthylamino)-1-ethylamino)-5-nitro-pyrimidine
HPLC/MS (method B): RT=3.8 min.; [M+H]+=435.2
(456) 2-(4-chlorophenylamino)-4-(2-(4-nitrophenyl)-1-ethylamino)-5-nitro-pyrimidine
HPLC/MS (method B): RT=3.5 min.; [M+H]+=415.3
(457) 2-(4-chlorophenylamino)-4-(3-ethoxycarbonyl-1-propylamino)-5-nitro-pyrimidine
melting point: 133-135° C.
(458) 2-(4-chlorophenylamino)-4-(aminocarbonylmethylamino)-5-nitro-pyrimidine
HPLC/MS (method B): RT=2.36 min.; [M+H]+=323.1
(459) 4-[4-{3-Amino-pyrrolidin-1-yl}-5-trifluoromethyl-pyrimidin-2-ylamino)-benzamide
Prepared analogously to 1(80).
R$_f$=0.13 (silica gel; methylene chloride:methanol=4:1)
HPLC/MS (method G): RT=2.59 min.; [M+H]+=367; Abs. λ max=281.7 nm
(460) 2-(4-chlorophenylamino)-4-(2-tert.-butyloxycarbonylamino-1-ethylamino)-5-nitro-pyrimidine
HPLC/MS (method B): RT=3.24 min.; [M+H]+=409.1
(461) 2-(4-chlorophenylamino)-4-(1-ethyl-2-pyrrolidinyl)-methylamino)-5-nitro-pyrimidine
HPLC/MS (method B): RT=2.28 min.; [M+H]+=377.2
(462) 2-(4-chlorophenylamino)-4-(2-(1-pyrrolidinyl)-1-ethylamino)-5-nitro-pyrimidine
HPLC/MS (method B): RT=2.25 min.; [M+H]+=363.2
(463) 2-(4-chlorophenylamino)-4-(2-tetrahydrofuryl-methylamino)-5-nitro-pyrimidine
(464) 2-(4-chlorophenylamino)-4-(2-(1-piperidinyl)-1-ethylamino)-5-nitro-pyrimidine
HPLC/MS (method B): RT=2.3 min.; [M+H]+=377.1
(465) 2-(4-chlorophenylamino)-4-(2-hydroxy-1-propylamino)-5-nitro-pyrimidine
HPLC/MS (method B): RT=2.85 min.; [M+H]+=324.2
(466) 2-(4-chlorophenylamino)-4-(2,3-dihydroxy-1-propylamino)-5-nitro-pyrimidine
HPLC/MS (method B): RT=2.41 min.; [M+H]+=340.2
(467) 2-(4-chlorophenylamino)-4-(2-diethylamino-1-ethylamino)-5-nitro-pyrimidine
HPLC/MS (method B): RT=2.27 min.; [M+H]+=365.2
(468) 2-(4-chlorophenylamino)-4-(2-(2-hydroxyethoxy)-1-ethylamino)-5-nitro-pyrimidine
HPLC/MS (method B): RT=2.71 min.; [M+H]+=354.2
(469) 2-(4-chlorophenylamino)-4-(2-hydroxy-1-ethylamino)-5-nitro-pyrimidine
melting point: 226-228° C.
(470) 2-(4-chlorophenylamino)-4-(3-diethylamino-1-propylamino)-5-nitro-pyrimidine
HPLC/MS (method B): RT=2.35 min.; [M+H]+=379.2
(471) 2-(4-chlorophenylamino)-4-(3-hydroxy-1-propylamino)-5-nitro-pyrimidine
melting point: 190-194° C.
(472) 2-(4-chlorophenylamino)-4-(2-(1-methyl-1H-pyrrol-2-yl)-1-ethylamino)-5-nitro-pyrimidine
HPLC/MS (method B): RT=3.41 min.; [M+H]+=373.2
(473) 2-(4-chlorophenylamino)-4-(4-hydroxy-3-methoxybenzylamino)-5-nitro-pyrimidine
HPLC/MS (method B): RT=3.15 min.; [M+H]+=402.1
(474) 2-(4-chlorophenylamino)-4-(2-methylsulphanyl-1-ethylamino)-5-nitro-pyrimidine
HPLC/MS (method B): RT=3.46 min.; [M+H]+=340.1
(475) 2-(4-chlorophenylamino)-4-(3-methoxy-1-propylamino)-5-nitro-pyrimidine
melting point: 148-150° C.
(476) 2-(4-chlorophenylamino)-4-(2,2-dimethyl-3-dimethylamino-1-propylamino)-5-nitro-pyrimidine
HPLC/MS (method B): RT=2.4 min.; [M+H]+=379.2
(477) 2-(4-chlorophenylamino)-4-(2,2-dimethyl-3-hydroxy-1-propylamino)-5-nitro-pyrimidine
HPLC/MS (method B): RT=3.17 min.; [M+H]+=352.2
(478) 2-(4-chlorophenylamino)-4-cyanomethylamino-5-nitro-pyrimidine
HPLC/MS (method B): RT=2.49 min.; [M+H]+=305.14
(479) 2-(4-chlorophenylamino)-4-(3-aminocarbonyl-1-piperidinyl)-5-nitro-pyrimidine
HPLC/MS (method B): RT=2.69 min.; [M+H]+=377.2
(480) 2-(4-chlorophenylamino)-4-(4-acetyl-1-piperazinyl)-5-nitro-pyrimidine
HPLC/MS (method B): RT=3.64 min.; [M+H]+=409.2
(481) 2-(4-chlorophenylamino)-4-(4-(1-piperidinyl)-1-piperidinyl)-5-nitro-pyrimidine
HPLC/MS (method B): RT=2.31 min.; [M+H]+=377.2
(482) 2-(4-chlorophenylamino)-4-(4-(morpholinocarbonyl-methyl)-1-piperazinyl)-5-nitro-pyrimidine
HPLC/MS (method B): RT=2.28 min.; [M+H]+=462.2
(483) 2-(4-chlorophenylamino)-4-piperazino-5-nitro-pyrimidine
Rf value: 0.20 (silica gel; methylene chloride/methanol/conc. aqueous ammonia=9:1:0.1)
(484) 2-(4-chlorophenylamino)-4-(3-[4-(3-amino-1-propyl)-1-piperazinyl]-1-propylamino)-5-nitro-pyrimidine
HPLC/MS (method B): RT=2.41 min.; [M+H]+=519.2
(485) 2-(4-chlorophenylamino)-4-(cis-4-carboxy-cyclohexylamino)-5-nitro-pyrimidine
HPLC/MS (method B): RT=2.38 min.; [M+H]+=392.0
(486) 2-(4-chlorophenylamino)-4-(3-dibenzylamino-1-propylamino)-5-nitro-pyrimidine
HPLC/MS (method B): RT=2.65 min.; [M+H]+=560.1

(487) 2-(4-chlorophenylamino)-4-(N-[4-methoxycarbonyl-cyclohexyl]-N-[3-pyridylmethyl]amino)-5-nitro-pyrimidine
(488) 2-(3,4-dichlorophenylamino)-4-(2-acetylamino-ethylamino)-5-dimethylaminomethyl-pyrimidine
(489) 2-(4-chlorophenylamino)-4-(2-phenyl-1-(4-phenyl-1-butyl-aminocarbonyl)-1-ethylamino)-5-nitro-pyrimidine
HPLC/MS (method B): RT=3.6 min.; [M+H]+=545
(490) 2-(4-chlorophenylamino)-4-(1-aminocarbonyl-2-(4-methoxyphenyl)-1-ethylamino)-5-nitro-pyrimidine
HPLC/MS (method B): RT=2.66 min.; [M+H]+=443.2
(491) 2-(4-chlorophenylamino)-4-(1-dimethylaminomethyl-carbonyl-4-piperidinyl-methylamino)-5-nitro-pyrimidine
(492) 2-(4-chlorophenylamino)-4-(N-ethyl-N-[4-pyridylmethyl]amino)-5-nitro-pyrimidine
HPLC/MS (method B): RT=2.38 min.; [M+H]+=385.1
(493) 2-(4-chlorophenylamino)-4-(3-phenyl-azepan-4-on-1-yl)-5-nitro-pyrimidine
(494) 2-(4-chlorophenylamino)-4-(2-(3-hydroxy-1-propyl)-1-piperidinyl)-5-nitro-pyrimidine
HPLC/MS (method B): RT=3.17 min.; [M+H]+=392.3
(495) 2-(4-chlorophenylamino)-4-(4-(8-methoxy-3,4-dihydro-1H-quinazolin-2-on-3-yl)-1-piperidinyl)-5-nitro-pyrimidine
HPLC/MS (method B): RT=3.03 min.; [M+H]+=510.1
(496) 2-(4-chlorophenylamino)-4-(4-(2-nitrophenyl)-1-piperazinyl)-5-nitro-pyrimidine
HPLC/MS (method B): RT=3.6 min.; [M+H]+=456.0
(497) 2-(4-chlorophenylamino)-4-(4-(3,4-dimethoxyphenyl)-1-piperazinyl)-5-nitro-pyrimidine
HPLC/MS (method B): RT=2.34 min.; [M+H]+=396.2
(498) 2-(4-chlorophenylamino)-4-(4-(4-cyanophenyl)-1-piperazinyl)-5-nitro-pyrimidine
HPLC/MS (method B): RT=3.62 min.; [M+H]+=436.2
(499) 2-(4-chlorophenylamino)-4-(1-benzyl-3-pyrrolidinyl-amino)-5-nitro-pyrimidine
HPLC/MS (method B): RT=2.58 min.; [M+H]+=425.3
(500) 2-(4-chlorophenylamino)-4-(1-hydroxy-2-propylamino)-5-nitro-pyrimidine
HPLC/MS (method B): RT=2.74 min.; [M+H]+=324.2
(501) 2-(4-chlorophenylamino)-4-(3-(1-piperidinyl)-1-propylamino)-5-nitro-pyrimidine
HPLC/MS (method B): RT=2.36 min.; [M+H]+=391.2
(502) 2-(4-chlorophenylamino)-4-(1-benzyl-4-piperidinyl-amino)-5-nitro-pyrimidine
HPLC/MS (method B): RT=2.47 min.; [M+H]+=439.2
(503) 2-(4-chlorophenylamino)-4-(4-aminomethyl-benzylamino)-5-nitro-pyrimidine
HPLC/MS (method B): RT=2.39 min.; [M+H]+=385.1
(504) 2-(4-chlorophenylamino)-4-(4-aminobutylamino)-5-nitro-pyrimidine
HPLC/MS (method B): RT=2.24 min.; [M+H]+=337.1
(505) 2-(4-chlorophenylamino)-4-(3-amino-2,2-dimethyl-1-propylamino)-5-nitro-pyrimidine
HPLC/MS (method B): RT=2.35 min.; [M+H]+=351.1
(506) 2-(4-chlorophenylamino)-4-(trans-2-amino-cyclohexylamino)-5-nitro-pyrimidine
HPLC/MS (method B): RT=2.5 min.; [M+H]+=363.2
(507) 2-(4-chlorophenylamino)-4-(2-(2-(2-amino-1-ethoxy)-1-ethoxy)-1-ethylamino)-5-nitro-pyrimidine
HPLC/MS (method B): RT=2.13 min.; [M+H]+=397.2
(508) 2-(4-chlorophenylamino)-4-(3-amino-benzylamino)-5-nitro-pyrimidine
HPLC/MS (method B): RT=2.26 min.; [M+H]+=371.1
(509) 2-(4-chlorophenylamino)-4-(3-amino-2-hydroxy-1-propylamino)-5-nitro-pyrimidine
(510) 2-(4-chlorophenylamino)-4-(2-(2-amino-1-ethylsulphanyl)-1-ethylamino)-5-nitro-pyrimidine
HPLC/MS (method B): RT=2.34 min.; [M+H]+=369.0
(511) 2-(4-chlorophenylamino)-4-(N-[2-dimethylamino-1-ethyl]-N-ethyl-amino)-5-nitro-pyrimidine
HPLC/MS (method B): RT=2.4 min.; [M+H]+=365.0
(512) 2-(4-chlorophenylamino)-4-(N-[3-dimethylamino-1-propyl]-N-methyl-amino)-5-nitro-pyrimidine
HPLC/MS (method B): RT=2.25 min.; [M+H]+=365.1
(513) 2-(4-chlorophenylamino)-4-(3-(4-methyl-1-piperazinyl)-1-propylamino)-5-nitro-pyrimidine
HPLC/MS (method B): RT=1.84 min.; [M+H]+=406.2
(514) 2-(4-chlorophenylamino)-4-(N-[2-cyano-1-ethyl]-N-[3-pyridylmethyl]-amino)-5-nitro-pyrimidine
HPLC/MS (method B): RT=2.38 min.; [M+H]+=410.2
(515) 2-(4-chlorophenylamino)-4-(4-(2-pyridyl)-1-piperazinyl)-5-nitro-pyrimidine
HPLC/MS (method B): RT=2.28 min.; [M+H]+=412.1
(516) 2-(4-chlorophenylamino)-4-(4-[bis-(4-methoxy-phenyl)]-methyl-1-piperazinyl)-5-nitro-pyrimidine
(517) 2-(4-chlorophenylamino)-4-(4-(3-methoxy-phenyl)-1-piperazinyl)-5-nitro-pyrimidine
HPLC/MS (method B): RT=3.51 min.; [M+H]+=441.2
(518) 2-(4-chlorophenylamino)-4-(N-benzyl-N-[2-cyano-1-ethyl]-amino)-5-nitro-pyrimidine
HPLC/MS (method B): RT=3.53 min.; [M+H]+=409.2
(519) 2-(4-chlorophenylamino)-4-(N-benzyl-N-[2-hydroxy-1-ethyl]-amino)-5-nitro-pyrimidine
HPLC/MS (method B): RT=3.27 min.; [M+H]+=400.2
(520) 2-(4-chlorophenylamino)-4-(3-carboxy-1-propyl-amino)-5-nitro-pyrimidine
Prepared from compound 457 of Example 1 by subsequently reacting with 1N sodium hydroxide solution in tetrahydrofuran.
melting point: 258-260° C.
(521) 2-(4-chlorophenylamino)-4-(N-benzyl-N-[ethoxycarbonylmethyl]-amino)-5-nitro-pyrimidine
HPLC/MS (method B): RT=3.76 min.; [M+H]+=442.2
(522) 2-(4-chlorophenylamino)-4-(N-[4-nitrobenzyl]-N-propyl-amino)-5-nitro-pyrimidine
HPLC/MS (method B): RT=3.87 min.; [M+H]+=443.2
(523) 2-(4-chlorophenylamino)-4-(cyano-phenyl-methylamino)-5-nitro-pyrimidine
HPLC/MS (method B): RT=3.91 min.; [M+H]+=459.1
(524) 2-(4-chlorophenylamino)-4-(N-benzyl-N-[4-hydroxy-1-butyl]-amino)-5-nitro-pyrimidine
HPLC/MS (method B): RT=3.45 min.; [M+H]+=378.2
(525) 2-(4-chlorophenylamino)-4-(N-benzyl-N-[2-hydroxymethyl-1-cyclohexyl]-amino)-5-nitro-pyrimidine
HPLC/MS (method B): RT=2.45 min.; [M+H]+=468.33
(526) 2-(4-chlorophenylamino)-4-(1-carboxy-2-(4-hydroxyphenyl)-1-ethyl-amino)-5-nitro-pyrimidine
HPLC/MS (method B): RT=2.43 min.; [M+H]+=430.24
(527) 2-(4-chlorophenylamino)-4-((1S)-1-carboxy-2-hydroxy-1-ethyl-amino)-5-nitro-pyrimidine
(528) 2-(4-chlorophenylamino)-4-(5-carboxy-1-pentyl-amino)-5-nitro-pyrimidine
HPLC/MS (method B): RT=3 min.; [M+H]+=380.0
(529) 2-(4-chlorophenylamino)-4-(1-carboxy-2-aminocarbonyl-1-ethyl-amino)-5-nitro-pyrimidine
HPLC/MS (method B): RT=1.88 min.; [M+H]+=381.15
(530) 2-(4-chlorophenylamino)-4-(2-carboxy-2-propyl-amino)-5-nitro-pyrimidine
HPLC/MS (method B): RT=2.59 min.; [M+H]+=352.2
(531) 2-(4-chlorophenylamino)-4-(1-carboxy-3-methyl-1-propylamino)-5-nitro-pyrimidine
HPLC/MS (method B): RT=2.8 min.; [M+H]+=366.19

(532) 2-(4-chlorophenylamino)-4-((1R)-1-carboxy-2-hydroxy-1-ethyl-amino)-5-nitro-pyrimidine
HPLC/MS (method B): RT=2.03 min.; [M+H]+=354.19
(533) 2-(4-chlorophenylamino)-4-(4-(2-amino-1-ethyl)-1-piperazinyl)-5-nitro-pyrimidine
(534) 2-(4-chlorophenylamino)-4-(3,5-dimethyl-1-piperazinyl)-5-nitro-pyrimidine
HPLC/MS (method B): RT=2.28 min.; [M+H]+=363.2
(535) 2-(4-chlorophenylamino)-4-(cis-2-amino-cyclohexylamino)-5-nitro-pyrimidine
HPLC/MS (method B): RT=2.51 min.; [M+H]+=363.2
(536) 2-(4-chlorophenylamino)-4-(N-methyl-N-[3-methylamino-1-propyl]-amino)-5-nitro-pyrimidine
(537) 2-(4-chlorophenylamino)-4-(3-hydroxy-8-aza-bicyclo[3.2.1]oct-8-yl)-5-nitro-pyrimidine
HPLC/MS (method B): RT=3.04 min.; [M+H]+=376.2
(538) 2-(4-chlorophenylamino)-4-(3-amino-1-pyrrolidinyl)-5-nitro-pyrimidine
HPLC/MS (method B): RT=2.16 min.; [M+H]+=335.1
(539) 2-(4-chlorophenylamino)-4-(4-benzyloxycarbonyl-1-piperazinyl)-5-nitro-pyrimidine
HPLC/MS (method B): RT=3.57 min.; [M+H]+=469.2
(540) 2-(4-chlorophenylamino)-4-(3-(2-(3-amino-1-propoxy)-1-ethoxy)-1-propylamino)-5-nitro-pyrimidine
HPLC/MS (method B): RT=2.46 min.; [M+H]+=425.2
(541) 2-(4-chlorophenylamino)-4-(N-benzyl-N-[2-hydroxy-1-phenyl-1-ethyl]-amino)-5-nitro-pyrimidine
HPLC/MS (method B): RT=3.66 min.; [M+H]+=476.1
(542) 2-(4-chlorophenylamino)-4-(1-homopiperazinyl)-5-nitro-pyrimidine
HPLC/MS (method B): RT=2.22 min.; [M+H]+=349.1
(543) 2-(4-chlorophenylamino)-4-(2-(2-(2-hydroxy-1-ethoxy)-1-ethoxy)-1-ethylamino)-5-nitro-pyrimidine
HPLC/MS (method B): RT=2.73 min.; [M+H]+=398.2
(544) 2-(4-chlorophenylamino)-4-(2-(3-methoxycarbonylphenyl)-1-ethyl-amino)-5-nitro-pyrimidine
HPLC/MS (method B): RT=3.58 min.; [M+H]+=428.2
(545) 2-(4-chlorophenylamino)-4-(2-hydroxy-3-(4-morpholinyl)-1-propyl-amino)-5-nitro-pyrimidine
HPLC/MS (method B): RT=2.14 min.; [M+H]+=409.2
(546) 2-(4-chlorophenylamino)-4-(N-methyl-N-[2-nitrobenzyl]-amino)-5-nitro-pyrimidine
(547) 2-(4-chlorophenylamino)-4-(2-carboxy-1-phenyl-1-ethyl)-amino)-5-nitro-pyrimidine
(548) 2-(4-chlorophenylamino)-4-(N-methyl-N-[6-[N-methyl-N-(2-phenyl-1-ethyl)-amino]-1-hexyl]-amino)-5-nitro-pyrimidine
HPLC/MS (method B): RT=2.95 min.; [M+H]+=497.4
(549) 2-(4-chlorophenylamino)-4-(2-(2-(2-amino-1-ethyl)-phenyl)-1-ethyl-amino)-5-nitro-pyrimidine
HPLC/MS (method B): RT=2.65 min.; [M+H]+=413.2
(550) 2-(4-chlorophenylamino)-4-(N-[2-diethylamino-1-ethyl]-N-ethyl-amino)-5-nitro-pyrimidine
HPLC/MS (method B): RT=2.51 min.; [M+H]+=393.1
(551) 2-(4-chlorophenylamino)-4-(2-ethoxycarbonyl-1-piperidinyl)-5-nitro-pyrimidine
HPLC/MS (method B): RT=3.81 min.; [M+H]+=406.2
(552) 2-(4-chlorophenylamino)-4-(4-methyl-1-homopiperazinyl)-5-nitro-pyrimidine
HPLC/MS (method B): RT=2.26 min.; [M+H]+=363.2
(553) 2-(4-chlorophenylamino)-4-(N-cyanomethyl-N-butyl-amino)-5-nitro-pyrimidine
HPLC/MS (method B): RT=3.52 min.; [M+H]+=361.1
(554) 2-(4-chlorophenylamino)-4-(N-[2-dimethylamino-1-ethyl]-N-methyl-amino)-5-nitro-pyrimidine
HPLC/MS (method B): RT=2.21 min.; [M+H]+=351.1
(555) 2-(4-chlorophenylamino)-4-(2-(1-pyrrolidinyl-methyl)-1-pyrrolidinyl)-5-nitro-pyrimidine HPLC/MS (method B): RT=2.41 min; [M+H]+=403.2
(556) 2-(4-chlorophenylamino)-4-(3-methoxycarbonylmethyl-1-piperidinyl)-5-nitro-pyrimidine
HPLC/MS (method B): RT=3.47 min.; [M+H]+=406.2
(557) 2-(4-chlorophenylamino)-4-(3-(3-diethylamino-1-propyl)-1-piperidinyl)-5-nitro-pyrimidine
HPLC/MS (method B): RT=2.75 min.; [M+H]+=447.4
(558) 2-(4-chlorophenylamino)-4-(5-hydroxy-2-methyl-2,8-diaza-spiro[5.5]undec-8-yl)-5-nitro-pyrimidine
HPLC/MS (method B): RT=2.26 min.; [M+H]+=433.2
(559) 2-(4-chlorophenylamino)-4-(3-(1-pyrrolidinyl-methyl)-1-piperidinyl)-5-nitro-pyrimidine
HPLC/MS (method B): RT=2.5 min.; [M+H]+=417.2
(560) 2-(4-chlorophenylamino)-4-(3-carboxy-1-piperidinyl)-5-nitro-pyrimidine
HPLC/MS (method B): RT=2.83 min.; [M+H]+=378.2
(561) 2-(4-chlorophenylamino)-4-(2-(2-(2-dimethylamino-1-ethyl)-1-piperidinyl)-1-ethylamino)-5-nitro-pyrimidine
HPLC/MS (method B): RT=1.82 min.; [M+H]+=448.2
(562) 2-(4-chlorophenylamino)-4-(3-(2-diethylaminomethyl-1-piperidinyl)-1-propylamino)-5-nitro-pyrimidine
HPLC/MS (method B): RT=1.97 min.; [M+H]+=476.2
(563) 2-(4-chlorophenylamino)-4-(4-(8-methyl-8-aza-bicyclo[3.2.1]oct-3-yl)-1-piperazinyl)-5-nitro-pyrimidine
HPLC/MS (method B): RT=2.04 min.; [M+H]+=458.3
(564) 2-(4-chlorophenylamino)-4-(1-carboxy-2-(4-chlorophenyl)-1-ethyl-amino)-5-nitro-pyrimidine
HPLC/MS (method B): RT=3.13 min.; [M+H]+=448.25
(565) 2-(4-chlorophenylamino)-4-(carboxymethylaminocarbonylmethylamino)-5-nitro-pyrimidine
HPLC/MS (method B): RT=1.93 min.; [M+H]+=381.29
(566) 2-(4-chlorophenylamino)-4-(carboxy-phenyl-methylamino)-5-nitro-pyrimidine
HPLC/MS (method B): RT=2.87 min.; [M+H]+=400.2
(567) 2-(4-chlorophenylamino)-4-(4'-hydroxy-biphenyl-4-ylmethylamino)-5-nitro-pyrimidine
HPLC/MS (method B): RT=3.4 min.; [M+H]+=448.1
(568) 2-(4-chlorophenylamino)-4-(N-[4-amino-benzyl]-N-[2-methoxy-1-ethyl]-amino)-5-nitro-pyrimidine
(569) 2-(4-chlorophenylamino)-4-(4-hydroxy-benzylamino)-5-nitro-pyrimidine
HPLC/MS (method B): RT=3.01 min.; [M+H]+=372.1
(570) 2-(4-chlorophenylamino)-4-(2-diphenylmethoxy-1-ethylamino)-5-nitro-pyrimidine
(571) 2-(4-chlorophenylamino)-4-(N-aminocarbonylmethyl-N-methyl-amino)-5-nitro-pyrimidine
(572) 2-(4-chlorophenylamino)-4-(2-methylaminocarbonyl-1-ethylamino)-5-nitro-pyrimidine
(573) 2-(4-chlorophenylamino)-4-(2-dimethylaminocarbonyl-1-ethylamino)-5-nitro-pyrimidine
(574) 2-(4-chlorophenylamino)-4-(2-(4-methyl-1-piperazinyl)-carbonyl-1-ethylamino)-5-nitro-pyrimidine
(575) 2-(4-chlorophenylamino)-4-(4-carboxy-3-thiazolidinyl)-5-nitro-pyrimidine
HPLC/MS (method B): RT=2.6 min.; [M+H]+=382
(576) 2-(4-chlorophenylamino)-4-((R)carboxy-(4-hydroxyphenyl)-methylamino)-5-nitro-pyrimidine
HPLC/MS (method B): RT=2.44 min.; [M+H]+=416.2
(577) 2-(4-chlorophenylamino)-4-(1-carboxy-5-benzyloxycarbonylamino-1-pentylamino)-5-nitro-pyrimidine
HPLC/MS (method B): RT=3.01 min.; [M+H]+=529.14
(578) 2-(4-chlorophenylamino)-4-(1H-benzimidazol-2-yl)-1-ethylamino)-5-nitro-pyrimidine
HPLC/MS (method B): RT=2.21 min.; [M+H]+=410.1

(579) 2-(4-chlorophenylamino)-4-(4-(4-ethoxycarbonyl-1-piperidinyl)-1-piperidinyl)-5-nitro-pyrimidine
HPLC/MS (method B): RT=2.6 min.; [M+H]+=489.3

(580) 2-(4-chlorophenylamino)-4-(4-(3-hydroxy-1-piperidinyl)-1-piperidinyl)-5-nitro-pyrimidine
HPLC/MS (method B): RT=2.31 min.; [M+H]+=433.3

(581) 2-(4-chlorophenylamino)-4-(N-methyl-N-[2-pyrazinyl-methyl]-amino)-5-nitro-pyrimidine
HPLC/MS (method B): RT=2.91 min.; [M+H]+=372.1

(582) 2-(4-chlorophenylamino)-4-((S)carboxy-(4-hydroxyphenyl)-methylamino)-5-nitro-pyrimidine
HPLC/MS (method B): RT=2.47 min.; [M+H]+=416.09

(583) 2-(4-chlorophenylamino)-4-(1-phenylsulphonyl-4-piperidinylamino)-5-nitro-pyrimidine (584) 2-(4-chlorophenylamino)-4-(4-(4-hydroxyphenyl)-1-butylamino)-5-nitro-pyrimidine
HPLC/MS (method B): RT=3.38 min.; [M+H]+=414.3

(585) N-(2-Methyl-2-{2-[4-(morpholin-4-sulphonyl)-phenylamino]-5-trifluoromethyl-pyrimidin-4-ylamino}-propyl)-acetamide
melting point: 69-70° C.
Rf value: 0.39 (silica gel; ethyl acetate)
HPLC/MS (method D): RT=5.86 min.; [M+H]+=517; Abs./max 302 nm (586) 2-(4-chlorophenylamino)-4-(4-(3-carboxy-1-propyl)-cyclohexylamino)-5-nitro-pyrimidine (587) 2-(4-chlorophenylamino)-4-(4-(2-carboxy-1-ethyl)-cyclohexylmethylamino)-5-nitro-pyrimidine
HPLC/MS (method B): RT=3.41 min.; [M+H]+=434.3

(588) 2-(4-chlorophenylamino)-4-(1-carboxy-2-propylamino)-5-nitro-pyrimidine
HPLC/MS (method B): RT=2.95 min.; [M+H]+=352.2

(589) 2-(4-chlorophenylamino)-4-(2-(2-hydroxyphenyl)-1-ethylamino)-5-nitro-pyrimidine (590) tert. butyl (2-[2-(4-carbamoyl-phenylamino)-5-trifluoromethyl-pyrimidin-4-ylamino]-ethyl)-3-yl)-methyl-carbaminate
melting point: 186-187° C.
$R_f$=0.24 (silica gel; methylene chloride:methanol=9:1)
HPLC/MS (method G): RT=3.58 min.; [M+H]+=455; Abs. λ max=279.8 nm (591) 2-(4-chlorophenylamino)-4-(3-carboxy-benzylamino)-5-nitro-pyrimidine
HPLC/MS (method B): RT=3.06 min.; [M+H]+=400.2

(592) 2-(4-chlorophenylamino)-4-(6-tert.-butyloxycarbonylamino-1-hexylamino)-5-nitro-pyrimidine
HPLC/MS (method B): RT=3.74 min.; [M+H]+=465.0

(593) 2-(4-chlorophenylamino)-4-(3-tert.-butyloxycarbonylamino-1-propylamino)-5-nitro-pyrimidine
HPLC/MS (method B): RT=3.41 min.; [M+H]+=423.0

(594) 2-(4-chlorophenylamino)-4-(4-carboxy-1-methyl-4-piperidinylamino)-5-nitro-pyrimidine
HPLC/MS (method B): RT=1.67 min.; [M+H]+=407.3

(595) 2-(4-chlorophenylamino)-4-(1-carboxy-2-(2-chlorophenyl)-1-ethylamino)-5-nitro-pyrimidine
HPLC/MS (method B): RT=3.1 min.; [M+H]+=448.18

(596) 2-(4-chlorophenylamino)-4-(N-benzyl-N-[1-methoxycarbonyl-1-ethyl]-amino)-5-nitro-pyrimidine
HPLC/MS (method B): RT=3.72 min.; [M+H]+=442.2

(597) 2-(4-chlorophenylamino)-4-(N-[ethoxycarbonylmethyl]-N-isopropyl-amino)-5-nitro-pyrimidine
HPLC/MS (method B): RT=3.53 min.; [M+H]+=394.1

(598) 2-(4-chlorophenylamino)-4-(2-(2-ethoxycarbonyl-1-ethyl)-1-pyrrolidinyl)-5-nitro-pyrimidine (599) 2-(4-chlorophenylamino)-4-(carbamimidoyl-methylamino)-5-nitro-pyrimidine
HPLC/MS (method B): RT=1.51 min.; [M+H]+=322.22

(600) 2-(4-chlorophenylamino)-4-(N-[4-hydroxycyclohexyl]-N-methylamino)-5-nitro-pyrimidine (601) 2-(4-chlorophenylamino)-4-(2-(6-methoxy-1H-benzimidazol-2-yl)-1-ethyl)-5-nitro-pyrimidine
HPLC/MS (method B): RT=2.31 min.; [M+H]+=440.1

(602) 2-(4-chlorophenylamino)-4-(2-carboxy-benzylamino)-5-nitro-pyrimidine
HPLC/MS (method B): RT=2.88 min.; [M+H]+=400.25

(603) 2-(4-chlorophenylamino)-4-(2-aminocarbonyl-1,3-dihydro-isoindol-5-yl-methylamino)-5-nitro-pyrimidine
HPLC/MS (method B): RT=2.84 min.; [M+H]+=440.2

(604) 2-(4-chlorophenylamino)-4-(3-(tert.-butyloxycarbonylaminomethyl)-cyclohexylmethylamino)-5-nitro-pyrimidine
HPLC/MS (method B): RT=3.97 min.; [M+H]+=491.0

(605) 2-(4-chlorophenylamino)-4-(2-methyl-4-phenylaminocarbonylamino-2-butylamino)-5-nitro-pyrimidine
HPLC/MS (method B): RT=3.18 min.; [M+H]+=470.1

(606) 2-(4-chlorophenylamino)-4-(3-dimethylaminocarbonyl-1-piperidinyl)-5-nitro-pyrimidine
HPLC/MS (method B): RT=2.99 min.; [M+H]+=405.2

(607) 2-(4-chlorophenylamino)-4-(2-hydroxy-cyclohexylamino)-5-nitro-pyrimidine
HPLC/MS (method B): RT=2.2 min.; [M+H]+=382.1

(608) 2-(4-chlorophenylamino)-4-(2-hydroxymethyl-1-piperidinyl)-5-nitro-pyrimidine
HPLC/MS (method B): RT=3.08 min.; [M+H]+=364.2

(609) 2-(4-chlorophenylamino)-4-(N-methyl-N-[2-pyridylmethyl]-amino)-5-nitro-pyrimidine
HPLC/MS (method B): RT=2.34 min.; [M+H]+=371.1

(610) 2-(4-chlorophenylamino)-4-(N-methyl-N-[3-pyridylmethyl]-amino)-5-nitro-pyrimidine
HPLC/MS (method B): RT=2.26 min.; [M+H]+=371.1

(611) 2-(4-chlorophenylamino)-4-(1-ethyl-3-piperidinylamino)-5-nitro-pyrimidine
HPLC/MS (method B): RT=2.34 min.; [M+H]+=377.2

(612) 2-(4-chlorophenylamino)-4-(2-dimethylamino-cyclohexylamino)-5-nitro-pyrimidine
HPLC/MS (method B): RT=2.53 min.; [M+H]+=391.2

(613) 2-(4-chlorophenylamino)-4-(4-(3-hydroxy-1-propyl)-1-piperidinyl)-5-nitro-pyrimidine
HPLC/MS (method B): RT=3.16 min.; [M+H]+=392.2

(614) 2-(4-chlorophenylamino)-4-(4-(3-hydroxy-1-propyl)-1-piperazinyl)-5-nitro-pyrimidine
HPLC/MS (method B): RT=2.19 min.; [M+H]+=393.2

(615) 2-(4-chlorophenylamino)-4-(N-methyl-N-[3-(4-pyridyl)-1-propyl]-amino)-5-nitro-pyrimidine
HPLC/MS (method B): RT=2.39 min.; [M+H]+=399.2

(616) 2-(4-chlorophenylamino)-4-(4-dimethylamino-2-phenyl-1-butylamino)-5-nitro-pyrimidine
HPLC/MS (method B): RT=2.6 min.; [M+H]+=441.2

(617) 2-(4-chlorophenylamino)-4-(2-(3-diethylamino-1-propyl)-1-piperidinyl)-5-nitro-pyrimidine
HPLC/MS (method B): RT=2.77 min.; [M+H]+=447.3

(618) 2-(4-chlorophenylamino)-4-(bis-[3-pyridylmethyl]-amino)-5-nitro-pyrimidine
HPLC/MS (method B): RT=1.85 min.; [M+H]+=448.2

(619) 2-(4-chlorophenylamino)-4-(4-(N-methyl-N-[2-methoxycarbonyl-1-ethyl]-amino)-1-piperidinyl)-5-nitro-pyrimidine
HPLC/MS (method B): RT=2.11 min.; [M+H]+=449.3

(620) 2-(4-chlorophenylamino)-4-(2-(4-(2H-pyridazin-3-on-6-yl)-phenyl)-1-ethylamino)-1-piperidinyl)-5-nitro-pyrimidine (621) 2-(4-chlorophenylamino)-4-(3-(4-amino-3,5-dichlorophenyl)-1-propylamino)-5-nitro-pyrimidine (622) 2-(4-chlorophenylamino)-4-(4-(2-(N-[dimethylaminocarbonylmethyl]-N-methyl-amino)-1-ethyl-amino)-1-piperidinyl)-5-nitro-pyrimidine
HPLC/MS (method B): RT=2.21 min.; [M+H]+=476.34
(623) 2-(4-chlorophenylamino)-4-(2-(2-(2-diethylamino-1-ethoxy)-1-ethyl)-1-piperidinyl)-5-nitro-pyrimidine
(624) 2-(4-chlorophenylamino)-4-(4-(2-(2-diethylamino-1-ethoxy)-1-ethyl)-1-piperidinyl)-5-nitro-pyrimidine
(625) 2-(4-chlorophenylamino)-4-(5-(3-carboxy-1-propyl)-indan-2-yl-amino)-5-nitro-pyrimidine
(626) 2-(4-chlorophenylamino)-4-(2-ethoxycarbonyl-1-(3-pyridyl)-1-ethyl-amino)-5-nitro-pyrimidine
HPLC/MS (method B): RT=2.43 min.; [M+H]+=443.2
(627) 2-(4-chlorophenylamino)-4-(1,1-dimethyl-3-(2-oxo-3-pyridin-4-yl-imidazolidin-1-yl)-propylamino)-5-nitro-pyrimidine
HPLC/MS (method B): RT=2.4 min.; [M+H]+=497.0
(628) 2-(2-bromo-benzylamino)-4-(S-oxido-thiomorpholino)-5-nitro-pyrimidine
Prepared from 2-chloro-4-thiocyanato-5-nitro-pyrimidine, 2-bromobenzylamine and Hünig base in dioxane, evaporating the reaction mixture and further reacting with thiomorpholine-S-oxide and Hünig base in DMF. (The intermediate product was not isolated.)
Melting point: 246-250° C.
Rf=0.41 (silica gel; cyclohexane:ethyl acetate:methanol=10:8:2)
(629) 2-(4-chlorophenylamino)-4-morpholino-5-nitro-pyrimidine
melting point: 218-220° C.
(630) 2-(4-chlorophenylamino)-4-(2-cyanethylamino)-5-nitro-pyrimidine
melting point: 203° C.
(631) 2-(4-chlorophenylamino)-4-(ethoxycarbonylmethylamino)-5-nitro-pyrimidine
melting point: 202-204° C.
(632) 2-(4-chlorophenylamino)-4-[2-(ethoxycarbonyl)ethylamino]-5-nitro-pyrimidine
melting point: 163-165° C.
(633) 2-(3,4-dichlorophenylamino)-4-[3-(dimethylamino)propylamino]-5-nitro-pyrimidine
melting point: 168-170° C.
(634) 2-(3,4-dichlorophenylamino)-4-(2-hydroxyethylamino)-5-nitro-pyrimidine
melting point: 196° C.
(635) 2-(3,4-dichlorophenylamino)-4-(2-methoxyethylamino)-5-nitro-pyrimidine
melting point: 165° C.
(636) 2-(3,4-dichlorophenylamino)-4-[2-(dimethylamino)ethylamino]-5-nitro-pyrimidine
melting point: 175-176° C.
(637) 2-(3,4-dichlorophenylamino)-4-(2-morpholinoethylamino)-5-nitro-pyrimidine
melting point: 190° C.
(638) 2-(3,4-dichlorophenylamino)-4-[4-(dimethylamino)butylamino]-5-nitro-pyrimidine
melting point: 110° C.
(639) 2-(3,4-dichlorophenylamino)-4-[(2-ethoxycarbonyl-ethyl)amino]-5-nitro-pyrimidine
melting point: 137° C.
(640) 2-(4-chlorophenylamino)-4-[2-(methansulphonylamino)ethylamino]-5-nitro-pyrimidine
Prepared from compound 140 of Example 1 by subsequent reaction with methanesulphonylchloride/triethylamine
melting point: 231-235° C.
(641) 2-(4-chlorophenylamino)-4-(carboxymethylamino)-5-nitro-pyrimidine
Prepared from compound 631 of Example 1 by subsequent reaction with 1N sodium hydroxide solution in tetrahydrofuran.
melting point: >300° C.
Rf value: 0.36 (silica gel; methylene chloride/methanol=9:1)
(642) 2-(3,4-dichlorophenylamino)-4-[(2-carboxyethyl)amino]-5-nitro-pyrimidine
Prepared from compound 639 of Example 1 by subsequent reaction with 1N sodium hydroxide solution in tetrahydrofuran.
Rf value: 0.16 (silica gel; cyclohexane/ethyl acetate/methanol=7:2:1)
(643) 2-(3-bromophenylamino)-4-[1-hydroxy-3-methyl-2-butylamino]-5-trifluoromethyl-pyrimidine
Prepared from compound 5 of Example 3.
(644) 2-[4-(1,2,4,5-tetrahydro-benzo[d]azepin-3-yl-methyl)-phenylamino]-4-morpholino-5-trifluoromethyl-pyrimidine
melting point: 172° C.
(645) 2-[4-(1,2,4,5-tetrahydro-benzo[d]azepin-3-yl-methyl)-phenylamino]-4-(4-methyl-1-piperazinyl)-5-trifluoromethyl-pyrimidine
melting point: 217° C. (decomposition)
(646) 2-[4-(1,2,4,5-tetrahydro-benzo[d]azepin-3-yl-methyl)-phenylamino]-4-(1,4,6,7-tetrahydro-imidazo[4,5-c]pyridin-5-yl)-5-trifluoromethyl-pyrimidine
melting point: 350° C. (decomposition)
(647) 2-[4-(1,2,4,5-tetrahydro-benzo[d]azepin-3-yl-methyl)-phenylamino]-4-[(2-carboxyethyl)amino]-5-trifluoromethyl-pyrimidine
melting point: 120° C. (decomposition)
Prepared using beta-alanine in sodium hydroxide solution.
(648) 2-[4-(1,2,4,5-tetrahydro-benzo[d]azepin-3-yl-methyl)-phenylamino]-4-(trans-4-dimethylamino-cyclohexylamino)-5-trifluoromethyl-pyrimidine-dihydrochloride
melting point: 293° C. (decomposition)
(649) 2-[4-(1,2,4,5-tetrahydro-benzo[d]azepin-3-yl-methyl)-phenylamino]-4-(2-acetylamino-ethylamino)-5-trifluoromethyl-pyrimidine-dihydrochlorideBIBX2827BS, LD3YED00783B.
melting point: 205° C. (decomposition)
(650) 4-[4-(2-Methylamino-ethylamino)-5-trifluoromethyl-pyrimidin-2-ylamino]-benzamide
Prepared analogously to 1(80).
melting point: 187-190° C.
$R_f$=0.08 (silica gel; methylene chloride:methanol=4:1)
HPLC/MS (method G): RT=2.45 min.; [M+H]+=355; Abs. λ max=277.9 nm
(651) N-{2-[2-(3-dimethylsulphamoyl-phenylamino)-5-trifluoromethyl-pyrimidin-4-ylamino]-ethyl}-acetamide
Melting point: 202-203° C.
Rf value: 0.57 (silica gel; methylene chloride/methanol=9:1)
HPLC/MS (method D): RT=5.33 min.; [M+H]+=447; Abs./max 235 nm
(652) N-{2-[5-Bromo-2-(4-dimethylsulphamoyl-phenylamino)-pyrimidin-4-ylamino]-ethyl}-acetamide
Melting point: 226
Rf value: 0.42 (silica gel; methylene chloride/methanol=9:1)
HPLC/MS (method D): RT=4.84 min.; [M+H]+=459; Abs./max 273 nm
(653) N-(2-{2-[3-(morpholine-4-sulphonyl)-phenylamino]-5-trifluoromethyl-pyrimidin-4-ylamino}-ethyl)-acetamide Melting point: 214° C.
Rf value: 0.51 (silica gel; methylene chloride/methanol=9:1)
HPLC/MS (method D): RT=5.31 min.; [M+H]+=489; Abs./max 235 nm (654) N-{2-[2-(1-methyl-1H-indazol-6-ylamino)-5-trifluoromethyl-pyrimidin-4-ylamino]-ethyl}-acetamide
Melting point: 260-261° C.
Rf value: 0.39 (silica gel; methylene chloride/methanol=9:1)
HPLC/MS (method D): RT=4.78 min.; [M+H]+=394; Abs./max 250 nm (655) N-{2-[2-(1-methyl-1H-indazol-5-ylamino)-5-trifluoromethyl-pyrimidin-4-ylamino]-ethyl}-acetamide
Melting point: 265-266° C.
Rf value: 0.25 (silica gel; methylene chloride/methanol=9:1)
HPLC/MS (method D): RT=4.47 min.; [M+H]+=394; Abs./max 254 nm (656) N-{2-[2-(2-methyl-2H-indazol-6-ylamino)-5-trifluoromethyl-pyrimidin-4-ylamino]-ethyl}-acetamide
Melting point: 254-255° C.
Rf value: 0.45 (silica gel; methylene chloride/methanol=9:1)
HPLC/MS (method D): RT=4.45 min.; [M−H]−=394; Abs./max 250 nm (657) {2-[5-Bromo-2-(3-dimethylsulphamoyl-phenylamino)-pyrimidin-4-ylamino]-ethyl}-acetamide
Melting point: 192° C.
Rf value: 0.43 (silica gel; methylene chloride/methanol=9:1)
HPLC/MS (method D): RT=4.75 min.; [M+H]+=459; Abs. λ max=268 nm (658) N-(2-{5-Bromo-2-[3-(morpholine-4-sulphonyl)-phenylamino]-pyrimidin-4-ylamino}-ethyl)-acetamide
Melting point: 212° C.
Rf value: 0.47 (silica gel; methylene chloride/methanol=9:1)
HPLC/MS (method D): RT=4.76 min.; [M+H]+=501; Abs. λ max=268 nm (659) N-(2-{2-[4-(2-dimethylamino-ethyl)-phenylamino]-5-trifluoromethyl-pyrimidin-4-ylamino}-ethyl)-acetamide
Melting point: 110° C.
$R_f$=0.13 (silica gel; methylene chloride:methanol=1:2)
HPLC/MS (method D): RT=1.96 min.; [M+H]+=411; Abs. λ max=256

(660) N-{2-[2-(4-piperidin-1-ylmethyl-phenylamino)-5-trifluoromethyl-pyrimidin-4-ylamino]-ethyl}-acetamide
Melting point: 223-226° C.
$R_f$=0.23 (silica gel; methylene chloride:methanol=1:1)
HPLC/MS (method D): RT=3.94 min.; [M+H]+=437; Abs. λ max=265 nm (661) 1-{3-[5-Bromo-2-(3,4-dichloro-phenylamino)-pyrimidin-4-ylamino]-propyl}-pyrrolidin-2-one
Melting point: 234° C.
$R_f$=0.56 (silica gel; methylene chloride:methanol=9:1)
HPLC/MS (method C): RT=4.30 min.; [M+H]+=460; Abs. λ max=274 nm (662) 1-{3-[5-Bromo-2-(3,4-dichloro-phenylamino)-pyrimidin-4-ylamino]-propyl}-pyrrolidin-2-one
Melting point: 216-218° C.
$R_f$=0.55 (methylene chloride:methanol=5:1)
HPLC/MS (method C): RT=3.11 min.; [M+H]+=435; Abd. λ max=278

(663) 4-[4-(2-acetylamino-ethylamino)-5-bromo-pyrimidin-2-ylamino]-benzamide
Melting point: 265-266° C.
$R_f$=0.22 (silica gel; methylene chloride:methanol=9:1)
HPLC/MS (method D): RT=3.93 min.; [M+H]+=395; Abs. λ max=278

(664) N-(2-{2-[3-(benzyl-methyl-sulphamoyl)-phenylamino]-5-trifluoromethyl-pyrimidin-4-ylamino}-ethyl)-acetamide
Melting point: 126° C.
$R_f$=0.61 (silica gel; methylene chloride:methanol=9:1)
HPLC/MS (method D): RT=6.33 min.; [M+H]+=523; Abs. λ max=238 nm (665) N-(2-{2-[3-(4-methyl-piperazin-1-sulphonyl)-phenylamino]-5-trifluoromethyl-pyrimidin-4-ylamino}-ethyl)-acetamide
Melting point: 247° C.
$R_f$=0.44 (silica gel; methylene chloride:methanol=9:1)
HPLC/MS (method D): RT=4.36 min.; [M+H]+=502; Abs. λ max=234 nm (666) 4-{4-[(3-aminomethyl-cyclohexylmethyl)-amino]-5-trifluoromethyl-pyrimidin-2-ylamino}-benzamide
Melting point: 209-212° C.
$R_f$=0.03 (silica gel; methylene chloride:methanol=4:1)
HPLC/MS (method G): RT=2.87 min.; [M+H]+=423; Abs. λ max=279.8 nm (667) N-{2-[2-(4-Morpholin-4-ylmethyl-phenylamino)-5-trifluoromethyl-pyrimidin-4-ylamino]-ethyl}-acetamide
Melting point: 70° C.
$R_f$=0.69 (silica gel; methylene chloride:methanol=9:1)
HPLC/MS (method D): RT=3.98 min.; [M+H]+=439; Abs. λ max=266 nm (668) N-{2-[2-(4-cyano-3-trifluoromethyl-phenylamino)-5-trifluoromethyl-pyrimidin-4-ylamino]-ethyl}-acetamide
Melting point: 237° C.
$R_f$=0.50 (silica gel; methylene chloride:methanol=9:1)
HPLC/MS (method D): RT=6.35 min.; [M+H]+=433; Abs. λ max=318 nm (669) N-{2-[2-(3-Chloro-4-cyano-phenylamino)-5-trifluoromethyl-pyrimidin-4-ylamino]-ethyl}-acetamide
Melting point: 250° C.
$R_f$=0.45 (silica gel; methylene chloride:methanol=9:1)
HPLC/MS (method D): RT=6.20 min.; [M+H]+=399; Abs. λ max=309 nm (670) 1-(2-{[2-(3,4-dichloro-phenylamino)-5-trifluoromethyl-pyrimidin-4-yl]-methyl-amino}-ethyl)-pyrrolidin-2-one
Melting point: 164° C.
$R_f$=0.11 (silica gel; hexane:ethyl acetate=1:1)
HPLC/MS (method D): RT=6.862 min.; [M+H]+=450; Abs. λ max=270 nm (671) 1-{2-[2-(3,4-dichloro-phenylamino)-5-trifluoromethyl-pyrimidin-4-ylamino]-ethyl}-pyrrolidin-2-one
Melting point: 218° C.
$R_f$=0.23 (silica gel; hexane:ethyl acetate=1:1)
HPLC/MS (method D): RT=6.496 min.; [M+H]+=436; Abs. λ max=274 nm (672) 4-[4-(4-methanesulphonylamino-piperidin-1-yl)-5-trifluoromethyl-pyrimidin-2-ylamino]-N,N-dimethyl-phenylsulphonamide
Melting point: 218° C.
$R_f$=0.46 (silica gel; hexane:ethyl acetate=33:67)
HPLC/MS (method D): RT=6.353 min.; [M+H]+=523; Abs. λ max=294 nm (673) 4-{4-[4-(methanesulphonyl-methyl-amino)-piperidin-1-yl]-5-trifluoromethyl-pyrimidin-2-ylamino}-N,N-dimethyl-phenylsulphonamide
Melting point: 226° C.
$R_f$=0.27 (silica gel; hexane:ethyl acetate=1:1)

HPLC/MS (method D): RT=6.652 min.; [M+H]+=537; Abs. λ max=294 nm
(674) 3-[2-(1-methyl-1H-indazol-6-ylamino)-5-trifluoromethyl-pyrimidin-4-ylamino]-propylamine 4.7 g of N—Z-1,3-diaminopropane hydrochloride, 10 ml of Hünig base and 5.2 g of 2-(1-methyl-1H-indazol-6-ylamino)-4-chloro-5-trifluoromethyl-pyrimidine are suspended in 160 ml of dioxane and DMF is added until all the components have dissolved. After 17 hours at 80° C. the mixture is taken up in ethyl acetate, extracted with $H_2O$, the organic phase is then dried and concentrated by rotary evaporation. The product is chromatographed with toluene: ethyl acetate (1:1) over silica gel.

The intermediate product is dissolved in ethanol, methanol and toluene (4:1:3, 800 ml), 1 g of $Pd(OH)_2$ is added and the mixture is hydrogenated at 50 psi and 40° C. over 28 hours. After the catalyst has been filtered off and the solution concentrated, the product remains.

Melting point: 201° C., Subl.
$R_f$=0.15 (silica gel; methylene chloride:methanol=95:5)
HPLC/MS (method B): RT=4.35 min.; [M+H]+=366; Abs. λ max=226 nm (675) N-{1-[2-(3,4-dichloro-phenylamino)-5-trifluoromethyl-pyrimidin-4-yl]-piperidin-4-yl}-methanesulphonamide
Melting point: 200° C.
$R_f$=0.42 (silica gel; hexane:ethyl acetate=1:1)
HPLC/MS (method D): RT=7.105 min.; [M+H]+=486; Abs. λ max=274 nm (676) (4-Chloro-phenyl)-[4-(1-oxo-1,4-thiomorpholin-4-yl)-5-trifluoromethyl-pyrimidin-2-yl]-amine
Melting point: 213-216° C.
$R_f$=0.42 (silica gel; hexane:ethyl acetate=2:1)
HPLC/MS (method D): RT=6.015 min.; [M+H]+=391; Abs. λ max=259 nm (677) (3-Chloro-phenyl)-[4-(4-pyridin-2-yl-piperazin-1-yl)-5-trifluoromethyl-pyrimidin-2-yl]-amine
Melting point: 146-147° C.
$R_f$=0.66 (silica gel; methylene chloride:methanol=95:5)
HPLC/MS (method D): RT=5.203 min.; [M+H]+=435; Abs. λ max=271 nm (678) 1-{3-[2-(3,5-dichloro-phenylamino)-5-trifluoromethyl-pyrimidin-4-ylamino]-propyl}-pyrrolidin-2-one
Melting point: 174-175° C.
$R_f$=0.10 (silica gel; hexane:ethyl acetate=1:1)
HPLC/MS (method D): RT=6.309 min.; [M+H]+=450; Abs. λ max=230 nm (679) (3-Chloro-phenyl)-[4-(1-oxo-1-thiomorpholin-4-yl)-5-trifluoromethyl-pyrimidin-2-yl]-amine
Melting point: 214-217° C.
$R_f$=0.51 (silica gel; methylene chloride:methanol=95:5)
HPLC/MS (method D): RT=5.571 min.; [M+H]+=391; Abs. λ max=270 nm (680) (4-Chloro-phenyl)-[4-(4-pyridin-2-yl-piperazin-1-yl)-5-trifluoromethyl-pyrimidin-2-yl]-amine
Melting point: 164-166° C.
$R_f$=0.43 (silica gel; hexane:ethyl acetate:methanol=5:4:1)

(681) methyl {1-[2-(4-chloro-phenylamino)-5-trifluoromethyl-pyrimidin-4-yl]-piperidin-4-yl}-acetate
$R_f$=0.86 (silica gel; hexane:ethyl acetate=1:1)
HPLC/MS (method D): RT=7.521 min.; [M+H]+=429; Abs. λ max=266 nm (682) {1-[2-(4-Chloro-phenylamino)-5-trifluoromethyl-pyrimidin-4-yl]-piperidin-4-yl}-acetic acid
Melting point: 200-201° C.
$R_f$=0.44 (silica gel; hexane:ethyl acetate=1:1)
HPLC/MS (method D): RT=6.623 min.; [M+H]+=415; Abs. λ max=270 nm (683) N,N-dimethyl-4-{4-[2-(2-oxo-pyrrolidin-1-yl)-ethylamino]-5-trifluoromethyl-pyrimidin-2-ylamino}-phenylsulphonamide
Melting point: 258-261° C.
$R_f$=0.14 (silica gel; hexane:ethyl acetate=1:2)
HPLC/MS (method D): RT=5.828 min.; [M+H]+=473; Abs. λ max=302 nm (684) N,N-dimethyl-4-(4-{methyl-[2-(2-oxo-pyrrolidin-1-yl)-ethyl]-amino}-5-trifluoromethyl-pyrimidin-2-ylamino)-benzenesulphonamide
Melting point: 147-150° C.
$R_f$=0.13 (silica gel; hexane:ethyl acetate=2:1)
HPLC/MS (method D): RT=6.15 min.; [M+H]+=487; Abs. λ max=290 nm (685) N-(1,1-dimethyl-2-{2-[4-(morpholine-4-sulphonyl)-phenylamino]-5-trifluoromethyl-pyrimidin-4-ylamino}-ethyl)-acetamide
Melting point: 105-107° C.
$R_f$=0.39 (silica gel; ethyl acetate)
HPLC/MS (method D): RT=5.89 min.; [M+H]+=517; Abs. λ max=302 nm (686) N4-methyl-N4-(2-methylamino-ethyl)-N2-[4-(morpholine-4-sulphonyl)-phenyl]-5-trifluoromethyl-pyrimidine-2,4-diamine formate
Melting point: 184-186° C.
$R_f$=0.09 (silica gel; methylene chloride:methanol=9:1)
HPLC/MS (method D): RT=4.83 min.; [M+H]+=475; Abs. λ max=302 nm (687) N,N-dimethyl-4-{4-[methyl-(2-methylamino-ethyl)-amino]-5-trifluoromethyl-pyrimidin-2-ylamino}-benzenesulphonamide hydrochloride
Melting point: 235-238° C.
$R_f$=0.10 (silica gel; methylene chloride:methanol=9:1)
HPLC/MS (method D): RT=4.86 min.; [M+H]+=433; Abs. λ max=298 nm (688) benzyl (2-{2-[4-(morpholin-4-sulphonyl)-phenylamino]-5-trifluoromethyl-pyrimidin-4-ylamino}-ethyl)-carbonate
Melting point: 166-169° C.
$R_f$=0.61 (silica gel; ethyl acetate)
HPLC/MS (method D): RT=6.64 min.; [M+H]+=581; Abs. λ max=306 nm (689) N4-(2-amino-ethyl)-N2-[4-(morpholine-4-sulphonyl)-phenyl]-5-trifluoromethyl-pyrimidine-2,4-diamine
Melting point: 169-170° C.
$R_f$=0.20 (silica gel; methylene chloride:methanol=1:1)
HPLC/MS (method D): RT=4.88 min.; [M+H]+=447; Abs. λ max=302 nm (690) N-(2-{[2-(4-dimethylsulphamoyl-phenylamino)-5-trifluoromethyl-pyrimidin-4-yl]-methyl-amino}-ethyl)-N-methyl-acetamide
Melting point: 156-158° C.
$R_f$=0.17 (silica gel; ethyl acetate)
HPLC/MS (method D): RT=6.12 min.; [M+H]+=475; Abs. λ max=282 nm (691) N-methyl-N-[2-(methyl-{2-[4-(morpholine-4-sulphonyl)-phenylamino]-5-trifluoromethyl-pyrimidin-4-yl}-amino)-ethyl]-acetamide
Melting point: 158-161° C.
$R_f$=0.15 (silica gel; ethyl acetate)
HPLC/MS (method D): RT=6.04 min.; [M+H]+=517; Abs. λ max=294 nm (692) N-(2-{2-[4-(propane-2-sulphonyl)-phenylamino]-5-trifluoromethyl-pyrimidin-4-ylamino}-ethyl)-acetamide
Melting point: 198-200° C.

$R_f$=0.60 (silica gel; methylene chloride:methanol=9:1)
HPLC/MS (method C): RT=3.97 min.; [M+H]+=446; Abs. λ max=302 nm (693) 4-[4-(3-aminopropylamino)-5-trifluoromethyl-pyrimidin-2-ylamino]benzamide
The compound was obtained analogously to Example 1 (674)

(694) N,N-dimethyl-4-[4-(3,4,6,7-tetrahydro-imidazo[4,5-c]pyridin-5-yl)-5-trifluoromethyl-pyrimidin-2-ylamino]-phenylsulphonamide
Melting point: 230° C. decomposition
$R_f$=0.28 (silica gel; methylene chloride:methanol=95:5)
HPLC/MS (method D): RT=5.20 min.; [M+H]+=468; Abs. λ max=286, 302 nm (695) [4-(Morpholin-4-sulphonyl)-phenyl]-[4-(3,4,6,7-tetrahydro-imidazo[4,5-5]pyridin-5-yl)-5-trifluoromethyl-pyrimidin-2-yl]-amine
Melting point: >270° C. decomposition
$R_f$=0.33 (silica gel; methylene chloride:methanol=95:5)
HPLC/MS (method D): RT=5.30 min.; [M+H]+=510; Abs. λ max=302 nm (696) benzyl {3-[2-(1-methyl-1H-indazol-6-ylamino)-5-trifluoromethyl-pyrimidin-4-ylamino]-propyl}-carbaminate
Melting point: 139° C.
$R_f$=0.30 (silica gel; toluene:ethyl acetate=1:1)
HPLC/MS (method D): RT=6.37 min.; [M+H]+=500; Abs. λ max=250 nm Example 2

2-(4-carboxyphenylamino)-4-(2-acetylamino-ethylamino)-5-nitro-pyrimidine-hydrochloride 100 mg of 4-aminobenzoic acid in 5 ml ethanol are added to 173 mg of 2-chloro-4-(2-acetylamino-ethylamino)-5-nitro-pyrimidine (compound (1) of Example II) in 5 ml ethanol at ambient temperature. Two drops of concentrated hydrochloric acid are added and the mixture is stirred for 12 h. Then 50 ml of water are added. The precipitate is suction filtered and dried in the air. The residue is stirred with 30 ml methylene chloride, suction filtered and dried.
Yield: 135 mg (51% of theory), Melting point: 290° C. (decomposition)
$R_f$=0.2 (silica gel; methylene chloride:methanol=9:1)
The following compounds are obtained analogously to Example 2:

(1) 2-(3,4-dichlorophenylamino)-4-(2-acetylamino-ethylamino)-5-trifluoromethylsulphanyl-pyrimidine-hydrochloride
Melting point: 196° C.
$R_f$=0.5 (silica gel; methylene chloride:methanol:conc. ammonia=16:3:1)
Prepared from compound (3) of Example II.

(2) 2-(3,4-dichlorophenylamino)-4-(2-acetylamino-ethylamino)-5-bromo-pyrimidine-hydrochloride
Melting point: 260° C. (decomposition)
Prepared from compound (4) of Example II.

(3) 2-(3,4-dichlorophenylamino)-4-(2-acetylamino-ethylamino)-5-trifluoromethyl-pyrimidine-hydrochloride
Melting point: 227° C.
Prepared from the compound of Example II.

(4) N-{2-[2-(4-amino-phenylamino)-5-trifluoromethyl-pyrimidin-4-ylamino]-ethyl}-acetamide
6.9 g of p-phenylenediamine are added to 3 g of N-[2-(2-chloro-5-trifluoromethyl-pyrimidin-4-ylamino)-ethyl]-acetamide in 25 ml glacial acetic acid and the mixture is stirred for 2 hours at ambient temperature. After removal of the acetic acid under reduced pressure the crude product is taken up in methylene chloride and extracted with 2 M sodium carbonate solution. The aqueous phase is washed with methylene chloride, the organic phases are combined and dried over sodium sulphate. After evaporation, the material is chromatographed over silica gel with methylene chloride/isopropanol (20:1).
Yield: 3 g
Melting point: 175° C. decomposition
$R_f$=0.35 (silica gel; methylene chloride:isopropanol=8:2)
APCI-MS [M+H]+=355
1H-NMR ($D_6$-DMSO, 300 MHz) δ: 1.80 (s, 3H), 3.25 (m, 2H), 3.47 (m, 2H), 4.78 (bs, 2H), 6.50 (d, 2H), 6.93 (bs, 2H), 7.29 (d, 2H), 7.90 (t, 1H), 8.08 (s, 1H), 9.13 (s, 1H).

(5) 2-(3,4-dichlorophenylamino)-4-(2-acetylamino-ethylamino)-5-methylsulphanyl-pyrimidine-hydrochloride
Melting point: 220° C.
Prepared from compound (2) of Example II.

(6) 2-(1-naphthylamino)-4-[N-(trans-4-hydroxy-cyclohexyl)-N-methyl-amino]-5-nitro-pyrimidine
HPLC/MS (Method B): RT=2.55 min.; [M+H]+=394.2

(7) 2-(4-bromophenylamino)-4-(2-acetylamino-ethylamino)-5-trifluoromethyl-pyrimidine
HPLC/MS (Method A): RT=5.83 min.; [M+H]+=420.1

(8) 2-(4-aminosulphonyl-phenylamino)-4-(2-acetylamino-ethylamino)-5-trifluoromethyl-pyrimidine
HPLC/MS (Method A): RT=4.95 min.; [M+H]+=419.1

(9) 2-(3-chloro-phenylamino)-4-(2-acetylamino-ethylamino)-5-trifluoromethyl-pyrimidine
HPLC/MS (Method A): RT=5.84 min.; [M+H]+=374.1

(10) 2-(3-Nitro-phenylamino)-4-(2-acetylamino-ethylamino)-5-trifluoromethyl-pyrimidine
Melting point: 201-204° C.
$R_f$=0.60 (silica gel; methylene chloride:methanol=95:5)
HPLC/MS (method D): RT=5.398 min.; [M+H]+=385; Abs. λ max=266 nm

(11) 2-(4-(N-Methyl-N-methylsulphonyl)amino-phenylamino)-4-(2-acetylamino-ethylamino)-5-trifluoromethyl-pyrimidine
HPLC/MS (method A): RT=5.15 min.; [M+H]+=447.2

(12) 2-(3-bromo-phenylamino)-4-(2-acetylamino-ethylamino)-5-trifluoromethyl-pyrimidine
$R_f$=0.60 (silica gel; cyclohexane:ethyl acetate=1:2)
HPLC/MS (method D): RT=5.68 min.; [M+H]+=419; Abs. λ max=254 nm

(13) 2-(4-chloro-3-trifluoromethyl-phenylamino)-4-(2-acetylamino-ethylamino)-5-trifluoromethyl-pyrimidine
HPLC/MS (method A): RT=6.71 min.; [M+H]+=442.1

(14) 2-(4-bromo-3-chloro-phenylamino)-4-(2-acetylamino-ethylamino)-5-trifluoromethyl-pyrimidine
HPLC/MS (method A): RT=6.57 min.; [M+H]+=454.0

(15) 2-(3,5-Dichloro-phenylamino)-4-(2-acetylamino-ethylamino)-5-trifluoromethyl-pyrimidine
HPLC/MS (method A): RT=6.73 min.; [M+H]+=408.1

(16) 2-(4-chloro-phenylamino)-4-(2-acetylamino-ethylamino)-5-trifluoromethyl-pyrimidine
HPLC/MS (method A): RT=5.71 min.; [M+H]+=374.1

(17) 2-(4-Morpholino-phenylamino)-4-(2-acetylamino-ethylamino)-5-nitro-pyrimidin
HPLC/MS (method A): RT=5.22 min.; [M+H]+=402.2

(18) 2-(4-(N-Methyl-N-methylsulphonyl)amino-phenylamino)-4-(N-(trans-4-hydroxy-cyclohexyl)-N-methyl-amino)-5-nitro-pyrimidine
HPLC/MS (method A): RT=5.89 min.; [M+H]+=451.2

(19) 2-(4-Diethylaminomethyl-phenylamino)-4-(2-acetylamino-ethylamino)-5-nitro-pyrimidine
HPLC/MS (method A): RT=4.7 min.; [M+H]+=402.2

(20) 2-(1,3-Dihydro-2-oxo-indol-6-ylamino)-4-[N-(trans-4-hydroxy-cyclohexyl)-N-methyl-amino]-5-nitro-pyrimidine
HPLC/MS (method A): RT=5.51 min.; [M+H]+=399.2

(21) 2-(4-(N-Methyl-N-methylsulphonyl)amino-phenylamino)-4-(2-acetylamino-ethylamino)-5-nitro-pyrimidine
HPLC/MS (method A): RT=5.46 min.; [M+H]+=424.2

(22) 2-(3-Hydroxy-4-methyl-phenylamino)-4-(trans-4-hydroxy-cyclohexylamino)-5-trifluoromethyl-pyrimidine
HPLC/MS (method B): RT=1.61 min.; [M+H]+=383.3

(23) 2-(3-Hydroxy-4-methyl-phenylamino)-4-[N-(trans-4-hydroxy-cyclohexyl)-N-methyl-amino]-5-nitro-pyrimidine
HPLC/MS (method B): RT=2.2 min.; [M+H]+=374.2

(24) 2-(6-Indazolylamino)-4-[N-(trans-4-hydroxy-cyclohexyl)-N-methyl-amino]-5-nitro-pyrimidine
HPLC/MS (method B): RT=2.26 min.; [M+H]+=384.2

(25) 2-(1-Naphthylamino)-4-(trans-4-hydroxy-cyclohexylamino)-5-trifluoromethyl-pyrimidine

(26) 2-(4-(3-Diethylamino-1-propyloxy)-phenylamino)-4-(2-pyridyl-methylamino)-5-nitro-pyrimidine
HPLC/MS (method B): RT=1.26 min.; [M+H]+=452.3

(27) 2-(3-Hydroxy-4-methyl-phenylamino)-4-(2-acetylamino-1-ethylamino)-5-trifluoromethyl-pyrimidine
HPLC/MS (method B): RT=1.49 min.; [M+H]+=370.2

(28) 2-(4-Benzylaminocarbonyl-phenylamino)-4-[N-(2-hydroxyethyl)-N-methyl-amino]-5-nitro-pyrimidine
HPLC/MS (method B): RT=2.47 min.; [M+H]+=423.2

(29) 2-(3-Carboxy-phenylamino)-4-[N-(trans-4-hydroxy-cyclohexyl)-N-methyl-amino]-5-nitro-pyrimidine
HPLC/MS (method B): RT=2.21 min.; [M+H]+=388.2

(30) 2-(5-Carboxy-2-naphthylamino)-4-(2-acetylamino-1-ethylamino)-5-nitro-pyrimidine
HPLC/MS (method B): RT=2.22 min.; [M+H]+=411.2

(31) 2-(5-Carboxy-2-naphthylamino)-4-(2-pyridyl-methylamino)-5-nitro-pyrimidine

(32) 2-(5-Carboxy-2-naphthylamino)-4-(ethoxycarbonyl-methylamino)-5-nitro-pyrimidine
HPLC/MS (method B): RT=2.71 min.; [M+H]+=412.2

(33) 2-(4-Phenylaminocarbonyl-phenylamino)-4-[N-(2-hydroxyethyl)-N-methyl-amino]-5-nitro-pyrimidine
HPLC/MS (method B): RT=2.56 min.; [M+H]+=409.2

(34) 2-(4-(4-Methyl-1-piperazinyl)-phenylamino)-4-[N-(trans-4-hydroxy-cyclohexyl)-N-methyl-amino]-5-nitro-pyrimidine
HPLC/MS (method B): RT=1.77 min.; [M+H]+=442.3

(35) 2-(3,4-Dichlorphenylamino)-4-(2-acetylamino-ethylamino)-5-methyl-pyrimidine-hydrochlorid
Melting point: 254° C.

(36) 1-{3-[2-(1H-Benzotriazol-5-ylamino)-5-trifluoromethyl-pyrimidin-4-ylamino]-propyl}-pyrrolidin-2-one
$R_f$=0.16 (silica gel; methylene chloride:methanol=95:5)
Melting point: 118° C.

(37) 1-{3-[2-(1H-Benzimidazol-5-ylamino)-5-trifluoromethyl-pyrimidin-4-ylamino]-propyl}-pyrrolidin-2-one
Melting point: 110-113° C.
$R_f$=0.43 (silica gel; methylene chloride:methanol=95:5)
HPLC/MS (method D): RT=5.00 min.; [M+H]+=420; Abs. λ max=246 nm

(38) 1-{3-[2-(1H-Indazol-6-ylamino)-5-trifluoromethyl-pyrimidin-4-ylamino]-propyl}-pyrrolidin-2-one
$R_f$=0.18 (silica gel; methylene chloride:methanol=95:5)
Melting point: 210° C.
HPLC/MS (method D): RT=5.20 min.; [M+H]+=420; Abs. λ max=246 nm

(39) 1-{3-[2-(1H-Indazol-5-ylamino)-5-trifluoromethyl-2,3-dihydro-pyrimidin-4-ylamino]-propyl}-pyrrolidin-2-one
$R_f$=0.27 (silica gel; methylene chloride:methanol=95:5)
Melting point: 202° C.
HPLC/MS (method D): RT=4.50 min.; [M+H]+=420; Abs. λ max=237 nm

(40) N-{2-[5-chloro-2-(1H-indazol-6-ylamino)-pyrimidin-4-ylamino]-ethyl}-acetamide
Melting point: >260° C. decomposition
$R_f$=0.29 (silica gel; methylene chloride:methanol=9:1)
HPLC/MS (method F): RT=3.04 min.; [M+H]+=346; Abs. λ max=284 nm

(41) N,N-Dimethyl-4-{4-[3-(2-oxo-pyrrolidin-1-yl)-propylamino]-5-trifluoromethyl-pyrimidin-2-ylamino}-phenyl-sulphonamide
$R_f$=0.43 (silica gel; methylene chloride:methanol=95:5)
Melting point: 190-193° C.
HPLC/MS [M−H]−=485

(42) N-{2-[2-(1H-Benzotriazol-5-ylamino)-5-trifluoromethyl-pyrimidin-4-ylamino]-ethyl}-acetamide
$R_f$=0.17 (silica gel; methylene chloride:methanol=95:5)
Melting point: >300° C., decomposition

(43) N-{2-[2-(1H-Benzimidazol-5-ylamino)-5-trifluoromethyl-pyrimidin-4-ylamino]-ethyl}-acetamide
$R_f$=0.33 (silica gel; methylene chloride:methanol=95:5)
Melting point: 208-210° C.
HPLC/MS (method D): RT=3.90 min.; [M+H]+=380; Abs. λ max=240 nm

(44) N-{2-[2-(1H-Indazol-6-ylamino)-5-trifluoromethyl-pyrimidin-4-ylamino]-ethyl}-acetamide
$R_f$=0.21 (silica gel; methylene chloride:methanol=95:5)
Melting point: >300° C.
HPLC/MS (method D): RT=4.80 min.; [M+H]+=380; Abs. λ max=244 nm

(45) N-{2-[2-(1H-Indazol-5-ylamino)-5-trifluoromethyl-pyrimidin-4-ylamino]-ethyl}-acetamide
$R_f$=0.17 (silica gel; methylene chloride:methanol=95:5)
Melting point: >300° C. decomposition
HPLC/MS (method D): RT=4.20 min.; [M+H]+=380; Abs. λ max=246 nm

(46) N-(2-{2-[4-(2H-Tetrazol-5-yl)-phenylamino]-5-trifluoromethyl-pyrimidin-4-ylamino}-ethyl)-acetamide
Melting point: >300° C. decomposition
$R_f$=0.86 (silica gel; methylene chloride:methanol=1:1)
HPLC/MS (method D): RT=5.00 min.; [M+H]+=408; Abs. λ max=290 nm

(47) N-{2-[2-(4-Dimethylsulphamoyl-phenylamino)-5-trifluoromethyl-pyrimidin-4-ylamino]-ethyl}-acetamide
Melting point: 204° C.
$R_f$=0.79 (silica gel; methylene chloride:methanol=95:5)
HPLC/MS (method D): RT=5.60 min.; [M+H]+=447; Abs. λ max=300 nm

(48) 1-{3-[5-chloro-2-(1H-indazol-6-ylamino)-pyrimidin-4-ylamino]-propyl}-pyrrolidin-2-on
Melting point: 188-191° C.
$R_f$=0.41 (silica gel; methylene chloride:methanol=9:1)
HPLC/MS (method F): RT=3.23 min.; [M+H]+=386; Abs. λ max=249 nm

(49) N,N-Dimethyl-4-{4-[2-(2-oxo-imidazolidin-1-yl)-ethylamino]-5-trifluoromethyl-pyrimidin-2-ylamino}-phenyl-sulphonamid
Melting point: 163-164° C.
$R_f$=0.13 (silica gel; methylene chloride:methanol=98:2)
HPLC/MS (method D): RT=6.82 min.; [M+H]+=474; Abs. λ max=306 nm

(50) 2-chloro-5-{4-[3-(2-oxo-pyrrolidin-1-yl)-propylamino]-5-trifluoromethyl-pyrimidin-2-ylamino}-benzoic acid
Melting point: 236-239° C.
$R_f$=0.1 (silica gel; methylene chloride:methanol=9:1)
HPLC/MS (method G): RT=3.35 min.; [M+H]+=458; Abs. λ max=267 nm

(51) 1-(2-{2-[4-(Morpholin-4-sulphonyl)-phenylamino]-5-trifluoromethyl-pyrimidin-4-ylamino}-ethyl)-imidazolidin-2-one
Melting point: 164° C.
$R_f$=0.10 (silica gel; methylene chloride:methanol=98:2)
HPLC/MS (method D): RT=5.63 min.; [M+H]+=516; Abs. λ max=302 nm

(52) 1-{3-[2-(4-Hydroxymethyl-phenylamino)-5-trifluoromethyl-pyrimidin-4-ylamino]-propyl}-pyrrolidin-2-one
Melting point: 153° C.
$R_f$=0.18 (silica gel; methylene chloride:methanol=9:1)
HPLC/MS (method D): RT=4.75 min.; [M+H]+=410; Abs. λ max=256 nm

(53) 2-{4-[4-(2-Acetylamino-ethylamino)-5-trifluoromethyl-pyrimidin-2-ylamino]-phenyl}-N,N-dimethyl-acetamide
Melting point: 182-184° C.
$R_f$=0.09 (silica gel; hexane:ethyl acetate:methanol=5:4:1)
HPLC/MS (method D): RT=4.357 min; [M+H]+=425; Abs. λ max=246 nm

(54) 1-[2-(3,4-Dichloro-phenylamino)-5-trifluoromethyl-pyrimidine-4-yl]-azepan-4-one
Melting point: 147-149° C.
$R_f$=0.82 (silica gel; methylene chloride:methanol=95:5)
HPLC/MS (method D): RT=7.27 min.; [M+H]+=421; Abs. λ max=274 nm

(55) (3,4-Dichloro-phenyl)-[4-(4,5,7,8-tetrahydro-1H-imidazo[4,5-d]azepin-6-yl)-5-trifluoromethyl-pyrimidine-2-yl]-amine
Melting point: 247° C. decomposition
$R_f$=0.19 (silica gel; methylene chloride:methanol=95:5)
HPLC/MS (method D): RT=5.51 min.; [M+H]+=443; Abs. λ max=274 nm

(56) (3,4-Dichloro-phenyl)-[4-(2-methyl-4,5,7,8-tetrahydro-1H-imidazo[4,5-d]azepin-6-yl)-5-trifluoromethyl-pyrimidine-2-yl]-amine
Melting point: 245° C. decomposition
$R_f$=0.14 (silica gel; methylene chloride:methanol=95:5)
HPLC/MS (method D): RT=5.59 min.; [M+H]+=459; Abs. λ max=274 nm

(57) N-(2-{2-[4-(Morpholin-4-sulphonyl)-phenylamino]-5-trifluoromethyl-pyrimidin-4-ylamino}-ethyl)-acetamide
Melting point: 73-75° C.
$R_f$=0.19 (silica gel; methylene chloride:methanol=95:5)
HPLC/MS (method D): RT=5.40 min.; [M−H]−=487; Abs. λ max=277 nm

(58) N-(2-{2-[4-(4-Methyl-piperazin-1-sulphonyl)-phenylamino]-5-trifluoromethyl-pyrimidin-4-ylamino}-ethyl)-acetamide
Melting point: 125-127° C.
$R_f$=0.10 (silica gel; methylene chloride:methanol=95:5)
HPLC/MS (method D): RT=4.40 min.; [M+H]+=502; Abs. λ max=270 nm

(59) N-(2-{2-[4-(Pyridin-2-ylsulphamoyl)-phenylamino]-5-trifluoromethyl-pyrimidin-4-ylamino}-ethyl)-acetamide
Melting point: 228° C.
$R_f$=0.54 (silica gel; methylene chloride:methanol=95:5)
HPLC/MS (method D): RT=4.80 min.; [M+H]+=496; Abs. λ max=246 nm

(60) N-(2-{2-[4-(Perhydro-1,4-diazepin-1-sulphonyl)-phenylamino]-5-trifluoromethyl-pyrimidin-4-ylamino}-ethyl)-acetamide
Melting point: 167-169° C.
$R_f$=0.36 (silica gel; methylene chloride:methanol=95:5)
HPLC/MS (method D): RT=4.40 min.; [M+H]+=502; Abs. λ max=270 nm

(61) N-(2-{2-[4-(3,5-Dimethyl-piperazin-1-sulphonyl)-phenylamino]-5-trifluoromethyl-pyrimidin-4-ylamino}-ethyl)-acetamide
Melting point: 117° C.
$R_f$=0.16 (silica gel; methylene chloride:methanol=95:5)
HPLC/MS (method D): RT=4.50 min.; [M+H]+=516; Abs. λ max=270 nm

(62) N-[2-(2-phenylamino-5-trifluoromethylpyrimidin-4-ylamino)-ethyl]-acetamide
350 mg of 2-chloro-4-(2-acetylamino-ethylamino)-5-trifluoromethyl-pyrimidine and 630 mg of 4-(4-[tert-butyl-oxycarbonyl]-homopiperazin-1-sulphonyl)-phenylamine are mixed with 3 ml of dioxane and N,N-dimethylformamide is added until all the components are dissolved. Then 0.25 ml of 4.0M hydrochloric acid in 1,4-dioxane are added dropwise and the mixture is heated to 80° C. for 2 hours with stirring. Then additional 4.0M hydrochloric acid in 1,4-dioxane (1 ml) is added and the mixture is heated to 85° C. for 15 minutes. The precipitate formed is filtered off and washed with dioxane. After dissolving in water the solution is purified through an RP C-18 column with $H_2O$/acetonitrile as eluant. After evaporation the product is left behind as a solid.
Melting point: 175° C. decomposition
Rf=0.44 (silica gel; methylene chloride:methanol=9:1)
HPLC/MS (method D): RT=4.605 min; [M+H]+=340

(63) 4-{5-isopropyl-4-[3-(2-oxo-pyrrolidin-1-yl)-propylamino]-pyrimidin-2-ylamino}-benzamide
melting point: 204-205° C.
Rf=0.13 (silica gel; methylene chloride:methanol=9:1)
HPLC/MS (method G): RT=2.99 min.; [M+H]+=397; Abs. λ max=279.8 nm

(64) 1-{3-[2-(3-Chloro-4-morpholine-4-yl-phenylamino)-5-trifluoromethyl-pyrimidin-4-ylamino]-propyl}-pyrrolidin-2-one
melting point: 131-134° C.
Rf=0.56 (silica gel; methylene chloride:methanol=9:1)
HPLC/MS (method G): RT=3.61 min.; [M+H]+=499; Abs. λ max=230 nm

(65) N-[2-(2-benzylamino-5-trifluoromethyl-pyrimidin-4-ylamino)-ethyl]-acetamide
melting point: 190-191° C.
Rf=0.57 (silica gel; methylene chloride:methanol=9:1)
HPLC/MS (method G): RT=3.37 min.; [M+H]+=354; Abs. λ max=230 nm

(66) N-(2-{2-[4-(4-methoxy-piperidin-1-ylmethyl)-phenylamino]-5-trifluoromethyl-pyrimidin-4-ylamino}-ethyl)-acetamide

(67) N-{2-[2-(3-amino-phenylamino)-5-trifluoromethyl-pyrimidin-4-ylamino]-ethyl}-acetamide
melting point: 198-200° C.
Rf=0.48 (silica gel; methylene chloride:methanol=9:1)
HPLC/MS (method F): RT=2.97 min.; [M+H]+=355; Abs. λ max=253 nm
1H-NMR ($D_6$-DMSO, 300 MHz) δ: 1.80 (s, 3H), 3.30 (m, 2H), 3.52 (m, 2H), 4.99 (m, 2H), 6.20 (d, 1H), 6.92-6.79 (m, 2H), 7.05 (m, 2H), 7.99 (t, 1H), 8.14 (s, 1H), 9.30 (s, 1H).

(68) 4-[4-(4-pyrimidin-2-yl-piperazin-1-yl)-5-trifluoromethyl-pyrimidin-2-ylamino]-benzamide
melting point: 260-262° C.
$R_f$=0.23 (silica gel; methylene chloride:methanol=9:1)

HPLC/MS (method G): RT=3.60 min.; [M+H]+=445; Abs. λ max=287.4 nm

(69) N-{2-[5-isopropyl-2-(4-piperidin-1-ylmethyl-phenylamino)-pyrimidin-4-ylamino]-ethyl}-acetamide
melting point: 165-168° C.
$R_f$=0.07 (silica gel; methylene chloride:methanol=4:1)
HPLC/MS (method F): RT=3.01 min.; [M+H]+=411; Abs. λ max=260.8 nm

(70) 1-{3-[5-methoxy-2-(4-piperidin-1-ylmethyl-phenylamino)-pyrimidin-4-ylamino]-propyl}-pyrrolidin-2-one
$R_f$=0.07 (silica gel; methylene chloride:methanol=4:1)
HPLC/MS (method F): RT=3.00 min.; [M+H]+=439; Abs. λ max=260.8 nm

(71) 4-{5-dimethylamino-4-[3-(2-oxo-pyrrolidin-1-yl)-propylamino]-pyrimidin-2-ylamino}-benzamide
melting point: 202-203° C.
$R_f$=0.14 (silica gel; methylene chloride:methanol=9:1)
HPLC/MS (method G): RT=2.88 min.; [M+H]+=398; Abs. λ max=295 nm

(72) 4-{4-[4-(2-nitro-phenyl)-piperazin-1-yl]-5-trifluoromethyl-pyrimidin-2-ylamino}-benzamide
melting point: 223-225° C.
$R_f$=0.06 (silica gel; methylene chloride:methanol=99:1)
HPLC/MS (method G): RT=4.45 min.; [M+H]+=488; Abs. λ max=258.9 nm

(73) N,N-dimethyl-4-[4-(4,5,7,8-tetrahydro-1H-imidazo[4,5-d]azepin-6-yl)-5-trifluoromethyl-pyrimidin-2-ylamino]-phenylsulphonamide
melting point: 152-155° C.
$R_f$=0.26 (silica gel; methylene chloride:methanol=95:5)
HPLC/MS (method D): RT=5.35 min.; [M+H]+=482; Abs. λ max=298 nm

(74) N-{2-[2-(1H-indazol-6-ylamino)-5-methyl-pyrimidin-4-ylamino]-ethyl}-acetamide
melting point: 240-243° C.
$R_f$=0.22 (silica gel; methylene chloride:methanol=4:1)
HPLC/MS (method F): RT=3.05 min.; [M+H]+=326; Abs. λ max=248 nm

(75) 1-{3-[2-(1H-indazol-6-ylamino)-5-methyl-pyrimidin-4-ylamino]-propyl}-pyrrolidin-2-one
melting point: 227-230° C.
$R_f$=0.17 (silica gel; methylene chloride:methanol=9:1)
HPLC/MS (method F): RT=3.24 min.; [M+H]+=366; Abs. λ max=248 nm

(76) 1-(3-{2-[4-(2H-tetrazol-5-yl)-phenylamino]-5-trifluoromethyl-pyrimidin-4-ylamino}-propyl)-pyrrolidin-2-one
melting point: >300° C. decomposition
$R_f$=0.06 (silica gel; methylene chloride:methanol=95:5)
HPLC/MS (method D): RT=5.10 min.; [M+H]+=448; Abs. λ max=236 nm

(77) N-{2-[2-(4-sulphamoyl-benzylamino)-5-trifluoromethyl-pyrimidin-4-ylamino]-ethyl}-acetamide
melting point: 205-207° C.
$R_f$=0.39 (silica gel; methylene chloride:methanol=85:15)
HPLC/MS (method G): RT=2.31 min.; [M+H]+=433; Abs. λ max=232 nm

(78) N-{2-[5-Bromo-2-(1H-indazol-6-ylamino)-pyrimidin-4-ylamino]-ethyl}-acetamide
melting point: 270-272° C.
$R_f$=0.32 (silica gel; methylene chloride:methanol=9:1)
HPLC/MS (method F): RT=3.09 min.; [M+H]+=391; Abs. λ max=251 nm

(79) 1-{3-[2-(3-dimethylamino-phenylamino)-5-trifluoromethyl-pyrimidin-4-ylamino]-propyl}-pyrrolidin-2-one
melting point: 152-155° C.
$R_f$=0.6 (silica gel; methylene chloride:methanol=9:1)
HPLC/MS (method G): RT=2.49 min.; [M+H]+=423; Abs. λ max=253 nm

(80) 1-{3-[2-(2,4-dichloro-phenylamino)-5-trifluoromethyl-pyrimidin-4-ylamino]-propyl}-pyrrolidin-2-one
melting point: 148-150° C.
$R_f$=0.67 (silica gel; methylene chloride:methanol=9:1)
HPLC/MS (method G): RT=4.3 min.; [M+H]+=449; Abs. λ max=234 nm

(81) 1-{3-[2-(4-methoxy-2-methyl-phenylamino)-5-trifluoromethyl-pyrimidin-4-ylamino]-propyl}-pyrrolidin-2-one
melting point: 127-130° C.
$R_f$=0.58 (silica gel; methylene chloride:methanol=9:1)
HPLC/MS (method G): RT=3.68 min.; [M+H]+=424; Abs. λ max=236 nm

(82) 1-{3-[2-(2,5-dichloro-phenylamino)-5-trifluoromethyl-pyrimidin-4-ylamino]-propyl}-pyrrolidin-2-one
$R_f$=0.65 (silica gel; methylene chloride:methanol=9:1)
HPLC/MS (method I): RT=3.66 min.; [M+H]+=449; Abs. λ max=244 nm

(83) 1-{3-[2-(3-fluoro-5-trifluoromethyl-phenylamino)-5-trifluoromethyl-pyrimidin-4-ylamino]-propyl}-pyrrolidin-2-one
melting point: 183-184° C.
$R_f$=0.6 (silica gel; methylene chloride:methanol=9:1)
HPLC/MS (method I): RT=4.07 min.; [M+H]+=466; Abs. λ max=257 nm

(84) 1-{3-[2-(2-fluoro-5-trifluoromethyl-phenylamino)-5-trifluoromethyl-pyrimidin-4-ylamino]-propyl}-pyrrolidin-2-one
melting point: 148-149° C.
$R_f$=0.65 (silica gel; methylene chloride:methanol=91:1)
HPLC/MS (method I): RT=3.51 min.; [M+H]+=466; Abs. λ max=244 nm

(85) N-{2-[2-(3-Bromo-benzylamino)-5-trifluoromethyl-pyrimidin-4-ylamino]-ethyl}-acetamide
melting point: 162-165° C.
$R_f$=0.44 (silica gel; methylene chloride:methanol=9:1)
HPLC/MS (method G): RT=3.65 min.; [M+H]+=433; Abs. λ max=236 nm

(86) N-{2-[2-(1-phenyl-ethylamino)-5-trifluoromethyl-pyrimidin-4-ylamino]-ethyl}-acetamide
melting point: 125-140° C.
$R_f$=0.46 (silica gel; methylene chloride:methanol=9:1)
HPLC/MS (method F): RT=3.53 min.; [M+H]+=368; Abs. λ max=230 nm

(87) 1-{3-[2-(2-isopropyl-phenylamino)-5-trifluoromethyl-pyrimidin-4-ylamino]-propyl}-pyrrolidin-2-one
melting point: 115-118° C.
$R_f$=0.26 (silica gel; methylene chloride:methanol=9:1)
HPLC/MS (method G): RT=3.94 min.; [M+H]+=422; Abs. λ max=232 nm

(88) 1-{3-[2-(Biphenyl-4-ylamino)-5-trifluoromethyl-pyrimidin-4-ylamino]-propyl}-pyrrolidin-2-one
melting point: 155-156° C.
$R_f$=0.74 (silica gel; methylene chloride:methanol=9:1)
HPLC/MS (method H): RT=4.07 min.; [M+H]+=456; Abs. λ max=242 nm

(89) 1-{3-[2-(2,4-Difluoro-phenylamino)-5-trifluoromethyl-pyrimidin-4-ylamino]-propyl}-pyrrolidin-2-one
melting point: 117-120° C.
$R_f$=0.76 (silica gel; methylene chloride:methanol=8:2)
HPLC/MS (method G): RT=3.76 min.; [M+H]+=416; Abs. λ max=238 nm

(90) 1-{3-[2-(2-Chloro-4-methyl-phenylamino)-5-trifluoromethyl-pyrimidin-4-ylamino]-propyl}-pyrrolidin-2-one
melting point: 110-113° C.
$R_f$=0.71 (silica gel; methylene chloride:methanol=9:1)

HPLC/MS (method G): RT=4.02 min.; [M+H]+=428; Abs. λ max=242 nm

(91) 1-{3-[2-(2-Chloro-5-trifluoromethyl-phenylamino)-5-trifluoromethyl-pyrimidin-4-ylamino]-propyl}-pyrrolidin-2-one
melting point: 139-140° C.
$R_f$=0.77 (silica gel; methylene chloride:methanol=9:1)
HPLC/MS (method H): RT=4.51 min.; [M+H]+=482; Abs. λ max=248 nm

(92) 1-{3-[2-(3,5-Difluoro-phenylamino)-5-trifluoromethyl-pyrimidin-4-ylamino]-propyl}-pyrrolidin-2-one
melting point: 210-212° C.
$R_f$=0.71 (silica gel; methylene chloride:methanol=9:1)
HPLC/MS (method G): RT=4.32 min.; [M+H]+=416; Abs. λ max=253 nm

(93) N-{2-[2-(3,4-dichloro-benzylamino)-5-trifluoromethyl-pyrimidin-4-ylamino]-ethyl}-acetamide
melting point: 168° C.
$R_f$=0.57 (silica gel; methylene chloride:methanol=9:1)
HPLC/MS (method G): RT=3.79 min.; [M+H]+=422; Abs. λ max=230 nm

(94) 1-{3-[5-trifluoromethyl-2-(2-trifluoromethyl-phenylamino)-pyrimidin-4-ylamino]-propyl}-pyrrolidin-2-one
$R_f$=0.65 (silica gel; methylene chloride:methanol=9:1)
HPLC/MS (method H): RT=3.29 min.; [M+H]+=448; Abs. λ max=234 nm

(95) 1-{3-[2-(4-isopropyl-phenylamino)-5-trifluoromethyl-pyrimidin-4-ylamino]-propyl}-pyrrolidin-2-one
melting point: 124-126° C.
$R_f$=0.62 (silica gel; methylene chloride:methanol=9:1)
HPLC/MS (method H): RT=3.75 min.; [M+H]+=422; Abs. λ max=259 nm

(96) 1-{3-[2-(4-dimethylamino-phenylamino)-5-trifluoromethyl-pyrimidin-4-ylamino]-propyl}-pyrrolidin-2-one
melting point: 156-158° C.
$R_f$=0.54 (silica gel; methylene chloride:methanol=9:1)
HPLC/MS (method F): RT=3.25 min.; [M+H]+=423; Abs. λ max=257 nm

(97) 1-{3-[2-(4-morpholin-4-yl-phenylamino)-5-trifluoromethyl-pyrimidin-4-ylamino]-propyl}-pyrrolidin-2-one
melting point: 115-118° C.
$R_f$=0.52 (silica gel; methylene chloride:methanol=9:1)
HPLC/MS (method H): RT=3.25 min.; [M+H]+=465; Abs. λ max=257 nm

(98) N-{2-[2-(4-dimethylsulphamoyl-phenylamino)-5-methyl-pyrimidin-4-ylamino]-ethyl}-acetamide
melting point: 204-206° C.
$R_f$=0.3 (silica gel; methylene chloride:methanol=9:1)
HPLC/MS (method F): RT=3.15 min.; [M+H]+=393; Abs. λ max=282 nm

(99) 4-[5-Chloro-4-(4,5,7,8-tetrahydro-1H-imidazo[4,5-d]azepin-6-yl)-pyrimidin-2-ylamino]-N,N-dimethyl-phenylsulphonamide
melting point: 160-162° C.
$R_f$=0.22 (silica gel; methylene chloride:methanol=9:1)
HPLC/MS (method F): RT=3.79 min.; [M+H]+=448; Abs. λ max=286 nm (100) 4-{5-Bromo-4-[3-(2-oxo-pyrrolidin-1-yl)-propylamino]-pyrimidin-2-ylamino}-N,N-dimethyl-phenylsulphonamide
melting point: 165.1-167.7° C.
$R_f$=0.51 (silica gel; methylene chloride:methanol=9:1)
HPLC/MS (method F): RT=3.85 min.; [M+H]+=498; Abs. λ max=284 nm (101) N-{2-[5-Chloro-2-(4-dimethylsulphamoyl-phenylamino)-pyrimidin-4-ylamino]-ethyl}-acetamide
melting point: >300° C. decomposition
$R_f$=0.42 (silica gel; methylene chloride:methanol=9:1)
HPLC/MS (method F): RT=3.58 min.; [M+H]+=413; Abs. λ max=284 nm (102) N-{2-[5-Bromo-2-(4-piperidin-1-ylmethyl-phenylamino)-pyrimidin-4-ylamino]-ethyl}-acetamide
melting point: 154-157° C.
$R_f$=0.1 (silica gel; methylene chloride:methanol=9:1)
HPLC/MS (method F): RT=2.7 min.; [M+H]+=448; Abs. λ max=253 nm (103) 1-{3-[5-Bromo-2-(4-piperidin-1-ylmethyl-phenylamino)-pyrimidin-4-ylamino]-propyl}-pyrrolidin-2-one
melting point: 137-138° C.
$R_f$=0.25 (silica gel; methylene chloride:methanol=9:1)
HPLC/MS (method F): RT=3.16 min.; [M+H]+=488; Abs. λ max=268 nm (104) N-{2-[5-methyl-2-(4-piperidin-1-ylmethyl-phenylamino)-pyrimidin-4-ylamino]-ethyl}-acetamide
melting point: 150-152° C.
$R_f$=0.06 (silica gel; methylene chloride:methanol=4:1)
HPLC/MS (method F): RT=2.52 min.; [M+H]+=383; Abs. λ max=263 nm (105) N,N-dimethyl-4-{5-methyl-4-[3-(2-oxo-pyrrolidin-1-yl)-propylamino]-pyrimidin-2-ylamino}-phenylsulphonamide
melting point: 186-189° C.
$R_f$=0.41 (silica gel; methylene chloride:methanol=9:1)
HPLC/MS (method F): RT=3.6 min.; [M+H]+=433; Abs. λ max=282 nm (106) 1-{3-[5-Bromo-2-(1H-indazol-6-ylamino)-pyrimidin-4-ylamino]-propyl}-pyrrolidin-2-one
melting point: 211-213° C.
$R_f$=0.44 (silica gel; methylene chloride:methanol=9:1)
HPLC/MS (method F): RT=3.62 min.; [M+H]+=431; Abs. λ max=251 nm (107) N-{2-[2-(2-fluoro-benzylamino)-5-trifluoromethyl-pyrimidin-4-ylamino]-ethyl}-acetamide
melting point: 188-189° C.
Rf=0.44 (silica gel; methylene chloride:methanol=9:1)
HPLC/MS (method G): RT=3.34 min.; [M+H]+=372; Abs. λ max=229 nm (108) N-(2-{2-[1-(4-Bromo-phenyl)-ethylamino]-5-trifluoromethyl-pyrimidin-4-ylamino}-ethyl)-acetamide
melting point: 143-145° C.
Rf=0.46 (silica gel; methylene chloride:methanol=9:1)
HPLC/MS (method H): RT=3.29 min.; [M+H]+=447; Abs. λ max=230 nm (109) 4-{5-Chloro-4-[3-(2-oxo-pyrrolidin-1-yl)-propylamino]-pyrimidin-2-ylamino}-N,N-dimethyl-phenylsulphonamide
melting point: 159-161° C.
Rf=0.53 (silica gel; methylene chloride:methanol=9:1)
HPLC/MS (method F): RT=3.55 min.; [M+H]+=453; Abs. λ max=284 nm (110) 1-{3-[5-Chloro-2-(4-piperidin-1-ylmethyl-phenylamino)-pyrimidin-4-ylamino]-propyl}-pyrrolidin-2-one
melting point: 137-138° C.
$R_f$=0.20 (silica gel; methylene chloride:methanol=9:1)
HPLC/MS (method F): RT=3.21 min.; [M+H]+=443; Abs. λ max=267 nm (111) 4-[4-(2-acetylamino-ethylamino)-5-dimethylamino-pyrimidin-2-ylamino]-benzamide
melting point: 218-220° C.
$R_f$=0.46 (silica gel; methylene chloride:methanol=4:1)
HPLC/MS (method G): RT=2.63 min.; [M+H]+=358; Abs. λ max=293.1 nm (112) 4-[4-(2-acetylamino-ethylamino)-5-isopropyl-pyrimidin-2-ylamino]-benzamide melting point: 229° C.
R$_f$=0.42 (silica gel; methylene chloride:methanol=4:1)
HPLC/MS (method G): RT=2.77 min.; [M+H]+=357; Abs. λ max=285.5 nm (113) 4-{5-methanesulphonyl-4-[3-(2-oxo-pyrrolidin-1-yl)-propylamino]-pyrimidin-2-ylamino}-benzamide
melting point: 244-246° C.
R$_f$=0.07 (silica gel; methylene chloride:methanol=99:1)
HPLC/MS (method F): RT=3.15 min.; [M+H]+=433; Abs. λ max=287.4 nm (114) 1-{3-[2-(3,4-dichloro-phenylamino)-5-methylsulphonyl-pyrimidin-4-ylamino]-propyl}-pyrrolidin-2-one
melting point: 200-203° C.
R$_f$=0.48 (silica gel; methylene chloride:methanol=99:1)
HPLC/MS (method G): RT=4.34 min.; [M+H]+=459; Abs. λ max=262.7 nm (115) 4-[5-dimethylamino-4-(4-pyridin-2-yl-piperazin-1-yl)-pyrimidin-2-ylamino]-benzamide
melting point: 237-238° C.
R$_f$=0.20 (silica gel; methylene chloride:methanol=9:1)
HPLC/MS (method G): RT=2.69 min.; [M+H]+=419; Abs. λ max=298.8 nm (116) 1-{3-[2-(3,4-dichloro-phenylamino)-5-isopropyl-pyrimidin-4-ylamino]-propyl}-pyrrolidin-2-one
melting point: 147-150° C.
R$_f$=0.08 (silica gel; methylene chloride:methanol=99:1)
HPLC/MS (method G): RT=4.00 min.; [M+H]+=423; Abs. λ max=264.6 nm (117) 4-{5-methoxy-4-[3-(2-oxo-pyrrolidin-1-yl)-propylamino]-pyrimidin-2-ylamino}-benzamide
melting point: 212-213° C.
R$_f$=0.12 (silica gel; methylene chloride:methanol=9:1)
HPLC/MS (method G): RT=2.74 min.; [M+H]+=385; Abs. λ max=291.2 nm (118) 1-{3-[2-(3,4-dichloro-phenylamino)-5-methoxy-pyrimidin-4-ylamino]-propyl}-pyrrolidin-2-one
melting point: 148-150° C.
R$_f$=0.05 (silica gel; methylene chloride:methanol=99:1)
HPLC/MS (method H): RT=3.39 min.; [M+H]+=411; Abs. λ max=264.6 nm (119) N-{2-[5-methoxy-2-(4-piperidin-1-ylmethyl-phenylamino)-pyrimidin-4-ylamino]-ethyl}-acetamide
melting point: 109-111° C.
R$_f$=0.09 (silica gel; methylene chloride:methanol=4:1)
HPLC/MS (method F): RT=2.89 min.; [M+H]+=399; Abs. λ max=257 nm (120) [5-methoxy-4-(4-pyridin-2-yl-piperazin-1-yl)-pyrimidin-2-yl]-(4-piperidin-1-ylmethyl-phenyl)-amine
melting point: 158-159° C.
R$_f$=0.12 (silica gel; methylene chloride:methanol=9:1)
HPLC/MS (method F): RT=2.92 min.; [M+H]+=460; Abs. λ max=266.5 nm (121) N-{2-[5-dimethylamino-2-(4-piperidin-1-ylmethyl-phenylamino)-pyrimidin-4-ylamino]-ethyl}-acetamide
R$_f$=0.08 (silica gel; methylene chloride:methanol=4:1)
HPLC/MS (method F): RT=2.94 min.; [M+H]+=412; Abs. λ max=257 nm (122) 1-{3-[2-(3,4-dichloro-phenylamino)-5-dimethylamino-pyrimidin-4-ylamino]-propyl}-pyrrolidin-2-one
melting point: 103-106° C.
R$_f$=0.22 (silica gel; methylene chloride:methanol=99:1)
HPLC/MS (method G): RT=3.87 min.; [M+H]+=424; Abs. λ max=268.4 nm (123) [5-isopropoxy-4-(4-pyridin-2-yl-piperazin-1-yl)-pyrimidin-2-yl]-(4-piperidin-1-ylmethyl-phenyl)-amine
melting point: 143-145° C.
R$_f$=0.13 (silica gel; methylene chloride:methanol=9:1)
HPLC/MS (method F): RT=3.06 min.; [M+H]+=488; Abs. λ max=272.2 nm (124) 1-{3-[5-isopropoxy-2-(4-piperidin-1-ylmethyl-phenylamino)-pyrimidin-4-ylamino]-propyl}-pyrrolidin-2-one
R$_f$=0.13 (silica gel; methylene chloride:methanol=9:1)
HPLC/MS (method F): RT=3.21 min.; [M+H]+=467; Abs. λ max=253.2 nm (125) N-{2-[5-isopropoxy-2-(4-piperidin-1-ylmethyl-phenylamino)-pyrimidin-4-ylamino]-ethyl}-acetamide
melting point: 105-107° C.
R$_f$=0.06 (silica gel; methylene chloride:methanol=9:1)
HPLC/MS (method F): RT=3.06 min.; [M+H]+=427; Abs. λ max=255.1 nm (126) N-{2-[2-(3,4-dichloro-phenylamino)-5-isopropyl-pyrimidin-4-ylamino]-ethyl}-acetamide
melting point: 206-207° C.
R$_f$=0.18 (silica gel; methylene chloride:methanol=99:1)
HPLC/MS (method G): RT=3.70 min.; [M+H]+=383; Abs. λ max=264.6 nm (127) N-{2-[2-(3,4-dichloro-phenylamino)-5-dimethylamino-pyrimidin-4-ylamino]-ethyl}-acetamide
melting point: 165-168° C.
R$_f$=0.05 (silica gel; methylene chloride:methanol=99:1)
HPLC/MS (method G): RT=3.57 min.; [M+H]+=384; Abs. λ max=264.6 nm (128) N-(2-[2-(4-amino-phenylamino)-5-trifluoromethyl-pyrimidin-4-ylamino]-ethyl)-acetamide
3 g of N-[2-(2-chloro-5-trifluoromethyl-pyrimidin-4-ylamino)-ethyl]-acetamide are combined with 6.9 g of p-phenylenediamine in 25 ml of glacial acetic acid and stirred for 4 hours at ambient temperature. After removal of the acetic acid in vacuo the reaction mixture is taken up in dichloromethane and washed with saturated sodium carbonate solution. The aqueous phase is extracted with dichloromethane. The combined organic phases are dried over sodium sulphate and evaporated down. The crude product is purified by chromatography (silica gel, CH$_2$Cl$_2$/iPrOH=20/1). 3.0 g of a grey solid are obtained.
R$_f$ (CH$_2$Cl$_2$/iPrOH=8/2+1% NH$_3$; SiO$_2$)=0.35
1H-NMR (D$_6$-DMSO, 300 MHz) δ: 1.80 (s, 3H), 3.25 (m, 2H), 3.47 (m, 2H), 4.78 (m, 2H), 6.50 (d, 1H), 6.93 (m, 1H), 7.29 (d, 2H), 7.90 (t, 1H), 8.08 (s, 1H), 9.13 (s, 1H).

(129) 1-{3-[5-isopropyl-2-(4-piperidin-1-ylmethyl-phenylamino)-pyrimidin-4-ylamino]-propyl}-pyrrolidin-2-one
melting point: 142-144° C.
R$_f$=0.05 (silica gel; methylene chloride:methanol=9:1)
HPLC/MS (method F): RT=3.2 min.; [M+H]+=451; Abs. λ max=253.2 nm (130) N-{2-[2-(4-methylamino-phenylamino)-5-trifluoromethyl-pyrimidin-4-ylamino]-ethyl}-acetamide
The compound is prepared from N-tert-butyl-oxycarbonyl-N-methyl-amino-4-aminobenzene and Example II. The intermediate product is combined with 5 eq. of 4.0M hydrochloric acid in 1,4-dioxane and heated to 85° C. for 0.5 hours with stirring. After elimination of the solvent in vacuo the crude product is taken up in dichloromethane and purified by chromatography (silica gel, CH$_2$Cl$_2$/methanol).
melting point: 169-171° C.
R$_f$=0.37 (silica gel; methylene chloride:methanol=9:1)
HPLC/MS (method F): RT=2.96 min.; [M+H]+=369; Abs. λ max=257 nm (131) N-{2-[2-(3-methylamino-phenylamino)-5-trifluoromethyl-pyrimidin-4-ylamino]-ethyl}-acetamide
Prepared analogously to 2 (130).
melting point: 191-193° C.
R$_f$=0.49 (silica gel; methylene chloride:methanol=9:1)

HPLC/MS (method G): RT=2.68 min.; [M+H]+=369; Abs. λ max=253 nm (132) N-{2-[2-(3-formyl-phenylamino)-5-trifluoromethyl-pyrimidin-4-ylamino]-ethyl}-acetamide 12 g of manganese dioxide are suspended in 200 ml of dichloromethane, cooled to 0° C. and a solution of N-{2-[2-(3-hydroxymethyl-phenylamino)-5-trifluoromethyl-pyrimidin-4-ylamino]-ethyl}-acetamide (prepared analogously to 2(52)) in 300 ml of THF is slowly added at 0° C. The reaction mixture is heated to ambient temperature and stirred for 6 h. After the reaction mixture has been filtered the filter cake is thoroughly washed with THF and the solution is evaporated down. The residue is taken up in ethyl acetate and after treatment in the ultrasound bath filtered again. The procedure is repeated with ethylether and finally a white solid is obtained in a 70% yield.

$R_f$=0.40 (silica gel; methylene chloride:methanol=20:1)
1H-NMR (D6-DMSO, 300 MHz) δ: 1.81 (s, 3H), 3.30 (m, 2H), 3.55 (m, 2H), 7.30 (m, 1H), 7.82 (m, 2H), 7.96 (m, 4H), 8.25 (s, 1H), 9.82 (s, 1H), 10.11 (s, 1H).

(133) N-{2-[2-(4-formyl-phenylamino)-5-trifluoromethyl-pyrimidin-4-ylamino]-ethyl}-acetamide N-{2-[2-(4-formyl-phenylamino)-5-trifluoromethyl-pyrimidin-4-ylamino]-ethyl}-acetamide is obtained analogously to 2(132) from N-{2-[2-(4-hydroxymethyl-phenylamino)-5-trifluoromethyl-pyrimidin-4-ylamino]-ethyl}-acetamide (prepared analogously to 2(52)) in a 76% yield.

$R_f$=0.35 (silica gel; methylene chloride:methanol=20:1)
HPLC/MS (method F): RT=3.48 min.; [M+H]+=368
1H-NMR (D6-DMSO, 300 MHz) δ: 1.80 (s, 3H), 3.31 (m, 2H), 3.57 (m, 2H), 7.22 (m, 1H), 7.51 (m, 2H), 7.91 (m, 3H), 8.21 (s, 1H), 8.42 (s, 1H), 9.90 (s, 1H), 9.93 (s, 1 H).

(134) [5-Chloro-4-(1,4,6,7-tetrahydro-imidazo[4,5-c]pyridin-5-yl)-pyrimidin-2-yl]-(1H-indazol-6-yl)-amine
melting point: >300° C. decomposition
$R_f$=0.42 (silica gel; methylene chloride:methanol=4:1)
HPLC/MS (method F): RT=3.09 min.; [M+H]+=367; Abs. λ max=282 nm (135) (1H-indazol-6-yl)-[5-methyl-4-(4,5,7,8-tetrahydro-1H-imidazo[4,5-d]azepin-6-yl)-pyrimidin-2-yl]-amine
melting point: >300° C. decomposition
$R_f$=0.08 (silica gel; methylene chloride:methanol=4:1)
HPLC/MS (method F): RT=2.92 min.; [M+H]+=361; Abs. λ max=246 nm (136) 4-[5-Chloro-4-(1,4,6,7-tetrahydro-imidazo[4,5-c]pyridin-5-yl)-pyrimidin-2-ylamino]-N,N-dimethyl-phenyl-sulphonamide
melting point: 171-173° C.
$R_f$=0.29 (silica gel; methylene chloride:methanol=9:1)
HPLC/MS (method F): RT=3.71 min.; [M+H]+=434; Abs. λ max=291 nm (137) [5-Chloro-4-(4,5,7,8-tetrahydro-1H-imidazo[4,5-d]azepin-6-yl)-pyrimidin-2-yl]-(1H-indazol-6-yl)-amine
melting point: >290° C. decomposition
$R_f$=0.19 (silica gel; methylene chloride:methanol=4:1)
HPLC/MS (method F): RT=3.03 min.; [M+H]+=381; Abs. λ max=282 nm (138) (1H-indazol-6-yl)-[5-methyl-4-(1,4,6,7-tetrahydro-imidazo[4,5-c]pyridin-5-yl)-pyrimidin-2-yl]-amine
melting point: >320° C. decomposition
$R_f$=0.3 (silica gel; methylene chloride:methanol=8:2)
HPLC/MS (method F): RT=2.87 min.; [M+H]+=; 347 Abs. λ max=251 nm (139) [5-methoxy-4-(1,4,6,7-tetrahydro-imidazo[4,5-c]pyridin-5-yl)-pyrimidin-2-yl]-(4-piperidin-1-ylmethyl-phenyl)-amine
melting point: 105-108° C.
$R_f$=0.06 (silica gel; methylene chloride:methanol=4:1)
HPLC/MS (method F): RT=2.83 min.; [M+H]+=420; Abs. λ max=268.4 nm (140) (3,4-dichloro-phenyl)-[5-methoxy-4-(1,4,6,7-tetrahydro-imidazo[4,5-c]pyridin-5-yl)-pyrimidin-2-yl]-amine
$R_f$=0.13 (silica gel; methylene chloride:methanol=9:1)
HPLC/MS (method G): RT=3.22 min.; [M+H]+=392; Abs. λ max=272.2 nm (141) [5-Bromo-4-(4,5,7,8-tetrahydro-1H-imidazo[4,5-d]azepin-6-yl)-pyrimidin-2-yl]-(1H-indazol-6-yl)-amine
melting point: 258-260° C.
$R_f$=0.22 (silica gel; methylene chloride:methanol=9:1)
HPLC/MS (method F): RT=3.05 min.; [M+H]+=426; Abs. λ max=283 nm (142) [5-Bromo-4-(1,4,6,7-tetrahydro-imidazo[4,5-c]pyridin-5-yl)-pyrimidin-2-yl]-(1H-indazol-6-yl)-amine
melting point: >300° C. decomposition
$R_f$=0.2 (silica gel; methylene chloride:methanol=9:1)
HPLC/MS (method F): RT=3.12 min.; [M+H]+=412; Abs. λ max=255 nm (143) N,N-dimethyl-4-[5-methyl-4-(1,4,6,7-tetrahydro-imidazo[4,5-c]pyridin-5-yl)-pyrimidin-2-ylamino]-phenyl-sulphonamide
melting point: 228-230° C.
$R_f$=0.27 (silica gel; methylene chloride:methanol=9:1)
HPLC/MS (method F): RT=3.14 min.; [M+H]+=414; Abs. λ max=282 nm (144) N,N-dimethyl-4-[5-methyl-4-(4,5,7,8-tetrahydro-1H-imidazo[4,5-d]azepin-6-yl)-pyrimidin-2-ylamino]-phenylsulphonamide
melting point: 173-176° C.
$R_f$=0.2 (silica gel; methylene chloride:methanol=9:1)
HPLC/MS (method F): RT=3.04 min.; [M+H]+=428; Abs. λ max=256 nm (145) $N^5,N^5$-dimethyl-$N^5$-(4-piperidin-1-ylmethyl-phenyl)-4-(1,4,6,7-tetrahydro-imidazo[4,5-c]pyridin-5-yl)-pyrimidine-2,5-diamine
melting point: 126-129° C.
$R_f$=0.08 (silica gel; methylene chloride:methanol=4:1)
HPLC/MS (method F): RT=2.89 min.; [M+H]+=433; Abs. λ max=257 nm (146) [5-isopropyl-4-(1,4,6,7-tetrahydro-imidazo[4,5-c]pyridin-5-yl)-pyrimidin-2-yl]-(4-piperidin-1-ylmethyl-phenyl)-amine
melting point: 234-237° C.
$R_f$=0.13 (silica gel; methylene chloride:methanol=9:1)
HPLC/MS (method F): RT=2.95 min.; [M+H]+=432; Abs. λ max=266.5 nm (147) N-{2-[2-(3,4-dichloro-phenylamino)-5-methanesulphonyl-pyrimidin-4-ylamino]-ethyl}-acetamide
melting point: 245-248° C.
$R_f$=0.36 (silica gel; methylene chloride:methanol=9:1)
HPLC/MS (method F): RT=4.15 min.; [M+H]+=419; Abs. λ max=276 nm (148) N2-{5-methyl-2-[3-(2,2,2-trifluoroethyl)-2,3,4,5-tetrahydro-1H-benzo[d]azepin-7-ylamino]-pyrimidin-4-ylamino}-ethyl)-acetamide
Melting point: 154-156° C.
$R_f$=0.27 (silica gel; methylene chloride:methanol=9:1)
HPLC/MS (method D): RT=2.12 min.; [M+H]+=437; Abs./max=253 nm (149) N2-{5-chloro-2-[3-(2,2,2-trifluoroethyl)-2,3,4,5-tetrahydro-1H-benzo[d]azepin-7-ylamino]-pyrimidin-4-ylamino}-ethyl)-acetamide
Melting point: 205-208° C.
$R_f$=0.44 (silica gel; methylene chloride:methanol=9:1)

HPLC/MS (method D): RT=3.07 min.; [M+H]+=457; Abs./max=263 nm (150) 1-(3-{2-[3-(2,2,2-trifluoroethyl)-2,3,4,5-tetrahydro-1H-benzo[d]azepin-7-ylamino]-5-trifluoromethyl-pyrimidin-4-ylamino}-propyl)-pyrrolidin-2-one
Melting point: 132-133° C.
$R_f$=0.62 (silica gel; methylene chloride:methanol=9:1)
HPLC/MS (method F): RT=2.95 min; [M+H]+=531; Abs./max=259 nm (151) N2-{5-bromo-2-[3-(2,2,2-trifluoroethyl)-2,3,4,5-tetrahydro-1H-benzo[d]azepin-7-ylamino]-pyrimidin-4-ylamino}-ethyl)-acetamide
Melting point: 186-191° C.
$R_f$=0.44 (silica gel; methylene chloride:methanol=9:1)
HPLC/MS (method D): RT=3.12 min.; [M+H]+=502; Abs./max=267 nm (152) 1-(3-{5-methyl-2-[3-(2,2,2-trifluoroethyl)-2,3,4,5-tetrahydro-1H-benzo[d]azepin-7-ylamino]-pyrimidin-4-ylamino}-propyl)-pyrrolidin-2-one
Melting point: oil
$R_f$=0.38 (silica gel; methylene chloride:methanol=9:1)
HPLC/MS (method D): RT=3.67 min.; [M+H]+=477; Abs./max=259 nm (153) 1-(3-{5-chloro-2-[3-(2,2,2-trifluoroethyl)-2,3,4,5-tetrahydro-1H-benzo[c]azepin-7-ylamino]-pyrimidin-4-ylamino}-propyl)-pyrrolidin-2-one
Melting point: 57-75° C.
$R_f$=0.79 (silica gel; methylene chloride:methanol=8:2)
HPLC/MS (method D): RT=3.70 min.; [M+H]+=497; Abs./max=265 nm (154) 1-(3-{5-bromo-2-[3-(2,2,2-trifluoroethyl)-2,3,4,5-tetrahydro-1H-benzo[d]azepin-7-ylamino]-pyrimidin-4-ylamino}-propyl)-pyrrolidin-2-one
Melting point: 138-144° C.
$R_f$=0.55 (silica gel; methylene chloride:methanol=8:2)
HPLC/MS (method D): RT=3.71 min.; [M+H]+=542; Abs./max=263 nm Example 3

N-{2-[2-(3,4-Dichloro-phenylamino)-5-trimethylsilanylethynyl-pyrimidin-4-ylamino]-ethyl}-acetamid hydrochlorid Analogously to Example 2, 229 mg of N-{2-[2-(3,4-dichloro-phenylamino)-5-trimethylsilanylethynyl-pyrimidin-4-ylamino]-ethyl}-acetamide hydrochloride were obtained from 104 mg of 3,4-dichloroaniline and 200 mg of N-[2-(2-chloro-5-trimethylsilanylethynyl-pyrimidin-4-ylamino)-ethyl]acetamide (Example II(10)).
Melting point: 206-208° C.
Rf (ethyl acetate; SiO2)=0.51
RT (HPLC, Method D)=7.29 min., UVmax=286 nm The following compound was obtained analogously to Example 3:
N-{2-[2-(4-Dimethylsulphamoyl-phenylamino)-5-trimethylsilanylethynyl-pyrimidin-4-ylamino]-ethyl}-acetamide hydrochloride Example 4

N-{2-[2-(3,4-dichloro-phenylamino)-5-ethynyl-pyrimidin-4-ylamino]-ethyl}-acetamide 145 mg of tetrabutylammonium fluoride×3H$_2$O is dissolved in 10 ml of methanol and combined with 100 mg of N-{2-[2-(3,4-dichloro-phenylamino)-5-trimethylsilanyl-ethynyl-pyrimidin-4-ylamino]-ethyl}-acetamide, homogenised in an ultrasound bath and stirred overnight at RT.

The mixture is then evaporated down in vacuo and filtered through silica gel with methanol/dichloromethane (1/10). 54 mg of N-{2-[2-(3,4-dichloro-phenylamino)-5-ethynyl-pyrimidin-4-ylamino]-ethyl}-acetamide is isolated in a 64% yield.
Melting point: 221-224° C.
Rf (ethyl acetate/SiO2)=0.32
RT (HPLC, method D)=5.30 min., UVmax=282 nm The following compound was obtained analogously to Example 4: 4(1) N-{2-[2-(4-dimethylsulphamoyl-phenylamino)-5-ethynyl-pyrimidin-4-ylamino]-ethyl}-acetamide
Melting point: 179-185° C.
Rf (ethyl acetate/SiO2)=0.14
RT (HPLC, method D)=4.71 min., UVmax=294 nm Example 5

N-{2-[2-(4-dimethylsulphamoyl-phenylamino)-5-ethyl-pyrimidin-4-ylamino]-ethyl}-acetamide hydrochloride 50 mg of N-{2-[2-(3,4-dichloro-phenylamino)-5-ethynyl-pyrimidin-4-ylamino]-ethyl}-acetamide are dissolved in 15 ml of ethanol and 15 ml of ethyl acetate and combined with 25 mg of Pd/C (5%). The mixture is hydrogenated in the shaking autoclave at ambient temperature and 3.5 bar (50 psi) for 3.5 hours.

Then the catalyst is filtered off, the solution is combined with HCl in dioxane and evaporated down. The product is obtained in a 50 mg yield.
Melting point: >219° C. decomposition
Rf (ethyl acetate/SiO2)=0.39
RT (HPLC, method D)=4.37 min., UVmax=282 nm Example 6

4-[4-(2-acetylamino-ethylamino)-5-isopropyl-pyrimidin-2-ylamino]-benzoic acid 150 mg of N-[2-(2-chloro-5-isopropyl-pyrimidin-4-ylamino)-ethyl]-acetamide, methyl-4-aminobenzoate (—Seq.) and 10 mg of 4-dimethylaminopyridine are heated to 150° C. in 2 ml of isopropanol in a sealed reaction vessel for 48 hours. After extraction with ethyl acetate from saturated bicarbonate solution the mixture is dried over sodium sulphate and evaporated down. Chromatography (CH$_2$Cl$_2$/MeOH gradient, silica gel) yields the methylester. This is taken up in 3 ml of methanol, combined with a 1 M LiOH solution (10 eq.) and treated at 50° C. for up to 24 hours. The pH is adjusted to 5 by adding a 10% NaH$_2$PO$_4$ solution (or alternatively to pH=4 with a 1 M HCl solution) and the product is precipitated. After filtration the product is washed with water, diethylether and ethyl acetate and dried in vacuo. 95 mg of product are obtained.
Melting point: 275-278° C.
$R_f$=0.04 (silica gel; methylene chloride:methanol=4:1)
HPLC/MS (method G): RT=3.01 min.; [M+H]+=358; Abs. λ max=291.2 nm The following compounds are obtained analogously to Example 6:
(1) 4-(5-methanesulphonyl-4-[3-(2-oxo-pyrrolidin-1-yl)-propylamino]-pyrimidin-2-ylamino}-benzoic acid
Melting point: >270° C. decomposition
$R_f$=0.17 (silica gel; methylene chloride:methanol=9:1)
HPLC/MS (method F): RT=3.43 min.; [M+H]+=434; Abs. λ max=293 nm (2) 4-(5-methoxy-4-[3-(2-oxo-pyrrolidin-1-yl)-propy-lamino]-pyrimidin-2-ylamino}-benzoic acid
Melting point: >218° C. decomposition
$R_f$=0.12 (silica gel; methylene chloride:methanol=9:1)
HPLC/MS (method J): RT=4.88 min.; [M+H]+=386; Abs.
λ max=298.8 nm
(3) 4-(5-dimethylamino-4-[3-(2-oxo-pyrrolidin-1-yl)-propy-lamino]-pyrimidin-2-ylamino}-benzoic acid
Melting point: >235° C. decomposition
$R_f$=0.1 (silica gel; methylene chloride:methanol=9:1)
HPLC/MS (method G): RT=3.08 min.; [M+H]+=399; Abs.
λ max=298.8 nm
(4) 4-[4-(2-acetylamino-ethylamino)-5-trifluoromethyl-pyrimidin-2-ylamino]-2-chloro-benzoic acid
Melting point: 261° C.
$R_f$=0.15 (silica gel; methylene chloride:methanol=4:1)
HPLC/MS (method G): RT=3.28 min.; [M+H]+=418; Abs.
λ max=251.3 nm
1H-NMR ($D_6$-DMSO, 300 MHz) δ: 1.80 (s, 3H), 3.34 (m, 2H), 3.54 (m, 2H), 7.54 (m, 1H), 7.78 (m, 1H), 7.84 (m, 1H), 8.03 (m, 2H), 8.30 (s, 1H), 10.23 (s, 1H).
(5) 4-[4-(2-acetylamino-ethylamino)-5-trifluoromethyl-pyrimidin-2-ylamino]-3-chloro-benzoic acid
Melting point: 245° C.
$R_f$=0.33 (silica gel; methylene chloride:methanol=4:1)
HPLC/MS (method G): RT=3.35 min.; [M+H]+=418; Abs.
λ max=253.2 nm
1H-NMR ($D_6$-DMSO, 300 MHz): 1.78 (s, 3H), 3.24 (m, 2H), 3.43 (m, 2H), 7.31 (t, 1H), 7.90 (m, 3H), 8.20 (m, 2H), 8.76 (s, 1H), 13.04 (s, 1H).
(6) 4-[5-methoxy-4-(4-pyridin-2-yl-piperazin-1-yl)-pyrimidin-2-ylamino]-benzoic acid
Melting point: >260° C. decomposition
$R_f$=0.23 (silica gel; methylene chloride:methanol=9:1)
HPLC/MS (method G): RT=2.84 min.; [M+H]+=407; Abs.
λ max=298.8 nm
(7) 4-(5-isopropyl-4-[3-(2-oxo-pyrrolidin-1-yl)-propy-lamino]-pyrimidin-2-ylamino}-benzoic acid
Melting point: >315° C.
$R_f$=0.08 (silica gel; methylene chloride:methanol=9:1)
HPLC/MS (method G): RT=3.21 min.; [M+H]+=398; Abs.
λ max=257 nm Example 7

N-(2-[2-(3,4-dichloro-phenylamino)-5-trifluoromethyl-pyrimidin-4-ylamino]-ethyl)-benzamide 100 mg of N4-(2-amino-ethyl)-N2-(3,4-dichloro-phenyl)-5-trifluoromethyl-pyrimidine-2,4-diamine were dissolved in pyridine/$CH_2Cl_2$ (1 ml/1 ml) and cooled to 0° C. and 1.1 eq of benzoic acid chloride were slowly added to 1 ml of $CH_2Cl_2$. The reaction mixture was allowed to heat up to ambient temperature and stirred overnight. After the addition of 2 ml of saturated $NaHCO_3$ solution the mixture was extracted with ethyl acetate, dried over $Na_2SO_4$ and evaporated down. Then the residue was washed with ethyl acetate, diethylether and dichloromethane and chromatographed over silica gel ($CH_2Cl_2$, MeOH).
A yield of 83 mg was obtained.
Melting point: 226-228° C.
$R_f$=0.57 (silica gel; methylene chloride:methanol=99:1)
HPLC/MS (method I): RT=4.04 min.; [M+H]+=471; Abs.
λ max=266.5 nm
The following compounds are obtained analogously to Example 7:

(1) N-(2-[2-(3,4-dichloro-phenylamino)-5-trifluoromethyl-pyrimidin-4-ylamino]-ethyl)-methanesulphonamide
100 mg of N4-(2-amino-ethyl)-N2-(3,4-dichloro-phenyl)-5-trifluoromethyl-pyrimidine-2,4-diamine were dissolved with diisopropylethylamine (4 eq.) in THF (2 ml) and 1.1 eq of methanesulphonic acid chloride were slowly added. The reaction mixture was stirred for 4 hours. After the addition of 2 ml of saturated. $NaHCO_3$ solution the mixture was extracted with ethyl acetate, dried over $Na_2SO_4$ and evaporated down. Then the residue was washed with ethyl acetate, diethylether and dichloromethane and chromatographed over silica gel ($CH_2Cl_2$, MeOH). A yield of 91 mg was obtained.
Melting point: 195-196° C.
$R_f$=0.50 (silica gel; methylene chloride:methanol=99:1)
HPLC/MS (method K): RT=2.44 min.; [M+H]+=445; Abs.
λ max=266.5 nm
(2) N-{3-[2-(1-methyl-1H-indazol-6-ylamino)-5-trifluoromethyl-pyrimidin-4-ylamino]-propyl}-isobutyramide
Prepared from compound 1 (674)
Melting point: 268° C.
$R_f$=0.38 (silica gel; methylene chloride:methanol=95:5)
HPLC/MS (method D): RT=5.50 min.; [M+H]+=436; Abs.
λ max=250 nm
(3) N-(2-[2-(3,4-dichloro-phenylamino)-5-trifluoromethyl-pyrimidin-4-ylamino]-ethyl)-dimethylamino-acetamide
100 mg of N4-(2-amino-ethyl)-N2-(3,4-dichloro-phenyl)-5-trifluoromethyl-pyrimidine-2,4-diamine[1(80)] were dissolved with dimethylaminoacetic acid (1 eq.), diisopropyl-ethylamine (2 eq.), HOBT (1.3 eq.) and HBTU (1.3 eq.) in DMF (2 ml) and stirred overnight at ambient temperature. After the addition of 2 ml of 2 M $NaHCO_3$ solution the mixture was extracted with ethyl acetate, dried over $Na_2SO_4$ and evaporated down. Then the residue was chromatographed over silica gel ($CH_2Cl_2$, MeOH). A yield of 62 mg was obtained.
Melting point: 165-167° C.
$R_f$=0.17 (silica gel; methylene chloride:methanol=99:1)
HPLC/MS (method H): RT=3.07 min.; [M+H]+=452; Abs.
λ max=264.6 nm
(4) N-(2-[2-(3,4-dichloro-phenylamino)-5-trifluoromethyl-pyrimidin-4-ylamino]-ethyl)-isobutyramide
Prepared from compound 1 (80).
Melting point: 232-235° C.
$R_f$=0.55 (silica gel; methylene chloride:methanol=99:1)
HPLC/MS (method I): RT=2.74 min.; [M+H]+=437; Abs.
λ max=266.5 nm
(5) N-(2-[2-(3,4-dichloro-phenylamino)-5-trifluoromethyl-pyrimidin-4-ylamino]-ethyl)-methoxy-acetamide
Prepared from compound 1 (80).
Melting point: 197-201° C.
$R_f$=0.45 (silica gel; methylene chloride:methanol=99:1)
HPLC/MS (method G): RT=3.27 min.; [M+H]+=439; Abs.
λ max=266.5 nm
(6) N-{3-[2-(1-methyl-1H-indazol-6-ylamino)-5-trifluoromethyl-pyrimidin-4-ylamino]-propyl}-propionamide
Prepared from compound 1 (674).
Melting point: 261° C.
$R_f$=0.37 (silica gel; methylene chloride:methanol=95:5)
HPLC/MS (method D): RT=5.30 min.
(7) N-{3-[2-(1-methyl-1H-indazol-6-ylamino)-5-trifluoromethyl-pyrimidin-4-ylamino]-propyl}-methane sulphonamide
Prepared from compound 1 (674)
Melting point: 230° C.
$R_f$=0.20 (silica gel; methylene chloride:methanol=95:5)
HPLC/MS (method D): RT=5.20 min.; [M+H]+=444; Abs.
λ max=250 nm (8) N-(2-[2-(3,4-dichloro-phenylamino)-5-trifluoromethyl-pyrimidin-4-ylamino]-ethyl)-N-methyl-isobutyramide
Prepared from compound 1 (240).
Melting point: 138-140° C.
$R_f$=0.33 (silica gel; methylene chloride:methanol=99:1)
HPLC/MS (method G): RT=4.80 min.; [M+H]+=451; Abs. λ max=274.1 nm (9) N-(2-[2-(3,4-dichloro-phenylamino)-5-trifluoromethyl-pyrimidin-4-ylamino]-ethyl)-N-methyl-acetamide
Prepared from compound 1 (240).
Melting point: 174-175° C.
$R_f$=0.14 (silica gel; methylene chloride:methanol=99:1)
HPLC/MS (method G): RT=4.19 min.; [M+H]+=423; Abs. λ max=266.5 nm

(10) N-(3-[2-(3,4-dichloro-phenylamino)-5-trifluoromethyl-pyrimidin-4-ylamino]-propyl)-acetamide
Prepared from compound 1 (35).
Melting point: 200-203° C.
$R_f$=0.32 (silica gel; methylene chloride:methanol=99:1)
HPLC/MS (method F): RT=4.19 min.; [M+H]+=423; Abs. λ max=266.5 nm

(11) N-(3-[2-(3,4-dichloro-phenylamino)-5-trifluoromethyl-pyrimidin-4-ylamino]-propyl)-2-methoxy-acetamide
Prepared from compound 1 (35).
Melting point: 160-162° C.
$R_f$=0.61 (silica gel; methylene chloride:methanol=99:1)
HPLC/MS (method G): RT=4.27 min.; [M+H]+=453; Abs. λ max=266.5 nm

(12) 4-fluoro-N-{3-[2-(1-methyl-1H-indazol-6-ylamino)-5-trifluoromethyl-pyrimidin-4-ylamino]-propyl}-benzensulphonamide
Prepared from compound 1 (674).
Melting point: 256° C.
$R_f$=0.30 (silica gel; methylene chloride:methanol=95:5)
HPLC/MS (method D): RT=6.20 min.; [M+H]+=524; Abs. λ max=242 nm

(13) 2-methoxy-N-{3-[2-(1-methyl-1H-indazol-6-ylamino)-5-trifluoromethyl-pyrimidin-4-ylamino]-propyl}-acetamide
Prepared from compound 1 (674)
Melting point: 241° C.
$R_f$=0.38 (silica gel; methylene chloride:methanol=95:5)
HPLC/MS (method D): RT=5.20 min.; [M+H]+=438; Abs. λ max=250 nm

(14) N-1-[2-(3,4-dichloro-phenylamino)-5-trifluoromethyl-pyrimidin-4-yl]-pyrrolidine-3-yl)-acetamide
Prepared from compound 1 (338).
Melting point: 244-245° C.
$R_f$=0.11 (silica gel; methylene chloride:methanol=99:1)
HPLC/MS (method F): RT=4.37 min.; [M+H]+=435; Abs. λ max=268.4 nm

(15) 3-methyl-N-{3-[2-(1-methyl-1H-indazol-6-ylamino)-5-trifluoromethyl-pyrimidin-4-ylamino]-propyl}-butyramide
Prepared from compound 1 (674)
Melting point: 254° C.
$R_f$=0.40 (silica gel; methylene chloride:methanol=95:5)
HPLC/MS (method D): RT=5.70 min.; [M+H]+=450; Abs. λ max=250 nm

(16) 2-fluoro-N-{3-[2-(1-methyl-1H-indazol-6-ylamino)-5-trifluoromethyl-pyrimidin-4-ylamino]-propyl}-benzensulphonamide
Prepared from compound 1 (674)
Melting point: 253° C.
$R_f$=0.32 (silica gel; methylene chloride:methanol=95:5)
HPLC/MS (method D): RT=6.10 min.; [M+H]+=524; Abs. λ max=250 nm

(17) 4-[4-(2-acetyl-methyl-amino)-ethylamino)-5-trifluoromethyl-pyrimidin-2-ylamino]-benzamide
Prepared from compound 1 (650).
Melting point: 250-252° C.
$R_f$=0.14 (silica gel; methylene chloride:methanol=9:1)
HPLC/MS (method G): RT=2.76 min.; [M+H]+=397; Abs. λ max=277.9 nm

(18) 4-}-4-[2-(2-dimethylamino-acetylamino)-ethylamino]-5-trifluoromethyl-pyrimidin-2-ylamino}-benzamide
Prepared from compound 1 (259)
Melting point: 215-218° C.
$R_f$=0.24 (silica gel; methylene chloride:methanol=4:1)
HPLC/MS (method F): RT=2.86 min.; [M+H]+=426; Abs. λ max=279.8 nm

(19) 4-[4-(2-isobutyrylamino-ethylamino)-5-trifluoromethyl-pyrimidin-2-ylamino]-benzamide
Prepared from compound 1 (259).
Melting point: 247-250° C.
$R_f$=0.16 (silica gel; methylene chloride:methanol=9:1)
HPLC/MS (method F): RT=3.18 min.; [M+H]+=411; Abs. λ max=279.8 nm

(20) 4-[4-(2-methanesulphonylamino-ethylamino)-5-trifluoromethyl-pyrimidin-2-ylamino]-benzamide Prepared from compound 1 (259).
Melting point: 255-256° C.
$R_f$=0.13 (silica gel; methylene chloride:methanol=9:1)
HPLC/MS (method G): RT=2.83 min.; [M+H]+=419; Abs. λ max=279.8 nm

(21) N-{3-[2-(1-methyl-1H-indazol-6-ylamino)-5-trifluoromethyl-pyrimidin-4-ylamino]-propyl}-2-phenyl-acetamide
Prepared from compound 1 (674).
Melting point: 230° C.
$R_f$=0.46 (silica gel; methylene chloride:methanol=95:5)
HPLC/MS (method D): RT=5.90 min.; [M+H]+=484; Abs. λ max=250 nm

(22) {3-[2-(1-methyl-1H-indazol-6-ylamino)-5-trifluoromethyl-pyrimidin-4-ylamino]-propyl}-methylcarbamate
Prepared from compound 1 (674).
Melting point: 136° C.
$R_f$=0.46 (silica gel; methylene chloride:methanol=95:5)
HPLC/MS (method D): RT=5.50 min.; [M+H]+=424; Abs. λ max=250 nm

(23) 4-(4-[2-(isobutyryl-methyl-amino)-ethylamino)-5-trifluoromethyl-pyrimidin-2-ylamino)-benzamide
Prepared from compound 1 (650).
Melting point: 250-253° C.
$R_f$=0.19 (silica gel; methylene chloride:methanol=9:1)
HPLC/MS (method G): RT=3.12 min.; [M+H]+=424; Abs. λ max=279.8 nm

(24) {3-[2-(1-methyl-1H-indazol-6-ylamino)-5-trifluoromethyl-pyrimidin-4-ylamino]-propyl}-isobutylcarbamate
Prepared from compound 1 (674).
Melting point: 226° C.
$R_f$=0.50 (silica gel; methylene chloride:methanol=95:5)
HPLC/MS (method C): RT=4.40 min.; [M+H]+=466; Abs. λ max=250 nm

(25) {3-[2-(1-methyl-1H-indazol-6-ylamino)-5-trifluoromethyl-pyrimidin-4-ylamino]-propyl}-2-chlorobenzylcarbamate
Prepared from compound 1 (674).
Melting point: 194° C.
$R_f$=0.60 (silica gel; methylene chloride:methanol=95:5)
HPLC/MS (method D): RT=6.60 min.; [M+H]+=536; Abs. λ max=254 nm

(26) N-(3-[2-(3,4-dichloro-phenylamino)-5-trifluoromethyl-pyrimidin-4-ylamino]-propyl)-2-dimethylamino-acetamide
Prepared from compound 1 (35).
Melting point: 187-189° C.
$R_f$=0.09 (silica gel; methylene chloride:methanol=99:1)
HPLC/MS (method G): RT=3.85 min.; [M+H]+=466; Abs. λ max=268.4 nm

(27) 4-[4-(3-acetylamino-propylamino)-5-trifluoromethyl-pyrimidin-2-ylamino]-benzamide
Prepared from compound 1 (697).
Melting point: 212-213° C.
$R_f$=0.13 (silica gel; methylene chloride:methanol=9:1)
HPLC/MS (method F): RT=3.01 min.; [M+H]+=397; Abs. λ max=279.8 nm

(28) 4-[4-(3-(2-methoxy-acetamino)-propylamino)-5-trifluoromethyl-pyrimidin-2-ylamino]-benzamide
Prepared from compound 1 (697).
Melting point: 212-213° C.
$R_f$=0.09 (silica gel; methylene chloride:methanol=99:1)
HPLC/MS (method F): RT=3.12 min.; [M+H]+=467; Abs. λ max=279.8 nm

(29) 4-(4-[3-(2-dimethylamino-acetylamino)-propylamino]-5-trifluoromethyl-pyrimidin-2-ylamino)-benzamide
Prepared from compound 1 (697).
Melting point: 184-187° C.
$R_f$=0.10 (silica gel; methylene chloride:methanol=9:1)
HPLC/MS (method F): RT=2.90 min.; [M+H]+=440; Abs. λ max=279.8 nm

(30) N-{3-[2-(1-methyl-1H-indazol-6-ylamino)-5-trifluoromethyl-pyrimidin-4-ylamino]-propyl}-benzensulphonamide
Prepared from compound 1 (674).
Melting point: 264° C.
$R_f$=0.28 (silica gel; methylene chloride:methanol=95:5)
HPLC/MS (method D): RT=6.10 min.; [M+H]+=506; Abs. λ max=238 nm

(31) 4-[4-{3-acetylamino-pyrrolidin-1-yl)-5-trifluoromethyl-pyrimidin-2-ylamino)-benzamide
Prepared from compound 1 (459).
Melting point: 244-246° C.
$R_f$=0.1 (silica gel; methylene chloride:methanol=9:1)
HPLC/MS (method F): RT=2.90 min.; [M+H]+=409; Abs. λ max=283.6 nm

(32) 1,1-diethyl-3-{3-[2-(1-methyl-1H-indazol-6-ylamino)-5-trifluoromethyl-pyrimidin-4-ylamino]-propyl}-urea
Prepared from compound 1 (674).
Melting point: 228° C.
$R_f$=0.36 (silica gel; methylene chloride:methanol=95:5)
HPLC/MS (method D): RT=5.70 min.; [M+H]+=465; Abs. λ max=250 nm

(33) 4-[4-(2-benzoylamino-ethylamino)-5-trifluoromethyl-pyrimidin-2-ylamino]-benzamide
Prepared from compound 1 (259)
Melting point: 238-240° C.
$R_f$=0.26 (silica gel; methylene chloride:methanol=9:1)
HPLC/MS (method G): RT=3.22 min.; [M+H]+=445; Abs. λ max=279.8 nm

(34) 4-(4-[2-(2-methoxy-acetylamino)-ethylamino]-5-trifluoromethyl-pyrimidin-2-ylamino]-benzamide
Prepared from compound 1 (259)
Melting point: 232-234° C.
$R_f$=0.29 (silica gel; methylene chloride:methanol=9:1)
HPLC/MS (method G): RT=2.77 min.; [M+H]+=413; Abs. λ max=279.8 nm

(35) 1,1-dimethyl-3-{3-[2-(1-methyl-1H-indazol-6-ylamino)-5-trifluoromethyl-pyrimidin-4-ylamino]-propyl}-urea
Prepared from compound 1 (674)
Melting point: 259° C.
$R_f$=0.59 (silica gel; methylene chloride:methanol=95:5)
HPLC/MS (method D): RT=5.20 min.; [M+H]+=437; Abs. λ max=250 nm

(36) 1-isopropyl-3-{3-[2-(1-methyl-1H-indazol-6-ylamino)-5-trifluoromethyl-pyrimidin-4-ylamino]-propyl}-urea
Prepared from compound 1 (674)
Melting point: 190° C.
$R_f$=0.08 (silica gel; methylene chloride:methanol=98:2)

Example 8

4-[4-(2-acetylamino-ethylamino)-5-trifluoromethyl-pyrimidin-2-ylamino]-N-methyl-benzamide 100 mg of 4-[4-(2-acetylamino-ethylamino)-5-trifluoromethyl-pyrimidin-2-ylamino]-benzoic acid 9(1), methylamine (1.3 eq.), HOBT (1.3 eq.), HBTU (1.3 eq.) and diisopropylethylamine (3 eq.) are added to 2 ml of DMF and stirred overnight. The reaction mixture is combined with saturated bicarbonate solution and extracted with ethyl acetate. Then the organic phase is washed with water, dried over sodium sulphate and evaporated down. The crude product is washed with ethyl acetate, diethylether and dichloromethane and optionally purified by chromatography (silica gel, $CH_2Cl_2$/MeOH gradient). A yield of 39 mg is obtained.
Melting point: 196° C.
$R_f$=0.11 (silica gel; methylene chloride:methanol=95:5)
Rt (HPLC, method F)=3.06 min; [M+H]+=397; Abs. λ max=279.8 nm The following compounds are obtained analogously to Example 8:
(1) 3-[4-(2-acetylamino-ethylamino)-5-trifluoromethyl-pyrimidin-2-ylamino]-N-methyl-benzamide
Prepared from compound 9 (0).
Melting point: 291° C.
$R_f$=0.12 (silica gel; methylene chloride:methanol=9:1)
HPLC/MS (method G): RT=2.88 min.; [M+H]+=397; Abs. λ max=239.9 nm (2) 4-[4-(2-acetylamino-ethylamino)-5-trifluoromethyl-pyrimidin-2-ylamino]-3-chloro-N-methyl-benzamide
Prepared from compound 6 (5)
Melting point: 252° C.
$R_f$=0.09 (silica gel; methylene chloride:methanol=9:1)
HPLC/MS (method G): RT=3.04 min.; [M+H]+=431; Abs. λ max=251.3 nm (3) 4-[4-(2-acetylamino-ethylamino)-5-trifluoromethyl-pyrimidin-2-ylamino]-2-chloro-N-methyl-benzamide
Prepared from compound 6 (4)
Melting point: 183° C.
$R_f$=0.10 (silica gel; methylene chloride:methanol=9:1)
HPLC/MS (method G): RT=2.89 min.; [M+H]+=431; Abs. λ max=270.3 nm (4) 4-[4-(2-acetylamino-ethylamino)-5-trifluoromethyl-pyrimidin-2-ylamino]-N,N-dimethyl-benzamide
Prepared from compound 9 (1).
Melting point: 185° C.
$R_f$=0.14 (silica gel; methylene chloride:methanol=9:1)
HPLC/MS (method G): RT=2.84 min.; [M+H]+=411; Abs. λ max=262.7 nm (5) 3-[4-(2-acetylamino-ethylamino)-5-trifluoromethyl-pyrimidin-2-ylamino]-N,N-dimethyl-benzamide
Prepared from compound 9 (0).

Melting point: 205° C.
$R_f$=0.19 (silica gel; methylene chloride:methanol=9:1)
HPLC/MS (method G): RT=2.88 min.; [M+H]+=411; Abs. λ max=245.6 nm (6) 4-[4-(2-acetylamino-ethylamino)-5-trifluoromethyl-pyrimidin-2-ylamino]-3-chloro-N,N-dimethyl-benzamide
Prepared from compound 6 (5).
Melting point: 135° C.
$R_f$=0.54 (silica gel; methylene chloride:methanol=9:1)
HPLC/MS (method G): RT=3.01 min.; [M+H]+=445; Abs. λ max=219 nm (7) 4-[4-(2-acetylamino-ethylamino)-5-trifluoromethyl-pyrimidin-2-ylamino]-2-chloro-N,N-dimethyl-benzamide
Prepared from compound 6 (4).
Melting point: 198° C.
$R_f$=0.14 (silica gel; methylene chloride:methanol=9:1)
HPLC/MS (method G): RT=3.09 min.; [M+H]+=445; Abs. λ max=253 nm (8) 4-[4-(2-acetylamino-ethylamino)-5-trifluoromethyl-pyrimidin-2-ylamino]-N-benzyl-N-methyl-benzamide
Prepared from compound 9 (1).
Melting point: 214° C.
$R_f$=0.18 (silica gel; methylene chloride:methanol=9:1)
HPLC/MS (method G): RT=3.52 min.; [M+H]+=487; Abs. λ max=253.2 nm (9) 3-[4-(2-acetylamino-ethylamino)-5-trifluoromethyl-pyrimidin-2-ylamino]-N-benzyl-N-methyl-benzamide
Prepared from compound 9 (0).
Melting point: 157° C.
$R_f$=0.24 (silica gel; methylene chloride:methanol=9:1)
HPLC/MS (method G): RT=3.59 min.; [M+H]+=487; Abs. λ max=203.8 nm

(10) 4-[4-(2-acetylamino-ethylamino)-5-trifluoromethyl-pyrimidin-2-ylamino]-3-chloro-N-benzyl-N-methyl-benzamide
Prepared from compound 6 (5).
Melting point: 152° C.
$R_f$=0.22 (silica gel; methylene chloride:methanol=9:1)
HPLC/MS (method G): RT=3.78 min.; [M+H]+=521; Abs. λ max=209.5 nm

(11) 4-[4-(2-acetylamino-ethylamino)-5-trifluoromethyl-pyrimidin-2-ylamino]-2-chloro-N-benzyl-N-methyl-benzamide
Prepared from compound 6 (4).
Melting point: 180° C.
$R_f$=0.20 (silica gel; methylene chloride:methanol=9:1)
HPLC/MS (method G): RT=3.85 min.; [M+H]+=522; Abs. λ max=268.4 nm

(12) N-(2-(2-[4-(piperidin-1-carbonyl)-phenylamino]-5-trifluoromethyl-pyrimidin-4-ylamino)-ethyl)-acetamide
Prepared from compound 9 (1).
Melting point: 199° C.
$R_f$=0.67 (silica gel; methylene chloride:methanol=85:15)
HPLC/MS (method G): RT=3.25 min.; [M+H]+=451; Abs. λ max=266.5 nm

(13) N-(2-(2-[3-(piperidin-1-carbonyl)-phenylamino]-5-trifluoromethyl-pyrimidin-4-ylamino)-ethyl)-acetamide
Prepared from compound 9 (0).
Melting point: 179° C.
$R_f$=0.21 (silica gel; methylene chloride:methanol=9:1)
HPLC/MS (method G): RT=3.30 min.; [M+H]+=451; Abs. λ max=245.6 nm

(14) N-(2-(2-[2-Chloro-4-(piperidin-1-carbonyl)-phenylamino]-5-trifluoromethyl-pyrimidin-4-ylamino)-ethyl)-acetamide
Prepared from compound 6 (5).
Melting point: 108° C.
$R_f$=0.22 (silica gel; methylene chloride:methanol=9:1)
HPLC/MS (method G): RT=3.44 min.; [M+H]+=485; Abs. λ max=243.7 nm

(15) N-(2-(2-[3-Chloro-4-(piperidin-1-carbonyl)-phenylamino]-5-trifluoromethyl-pyrimidin-4-ylamino)-ethyl)-acetamide
Prepared from compound 6 (4).
Melting point: 193° C.
$R_f$=0.22 (silica gel; methylene chloride:methanol=9:1)
HPLC/MS (method G): RT=3.52 min.; [M+H]+=485; Abs. λ max=266.5 nm

(16) N-(2-(2-[4-(Morpholin-4-carbonyl)-phenylamino]-5-trifluoromethyl-pyrimidin-4-ylamino)-ethyl)-acetamide
Prepared from compound 9 (1).
Melting point: 221° C.
$R_f$=0.65 (silica gel; methylene chloride:methanol=85:15)
HPLC/MS (method G): RT=2.85 min.; [M+H]+=453; Abs. λ max=262.7 nm

(17) N-(2-(2-[3-(Morpholin-4-carbonyl)-phenylamino]-5-trifluoromethyl-pyrimidin-4-ylamino)-ethyl)-acetamide
Prepared from compound 9 (0).
Melting point: 196° C.
$R_f$=0.18 (silica gel; methylene chloride:methanol=9:1)
HPLC/MS (method G): RT=2.89 min.; [M+H]+=453; Abs. λ max=245.6 nm

(18) N-(2-(2-[2-Chloro-4-(morpholine-4-carbonyl)-phenylamino]-5-trifluoromethyl-pyrimidin-4-ylamino)-ethyl)-acetamide
Prepared from compound 6 (5).
Melting point: 40° C.
$R_f$=0.20 (silica gel; methylene chloride:methanol=9:1)
HPLC/MS (method G): RT=3.31 min.; [M+H]+=487; Abs. λ max=220.9 nm

(19) N-(2-(2-[3-Chloro-4-(morpholine-4-carbonyl)-phenylamino]-5-trifluoromethyl-pyrimidin-4-ylamino)-ethyl)-acetamide
Prepared from compound 6 (4).
Melting point: 197° C.
$R_f$=0.20 (silica gel; methylene chloride:methanol=9:1)
HPLC/MS (method G): RT=3.09 min.; [M+H]+=487; Abs. λ max=266.5 nm

(20) N-(2-{2-[4-(4-methyl-piperazin-1-carbonyl)-phenylamino]-5-trifluoromethyl-pyrimidin-4-ylamino}-ethyl)-acetamide
Prepared from compound 9 (1).
Melting point: 228° C.
$R_f$=0.37 (silica gel; methylene chloride:methanol=85:15)
HPLC/MS (method G): RT=2.39 min.; [M+H]+=466; Abs. λ max=272.2 nm

(21) N-(2-(2-[3-(4-methyl-piperazin-1-carbonyl)-phenylamino]-5-trifluoromethyl-pyrimidin-4-ylamino)-ethyl)-acetamide
Prepared from compound 9 (—O).
Melting point: 186° C.
$R_f$=0.54 (silica gel; methylene chloride:methanol=4:1)
HPLC/MS (method G): RT=2.50 min.; [M+H]+=466; Abs. λ max=245.6 nm

(22) 4-[4-(2-acetylamino-ethylamino)-5-trifluoromethyl-pyrimidin-2-ylamino]-N-pyridin-2-ylmethyl-benzamide
Prepared from compound 9 (1).
Melting point: 229° C.
$R_f$=0.61 (silica gel; methylene chloride:methanol=85:15)
HPLC/MS (method G): RT=2.68 min.; [M+H]+=474; Abs. λ max=281.7 nm

(23) 3-[4-(2-acetylamino-ethylamino)-5-trifluoromethyl-pyrimidin-2-ylamino]-N-pyridin-2-ylmethyl-benzamide
Prepared from compound 9 (—O).

Melting point: 216° C.
$R_f$=0.69 (silica gel; methylene chloride:methanol=85:15)
HPLC/MS (method G): RT=2.70 min.; [M+H]+=474; Abs. λ max=260.8 nm

(24) 4-[4-(2-acetylamino-ethylamino)-5-trifluoromethyl-pyrimidin-2-ylamino]-N-pyridin-2-yl-benzamide
Prepared from compound 9 (1).
Melting point: 225° C.
$R_f$=0.09 (silica gel; methylene chloride:methanol=85:15)
HPLC/MS (method G): RT=4.24 min.; [M+H]+=460; Abs. λ max=205.7 nm

(25) 3-[4-(2-acetylamino-ethylamino)-5-trifluoromethyl-pyrimidin-2-ylamino]-N-pyridin-2-yl-benzamide
Prepared from compound 9 (—O).
Melting point: 251° C.
$R_f$=0.20 (silica gel; methylene chloride:methanol=9:1)
HPLC/MS (method G): RT=2.99 min.; [M+H]+=460; Abs. λ max=247.5 nm

(26) 4-[4-(2-acetylamino-ethylamino)-5-trifluoromethyl-pyrimidin-2-ylamino]-N-(3,5-difluorobenzyl)-benzamide
Prepared from compound 9 (1).
Melting point: 231° C.
$R_f$=0.11 (silica gel; methylene chloride:methanol=9:1)
HPLC/MS (method G): RT=3.67 min.; [M+H]+=509; Abs. λ max=281.7 nm

(27) 3-[4-(2-acetylamino-ethylamino)-5-trifluoromethyl-pyrimidin-2-ylamino]-N-(3,5-difluorobenzyl)-benzamide
Prepared from compound 9 (0).
Melting point: 226° C.
$R_f$=0.72 (silica gel; methylene chloride:methanol=85:15)
HPLC/MS (method G): RT=3.71 min.; [M+H]+=509; Abs. λ max=239.9 nm

(28) 4-[4-(2-acetylamino-ethylamino)-5-trifluoromethyl-pyrimidin-2-ylamino]-N-(1-phenyl-ethyl)-benzamide
Prepared from compound 9 (1).
Melting point: 237° C.
$R_f$=0.10 (silica gel; methylene chloride:methanol=9:1)
HPLC/MS (method G): RT=3.60 min.; [M+H]+=487; Abs. λ max=279.8 nm

(29) 3-[4-(2-acetylamino-ethylamino)-5-trifluoromethyl-pyrimidin-2-ylamino]-N-(1-phenyl-ethyl)-benzamide
Prepared from compound 9 (—O).
Melting point: 234° C.
$R_f$=0.23 (silica gel; methylene chloride:methanol=9:1)
HPLC/MS (method G): RT=3.66 min.; [M+H]+=487; Abs. λ max=241.8 nm Example 9

3-[4-(2-acetylamino-ethylamino)-5-trifluoromethyl-pyrimidin-2-ylamino]-benzoic acid N-[2-(2-Chloro-5-trifluoromethyl-pyrimidin-4-ylamino)-ethyl]-acetamide (1 eq.), 3-aminobenzoic acid (4 eq.) and isopropanol are heated overnight at 60° C. The reaction mixture is diluted with ethyl acetate and washed with 0.01 N HCL solution. The solid formed is filtered off and washed with ethyl acetate by centrifugation and if necessary purified by chromatography (silica gel $CH_2Cl_2$/MeOH/AcOH=10:1: 0.1). A white solid is obtained in an 89% yield.
Melting point: 282° C.
$R_f$=0.33 (silica gel; methylene chloride:methanol=4:1)
HPLC/MS (method G): RT=3.02 min.; [M+H]+=384; Abs. λ max=238 nm
1H-NMR ($D_6$-DMSO, 300 MHz) δ: 1.81 (s, 3H), 3.32 (m, 2H), 3.55 (m, 2H), 7.22 (m, 1H), 7.42 (m, 1H), 7.56 (m, 1H), 7.90 (m, 2H), 8.22 (s, 1H), 8.52 (s, 1H), 8.85 (s, 1H).

The following compound was obtained analogously to Example 9:
(1) 4-[4-(2-acetylamino-ethylamino)-5-trifluoromethyl-pyrimidin-2-ylamino]-benzoic
acid Melting point: 260° C.
$R_f$=0.33 (silica gel; methylene chloride:methanol:conc. ammonia=4:1:0.25)
Rt (HPLC, method E)=3.21 min.
1H-NMR ($D_6$-DMSO, 300 MHz) δ: 1.82 (s, 3H), 3.33 (m, 2H), 3.54 (m, 2H), 7.29 (m, 1H), 7.88 (m, 5H), 8.00 (m, 1H), 8.25 (s, 1H), 10.00 (s, 1H).

Example 10

N-(2-[2-(3-acetylamino-phenylamino)-5-trifluoromethyl-pyrimidin-4-ylamino]-ethyl)-acetamide 100 mg of N-(2-[2-(3-amino-phenylamino)-5-trifluoromethyl-pyrimidin-4-ylamino]-ethyl)-acetamide[2(67)] in 1 ml of pyridine and 1 ml dichloromethane are mixed at 0° C. with acetylchloride (1.1 eq.) in 0.5 ml of dichloromethane, heated to ambient temperature and stirred overnight. The reaction mixture is mixed with 2 ml saturated bicarbonate solution and extracted with ethyl acetate. The organic phases are dried over sodium sulphate and evaporated down. The crude product is washed with ethyl acetate, diethylether and dichloromethane and optionally purified by chromatography (silica gel, $CH_2Cl_2$/MeOH gradient). 102 mg of a solid are obtained.
Melting point: 220° C.
$R_f$=0.11 (silica gel; methylene chloride:methanol=9:1)
HPLC/MS (method F): RT=3.12 min.; [M+H]+=397; Abs. λ max=245.6 nm (1) pyridine-2-carboxylic acid (3-[4-(2-acetylamino-ethylamino)-5-trifluoromethyl-pyrimidin-2-ylamino]-phenyl)-amide
100 mg of N-(2-[2-(3-amino-phenylamino)-5-trifluoromethyl-pyrimidin-4-ylamino]-ethyl)-acetamide[2(67)] are stirred overnight at ambient temperature with 2-pyridinecarboxylic acid (1.2 eq.), HOBT (1.2 eq.), HBTU (1.2 eq.) and diisopropylethylamine (2 eq.) in 2 ml of DMF. The reaction mixture is combined with 2 ml of saturated bicarbonate solution and extracted with ethyl acetate. The organic phases are dried over sodium sulphate and evaporated down. The crude product is washed with ethyl acetate, diethylether and dichloromethane and optionally purified by chromatography (silica gel, $CH_2Cl_2$/MeOH gradient). 109 mg of a solid are obtained.
Melting point: 184° C.
$R_f$=0.24 (silica gel; methylene chloride:methanol=9:1)
HPLC/MS (method F): RT=3.69 min.; [M+H]+=460; Abs. λ max=262.7 nm
The following compounds are obtained analogously to Example 10 or 10 (1):
(2) N-{4-[4-(2-acetylamino-ethylamino)-5-trifluoromethyl-pyrimidin-2-ylamino]-phenyl}-3,5-difluoro-N-methyl-benzamide
Prepared from compound 2 (130).
Melting point: 103-106° C.
$R_f$=0.45 (silica gel; methylene chloride:methanol=9:1)
HPLC/MS (method F): RT=3.83 min.; [M+H]+=509; Abs. λ max=261 nm
(3) N-(2-[2-(4-acetylamino-phenylamino)-5-trifluoromethyl-pyrimidin-4-ylamino]-ethyl)-acetamide
Prepared from compound 2 (4)
Melting point: 222° C.
$R_f$=0.65 (silica gel; methylene chloride:methanol=4:1)
HPLC/MS (method F): RT=3.05 min.; [M+H]+=397; Abs. λ max=266.5 nm (4) N-(3-[4-(2-acetylamino-ethylamino)-5-trifluoromethyl-pyrimidin-2-ylamino]-phenyl)-benzamide
Prepared from compound 2 (67).
Melting point: 215° C.
$R_f$=0.29 (silica gel; methylene chloride:methanol=9:1)
HPLC/MS (method F): RT=3.67 min.; [M+H]+=459; Abs. λ max=257 nm (5) N-(4-[4-(2-acetylamino-ethylamino)-5-trifluoromethyl-pyrimidin-2-ylamino]-phenyl)-benzamide
Prepared from compound 2 (4)
Melting point: 252° C.
$R_f$=0.17 (silica gel; methylene chloride:methanol=9:1)
HPLC/MS (method F): RT=3.59 min.; [M+H]+=459; Abs. λ max=219 nm (6) pyridine-2-carboxylic acid (4-[4-(2-acetylamino-ethylamino)-5-trifluoromethyl-pyrimidin-2-ylamino]-phenyl)-amide
Prepared from compound 2 (4).
Melting point: 215° C.
$R_f$=0.22 (silica gel; methylene chloride:methanol=9:1)
HPLC/MS (method F): RT=3.61 min.; [M+H]+=460; Abs. λ max=220.9 nm (7) pyridine-2-carboxylic acid {-4-[4-(2-acetylamino-ethylamino)-5-trifluoromethyl-pyrimidin-2-ylamino]-phenyl}-methyl-amide
Prepared from compound 2 (130).
Melting point: 144-145° C.
$R_f$=0.43 (silica gel; methylene chloride:methanol=9:1)
HPLC/MS (method F): RT=3.32 min.; [M+H]+=474; Abs. λ max=263 nm (8) N-(2-{2-[4-(phenylsulphonyl-methyl-amino)-phenylamino]-5-trifluoromethyl-pyrimidin-4-ylamino}-ethyl)-acetamide
Prepared from compound 2 (130).
Melting point: 162-164° C.
$R_f$=0.56 (silica gel; methylene chloride:methanol=9:1)
HPLC/MS (method F): RT=3.99 min.; [M+H]+=509; Abs. λ max=267 nm (9) N-{3-[4-(2-acetylamino-ethylamino)-5-trifluoromethyl-pyrimidin-2-ylamino]-phenyl}-3,5-difluoro-N-methyl-benzamide
Prepared from compound 2 (131).
Melting point: 193-195° C.
$R_f$=0.43 (silica gel; methylene chloride:methanol=9:1)
HPLC/MS (method H): RT=3.31 min.; [M+H]+=509; Abs. λ max=253 nm

(10) pyridine-2-carboxylic acid {3-[4-(2-acetylamino-ethylamino)-5-trifluoromethyl-pyrimidin-2-ylamino]-phenyl}-methyl-amide
Prepared from compound 2 (131).
Melting point: 188-190° C.
$R_f$=0.49 (silica gel; methylene chloride:methanol=9:1)
HPLC/MS (method G): RT=3.16 min.; [M+H]+=474; Abs. λ max=253 nm

(11) N-(2-{2-[3-(phenylsulphonyl-methyl-amino)-phenylamino]-5-trifluoromethyl-pyrimidin-4-ylamino}-ethyl)-acetamide
Prepared from compound 2 (131).
Melting point: 117-120° C.
$R_f$=0.62 (silica gel; methylene chloride:methanol=9:1)
HPLC/MS (method F): RT=3.97 min.; [M+H]+=; 509 Abs. λ max=234 nm

(12) N-(4-[4-(2-acetylamino-ethylamino)-5-trifluoromethyl-pyrimidin-2-ylamino]-phenyl)-3,5-difluoro-benzamide
Prepared from compound 2 (4).
Melting point: 277° C.
$R_f$=0.18 (silica gel; methylene chloride:methanol=9:1)
HPLC/MS (method G): RT=3.74 min.; [M+H]+=495; Abs. λ max=219 nm

(13) N-(2-[2-(3-methanesulphonylamido-phenylamino)-5-trifluoromethyl-pyrimidin-4-ylamino]-ethyl)-acetamide
Prepared from compound 2 (67).
Melting point: 188° C.
$R_f$=0.15 (silica gel; methylene chloride:methanol=9:1)
HPLC/MS (method F): RT=3.22 min.; [M+H]+=433; Abs. λ max=243.7 nm

(14) N-(2-[2-(4-methanesulphonylamido-phenylamino)-5-trifluoromethyl-pyrimidin-4-ylamino]-ethyl)-acetamide
Prepared from compound 2 (4).
Melting point: 237° C.
$R_f$=0.17 (silica gel; methylene chloride:methanol=9:1)
HPLC/MS (method F): RT=3.14 min.; [M+H]+=433; Abs. λ max=263 nm

(15) N-(2-[2-(3-phenylsulphonylamido-phenylamino)-5-trifluoromethyl-pyrimidin-4-ylamino]-ethyl)-acetamide
Prepared from compound 2 (67).
Melting point: 208° C.
$R_f$=0.20 (silica gel; methylene chloride:methanol=9:1)
HPLC/MS (method F): RT=3.75 min.; [M+H]+=495; Abs. λ max=236.1 nm

(16) N-(2-[2-(4-phenylsulphonylamido-phenylamino)-5-trifluoromethyl-pyrimidin-4-ylamino]-ethyl)-acetamide
Prepared from compound 2 (4).
Melting point: 242° C.
$R_f$=0.22 (silica gel; methylene chloride:methanol=9:1)
HPLC/MS (method F): RT=3.58 min.; [M+H]+=495; Abs. λ max=264.6 nm

(17) N-(3-[4-(2-acetylamino-ethylamino)-5-trifluoromethyl-pyrimidin-2-ylamino]-phenyl)-3,5-difluoro-benzamide
Prepared from compound 2 (67).
Melting point: 231° C.
$R_f$=0.24 (silica gel; methylene chloride:methanol=9:1)
HPLC/MS (method F): RT=4.00 min.; [M+H]+=495; Abs. λ max=262.7 nm Example 11

N-{2-[2-(3-piperidin-1-ylmethyl-phenylamino)-5-trifluoromethyl-pyrimidin-4-ylamino]-ethyl}-acetamide 80 mg of N-{2-[2-(3-formyl-phenylamino)-5-trifluoromethyl-pyrimidin-4-ylamino]-ethyl}-acetamide, 1.1 eq. of piperidine and 2 eq. of NaBH(OAc)$_3$ are dissolved in 2 ml of THF and the mixture is stirred overnight at ambient temperature. The reaction is stopped by the addition of 2 ml of saturated aqueous sodium carbonate solution and extracted twice with 10 ml of methylene chloride. The organic phase is washed with water, dried over sodium sulphate and evaporated to dryness. The crude product is purified over silica gel with methylene chloride/methanol.
Melting point: 154-155° C.
$R_f$=0.11 (silica gel; methylene chloride:methanol=9:1)
HPLC/MS (method F): RT=3.35 min.; [M+H]+=437; Abs. λ max=253 nm The following compounds are obtained analogously to Example 11:

(1) N-(2-{2-[3-(3-oxo-piperazin-1-ylmethyl)-phenylamino]-5-trifluoromethyl-pyrimidin-4-ylamino}-ethyl)-acetamide
Melting point: 196-198° C.
$R_f$=0.23 (silica gel; methylene chloride:methanol=9:1)

HPLC/MS (method F): RT=3.14 min.; [M+H]+=452; Abs. λ max=255 nm (2) N-{2-[2-(3-pyrrolidin-1-ylmethyl-phenylamino)-5-trifluoromethyl-pyrimidin-4-ylamino]-ethyl}-acetamide
Melting point: 172-173° C.
R$_f$=0.16 (silica gel; methylene chloride:methanol=85:15)
HPLC/MS (method F): RT=3.25 min.; [M+H]+=423; Abs. λ max=255 nm (3) N-{2-[2-(3-dimethylaminomethyl-phenylamino)-5-trifluoromethyl-pyrimidin-4-ylamino]-ethyl}-acetamide
Melting point: 140-141° C.
R$_f$=0.21 (silica gel; methylene chloride:methanol=85:15)
HPLC/MS (method F): RT=3.22 min.; [M+H]+=397; Abs. λ max=253 nm (4) 1-{3-[2-(3-dimethylaminomethyl-phenylamino)-5-trifluoromethyl-pyrimidin-4-ylamino]-propyl}-pyrrolidin-2-one
Melting point: 126-128° C.
R$_f$=0.19 (silica gel; methylene chloride:methanol=9:1)
HPLC/MS (method F): RT=3.43 min.; [M+H]+=437; Abs. λ max=253 nm (5) 1-{3-[2-(3-pyrrolidin-1-ylmethyl-phenylamino)-5-trifluoromethyl-pyrimidin-4-ylamino]-propyl}-pyrrolidin-2-one
Melting point: 122-124° C.
R$_f$=0.14 (silica gel; methylene chloride:methanol=9:1)
HPLC/MS (method F): RT=3.5 min.; [M+H]+=463; Abs. λ max=253 nm (6) 1-{3-[2-(3-piperidin-1-ylmethyl-phenylamino)-5-trifluoromethyl-pyrimidin-4-ylamino]-propyl}-pyrrolidin-2-one
Melting point: 130-132° C.
R$_f$=0.23 (silica gel; methylene chloride:methanol=9:1)
HPLC/MS (method F): RT=3.52 min.; [M+H]+=477; Abs. λ max=253 nm (7) 1-{3-[2-(4-dimethylaminomethyl-phenylamino)-5-trifluoromethyl-pyrimidin-4-ylamino]-propyl}-pyrrolidin-2-one
Melting point: 93-95° C.
R$_f$=0.09 (silica gel; methylene chloride:methanol=9:1)
HPLC/MS (method G): RT=3.03 min.; [M+H]+=437; Abs. λ max=259 nm (8) N-[2-(2-{4-[(isobutyl-methyl-amino)-methyl]-phenylamino}-5-trifluoromethyl-pyrimidin-4-ylamino)-ethyl]-acetamide
Melting point: 162-163° C.
R$_f$=0.38 (silica gel; methylene chloride:methanol=85:15)
HPLC/MS (method G): RT=3.11 min.; [M+H]+=439; Abs. λ max=255 nm (9) N-{2-[2-(4-pyrrolidin-1-ylmethyl-phenylamino)-5-trifluoromethyl-pyrimidin-4-ylamino]-ethyl}-acetamide
Melting point: 170-173° C.
R$_f$=0.18 (silica gel; methylene chloride:methanol=85:15)
HPLC/MS (method G): RT=2.83 min.; [M+H]+=423; Abs. λ max=261 nm

(10) 1-{3-[2-(4-pyrrolidin-1-ylmethyl-phenylamino)-5-trifluoromethyl-pyrimidin-4-ylamino]-propyl}-pyrrolidin-2-one
Melting point: 122-125° C.
R$_f$=0.23 (silica gel; methylene chloride:methanol=85:15)
HPLC/MS (method G): RT=3.11 min.; [M+H]+=463; Abs. λ max=263 nm

(11) 1-{3-[2-(4-Morpholin-4-ylmethyl-phenylamino)-5-trifluoromethyl-pyrimidin-4-ylamino]-propyl}-pyrrolidin-2-one
Melting point: 128-130° C.
R$_f$=0.51 (silica gel; methylene chloride:methanol=9:1)
HPLC/MS (method G): RT=3.02 min.; [M+H]+=479; Abs. λ max=259 nm

(12) 1-(3-{2-[4-(3,5-dimethyl-piperazin-1-ylmethyl)-phenylamino]-5-trifluoromethyl-pyrimidin-4-ylamino}-propyl)-pyrrolidin-2-one
Melting point: 83-85° C.
R$_f$=0.11 (silica gel; methylene chloride:methanol=9:1)
HPLC/MS (method G): RT=2.95 min.; [M+H]+=506; Abs. λ max=265 nm

(13) N-[2-(2-{3-[(diisopropylamino)-methyl]-phenylamino}-5-trifluoromethyl-pyrimidin-4-ylamino)-ethyl]-acetamide
Melting point: 60-63° C.
R$_f$=0.21 (silica gel; methylene chloride:methanol=9:1)
HPLC/MS (method F): RT=3.03 min.; [M+H]+=453; Abs. λ max=253 nm

(14) 1-(3-{2-[4-(4-acetyl-piperazin-1-ylmethyl)-phenylamino]-5-trifluoromethyl-pyrimidin-4-ylamino}-propyl)-pyrrolidin-2-one
Melting point: 163-163° C.
R$_f$=0.46 (silica gel; methylene chloride:methanol=9:1)
HPLC/MS (method F): RT=3.00 min.; [M+H]+=520; Abs. λ max=263 nm

(15) N-{2-[2-(4-methylaminomethyl-phenylamino)-5-trifluoromethyl-pyrimidin-4-ylamino]-ethyl}-acetamide
Melting point: 130-132° C.
R$_f$=0.05 (silica gel; methylene chloride:methanol=8:2)
HPLC/MS (method F): RT=2.8 min.; [M+H]+=383; Abs. λ max=261 nm

(16) 1-[3-(2-{3-[(diisopropylamino)-methyl]-phenylamino}-5-trifluoromethyl-pyrimidin-4-ylamino)-propyl]-pyrrolidin-2-one
Melting point: 141-143° C.
R$_f$=0.37 (silica gel; methylene chloride:methanol=9:1)
HPLC/MS (method F): RT=3.24 min.; [M+H]+=493; Abs. λ max=249 nm

(17) 1-{3-[2-(3-methylaminomethyl-phenylamino)-5-trifluoromethyl-pyrimidin-4-ylamino]-propyl}-pyrrolidin-2-one
Melting point: 65-68° C.
HPLC/MS (method F): RT=2.98 min.; [M+H]+=423; Abs. λ max=251 nm

(18) N-[2-(2-{4-[(diisopropylamino)-methyl]-phenylamino}-5-trifluoromethyl-pyrimidin-4-ylamino)-ethyl]-acetamide
Melting point: 140-143° C.
R$_f$=0.26 (silica gel; methylene chloride:methanol=85:15)
HPLC/MS (method F): RT=3.04 min.; [M+H]+=453; Abs. λ max=251 nm

(19) N-{2-[2-(3-methylaminomethyl-phenylamino)-5-trifluoromethyl-pyrimidin-4-ylamino]-ethyl}-acetamide
Melting point: 137-140° C.
R$_f$=0.09 (silica gel; methylene chloride:methanol=9:1)
HPLC/MS (method F): RT=2.77 min.; [M+H]+=383; Abs. λ max=253 nm

(20) 1-[3-(2-{4-[(isobutyl-methyl-amino)-methyl]-phenylamino}-5-trifluoromethyl-pyrimidin-4-ylamino)-propyl]-pyrrolidin-2-one
Melting point: 110-113° C.
R$_f$=0.36 (silica gel; methylene chloride:methanol=9:1)
HPLC/MS (method G): RT=3.31 min.; [M+H]+=479; Abs. λ max=265 nm

(21) N-{2-[2-(4-Azepan-1-ylmethyl-phenylamino)-5-trifluoromethyl-pyrimidin-4-ylamino]-ethyl}-acetamide
Melting point: 170-172° C.
R$_f$=0.11 (silica gel; methylene chloride:methanol=85:15)

(22) 1-{3-[2-(4-Azepan-1-ylmethyl-phenylamino)-5-trifluoromethyl-pyrimidin-4-ylamino]-propyl}-pyrrolidin-2-one
Melting point: 142-145° C.
$R_f$=0.19 (silica gel; methylene chloride:methanol=85:15)
HPLC/MS (method G): RT=3.31 min.; [M+H]+=491; Abs. λ max=265 nm

(23) N-(2-{2-[4-(isobutylamino-methyl)-phenylamino]-5-trifluoromethyl-pyrimidin-4-ylamino}-ethyl)-acetamide
Melting point: 163-165° C.
$R_f$=0.13 (silica gel; methylene chloride:methanol=9:1)
HPLC/MS (method G): RT=3.06 min.; [M+H]+=; 425 Abs. λ max=261 nm

(24) 1-{3-[5-methyl-2-(4-piperidin-1-ylmethyl-phenylamino)-pyrimidin-4-ylamino]-propyl}-pyrrolidin-2-one
Melting point: 144-145° C.
$R_f$=0.10 (silica gel; methylene chloride:methanol=8:2)
HPLC/MS (method F): RT=2.12 min.; [M+H]+=423; Abs. λ max=263 nm

(25) 1-(3-{2-[4-(isobutylamino-methyl)-phenylamino]-5-trifluoromethyl-pyrimidin-4-ylamino}-propyl)-pyrrolidin-2-one
Melting point: 112-114° C.
$R_f$=0.21 (silica gel; methylene chloride:methanol=9:1)
HPLC/MS (method G): RT=3.28 min.; [M+H]+=465; Abs. λ max=261 nm

(26) N-(2-{2-[4-(3,5-dimethyl-piperazin-1-ylmethyl)-phenylamino]-5-trifluoromethyl-pyrimidin-4-ylamino}-ethyl)-acetamide
Melting point: 186-189° C.
$R_f$=0.10 (silica gel; methylene chloride:methanol=85:15)
HPLC/MS (method F): RT=3 min.; [M+H]+=466; Abs. λ max=261 nm

(27) N-{2-[5-Chloro-2-(4-piperidin-1-ylmethyl-phenylamino)-pyrimidin-4-ylamino]-ethyl}-acetamide
Melting point: 162-164° C.
$R_f$=0.25 (silica gel; methylene chloride:methanol=4:1)
HPLC/MS (method F): RT=2.88 min.; [M+H]+=; 403 Abs. λ max=267 nm

(28) N-(2-{2-[4-(4-acetyl-piperazin-1-ylmethyl)-phenylamino]-5-trifluoromethyl-pyrimidin-4-ylamino}-ethyl)-acetamide
Melting point: 80-83° C.
$R_f$=0.31 (silica gel; methylene chloride:methanol=9:1)
HPLC/MS (method F): RT=3.01 min.; [M+H]+=480; Abs. λ max=257 nm

(29) 1-{3-[2-(4-methylaminomethyl-phenylamino)-5-trifluoromethyl-pyrimidin-4-ylamino]-propyl}-pyrrolidin-2-one
HPLC/MS (method F): RT=2.28 min.; [M+H]+=423; Abs. λ max=261 nm

(30) 1-(3-{2-[4-(2,5-dimethyl-pyrrolidin-1-ylmethyl)-phenylamino]-5-trifluoromethyl-pyrimidin-4-ylamino}-propyl)-pyrrolidin-2-one
Melting point: 131-134° C.
$R_f$=0.18 (silica gel; methylene chloride:methanol=9:1)
HPLC/MS (method G): RT=3.09 min.; [M+H]+=491; Abs. λ max=263 nm

(31) 1-{3-[2-(3-Morpholin-4-ylmethyl-phenylamino)-5-trifluoromethyl-pyrimidin-4-ylamino]-propyl}-pyrrolidin-2-one
Melting point: 132-135° C.
$R_f$=0.47 (silica gel; methylene chloride:methanol=9:1)
HPLC/MS (method G): RT=2.88 min.; [M+H]+=479; Abs. λ max=253 nm

(32) 1-[3-(2-{4-[(diisopropylamino)-methyl]-phenylamino}-5-trifluoromethyl-pyrimidin-4-ylamino)-propyl]-pyrrolidin-2-one
Melting point: 121° C.
$R_f$=0.31 (silica gel; methylene chloride:methanol=9:1)
HPLC/MS (method F): RT=3.42 min.; [M+H]+=493; Abs. λ max=263 nm

(33) N-{2-[2-(3-Morpholin-4-ylmethyl-phenylamino)-5-trifluoromethyl-pyrimidin-4-ylamino]-ethyl}-acetamide
Melting point: 169-170° C.
$R_f$=0.443 (silica gel; methylene chloride:methanol=9:1)
HPLC/MS (method F): RT=2.53 min.; [M+H]+=439; Abs. λ max=255 nm

(34) 1-[3-(2-{3-[(2,2,2-Trifluoro-ethylamino)-methyl]-phenylamino}-5-trifluoromethyl-pyrimidin-4-ylamino)-propyl]-pyrrolidin-2-one
Melting point: 93-94° C.
$R_f$=0.61 (silica gel; methylene chloride:methanol=9:1)
HPLC/MS (method E): RT=2.92 min.; [M+H]+=491; Abs. λ max=253 nm

(35) N-[2-(2-{3-[(2,2,2-Trifluoro-ethylamino)-methyl]-phenylamino}-5-trifluoromethyl-pyrimidin-4-ylamino)-ethyl]-acetamide
Melting point: 139-144° C.
Rf=0.44 (silica gel; methylene chloride:methanol=9:1)
HPLC/MS (method E): RT=3.11 min.; [M+H]+=451; Abs. λ max=255 nm

(36) 1-[3-(2-{4-[(2,2,2-Trifluoro-ethylamino)-methyl]-phenylamino}-5-trifluoromethyl-pyrimidin-4-ylamino)-propyl]-pyrrolidin-2-one
Melting point: 92-98° C.
Rf=0.61 (silica gel; methylene chloride:methanol=9:1)
HPLC/MS (method E): RT=3.23 min.; [M+H]+=491; Abs. λ max=251 nm

(37) N-[2-(2-{4-[(2,2,2-Trifluoro-ethylamino)-methyl]-phenylamino}-5-trifluoromethyl-pyrimidin-4-ylamino)-ethyl]-acetamide
Melting point: 156-165° C.
Rf=0.45 (silica gel; methylene chloride:methanol=9:1)
HPLC/MS (method E): RT=2.92 min.; [M+H]+=451; Abs. λ max=257 nm Example 12

Preparation of Recombinant Cyclin-CDK Enzymes

The corresponding cDNAs for human cyclin B1 (cyclin E, or. cyclin D1) and human CDK1 (CDK2, or. CDK4) were cloned by standard methods using RT-PCR, and cloned into a transfer vector (cyclin in pAcG2T made by Pharmingen, CDKs in p2Bac made by Invitrogen) for the baculovirus system. Recombinant cyclin B1-CDK1 (or cyclin E-CDK2, cyclin D1-CDK4) was expressed in High Five insect cells (*Trichoplusia ni*) by coinfection with both recombinant baculoviruses (after the 4th round of amplification, >1×10$^8$ viruses/ml). 72 h after the infection the High Five cells were harvested, and deep-frozen in liquid nitrogen. After thawing the cells were resuspended in lysing buffer (50 mM HEPES pH 7.5, 10 mM MgCl$_2$, 1 mM DTT, 5 µg/ml leupeptin, 5 µg/ml aprotinin, 100 µM NaF, 100 µM PMSF, 10 mM β-glycerolphosphate, 100 µM Na$_3$VO$_4$, 30 mM nitrophenylphosphate, 17.5 ml of lysing buffer per 10$^8$ cells) and incubated on ice for 30 min. The cell lysate was freed from the cell debris by centrifugation and the quantity of recombinant cyclin B1-CDK1 enzyme (or cyclin E-CDK2, cyclin D1-CDK4) in the total lysate (about 1-5 mg/ml) was determined by SDS-polyacrylamide gel electrophoresis. Cyclin D1-CDK4 was purified by means of a GST-tag on cyclin D1 and then using glutathione beads (total protein about 0.2 mg/ml).

Example 13

Cyclin B1-CDK1 Kinase Inhibition Test

All the kinase tests were carried out in 96-well microtitre plates (Greiner PS) in a final volume of 60 µl. The kinase test contained 1% DMSO (v/v), 5 µg of histone H1 (calf thymus, Roche Molecular Biochemicals), 1 to 5 µg of a cell lysate with recombinant cyclin B1/CDK1, the test substance (in a final concentration of 1 nM to 10 µM) and kinase buffer (15 mM MgCl$_2$, 25 mM MOPS, pH 7.0, 0.1 mM DTT). As a negative control the kinase reaction was carried out in the absence of the substrate histone H1. As a positive control the kinase reaction was carried out in the absence of a test substance. As an internal control 30 µM and 300 µM (final concentration) of the kinase inhibitor olomoucin (Alexis) were used.

The PS microtitre plates were placed on ice, and 10 µl of the test substance, in different concentrations (in each case in 6% DMSO), 20 µl of the histone H1 (250 µg/ml in kinase buffer) and 20 µl of cyclin B1/CDK1 (1 to 5 µg of the recombinant cell lysate in 20 µl of kinase buffer) were pipetted in and mixed together. The kinase reaction is started by the addition of 10 µl of ATP mix (0.045 mM ATP, 0.5 µCi $^{33}$P-ATP in kinase buffer) and incubated for 30 min at 30° C. and 600 rpm in a shaking incubator. After incubation the plates were placed on ice and the proteins were precipitated by the addition of 125 µl of ice-cold 5% trichloroacetic acid. After 15 min on ice the precipitates were transferred onto Packard Unifilter 96 GF/B plates with the Packard Harvester System, and collected by vacuum filtration. The precipitates were washed 4 times with dist. H$_2$O at ambient temperature. The filter plates were then dried at 60° C. and 50 µl of scintillation liquid were added to each well (Ultima Gold, Packard). The plate was sealed up with Sealing Tape and after 1 h measured in a scintillation measuring apparatus (Micro Beta made by Wallac).

The inhibition of the substances was calculated as a percentage of the control (cyclin B1-CDK1 without inhibitor) and the active substance concentration which inhibits the enzyme activity by 50% (IC50) was derived.

Example 14

Cyclin E-CDK2 Kinase Inhibition Test

The inhibition test with cyclin E-CDK2 was carried out using the same method as for cyclin B1-CDK1, except that recombinant cyclin E-CDK2 was used as the enzyme.

Example 15

Cyclin D1-CDK4 Kinase Inhibition Test

For the inhibition test with cyclin D1-CDK4, recombinant Retinoblastoma Protein (pRB) from aa379-928, which contains a GST-tag at the N-terminus, was used as the substrate. GST-pRB was expressed in bacteria and then purified using glutathione beads (about 0.2 mg/ml).

The kinase test contained 1% DMSO (v/v), 10 µg pRB, 0.4 µg of a cell lysate with recombinant cyclin D1-CDK4, the test substance (final concentration from 1 nM to 10 µM) and kinase buffer (15 mM MgCl$_2$, 25 mM MOPS, pH 7.0, 0.1 mM DTT). As a negative control the kinase reaction was carried out in the absence of the substrate pRB. As a positive control the kinase reaction was carried out in the absence of a test substance. As an internal control 30 µM and 300 µM (final concentration) of the kinase inhibitor olomoucin (Alexis) were used.

The PS microtitre plates were placed on ice, and 10 µl of the test substance, in different concentrations (in each case in 6% DMSO), 20 µl of pRB (10 µg in kinase buffer) and 20 µl of cyclin D1-CDK4 (0.4 µg of the recombinant cell lysate in 20 µl of kinase buffer) were pipetted in and mixed together. The kinase reaction was started by the addition of 10 µl of ATP mix (0.045 mM ATP, 1 µCi $^{33}$P-ATP in kinase buffer) and incubated for 45 min at 32° C. and 600 rpm in a vibrating incubator. After incubation, 50 µl of the reaction mixture were pipetted onto P81 filters (Whatmann). After 20 sec reaction time the filters were washed 4 times with 1.5% phosphoric acid (about 5 min per washing step) while shaking them gently. After washing the filters were dried at 85° C., scintillation liquid was added and the scintillation was measured in a scintillation counter (Micro Beta made by Wallac).

Example 16

Measurement of the Cytotoxicity on Cultivated Human Tumour Cells

Cells of the non-small cell lung tumour cell line NCI H-460 (obtained from American Type Culture Collection (ATCC)) were cultivated in RPMI1640 medium (Gibco) and 10% foetal calf serum (Gibco) and harvested in the log growth phase. Then the NCI H-460 cells were placed in 96-well plates (Costar) at a density of 1000 cells per well and incubated overnight in an incubator (at 37° C. and 5% CO$_2$), each plate containing 6 wells which were filled only with medium (3 wells as a medium control and 3 wells for incubation with reduced AlamarBlue). The active substances were added to the cells in various concentrations (dissolved in DMSO; final concentration: 1%) (each measurement being done three times). After 72 hours incubation 20 µl AlamarBlue (AccuMed International) were added to each well, and the cells were incubated for a further 5 hours. As a control 20 µl of reduced Alamar Blue were added to three wells (AlamarBlue Reagent autoclaved for 30 min) After 5 h incubation the colour change of the AlamarBlue Reagent in the individual wells was determined in an Perkin Elmer Fluorescence spectrophotometer (excitation 530 nm, emission 590 nm, slits 15, integrate time 0.1). The quantity of AlamarBlue Reagent reacted represents the metabolic activity of the cells. The relative cell activity was calculated as a percentage of the control (NCI H-460 cells without an inhibitor) and the active substance concentration which inhibits the cell activity by 50% (IC50) was derived. The values were calculated from the average of three separate measurements, correcting for the control value (medium control).

ABBREVIATIONS USED

ATP Adenosine triphosphate
Ci Curie
DTT 1,4-dithiothreitol
DMSO dimethylsulphoxide
GST Glutathion-5-transferase
HEPES N2-hydroxyethylpiperazine-N'-2'-ethanesulphonic acid
MOPS 3-(N-morpholino)-propanesulphonic acid
NaF sodium fluoride
PMSF phenylmethylsulphonyl fluoride The following compounds according to the invention have a CDK1/cyclinB1 $IC_{50}$ value of less than 100 nM in the CDK1 tests (Example 13):

Example 1

Serial numbers: 003, 004, 005, 008, 009, 010, 011, 012, 014, 015, 016, 017, 018, 019, 020, 021, 022, 023, 024, 025, 026, 027, 028, 029, 030, 031, 032, 033, 034, 035, 037, 038, 039, 040, 041, 042, 043, 044, 045, 046, 047, 049, 050, 052, 053, 054, 055, 067, 073, 077, 079, 080, 088, 093, 104, 107, 109, 111, 112, 113, 115, 116, 117, 118, 119, 120, 152, 304, 349, 388, 585, 628, 651, 652, 654, 655, 656, 661, 662, 663, 683, 685, 689, 690, 692, 693, 694, 695

Example 2

Serial numbers: 002, 003, 004, 007, 008, 009, 010, 011, 012, 013, 014, 015, 016, 036, 037, 038, 041, 042, 043, 044, 045, 046, 047, 048, 051, 052, 053, 057, 058, 059, 060, 061, 062, 075, 076, 106, 109, 134, 136, 141, 142

Example 4

Serial number: 001

Example 5

Serial number: 000

Example 7

Serial numbers: 001, 002, 006, 010, 012, 013, 015, 021, 022, 024, 027, 028, 029, 032, 035, 036

Example 8

Serial numbers: 003, 007, 024, 026, 028

Example 9

Serial number: 001

Example 10

Serial numbers: 000, 014, 015, 016

Example 11

Serial number: 034

Preparations for Administration

The compounds according to the invention may be administered by oral, transdermal or parenteral route or by inhalation. The compounds according to the invention are present as active ingredients in conventional preparations, e.g. in compositions consisting essentially of an inert pharmaceutical carrier and an effective dose of the active substance, such as for example plain or coated tablets, capsules, lozenges, powders, solutions, suspensions, emulsions, syrups, suppositories, transdermal systems, etc. An effective dose of the compounds according to the invention is between 1 and 100, preferably between 1 and 50, most preferably between 5-30 mg/dose, for oral administration, and between 0.001 and 50, preferably between 0.1 and 10 mg/dose for intravenous or intramuscular administration. For inhalation, solutions containing 0.01 to 1.0, preferably 0.1 to 0.5% of active substance are suitable according to the invention. For inhalation, the use of powders is preferred. It is also possible to use the compounds according to the invention as a solution for infusion, preferably in physiological saline or nutrient salt solution.

The compounds according to the invention may be used on their own or in conjunction with other active substances according to the invention, optionally also in conjunction with other pharmacologically active substances. Suitable preparations include for example tablets, capsules, suppositories, solutions, elixirs, emulsions or dispersible powders. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dose is between 1 and 800 mg, preferably 10-300 mg, in adults.

The Examples that follow illustrate the present invention without, however, restricting its scope.

Examples of Pharmaceutical Formulations

| A) Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Coated tablets | per coated tablet |
|---|---|
| Active substance | 5 mg |
| Corn starch | 41.5 mg |
| Lactose | 30 mg |
| Polyvinylpyrrolidone | 3 mg |
| Magnesium stearate | 0.5 mg |
| | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) Capsules | per capsule |
|---|---|
| Active substance | 50 mg |
| Corn starch | 268.5 mg |
| Magnesium stearate | 1.5 mg |
| | 320 mg |

The substance and corn starch are mixed and moistened with water. The moist mass is screened and dried. The dry granules are screened and mixed with magnesium stearate. The finished mixture is packed into size 1 hard gelatine capsules.

| E) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) Suppositories | |
|---|---|
| Active substance | 50 mg |
| Solid fat | 1650 mg |
| | 1700 mg |

The hard fat is melted. At 40° C. the ground active substance is homogeneously dispersed. It is cooled to 38° C. and poured into slightly chilled suppository moulds.

The invention claimed is:
1. A trisubstituted pyrimidine of formula (I):

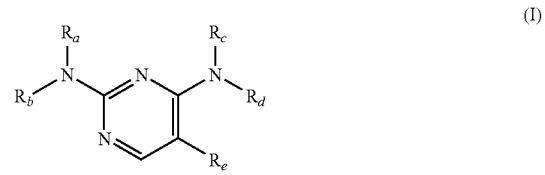

wherein
$R_a$ denotes a hydrogen atom or an alkyl group,
$R_b$ denotes an aralkyl group optionally substituted in the alkylene moiety by one or two alkyl groups, which may be substituted in the aryl moiety by a carboxy, alkoxycarbonyl, aminocarbonyl, alkylaminocarbonyl, dialkylaminocarbonyl, amino, alkylamino, dialkylamino, cyano, trifluoromethyl or nitro group or one or two fluorine, chlorine, bromine or iodine atoms or one or two hydroxy, alkyl or alkoxy groups, while the substituents may be identical or different, or by a 5- to 7-membered alkyleneimino group, while in each case one or two methylene groups adjacent to the nitrogen atom may be replaced in each case by a carbonyl group or in the abovementioned 6- to 7-membered alkyleneimino groups a methylene group in the 4-position may be replaced by an oxygen atom, by an imino, N-aryl-imino or N-alkyl-imino group, or
denotes a phenyl group optionally substituted by the groups $R_1$ to $R_3$, while
$R_1$ and $R_2$ in each case independently of one another denote
a fluorine, chlorine, bromine or iodine atom, or
a $C_{1-2}$-alkyl or hydroxy group,
a $C_{3-7}$-cycloalkyl or $C_{4-7}$-cycloalkoxy group which may be substituted in each case by one or two alkyl groups or by an aryl group, a C$_{2-5}$-alkenyl group optionally substituted by an aryl group, a C$_{2-5}$-alkynyl group optionally substituted by an aryl group an aryl, aryloxy, aralkyl, aralkoxy, alkylsulphenyl, alkylsulphinyl, alkylsulphonyl, alkylsulphonyloxy, trifluoromethylsulphenyl, trifluoromethylsulphinyl, trifluoromethylsulphonyl, arylsulphenyl, arylsulphinyl, arylsulphonyl, aralkylsulphenyl, aralkylsulphinyl or aralkylsulphonyl group, a methyl or methoxy group substituted by 1 to 3 fluorine atoms, a C$_{2-4}$-alkyl or C$_{2-4}$-alkoxy group substituted by 1 to 5 fluorine atoms, a nitro, amino, alkylamino, dialkylamino, C$_{3-7}$-cycloalkylamino, N-alkyl-C$_{3-7}$-cycloalkylamino, arylamino, N-alkyl-arylamino, aralkylamino or N-alkyl-aralkylamino group, a 4- to 7-membered alkyleneimino group optionally substituted by 1 to 4 alkyl groups, while in the abovementioned 5- to 7-membered alkyleneimino groups in each case one or two methylene groups adjacent to the nitrogen atom may be replaced in each case by a carbonyl group or in the abovementioned 6- to 7-membered alkyleneimino groups a methylene group in the 4-position may be replaced by an oxygen or sulphur atom, by a sulphinyl, sulphonyl, imino, N-alkyl-imino, N-alkylcarbonyl-imino, N-alkylsulphonyl-imino, N-arylcarbonyl-imino, N-arylsulphonyl-imino, N-aryl-imino or N-aralkyl-imino group, an (alkyleneimino)carbonyl or (alkyleneimino)sulphonyl group with in each case 4 to 7 cyclic atoms in the alkyleneimino moiety, optionally substituted by 1 to 4 alkyl groups, while in the abovementioned 6- to 7-membered alkyleneimino moieties in each case a methylene group in the 4-position may be replaced by an oxygen or sulphur atom, by a sulphinyl, sulphonyl, imino, N-alkyl-imino, N-alkylcarbonyl-imino, N-alkylsulphonyl-imino, N-arylcarbonyl-imino, N-arylsulphonyl-imino, N-aryl-imino or N-aralkyl-imino group, an alkylcarbonylamino, N-alkyl-alkylcarbonylamino, alkyl-sulphonylamino, N-alkyl-alkylsulphonylamino, arylcarbonylamino, N-alkyl-arylcarbonylamino, arylsulphonylamino, N-alkyl-arylsulphonylamino, aralkylcarbonylamino, N-alkyl-aralkylcarbonylamino, aralkylsulphonylamino, N-alkyl-aralkylsulphonylamino, perfluoroalkylsulphonylamino, N-alkyl-perfluoroalkylsulphonylamino, alkylcarbonyl, arylcarbonyl, aralkylcarbonyl, aryl-hydroxymethyl, aralkyl-hydroxymethyl, carboxy, alkoxycarbonyl, aralkoxycarbonyl, aminocarbonyl, alkylaminocarbonyl, dialkylaminocarbonyl, arylaminocarbonyl, N-alkyl-arylaminocarbonyl, aralkylaminocarbonyl, N-alkyl-aralkylaminocarbonyl, N-hydroxy-aminocarbonyl, N-hydroxy-alkylaminocarbonyl, N-alkoxy-aminocarbonyl, N-alkoxy-alkylaminocarbonyl, cyano, azido, N-cyano-amino or N-cyano-alkylamino group, a sulpho, alkoxysulphonyl, aminosulphonyl, alkylaminosulphonyl, dialkylaminosulphonyl, arylaminosulphonyl, pyridylaminosulphonyl, pyrimidinylaminosulphonyl, N-alkyl-arylaminosulphonyl, aralkylaminosulphonyl or N-alkyl-aralkylaminosulphonyl group, a phosphono, O-alkyl-phosphono, O,O'-Dialkyl-phosphono, O-aralkyl-phosphono or O,O'-diaralkyl-phosphono group, or a C$_{1-2}$ alkyl group substituted by R$_4$, wherein R$_4$ denotes a hydroxy, alkoxy, aryloxy, aralkoxy, amino, alkylamino, dialkylamino, alkylsulphenyl, alkylsulphinyl, alkylsulphonyl, arylsulphenyl, arylsulphinyl, arylsulphonyl, aralkylsulphenyl, aralkylsulphinyl, aralkylsulphonyl, carboxy, alkoxycarbonyl, aminocarbonyl, alkylaminocarbonyl, dialkylaminocarbonyl or cyano group, a 4- to 7-membered alkyleneimino group optionally substituted by 1 to 4 alkyl groups, while in the abovementioned 5- to 7-membered alkyleneimino groups one or two methylene groups adjacent to the nitrogen atom may be replaced in each case by a carbonyl group or in the abovementioned 6- to 7-membered alkyleneimino groups a methylene group in the 4-position may be replaced by an oxygen or sulphur atom, by a sulphinyl, sulphonyl, imino, N-alkyl-imino, N-alkylcarbonyl-imino, N-alkylsulphonyl-imino, N-arylcarbonyl-imino, N-arylsulphonyl-imino, N-aryl-imino or N-aralkyl-imino group, or a 4- to 7-membered alkyleneimino group optionally substituted by 1 to 4 alkyl groups, while in the abovementioned 5- to 7-membered alkyleneimino groups in each case one or two methylene groups adjacent to the nitrogen atom may be substituted by a carbonyl group or in the abovementioned 6- to 7-membered alkyleneimino groups may be substituted by one or two hydroxy, alkoxy, aminocarbonyl, alkylaminocarbonyl, dialkylaminocarbonyl, amino, alkylamino and dialkylamino group, an (alkyleneimino)carbonyl group optionally substituted by 1 to 4 alkyl groups with 4 to 7 cyclic atoms in the alkyleneimino moiety in each case, while in the abovementioned 6- to 7-membered alkyleneimino moieties in each case a methylene group may be replaced in the 4-position by an oxygen or sulphur atom, by a sulphinyl, sulphonyl, imino, N-alkyl-imino, N-alkylcarbonyl-imino, N-alkylsulphonyl-imino, N-arylcarbonyl-imino, N-arylsulphonyl-imino, N-aryl-imino or N-aralkyl-imino group, or a group of formula

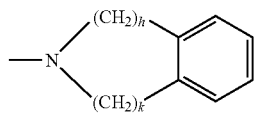

wherein h and k, which may be identical or different, represent the numbers 1 to 3 or h denotes the number 0 and k denotes the number 2, 3 or 4, while additionally the above benzo moiety may be mono- or disubstituted by fluorine, chlorine, bromine or iodine atoms, by alkyl, trifluoromethyl, hydroxy, alkoxy, carboxy or cyano groups, while the substituents in each case may be identical or different, and the above saturated cyclic alkyleneimino moiety may be substituted by 1 or 2 alkyl groups, $R_3$ denotes a fluorine, chlorine or bromine atom, a $C_{1-2}$ alkyl, $C_{1-2}$ alkoxy or trifluoromethyl group, or
a sulpho, alkoxysulphonyl, aminosulphonyl, alkylaminosulphonyl, dialkylaminosulphonyl, arylaminosulphonyl, pyridylaminosulphonyl, pyrimidinylaminosulphonyl, N-alkyl-arylaminosulphonyl, aralkylaminosulphonyl or N-alkyl-aralkylaminosulphonyl group, or $R_2$ together with $R_3$, if they are bound to adjacent carbon atoms, denote
a methylenedioxy group optionally substituted by one or two alkyl groups, or
an n-$C_{3-6}$-alkylene group optionally substituted by one or two alkyl groups, wherein a methylene group may be replaced by an oxygen or sulphur atom, by a sulphinyl, sulphonyl, N-alkylcarbonyl-imino, N-alkylsulphonyl-imino, N-arylcarbonyl-imino or N-arylsulphonyl-imino group, or
a 1,3-butadiene-1,4-diylene group optionally substituted by one or two fluorine, chlorine, bromine or iodine atoms, by one or two hydroxy, alkyl, alkoxy, trifluoromethyl, carboxy, alkoxycarbonyl, aminocarbonyl, alkylaminocarbonyl, dialkylaminocarbonyl or cyano groups, while the substituents may be identical or different, or
a group of formula —(CH$_2$)$_m$—N(R$_5$)—(CH$_2$)$_n$—, wherein
the methylene groups of the cyclic alkyleneimino moieties thus formed may additionally be substituted by 1 or 2 alkyl groups,
$R_5$ denotes a hydrogen atom or an alkyl, aryl or aralkyl group, and
m and n, which may be identical or different, represent the numbers 1, 2 or 3, while in the alkyleneimino moieties thus formed one or two methylene groups adjacent to the nitrogen atom may be replaced in each case by a carbonyl group, or
m denotes the number 0 and n denotes the number 2, 3 or 4, while in the alkyleneimino moieties thus formed in each case the methylene group adjacent to the nitrogen atom may be replaced by a carbonyl group, or
R2 together with R3 denotes a group of formula —NH—C(═O)—(CH$_2$)—, —NH—C(═O)—(CH$_2$)$_2$, —NH—N═N, —NH—N═CH, —NH—CH═N—, —O—CH═N, —S—CH═N or —NH—CH═CH— and the tautomers of the ring systems defined by —NH—N═N, —NH—N═CH, —NH—CH═N—, while each hydrogen atom may be substituted by an alkyl, aryl or aralkyl group, or $R_a$ together with $R_1$, if $R_1$ is in the o-position to the nitrogen atom substituted by $R_a$, also denote an n-$C_{2-4}$-alkylene group optionally substituted by one or two alkyl groups, and $R_c$NR$_d$ together denotes a 4- to 8-membered alkyleneimino group optionally substituted by 1 to 4 alkyl groups or 1 to 2 aryl groups, which is additionally substituted by the group $R_6$, while $R_6$ denotes a carboxy, alkoxycarbonyl, aminocarbonyl, alkylaminocarbonyl, dialkylaminocarbonyl, cyano, hydroxy, alkoxy, aryloxy, aralkoxy, alkylcarbonyloxy, arylcarbonyloxy, amino, alkylamino, hydroxy-$C_{2-4}$-alkylamino, dialkylamino, cyanamino, formylamino, N-(alkyl)-N-(hydroxy-$C_{2-4}$-alkyl)amino, bis-(hydroxy-$C_{2-4}$-alkyl)-amino group, alkylsulphenyl, alkylsulphinyl, alkylsulphonyl, arylsulphenyl, arylsulphinyl, arylsulphonyl, aralkylsulphenyl, aralkylsulphinyl, aralkylsulphonyl, an alkylcarbonylamino, N-alkyl-alkylcarbonylamino, alkylsulphonylamino, N-alkyl-alkylsulphonylamino, arylcarbonylamino, N-alkyl-arylcarbonylamino, arylsulphonylamino, N-alkyl-arylsulphonylamino, aralkylcarbonylamino, N-alkyl-aralkylcarbonylamino, aralkylsulphonylamino, N-alkyl-aralkylsulphonylamino, alkoxycarbonylamino, N-alkyl-alkoxycarbonylamino, alkoxycarbonylalkylamino, N-(alkyl)-N-(alkoxycarbonylalkyl)-amino, aralkoxycarbonylamino or N-alkyl-aralkoxycarbonylamino group,
an (NR$_8$R$_9$)CONR$_7$ or (NR$_8$R$_9$)SO$_2$NR$_7$-group, wherein
$R_7$, $R_8$ and $R_9$, which may be identical or different, in each case denote a hydrogen atom or an alkyl, aryl or pyridyl group, or
$R_7$ and $R_8$ together denote an n-$C_{2-4}$-alkylene group and $R_9$ denotes a hydrogen atom or an alkyl, aryl or pyridyl group,
an (alkyleneimino)carbonyl group optionally substituted by 1 to 4 alkyl groups with in each case 4 to 7 cyclic atoms in the alkyleneimino moiety, while in the abovementioned 6- to 7-membered alkyleneimino moieties in each case a methylene group in the 4-position may be replaced by an oxygen or sulphur atom, by a sulphinyl, sulphonyl, imino, N-alkyl-imino, N-alkylcarbonyl-imino, N-alkylsulphonyl-imino, N-aryl-imino or N-aralkyl-imino group,
a 4- to 7-membered alkyleneimino group optionally substituted by 1 to 4 alkyl groups or a hydroxyalkyl group, while in the abovementioned 5- to 7-membered alkyleneimino groups in each case one or two methylene groups adjacent to the nitrogen atom may be replaced by a carbonyl group,
a 6 or 7-membered alkyleneimino group optionally substituted by 1 to 4 alkyl groups or a hydroxyalkyl group, while in each case a methylene group in the 4-position of the alkyleneimino moiety is replaced by an oxygen or sulphur atom, by a carbonyl, sulphinyl, sulphonyl, imino, N-alkylimino, N-alkylcarbonyl-imino, N-alkylsulphonyl-imino, N-arylimino or N-aralkyl-imino group and additionally in the alkyleneimino moiety of the abovementioned groups in each case one or two of the methylene groups adjacent to the nitrogen atoms may be replaced by a carbonyl group,
a 4- to 7-membered alkyleneimino group substituted by a hydroxy, alkoxy, amino, alkylamino, dialkylamino, alkylcarbonylamino, N-alkyl-alkylcarbonylamino, alkylsulphonylamino, N-alkyl-alkylsulphonylamino, carboxy, alkoxycarbonyl, aminocarbonyl, alkylaminocarbonyl or dialkylaminocarbonyl group,
an alkyl group substituted by a carboxy, alkoxycarbonyl, aminocarbonyl, alkylaminocarbonyl or dialkylaminocarbonyl, cyano, hydroxy, alkoxy, aryloxy, amino, alkylamino, dialkylamino, alkylcarbonylamino, N-alkyl-alkylcarbonylamino, alkoxycarbonylamino, N-alkyl-alkoxycarbonylamino, alkylsulphonylamino, N-alkyl-alkylsulphonylamino, arylcarbonylamino, N-alkyl-arylcarbonylamino, arylsulphonylamino, N-alkyl-arylsulphonylamino, aminocarbonylalkylamino, N-(alkyl)-N-(aminocarbonylalkyl)-amino, alkylaminocarbonylalkylamino, N-(alkyl)-N-(alkylaminocarbonylalkyl)-amino, dialkylaminocarbonylalkylamino, N-(alkyl)-N-(dialkylaminocarbonylalkyl)-amino, dialkylaminoalkoxy, alkylsulphenyl, alkylsulphinyl, alkylsulphonyl, arylsulphenyl, arylsulphinyl or arylsulphonyl group, an (alkyleneimino)alkyl group optionally substituted by 1 to 4 alkyl groups with in each case 4 to 7 cyclic atoms in the alkyleneimino moiety, while in the abovementioned 6- to 7-membered alkyleneimino moieties a methylene group in the 4-position may be replaced in each case by an oxygen or sulphur atom, by a sulphinyl, sulphonyl, imino, N-alkyl-imino or N-alkylcarbonyl-imino group, an (alkyleneimino)carbonylalkyl group optionally substituted by 1 to 4 alkyl groups with in each case 4 to 7 cyclic atoms in the alkyleneimino moiety, while in the abovementioned 6- to 7-membered alkyleneimino moieties a methylene group in the 4-position may be replaced in each case by an oxygen or sulphur atom, by a sulphinyl, sulphonyl, imino or N-alkyl-imino group, a (carboxyalkyl)oxy, (alkoxycarbonylalkyl)oxy, (aminocarbonylalkyl)oxy, (alkylaminocarbonylalkyl)oxy or (dialkylaminocarbonylalkyl)oxy group, an [(alkyleneimino)carbonylalkyl]oxy-group optionally substituted by 1 to 4 alkyl groups with in each case 4 to 7 cyclic atoms in the alkyleneimino moiety, while in the abovementioned 6- to 7-membered alkyleneimino moieties a methylene group in the 4-position may be replaced in each case by an oxygen or sulphur atom, by a sulphinyl, sulphonyl, imino or N-alkyl-imino group, a $C_{5-7}$-cycloalkyl group wherein a methylene group is replaced by an oxygen or sulphur atom, by a sulphinyl, sulphonyl, imino or N-alkyl-imino, alkylcarbonylimino or alkylsulphonylimino group, or a 3,4-dihydro-1H-quinazolin-2-on-3-yl or 1H-benzimidazol-2-on-1-yl-group optionally substituted in the aryl moiety by one or two fluorine, chlorine, bromine or iodine atoms or one or two nitro, alkyl, alkoxy or cyano groups in each case, while the substituents may be identical or different, or $R_cNR_d$ together denotes a 6- to 8-membered alkyleneimino group optionally substituted by 1 to 4 alkyl groups or by an aryl group, which may additionally be substituted by the group $R_6$, while in the abovementioned alkyleneimino groups a methylene group in the 4-position is replaced by an oxygen or sulphur atom, by a carbonyl, sulphinyl, sulphonyl, N-oxido-N-alkylimino or $R_{10}N$-group in each case, while $R_{10}$ denotes a hydrogen atom, an alkyl, hydroxy-$C_{2-4}$-alkyl, alkoxy-$C_{2-4}$-alkyl, amino-$C_{2-4}$-alkyl, alkylamino-$C_{2-4}$-alkyl, dialkylamino-$C_{2-4}$-alkyl, (hydroxy-$C_{2-4}$-alkoxy)-$C_{2-4}$-alkyl, aminocarbonylalkyl, alkylaminocarbonylalkyl, dialkylaminocarbonylalkyl, aryl, formyl, alkylcarbonyl, alkylsulphonyl, arylcarbonyl, aryl-sulphonyl, aralkylcarbonyl, aralkylsulphonyl, alkoxycarbonyl, aralkoxycarbonyl, cyano, aminocarbonyl, alkylaminocarbonyl or dialkylaminocarbonyl group, an amino-alkylcarbonyl, alkylamino-alkylcarbonyl, dialkylamino-alkylcarbonyl group, an alkyl group substituted by one, two or three aryl groups, an 8-alkyl-8-aza-bicyclo[3.2.1]oct-3-yl group, an aryl or a 2-, 3- or 4-pyridyl group or 2-, 4- or 5-pyrimidinyl group an (alkyleneimino)carbonyl or (alkyleneimino)carbonylalkyl group with 4 to 7 cyclic atoms in the alkyleneimino moiety in each case, while in the abovementioned 6- to 7-membered alkyleneimino moieties a methylene group in the 4-position may be replaced in each case by an oxygen or sulphur atom, by a sulphinyl, sulphonyl, imino, N-alkyl-imino, N-alkylcarbonyl-imino or N-aralkyl-imino group, or $R_cNR_d$ together denotes a 3-thiazolidinyl-group substituted in the 4-position by a carboxy, alkoxycarbonyl, aminocarbonyl, alkylaminocarbonyl, dialkylaminocarbonyl group, or $R_cNR_d$ together denotes:

a 1-pyrrolidinyl group optionally substituted by 1 to 4 alkyl groups, wherein two hydrogen atoms on the carbon skeleton are replaced by a straight-chain alkylene bridge, this bridge containing 2 to 6 carbon atoms if the two hydrogen atoms are located on the same carbon atom, or 1 to 5 carbon atoms if the two hydrogen atoms are located on adjacent carbon atoms, or 2 to 4 carbon atoms if the two hydrogen atoms are located on carbon atoms separated by one atom, while the abovementioned 1-pyrrolidinyl groups are additionally substituted by the group $R_6$, which is as hereinbefore defined, a 1-piperidinyl or 1-azacyclohept-1-yl group optionally substituted by 1 to 4 alkyl groups, wherein two hydrogen atoms on the carbon skeleton are replaced by a straight-chain alkylene bridge, this bridge containing 2 to 6 carbon atoms if the two hydrogen atoms are located on the same carbon atom, or 1 to 5 carbon atoms if the two hydrogen atoms are located on adjacent carbon atoms, or 1 to 4 carbon atoms if the two hydrogen atoms are located on carbon atoms separated by an atom, or 1 to 3 carbon atoms if the two hydrogen atoms are located on carbon atoms separated by two atoms, while the abovementioned 1-piperidinyl- and 1-azacyclohept-1-yl groups are additionally substituted by the group $R_6$, which is as hereinbefore defined, a 1-pyrrolidinyl group optionally substituted by 1 to 4 alkyl groups, wherein two hydrogen atoms in the 3 position are substituted by a —O—$CH_2CH_2$—O or —O—$CH_2CH_2CH_2$—O-group, a 1-piperidinyl or 1-azacyclohept-1-yl group optionally substituted by 1 to 4 alkyl groups, wherein in the 3 position or in the 4 position two hydrogen atoms are substituted by a —O—$CH_2CH_2$—O or —O—$CH_2CH_2CH_2$—O-group in each case, a 1-azetidinyl group optionally substituted by an alkyl group, wherein the two hydrogen atoms of a methylene group are replaced by a straight-chain $C_{4-6}$-alkylene bridge, while in each case a methylene group in the $C_{4-6}$-alkylene bridge is replaced by a $R_{10}N$-group, where $R_{10}$ is as hereinbefore defined, while the bicyclic ring thus formed may additionally be substituted by a hydroxy, alkoxy, amino, alkylamino, dialkylamino, cyano, alkylcarbonylamino, alkylsulphonylamino, alkoxycarbonylamino, arylcarbonyl, carboxy, alkoxycarbonyl, aminocarbonyl, alkylaminocarbonyl or dialkylaminocarbonyl group, a 1-pyrrolidinyl, 1-piperidinyl or 1-azacyclohept-1-yl group optionally substituted by 1 to 2 alkyl groups, wherein the two hydrogen atoms of a methylene group are replaced by a straight-chain $C_{3-6}$-alkylene bridge, while in each case a methylene group in the $C_{3-6}$-alkylene bridge is replaced by a $R_{10}N$-group, while $R_{10}$ is as hereinbefore defined, while the bicyclic ring thus formed may additionally be substituted by a hydroxy, alkoxy, amino, alkylamino, dialkylamino, cyano, alkylcarbonylamino, alkylsulphonylamino, alkoxycarbonylamino, arylcarbonyl, carboxy, alkoxycarbonyl, aminocarbonyl, alkylaminocarbonyl or dialkylaminocarbonyl group, or a group of the structure

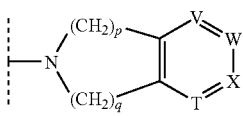

optionally substituted in the alkylene moieties by 1 or 2 alkyl groups, wherein p and q, which may be identical or different, represent the number 1 or 2, and the unit -V=W—X=Y— denotes one of the groups (a), (b), (c), (d) or (e):

  (a),

  (b),

  (c),

  (d),

  (e), or —V=W— taken together represent an oxygen or sulphur atom and —X=Y— represents one of the groups —N=C, —C=N or —C=C—, or —V=W— taken together represent an imino, N-alkyl-imino, N-aralkyl-imino or N-aryl-imino group and —X=Y— represents one of the groups —N=N, —N=C, —C=N or —C=C—, or, if p and q are not the same, —X=Y— taken together represent an oxygen or sulphur atom and —V=W— represents one of the groups —N=C, —C=N or —C=C—, or —X=Y— taken together represent an imino, N-alkyl-imino, N-aralkyl-imino or N-aryl-iminogroup and —V=W— represents one of the groups —N=N, —N=C, —C=N or —C=C—, while one or two of the available carbon atoms of the unit —V=W—X=Y— may be substituted in each case by a hydroxy, alkoxy, amino, alkylamino, dialkylamino, carboxy, alkoxycarbonyl, aminocarbonyl, alkylaminocarbonyl, dialkylaminocarbonyl or hydrazinocarbonyl group, while the substituents may be identical or different, and the remaining available carbon atoms of the unit —V=W—X=Y— are substituted by a hydrogen atom, an alkyl, aralkyl or aryl group, and $R_e$ denotes a fluorine, chlorine, bromine or iodine atom, a nitro, alkyl, alkoxy, dialkylamino, alkylamino, alkylcarbonyl, alkylsulphenyl, alkylsulphinyl, alkylsulphonyl, alkoxyalkyl-alkylcarbonyl-N-alkyl-aminoalkyl, alkylcarbonyl-aminoalkyl, alkylsulphonyl-aminoalkyl, aminocarbonyl, dialkylaminocarbonyl, aminoalkyl, alkylaminoalkyl or dialkylaminoalkyl group, a methyl, methylsulphenyl or methoxy group substituted by 1 to 3 fluorine atoms, a $C_{2-4}$-alkyl, $C_{2-4}$-alkylsulphenyl or $C_{2-4}$-alkoxy group substituted by 1 to 5 fluorine atoms, an $C_{3-6}$-cycloalkyl-$C_{1-3}$-alkyl group optionally substituted by 1-6 fluorine atoms, a $C_{2-5}$-alkenyl or $C_{3-5}$-alkenyloxy group, while the vinyl moiety may not be attached to the oxygen atom, a $C_{2-6}$-alkynyl or $C_{3-6}$-alkynyloxy group, while the ethynyl moiety may not be attached to the oxygen atom, or an alkyleneimino or alkyleneimino-alkyl group with in each case 4 to 7 cyclic atoms in the alkyleneimino moiety optionally substituted by 1 to 4 alkyl groups, while in a 6- or 7-membered alkyleneimino moiety a methylene group in the 4-position may be replaced in each case by an oxygen or sulphur atom, by a sulphinyl, sulphonyl, imino, N-alkyl-imino, N-alkylcarbonyl-imino, N-alkylsulphonyl-imino, N-aryl-imino or N-aralkyl-imino group, or a tautomer, racemate, enantiomer, diastereomer or mixture thereof, or a pharmacologically acceptable acid addition salt thereof, wherein, unless otherwise stated, by the aryl moieties set forth above, either alone or as part of another group, is meant a phenyl group, wherein one or two carbon atoms may be replaced by a nitrogen atom in each case, wherein the abovementioned aryl moieties in each case may be monosubstituted by $R_{11}$, mono, di or trisubstituted by $R_{12}$ or monosubstituted by $R_{11}$ and additionally mono- or disubstituted by $R_{12}$, while the substituents may be identical or different, and $R_{11}$ denotes a cyano, carboxy, aminocarbonyl, alkylaminocarbonyl, dialkylaminocarbonyl, alkoxycarbonyl, alkylcarbonyl, alkylsulphenyl, alkylsulphinyl, alkylsulphonyl, alkylsulphonyloxy, perfluoroalkyl, perfluoroalkoxy, nitro, amino, alkylcarbonylamino, N-alkylalkylcarbonylamino, alkylamino, dialkylamino, hydroxy-$C_{2-4}$-alkylamino, N-alkyl-(hydroxy-$C_{2-4}$-alkyl)amino, bis-(hydroxy-$C_{2-4}$-alkyl)amino, phenylalkylcarbonylamino, phenylcarbonylamino, alkylsulphonylamino, phenylalkylsulphonylamino, phenylsulphonylamino, N-alkyl-phenylalkylcarbonylamino, N-alkyl-phenylcarbonylamino, N-alkyl-alkylsulphonylamino, N-alkyl-phenylalkylsulphonylamino, N-alkyl-phenylsulphonylamino, aminosulphonyl, alkylaminosulphonyl, dialkylaminosulphonyl, $(R_9NR_8)$—CO—$NR_7$ or $(R_9NR_8)$—$SO_2$—$NR_7$ group, where $R_7$, $R_8$ and $R_9$ are as hereinbefore defined, a 5- to 7-membered alkyleneimino group optionally substituted by 1 to 4 alkyl groups or a hydroxyalkyl group, while in the abovementioned 6- to 7-membered alkyleneimino groups a methylene group in the 4-position may be replaced in each case by an oxygen atom or an $R_{10}N$ group, where $R_{10}$ is as hereinbefore defined, a 5- to 7-membered alkyleneimino group optionally substituted by 1 to 4 alkyl groups or a hydroxyalkyl group, while in each case one or two methylene groups adjacent to the nitrogen atom is replaced by a carbonyl group in each case, and $R_{12}$ denotes an alkyl, hydroxy or alkoxy group, a fluorine, chlorine, bromine or iodine atom, while two groups $R_{12}$, if they are bound to adjacent carbon atoms, may also denote an alkylene group with 3 to 6 carbon atoms, a 1,3-butadiene-1,4-diylene group or a methylenedioxy group, and, unless stated to the contrary, the abovementioned alkyl, alkylene and alkoxy moieties each contain 1 to 4 carbon atoms, wherein, unless otherwise stated, each carbon atom in the abovementioned alkyl, alkylene or cycloalkylene moieties, which is bound to a nitrogen, oxygen or sulphur atom, cannot be bound to any other halogen, nitrogen, oxygen or sulphur atom.

2. A compound of formula I according to claim 1, wherein $R_a$ denotes a hydrogen atom or an alkyl group, $R_b$ denotes an aralkyl group which may be substituted in the aryl moiety by a carboxy, alkoxycarbonyl, aminocarbonyl, alkylaminocarbonyl, dialkylaminocarbonyl, amino, alkylamino, dialkylamino, cyano, trifluoromethyl or nitro group or one or two fluorine, chlorine, bromine or iodine atoms or one or two hydroxy, alkyl or alkoxy groups, while the substituents may be identical or different, or by a 5- to 7-membered alkyleneimino group, while in each case one or two methylene groups adjacent to the nitrogen atom may be replaced in each case by a carbonyl group or in the abovementioned 6- to 7-membered alkyleneimino groups a methylene group in the 4-position may be replaced by an oxygen atom, by an imino, N-aryl-imino or N-alkyl-imino group, and wherein the alkylene moiety of the abovementioned aralkyl groups may be substituted by one or two alkyl groups, or a phenyl group optionally substituted by the groups $R_1$ to $R_3$, while $R_1$ denotes a fluorine, chlorine, bromine or iodine atom,
a $C_{1-2}$-alkyl or hydroxy group,
a $C_{3-6}$-cycloalkyl or $C_{5-6}$-cycloalkoxy group,
a $C_{2-5}$-alkenyl group,
a $C_{2-5}$-alkynyl group,
an aryl, aryloxy, aralkyl, aralkoxy, alkylsulphenyl, alkylsulphinyl, alkylsulphonyl, alkylsulphonyloxy, trifluoromethylsulphenyl, trifluoromethylsulphonyl, arylsulphenyl, arylsulphinyl, arylsulphonyl, aralkylsulphenyl, aralkylsulphinyl or aralkylsulphonyl group,
a methyl or methoxy group substituted by 1 to 3 fluorine atoms,
a $C_{2-4}$-alkyl or $C_{2-4}$-alkoxy group substituted by 1 to 5 fluorine atoms,
a nitro, amino, alkylamino, dialkylamino, $C_{3-6}$-cycloalkylamino, N-alkyl-$C_{3-6}$-cycloalkylamino, arylamino, N-alkyl-arylamino, aralkylamino or N-alkyl-aralkylamino group,
a 5- to 7-membered alkyleneimino group, while in each case one or two methylene groups adjacent to the nitrogen atom may be replaced in each case by a carbonyl group or in the abovementioned 6- to 7-membered alkyleneimino groups a methylene group in the 4-position may be replaced by an oxygen atom, by an imino, N-aryl-imino or N-alkyl-imino group and the alkyleneimino groups may additionally be substituted by 1-2 methyl groups, an (alkyleneimino)carbonyl or (alkyleneimino)sulphonyl group with in each case 5 to 7 cyclic atoms in the alkyleneimino moiety, while in the abovementioned 6- to 7-membered alkyleneimino moieties a methylene group in the 4-position may be replaced in each case by an oxygen atom, by an imino, N-aryl-imino or N-alkyl-imino group, an alkylcarbonylamino, N-alkyl-alkylcarbonylamino, alkyl-sulphonylamino, N-alkyl-alkylsulphonylamino, arylcarbonylamino, N-alkyl-arylcarbonylamino, arylsulphonylamino, N-alkyl-arylsulphonylamino, aralkylcarbonylamino, N-alkyl-aralkylcarbonylamino, aralkylsulphonylamino, N-alkyl-aralkylsulphonylamino, trifluoromethylsulphonylamino, N-alkyl-trifluoromethylsulphonylamino, alkylcarbonyl, arylcarbonyl, aralkylcarbonyl, carboxy, alkoxycarbonyl, aminocarbonyl, alkylaminocarbonyl, dialkylaminocarbonyl, arylaminocarbonyl, N-alkyl-arylaminocarbonyl, aralkylaminocarbonyl, N-alkyl-aralkylaminocarbonyl, N-hydroxy-aminocarbonyl, N-hydroxy-alkylaminocarbonyl, N-alkoxy-aminocarbonyl, N-alkoxy-alkylaminocarbonyl, cyano, azido, N-cyano-amino or N-cyano-alkylamino group, a sulpho, aminosulphonyl, alkylaminosulphonyl, dialkylaminosulphonyl, arylaminosulphonyl, pyridylaminosulphonyl, N-alkyl-arylaminosulphonyl, aralkylaminosulphonyl or N-alkyl-aralkylaminosulphonyl group, or a $C_{1-2}$ alkyl group substituted by $R_4$, wherein $R_4$ denotes a hydroxy, alkoxy, aryloxy, amino, alkylamino, dialkylamino, alkylsulphenyl, alkylsulphinyl, alkylsulphonyl, arylsulphenyl, arylsulphinyl, arylsulphonyl, carboxy, alkoxycarbonyl, aminocarbonyl, alkylaminocarbonyl, dialkylaminocarbonyl or cyano group, a 5- to 7-membered alkyleneimino group optionally substituted by one or two alkyl groups, while in the abovementioned 6- to 7-membered alkyleneimino groups a methylene group in the 4-position may be replaced by an oxygen or sulphur atom, by an imino, N-alkyl-imino, N-alkylcarbonyl-imino, N-alkylsulphonyl-imino, N-arylcarbonyl-imino, N-arylsulphonyl-imino, N-aryl-imino or N-aralkyl-imino group, or may be substituted by a hydroxy, alkoxy, aminocarbonyl, alkylaminocarbonyl, dialkylaminocarbonyl, amino, alkylamino- and dialkylamino group, or an (alkyleneimino)carbonyl group with in each case 5 to 7 cyclic atoms in the alkyleneimino moiety optionally substituted by one or two alkyl groups, while in the abovementioned 6- to 7-membered alkyleneimino moieties a methylene group in the 4-position may be replaced in each case by an oxygen or sulphur atom, by an imino, N-alkyl-imino or N-alkylcarbonyl-imino group, or a group of formula

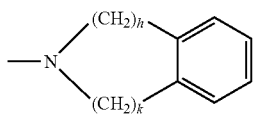

wherein
h and k, which may be identical or different, represent the numbers 1 to 2 or h denotes the number 0 and k denotes the number 2 or 3, while additionally the above benzo portion may be substituted by a fluorine, chlorine, bromine or iodine atom or by an alkyl, trifluoromethyl, hydroxy, alkoxy, carboxy or cyano group and the above saturated cyclic imino moiety may be substituted by 1 or 2 alkyl groups, $R_2$ denotes a fluorine, chlorine or bromine atom, a $C_{1-2}$ alkyl, trifluoromethyl, hydroxy, amino, alkylamino, dialkylamino, alkylcarbonylamino, N-alkyl-alkylcarbonylamino, alkylsulphonylamino, N-alkyl-alkylsulphonylamino, trifluoromethylsulphonylamino, N-alkyl-trifluoromethylsulphonylamino or cyano group, and $R_3$ denotes a fluorine, chlorine or bromine atom, a $C_{1-2}$ alkyl, trifluoromethyl or alkoxy group,
a sulpho, aminosulphonyl, alkylaminosulphonyl, dialkylaminosulphonyl, arylaminosulphonyl, pyridylaminosulphonyl, N-alkyl-arylaminosulphonyl, aralkylaminosulphonyl or N-alkyl-aralkylaminosulphonyl group, or $R_2$ together with $R_3$, if they are bound to adjacent carbon atoms, denote
a methylenedioxy group optionally substituted by one or two alkyl groups, or an n-$C_{3-5}$-alkylene group optionally substituted by one or two alkyl groups wherein a methylene group may be replaced by an oxygen atom, by an imino, N-alkyl-imino or N-aralkyl-imino group, or
a 1,3-butadiene-1,4-diylene group optionally substituted by a fluorine, chlorine or bromine atom, by a hydroxy, alkyl, alkoxy, trifluoromethyl, carboxy or cyano group or
a group of formula —NH—C(=O)—(CH$_2$) or —NH—C(=O)—(CH$_2$)$_2$, which may additionally be substituted in the alkylene moiety by 1 or 2 alkyl groups, or a group of formula —NH—N=N, —NH—N=CH, —NH—CH=N—, —O—CH=N, —S—CH=N, —NH—CH=CH— and the tautomers thereof, while each hydrogen atom may be substituted by an alkyl, aryl or aralkyl group,
or $R_a$ together with $R_1$, if $R_1$ is in the o-position to the nitrogen atom substituted by $R_a$, also denote an n-$C_{2-3}$-alkylene group optionally substituted by one or two alkyl groups, and $R_cNR_d$ together represents a 4- to 7-membered alkyleneimino group optionally substituted by 1 to 2 alkyl or aryl groups which is additionally substituted by the group $R_6$, where $R_6$ denotes a carboxy, alkoxycarbonyl, aminoalkyl, aminocarbonyl, alkylaminocarbonyl, dialkylaminocarbonyl, cyano, hydroxy, alkoxy, aryloxy, aralkoxy, alkylcarbonyloxy, arylcarbonyloxy, amino, alkylamino, hydroxy-$C_{2-4}$-alkylamino, dialkylamino, cyanamino, formylamino, alkylsulphenyl, alkylsulphinyl, alkylsulphonyl, arylsulphenyl, arylsulphinyl, arylsulphonyl, aralkylsulphenyl, aralkylsulphinyl or aralkylsulphonyl group,
an alkylcarbonylamino, N-alkyl-alkylcarbonylamino, alkylsulphonylamino, N-alkyl-alkylsulphonylamino, arylcarbonylamino, N-alkyl-arylcarbonylamino, arylsulphonylamino, N-alkyl-arylsulphonylamino, aralkylcarbonylamino, N-alkyl-aralkylcarbonylamino, aralkylsulphonylamino, N-alkyl-aralkylsulphonylamino, alkoxycarbonylamino, N-alkyl-alkoxycarbonylamino, alkoxycarbonylalkylamino, N-(alkyl)-N-(alkoxycarbonylalkyl)-amino, aralkoxycarbonylamino or N-alkyl-aralkoxycarbonylamino group,
a (NR$_8$R$_9$)CONR$_7$ group wherein
$R_7$ and $R_8$ in each case denote a hydrogen atom or an alkyl group and $R_9$ denotes a hydrogen atom or an alkyl, aryl or pyridyl group, while the groups $R_7$, $R_8$ and $R_9$ may be identical or different, or
$R_7$ and $R_8$ together denote a n-$C_{2-4}$-alkylene group and $R_9$ is a hydrogen atom or an alkyl, aryl or pyridyl group,
an alkyleneimino group with 5 to 7 cyclic atoms in the alkyleneimino moiety optionally substituted by 1 to 2 alkyl groups, while in the abovementioned 6- to 7-membered alkyleneimino moieties a methylene group in the 4-position of the alkyleneimino moiety may be replaced in each case by an oxygen or sulphur atom, by a carbonyl, sulphinyl, sulphonyl, imino, N-alkylimino, N-alkylcarbonyl-imino, N-alkylsulphonyl-imino, N-arylimino or N-aralkyl-imino group,
an (alkyleneimino)carbonyl group with in each case 4 to 7 cyclic atoms in the alkyleneimino moiety optionally substituted by 1 to 2 alkyl groups, while in the abovementioned 6- to 7-membered alkyleneimino moieties a methylene group in the 4-position may be replaced in each case by an oxygen or sulphur atom, by a sulphinyl, sulphonyl, imino, N-alkyl-imino, N-alkylcarbonyl-imino, N-alkylsulphonyl-imino, N-aryl-imino or N-aralkyl-imino group,
a 4- to 7-membered alkyleneimino group substituted by a hydroxy, alkoxy, amino, alkylamino, dialkylamino, alkylcarbonylamino, N-alkyl-alkylcarbonylamino, alkylsulphonylamino, N-alkyl-alkylsulphonylamino, hydroxyalkyl, carboxy, alkoxycarbonyl, aminocarbonyl, alkylaminocarbonyl or dialkylaminocarbonyl group,
an alkyl group substituted by a carboxy, alkoxycarbonyl, aminocarbonyl, alkylaminocarbonyl, dialkylaminocarbonyl, cyano, hydroxy, alkoxy, aryloxy, amino, alkylamino, dialkylamino, alkylcarbonylamino, N-alkyl-alkylcarbonylamino, alkoxycarbonylamino, N-alkyl-alkoxycarbonylamino, alkylsulphonylamino, N-alkyl-alkylsulphonylamino, arylcarbonylamino, N-alkyl-arylcarbonylamino, arylsulphonylamino, N-alkyl-arylsulphonylamino, dialkylaminocarbonylalkylamino, N-(alkyl)-N-(dialkylaminocarbonylalkyl)-amino, dialkylaminoalkoxy, alkylsulphenyl, alkylsulphinyl, alkylsulphonyl, arylsulphenyl, arylsulphinyl or arylsulphonyl group,
an (alkyleneimino)alkyl group with in each case 4 to 7 cyclic atoms in the alkyleneimino moiety optionally substituted by 1 to 2 alkyl groups, while in the abovementioned 6- to 7-membered alkyleneimino moieties a methylene group in the 4-position may be replaced in each case by an oxygen or sulphur atom, by a sulphinyl, sulphonyl, imino, N-alkyl-imino or N-alkylcarbonyl-imino group, an (alkyleneimino)carbonylalkyl group with in each case 4 to 7 cyclic atoms in the alkyleneimino moiety optionally substituted by 1 to 2 alkyl groups, while in the abovementioned 6- to 7-membered alkyleneimino moieties a methylene group in the 4-position may be replaced in each case by an oxygen or sulphur atom, by a sulphinyl, sulphonyl, imino or N-alkyl-imino group, a (carboxyalkyl)oxy, (alkoxycarbonylalkyl)oxy, (aminocarbonylalkyl)oxy, (alkylaminocarbonylalkyl)oxy or (dialkylaminocarbonylalkyl)oxy group, or a 3,4-dihydro-1H-quinazolin-2-on-3-yl or 1H-benzimidazol-2-on-1-yl group optionally substituted in the aryl moiety by one or two fluorine, chlorine, bromine or iodine atoms or one or two nitro, alkyl, alkoxy or cyano groups in each case, while the substituents may be identical or different, or $R_cNR_d$ together denotes a 6- to 7-membered alkyleneimino group optionally substituted by 1 to 2 alkyl groups or by an aryl group, which may additionally be substituted by the group $R_6$, while in the abovementioned alkyleneimino groups a methylene group in the 4-position is replaced in each case by an oxygen or sulphur atom, by a carbonyl, sulphinyl, sulphonyl or $R_{10}N$ group, where $R_{10}$ denotes a hydrogen atom, an alkyl, hydroxy-$C_{2-4}$-alkyl, amino-$C_{2-4}$-alkyl, alkylamino-$C_{2-4}$-alkyl, dialkylamino-$C_{2-4}$-alkyl, (hydroxy-$C_{2-4}$-alkoxy)-$C_{2-4}$-alkyl, aminocarbonylalkyl, alkylaminocarbonylalkyl, dialkylaminocarbonylalkyl, aryl, formyl, alkylcarbonyl, alkylsulphonyl, arylcarbonyl, arylsulphonyl, aralkylcarbonyl, aralkylsulphonyl, alkoxycarbonyl, aralkoxycarbonyl, cyano, aminocarbonyl, alkylaminocarbonyl or dialkylaminocarbonyl group, an amino-alkylcarbonyl, alkylamino-alkylcarbonyl, dialkylamino-alkylcarbonyl-group, a methyl group substituted by one or two aryl groups, while the aryl moieties may be substituted independently of one another by one or two fluorine, chlorine, bromine or iodine atoms or one or two nitro, alkyl, hydroxy or alkoxy groups in each case, while the substituents may be identical or different, a 2-, 3- or 4-pyridyl group, a 2-, 4- or 5-pyrimidyl group, a phenyl group optionally substituted by one or two fluorine, chlorine, bromine or iodine atoms or one or two nitro, trifluoromethyl, alkyl, hydroxy, alkoxy, amino, alkylamino, dialkylamino, carboxy, alkoxycarbonyl, aminocarbonyl, alkylaminocarbonyl, dialkylaminocarbonyl or cyano groups, while the substituents may be identical or different, a 8-methyl-8-aza-bicyclo[3.2.1]oct-3-yl group, or or an (alkyleneimino)carbonyl or (alkyleneimino)carbonylalkyl group with in each case 5 to 7 cyclic atoms in the alkyleneimino moiety, while in the abovementioned 6- to 7-membered alkyleneimino moieties a methylene group in the 4-position may be replaced in each case by an oxygen or sulphur atom, by a sulphinyl, sulphonyl, imino, N-alkyl-imino, N-alkylcarbonyl-imino or N-aralkyl-imino group, or $R_cNR_d$ together denotes a 3-thiazolidinyl group substituted in the 4-position by a carboxy, alkoxycarbonyl, aminocarbonyl, alkylaminocarbonyl or dialkylaminocarbonyl group, or $R_cNR_d$ together denotes:

a 1-piperidinyl group optionally substituted by 1 to 2 alkyl groups, wherein two hydrogen atoms on the carbon skeleton are replaced by a straight-chain alkylene bridge, this bridge containing 2 to 6 carbon atoms, if the two hydrogen atoms are located on the same carbon atom, or 1 to 5 carbon atoms if the two hydrogen atoms are located on adjacent carbon atoms, or 1 to 4 carbon atoms if the two hydrogen atoms are located on carbon atoms which are separated by one atom, or 1 to 3 carbon atoms if the two hydrogen atoms are located on carbon atoms which are separated by two atoms, while the abovementioned 1-piperidinyl groups are additionally substituted by the group $R_6$, which is as hereinbefore defined, a 1-pyrrolidinyl or 1-piperidinyl group optionally substituted by 1 to 2 alkyl groups, wherein the two hydrogen atoms of a methylene group are replaced by a straight-chain C3-6-alkylene bridge, while in each case a methylene group in the $C_{3-6}$-alkylene bridge is replaced by a $R_{10}N$ group, where $R_{10}$ is as hereinbefore defined, while the bicyclic ring thus formed is optionally additionally substituted by a hydroxy, alkoxy, amino, alkylamino, dialkylamino, cyano, alkylcarbonylamino, alkylsulphonylamino, alkoxycarbonylamino, arylcarbonyl, carboxy, alkoxycarbonyl, aminocarbonyl, alkylaminocarbonyl or dialkylaminocarbonyl group, or a group of the structure

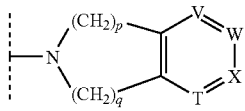

optionally substituted by 1 or 2 alkyl groups in the alkylene moieties wherein p and q, which may be identical or different, independently of one another denote the number 1 or 2, and the unit —V=W—X=Y— denotes one of the groups (a) or (b):

—N=C—C=C— (a),

—C=N—C=C— (b), while one of the available carbon atoms of the groups (a) or (b) may be substituted by a hydroxy, alkoxy, amino, alkylamino or dialkylamino group and the remaining available carbon atoms of the groups (a) or (b) are substituted by a hydrogen atom, an alkyl or aryl group, or —V=W— taken together represent an oxygen or sulphur atom or an imino, N-alkyl-imino or N-arylimino group and —X=Y— represents one of the groups —N=C or —C=N—, or, if n and m are not the same, —X=Y— taken together represent an oxygen or sulphur atom or an imino, N-alkyl-imino or N-arylimino group and —V=W— represents one of the groups —N=C or —C=N—, and $R_e$ denotes a fluorine, chlorine, bromine or iodine atom, an alkyl, alkoxy, dialkylamino, allyl, ethynyl, methylsulphenyl, methylsulphonyl, alkoxymethyl, nitro or dialkylaminomethyl group, a methyl, ethyl, methylsulphenyl or methoxy group substituted by 1 to 3 fluorine atoms, or an alkyleneimino or alkyleneimino-methyl group with 4 to 7 cyclic atoms in the alkyleneimino moiety in each case, while in a 6 or 7-membered alkyleneimino moiety a methylene group in the 4-position may be replaced in each case by an oxygen or sulphur atom, by an N-alkyl-imino, N-alkylcarbonyl-imino, N-alkylsulphonyl-imino, N-aryl-imino or N-aralkyl-imino group, while, unless otherwise specified, the abovementioned alkyl, alkylene and alkoxy moieties in each case contain 1 to 4 carbon atoms, or a tautomer, racemate, enantiomer, diastereomer or mixture thereof, or a pharmacologically acceptable acid addition salt thereof, wherein, unless otherwise stated, each carbon atom in the abovementioned alkyl, alkylene or cycloalkylene moieties which is bound to a nitrogen, oxygen or sulphur atom, cannot be bound to any other halogen, nitrogen, oxygen or sulphur atom.

3. A compound of formula I according to claim 2, wherein $R_a$ denotes a hydrogen atom or a methyl group, $R_b$ denotes a naphthyl group optionally substituted by a fluorine, chlorine or bromine atom or by a carboxy, $C_{1-2}$ alkyl, $C_{1-2}$ alkoxy, cyano or trifluoromethyl group, a benzyl or 2-phenethyl group optionally substituted in the aryl moiety by a hydroxy, cyano, trifluoromethyl, nitro, carboxy, alkoxycarbonyl, aminocarbonyl, alkylaminocarbonyl, dialkylaminocarbonyl, amino, alkylamino or dialkylamino group or one or two fluorine, chlorine or bromine atoms or one or two alkyl or alkoxy groups, while the substituents may be identical or different, and while the alkylene moiety of the abovementioned aralkyl groups may be substituted by one or two methyl groups, or a 5 or 6-indazolyl group, or a 1,3-dihydro-2-oxo-indol-6-yl group, or a phenyl group optionally substituted by the groups $R_1$ to $R_3$, where $R_1$ denotes a fluorine, chlorine, bromine or iodine atom, a $C_{1-2}$ alkyl, trifluoromethyl, aminocarbonyl, carboxy, alkoxycarbonyl, cyano, phenylaminocarbonyl, benzylaminocarbonyl, aminosulphonyl, methylaminosulphonyl, dimethylaminosulphonyl, morpholinosulphonyl, N-methylpiperazinosulphonyl, homopiperazinosulphonyl, 2,6-dimethylpiperazin-4-yl, 2-aminopyridyl-N-sulphonyl, morpholino, 4-methyl-1-piperazinyl, (N-methyl-N-methylsulphonyl)amino, 2-carboxy-1-ethyl, dimethylamino-1-ethyl or nitro group, or a methyl group which is substituted by a 1,2,4,5-tetrahydro-benzo[d]azepin-3-yl, a dialkylamino or a pyrrolidino, piperidino, 2,6-dimethyl-piperidino-1-yl, 4-methoxy-piperidino-1-yl, morpholino, S-dioxo-thiomorpholino, piperazino or 4-methyl-1-piperazinyl group, $R_2$ denotes a fluorine or chlorine atom, a hydroxy, amino or methyl group and $R_3$ denotes a chlorine atom, or an aminosulphonyl, methylaminosulphonyl, dimethylaminosulphonyl, morpholinosulphonyl, N-methylpiperazinosulphonyl, homopiperazinosulphonyl or 2-aminopyridyl-N-sulphonyl group, the group $R_cNR_d$ together denotes:

a 5- to 7-membered alkyleneimino group substituted by the group $R_6$, while $R_6$ denotes a hydroxy, alkoxy, aryloxy, amino, alkylamino, dialkylamino, alkylcarbonylamino, N-alkyl-alkylcarbonylamino, alkoxycarbonylalkylamino, N-(alkyl)-N-(alkoxycarbonylalkyl)-amino, alkylsulphenyl, alkylsulphinyl, alkylsulphonyl, arylsulphenyl, arylsulphinyl, arylsulphonyl, carboxy, alkoxycarbonyl, aminocarbonyl, alkylaminocarbonyl, dialkylaminocarbonyl or cyano group, an alkyl group which is substituted by a hydroxy, amino, alkylamino, dialkylamino, alkylcarbonylamino, N-alkyl-alkylcarbonylamino, dialkylaminocarbonylalkylamino, N-(alkyl)-N-(dialkylaminocarbonylalkyl)-amino, alkoxycarbonyl, carboxy or dialkylaminoalkoxy group or by a 5- to 7-membered alkyleneimino group, while in the abovementioned 6- to 7-membered alkyleneimino groups a methylene group in the 4-position may be replaced by an oxygen or sulphur atom or by an imino, N-alkyl-imino or N-alkylcarbonyl-imino group, an alkyleneimino group with 5 to 7 cyclic atoms in the alkyleneimino moiety, while in the abovementioned 6- to 7-membered alkyleneimino moieties a methylene group in the 4-position may be replaced in each case by an oxygen or sulphur atom, by an N-alkyl-imino, N-alkylcarbonyl-imino or N-aralkyl-imino group, an alkyleneimino group with 5 to 7 cyclic atoms in the alkyleneimino moiety substituted by a hydroxy, amino, alkylamino, dialkylamino, carboxy, alkoxycarbonyl, aminocarbonyl, alkylaminocarbonyl or dialkylaminocarbonyl group, or a 3,4-dihydro-1H-quinazolin-2-on-3-yl or a 1H-benzimidazol-2-on-1-yl group optionally substituted in the aryl moiety by a fluorine, chlorine or bromine atom or a nitro, alkyl, alkoxy or cyano group in each case, a 6- to 7-membered alkyleneimino group optionally substituted by 1 or 2 alkyl groups, while a methylene group in the 4-position is replaced by an oxygen or sulphur atom, by a sulphinyl, sulphonyl or an $NR_{10}$ group, where $R_{10}$ denotes a hydrogen atom or an alkyl, aralkyl, amino-$C_{2-4}$-alkyl, hydroxy-C2-4-alkyl, alkylcarbonyl, aralkoxycarbonyl, alkylsulphonyl, arylcarbonyl, arylsulphonyl, an (alkyleneimino)carbonylalkyl group with 5 to 7 cyclic atoms in the alkyleneimino moiety, while in the abovementioned 6- to 7-membered alkyleneimino moieties a methylene group in the 4-position may be replaced in each case by an oxygen or sulphur atom, by an N-alkyl-imino, N-alkylcarbonyl-imino or N-aralkyl-imino group, a 2-, 3- or 4-pyridyl group, a 2-, 3- or 4-pyrimidyl group, a phenyl group optionally substituted by one or two fluorine, chlorine, bromine or iodine atoms or one or two nitro, alkyl, hydroxy, alkoxy, amino, alkylamino, dialkylamino, carboxy, alkoxycarbonyl, aminocarbonyl, alkylaminocarbonyl, dialkylaminocarbonyl or cyano groups, while the substituents may be identical or different, an 8-methyl-8-aza-bicyclo[3.2.1]oct-3-yl group, a benzhydryl group, wherein independently of one another each phenyl moiety may be substituted by a fluorine, chlorine, bromine or iodine atom or a nitro, alkyl, hydroxy, alkoxy group, while the substituents may be identical or different, a 6 or 7-membered alkyleneimino group substituted by a phenyl group, which is additionally substituted by a hydroxy, carboxy, alkoxycarbonyl or cyano group or wherein a methylene group in the 4-position is replaced by a carbonyl group, a 3-thiazolidinyl group substituted in the 4-position by a carboxy, alkoxycarbonyl, aminocarbonyl, alkylaminocarbonyl or dialkylaminocarbonyl group, a group of the structure

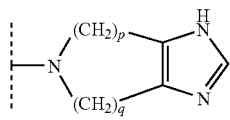

wherein p and q, which may be identical or different, independently of one another represent the number 1 or 2, while the imidazo ring may be substituted by one or two alkyl or aryl groups, while the substituents may be identical or different, a 1-pyrrolidinyl or 1-piperidinyl group, wherein the two hydrogen atoms of a methylene group are replaced by a straight-chain $C_{3-5}$-alkylene bridge, while in each case a methylene group in the $C_{3-5}$-alkylene bridge is replaced by an imino, N-alkyl-imino or N-(aralkyl)imino group, while the bicyclic ring thus formed is optionally additionally substituted by a hydroxy group, or a 1-piperidinyl group which is substituted in the 4-position by a hydroxy, alkoxy or aralkoxy group and wherein additionally one of the hydrogen atoms in each of positions 2 and 6 of the piperidinyl structure are together replaced by an ethylene bridge, and $R_e$ denotes a fluorine, chlorine bromine or iodine atom, an alkyl, alkoxy, dimethylamino, allyl, ethynyl, trifluoromethyl, methyldifluoromethylene, methylsulphenyl, trifluoromethylsulphenyl, methylsulphonyl, methoxymethyl, nitro or dimethylaminomethyl group, while, unless otherwise specified, the abovementioned alkyl, alkylene and alkoxy moieties each contain 1 to 4 carbon atoms, or a tautomer, racemate, enantiomer, diastereomer or mixture thereof, or a pharmacologically acceptable acid addition salt thereof, wherein, unless otherwise stated, each carbon atom in the abovementioned alkyl, alkylene or cycloalkylene moieties which is bound to a nitrogen, oxygen or sulphur atom cannot be bound to any other halogen, nitrogen, oxygen or sulphur atom.

4. A compound of formula I according to claim 3, wherein $R_a$ denotes a hydrogen atom, $R_b$ denotes a 1-naphthyl group or a 2-naphthyl group optionally substituted in the 5 position by a carboxy group, a benzyl group optionally substituted in the 2 position of the phenyl moiety by a chlorine or bromine atom, a 1,3-dihydro-2-oxo-indol-6-yl group, benzotriazol-5-yl, benzimidazol-5-yl, indazol-5-yl, or indazol-6-yl group, a phenyl group optionally substituted in the 4 position of the phenyl moiety by a fluorine, chlorine or bromine atom, by a cyano, aminosulphonyl, methylaminosulphonyl, dimethylaminosulphonyl, morpholinosulphonyl, N-methylpiperazinosulphonyl, homopiperazinosulphonyl, 2,6-dimethylpiperazin-4-yl, 2-aminopyridyl-N-sulphonyl, carboxy, piperidinomethyl, 1,2,4,5-tetrahydro-benzo[d]azepin-3-yl-methyl, 2-carboxy-1-ethyl, phenylaminocarbonyl, benzylaminocarbonyl, aminocarbonyl, methoxycarbonyl, (N-methyl-N-methylsulphonyl)amino, diethylaminomethyl, 3-diethylamino-1-propyloxy, morpholino, 4-methyl-1-piperazinyl or nitro group, a phenyl group substituted in the 3 position of the phenyl moiety by a chlorine or bromine atom, by a cyano, aminocarbonyl, carboxy, ethoxycarbonyl or nitro group, or a 3,4-dichlorophenyl, 3,5-dichlorophenyl, 4-amino-3,5-dichlorophenyl, 3-chloro-4-fluorophenyl, 4-chloro-3-methylphenyl, 4-chloro-3-trifluoromethylphenyl, 4-bromo-3-chlorophenyl or 3-hydroxy-4-methylphenyl group, the group $R_cNR_d$ together denotes:

a 1-pyrrolidinyl group substituted in the 2 position by a hydroxymethyl, 1-pyrrolidinylmethyl or 2-ethoxycarbonyl-1-ethyl group, a 1-pyrrolidinyl group substituted in the 3 position by an amino, acetylamino, N-methyl-acetylamino or tert.butyloxycarbonylamino, a 4-carboxy-3-thiazolidinyl, a 7-methyl-2,7-diaza-spiro[4.4]non-2-yl or a 5-hydroxy-2-methyl-2,8-diaza-spiro[5.5]undec-8-yl group, a morpholino or S-oxido-thiomorpholino group, a 1-piperidinyl group substituted in the 2 position by a ethoxycarbonyl, hydroxymethyl, 3-hydroxypropyl, 3-diethylamino-1-propyl or 2-(2-diethylaminoethoxy)-1-ethyl group, a 1-piperidinyl group substituted in the 3 position by a hydroxy, hydroxymethyl, 3-diethylamino-1-propyl, aminocarbonyl, dimethylaminocarbonyl, carboxy, 1-pyrrolidinylmethyl, 4-(1-pyrrolidinyl)-1-butyl, methoxycarbonylmethyl or acetylaminomethyl group, a 1-piperidinyl group substituted in the 4-position by an ethoxycarbonyl, 3-hydroxypropyl, hydroxy, aminomethyl, 2-(2-diethylaminoethoxy)-1-ethyl, 2-carboxy-1-ethyl, N-(2-methoxycarbonyl-1-ethyl)-N-methyl-amino, 2-(N-(dimethylaminocarbonylmethyl-)-N-methyl-amino)-1-ethyl, N-acetyl-N-methyl-aminomethyl, 8-methoxy-3,4-dihydro-1H-quinazolin-2-on-3-yl, 1-piperidinyl, 3-hydroxy-1-piperidinyl or 4-ethoxycarbonyl-1-piperidinyl group, a 3,5-dimethyl-1-piperazinyl, 1,4,6,7-tetrahydro-imidazo[4,5-c]pyridin-5-yl, 2-methyl-1,4,6,7-tetrahydro-imidazo[4,5-c]pyridin-5-yl, 1,4,5,6,7,8-hexahydro-imidazo[4,5-d]azepin-6-yl, 2-methyl-1,4,5,6,7,8-hexahydro-imidazo[4,5-d]azepin-6-yl, 3-phenyl-azepan-4-on-1-yl or 4-carboxy-4-phenyl-1-piperidinyl group, a 1-piperazinyl group which is optionally substituted in the 4-position by a methyl, acetyl, benzyloxycarbonyl, 2-pyridyl, 2-pyrimidinyl, 2-nitrophenyl, 3-methoxyphenyl, 4-cyanophenyl, 3,4-dimethoxyphenyl, 4-[bis-(4-methoxy-phenyl)]-methyl, 8-methyl-8-aza-bicyclo[3.2.1]oct-3-yl, morpholinocarbonylmethyl, 2-amino-1-ethyl or 3-hydroxy-1-propyl group, a 1-homopiperazinyl group which is optionally substituted in the 4-position by a methyl group, or a 3-hydroxy-8-aza-bicyclo[3.2.1]oct-8-yl group, and $R_e$ denotes a bromine atom or a methyl, ethyl, ethynyl, trifluoromethyl, methylsulphenyl, trifluoromethylsulphenyl or nitro group, or a tautomer, racemate, enantiomer, diastereomer or mixtures thereof, or a pharmacologically acceptable acid addition salt thereof.

5. A compound of formula I according to claim 4, wherein: $R_a$ denotes hydrogen.

6. A compound of formula I according to claim 4, wherein: $R_b$ denotes a phenyl group optionally substituted in the 4 position of the phenyl moiety by a fluorine, chlorine or bromine atom, by a cyano, aminosulphonyl, dimethylaminosulphonyl, carboxy, piperidinomethyl, 1,2,4,5-tetrahydro-benzo[d]azepin-3-yl-methyl, 2-carboxy-1-ethyl, phenylaminocarbonyl, benzylaminocarbonyl, aminocarbonyl, methoxycarbonyl, (N-methyl-N-methylsulphonyl)amino, diethylaminomethyl, 3-diethylamino-1-propyloxy, morpholino, 4-methyl-1-piperazinyl or nitro group, or a phenyl group substituted in the 3 position of the phenyl moiety by a chlorine or bromine atom, a cyano, aminocarbonyl, carboxy, ethoxycarbonyl, or nitro group, or a 3,4-dichlorophenyl, 3,5-dichlorophenyl, 4-amino-3,5-dichlorophenyl, 3-chloro-4-fluorophenyl, 4-chloro-3-methylphenyl, 4-chloro-3-trifluoromethylphenyl, 4-bromo-3-chlorophenyl, 3-hydroxy-4-methylphenyl group, benzotriazol-5-yl, benzimidazol-5-yl, indazol-5-yl or indazol-6-yl.

7. A compound of formula I according to claim 6, wherein: $R_e$ denotes a trifluoromethyl, ethyl, ethynyl or nitro group.

8. A compound of formula I according to claim 7, wherein: $R_e$ denotes a trifluoromethyl or nitro group.

9. A compound of formula I according to claim 8, wherein: the group $R_cNR_d$ together is selected from the following groups:
1,4,6,7-tetrahydro-imidazo[4,5-c]pyridin-5-yl, 2-hydroxymethyl-pyrrolidin-1-yl, 4-aminomethyl-piperidin-1-yl, 3-hydroxymethyl-piperidin-1-yl, 3-acetylaminomethyl-piperidin-1-yl, 4-(N-acetyl-N-methyl-aminomethyl)-piperidin-1-yl, 3-(4-(pyrrolidin-1-yl)butyl)-piperidin-1-yl, and 7-methyl-2,7-diaza-spiro[4.4]non-2-yl.

10. A physiologically acceptable salt of the compound of formula I according to claim 1.

11. A process for preparing a compound of formula I according to claim 1, wherein:
a. a compound of formula (II)

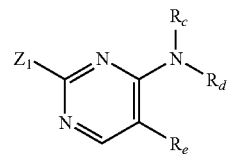

(II)

wherein
$R_c$ to $R_e$ are defined as in claim 1 and
$Z_1$ denotes a leaving group, is reacted with an amine of formula (III)

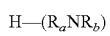

(III)

wherein
$R_a$ and $R_b$ are defined as in claim 1; or
b. a compound of formula IV

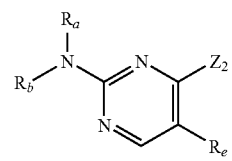

(IV)

wherein
$R_a$, $R_b$ and $R_e$ are defined as in claim 1, and
$Z_2$ denotes a leaving group, is reacted with an amine of formula (V)

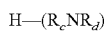

(V)

wherein
$R_c$ and $R_d$ are defined as in claim 1.

12. A pharmaceutical composition comprising one or more compounds of formula (I) according to claim 1.

* * * * *